US009284297B2

(12) United States Patent
Keller et al.

(10) Patent No.: US 9,284,297 B2
(45) Date of Patent: Mar. 15, 2016

(54) HALOFUGINONE ANALOGS FOR INHIBITION OF TRNA SYNTHETASES AND USES THEREOF

(75) Inventors: Tracy Keller, Jamaica Plain, MA (US); Ralph Mazitschek, Belmont, MA (US); Malcolm Whitman, Jamaica Plain, MA (US); Jinbo Lee, Andover, MA (US); Mark S. Sundrud, Jupiter, FL (US); Anjana Rao, La Jolla, CA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 613 days.

(21) Appl. No.: 13/058,486

(22) PCT Filed: Aug. 11, 2009

(86) PCT No.: PCT/US2009/004581
§ 371 (c)(1),
(2), (4) Date: May 27, 2011

(87) PCT Pub. No.: WO2010/019210
PCT Pub. Date: Feb. 18, 2010

(65) Prior Publication Data
US 2011/0263532 A1 Oct. 27, 2011

Related U.S. Application Data

(60) Provisional application No. 61/153,866, filed on Feb. 19, 2009, provisional application No. 61/188,740, filed on Aug. 11, 2008.

(51) Int. Cl.
| | |
|---|---|
| A61K 31/4184 | (2006.01) |
| C07D 401/06 | (2006.01) |
| C07D 401/14 | (2006.01) |
| C07D 403/06 | (2006.01) |
| C07D 405/14 | (2006.01) |
| C07D 491/04 | (2006.01) |
| C07D 495/04 | (2006.01) |
| C07F 9/6558 | (2006.01) |

(52) U.S. Cl.
CPC .......... *C07D 401/06* (2013.01); *A61K 31/4184* (2013.01); *C07D 401/14* (2013.01); *C07D 403/06* (2013.01); *C07D 405/14* (2013.01); *C07D 491/04* (2013.01); *C07D 495/04* (2013.01); *C07F 9/65583* (2013.01)

(58) Field of Classification Search
CPC ............. A61K 31/4184; C07D 401/06; C07D 401/14; C07D 403/06; C07D 405/14; C07D 491/04; C07D 495/04; C07F 9/65583
See application file for complete search history.

(56) References Cited

U.S. PATENT DOCUMENTS

| | | | |
|---|---|---|---|
| 2,694,711 A | 11/1954 | Baker et al. | |
| 3,320,124 A * | 5/1967 | Waletzky et al. | ........ 514/266.22 |
| 3,410,645 A | 11/1968 | Schwartzman | |
| 3,418,055 A | 12/1968 | Schwartzman | |
| 3,669,323 A | 6/1972 | Harker et al. | |
| 3,748,327 A * | 7/1973 | Beyerle | ........................ 544/58.6 |
| 4,254,105 A | 3/1981 | Fukuda | |
| 4,340,596 A | 7/1982 | Schein | |
| 4,620,648 A | 11/1986 | Schwartzman | |
| 4,693,623 A | 9/1987 | Schwartzman | |
| 4,725,599 A | 2/1988 | Glazer et al. | |
| 4,762,838 A | 8/1988 | Glazer | |
| 4,800,197 A | 1/1989 | Kowcz et al. | |
| 4,891,227 A | 1/1990 | Thaman et al. | |
| 4,891,228 A | 1/1990 | Thaman et al. | |
| 4,919,934 A | 4/1990 | Deckner et al. | |
| 4,937,370 A | 6/1990 | Sabatelli | |
| 4,960,764 A | 10/1990 | Figueroa, Jr. et al. | |
| 4,999,186 A | 3/1991 | Sabatelli et al. | |
| 5,073,371 A | 12/1991 | Turner et al. | |
| 5,073,372 A | 12/1991 | Turner et al. | |
| 5,087,445 A | 2/1992 | Haffey et al. | |
| 5,223,409 A | 6/1993 | Ladner et al. | |
| 5,449,678 A | 9/1995 | Pines et al. | |
| 5,759,833 A | 6/1998 | Shiba et al. | |
| 6,028,075 A | 2/2000 | Pines et al. | |
| 6,358,539 B1 | 3/2002 | Murad | |
| 6,446,032 B1 | 9/2002 | Schimmel | |
| 2005/0227935 A1 | 10/2005 | McSwiggen et al. | |

(Continued)

FOREIGN PATENT DOCUMENTS

| | | |
|---|---|---|
| CN | 1583729 A | 2/2005 |
| JP | 2002-201192 A | 7/2002 |

(Continued)

OTHER PUBLICATIONS

Kikuchi et. al., Journal of Medicinal Chemistry, 2002, American Chemical Society, vol. 45, pp. 2563-2570.*

(Continued)

*Primary Examiner* — Sarah Pihonak
(74) *Attorney, Agent, or Firm* — Wolf, Greenfield & Sacks, P.C.

(57) ABSTRACT

The present invention provides novel analogs and derivatives of halofuginone. The invention also provides pharmaceutical and cosmetic compositions thereof and methods for using halofuginone analogs in treating chronic inflammatory diseases, autoimmune diseases, dry eye syndrome, fibrosis, scar formation, angiogenesis, viral infections, ischemic damage, transplant and implant rejection, neurodegenerative diseases, and cosmetic applications.

29 Claims, 49 Drawing Sheets

(56) References Cited

U.S. PATENT DOCUMENTS

| | | | |
|---|---|---|---|
| 2008/0025917 A1 | 1/2008 | Whitman et al. |
| 2008/0188498 A1 | 8/2008 | Zhu |
| 2009/0123389 A1 | 5/2009 | Whitman et al. |
| 2011/0212100 A1 | 9/2011 | Keller et al. |
| 2011/0311519 A1 | 12/2011 | Teitelbaum et al. |
| 2012/0058133 A1 | 3/2012 | Whitman et al. |
| 2015/0057297 A1 | 2/2015 | Whitman et al. |

FOREIGN PATENT DOCUMENTS

| | | | |
|---|---|---|---|
| WO | WO 00/09070 A2 | 2/2000 |
| WO | WO 01/17498 A1 | 3/2001 |
| WO | WO 03/016860 A2 | 2/2003 |
| WO | WO 2004069793 A2 * | 8/2004 |
| WO | WO 2007/058990 A2 | 5/2007 |
| WO | WO 2007109192 A2 * | 9/2007 |
| WO | WO 2008094909 A2 * | 8/2008 |
| WO | WO 2008/157791 A2 | 12/2008 |
| WO | WO 2009/023267 A2 | 2/2009 |
| WO | WO 2010/019210 A2 | 2/2010 |
| WO | WO 2010/096170 A2 | 8/2010 |
| WO | WO 2013/106702 A1 | 7/2013 |

OTHER PUBLICATIONS

Baker et. al., The Journal of Organic Chemistry, 1952, American Chemical Society, vol. 17, issue 1, pp. 141-148.*
Baker et. al., The Journal of Organic Chemistry, 1952, American Chemical Society, vol. 17, issue 1, pp. 116-131.*
Kikuchi et. al., Journal of Medicinal Chemistry, 2006, American Chemical Society, vol. 49, pp. 4698-4706.*
Baker et. al., Journal of Organic Chemistry, 1952, American Chemical Society, vol. 17, pp. 35-51.*
Zhu et. al., Bioorganic and Medicinal Chemistry Letters, 2006, Elsevier, vol. 16, pp. 1854-1858.*
International Preliminary Report on Patentability for PCT/US2010/000460, mailed Sep. 1, 2011.
Extended European Search Report for EP 09806950.3, mailed Nov. 30, 2012.
International Search Report and Written Opinion for PCT/US2007/008752, mailed Oct. 9, 2007.
International Preliminary Report on Patentability for PCT/US2007/008752, mailed Oct. 23, 2008.
Office Communication, mailed Jun. 23, 2009, for U.S. Appl. No. 11/786,151.
Office Communication, mailed Jan. 19, 2010, for U.S. Appl. No. 11/786,151.
Office Communication, mailed Aug. 3, 2011, for U.S. Appl. No. 11/786,151.
Office Communication, mailed May 9, 2012, for U.S. Appl. No. 11/786,151.
[No Author Listed] Department of Health, Education, and Welfare. Federal Register. 1978;43(166):38206-69.
Burgess et al., PPARgamma agonists inhibit TGF-beta induced pulmonary myofibroblast differentiation and collagen production: implications for therapy of lung fibrosis. Am J Physiol Lung Cell Mol Physiol. Jun. 2005;288(6):L1146-53. Epub Feb. 25, 2005.
Campbell et al., A multi-station culture force monitor system to study cellular contractility. J Biomech. Jan. 2003;36(1):137-40.
Carell et al., A Solution-Phase Screening Procedure for the Isolation of Active Compounds from a Library of Molecules. Angew Chem Intl Ed Engl. 1994;33(20):2061-64.
Eastwood et al., Quantitative analysis of collagen gel contractile forces generated by dermal fibroblasts and the relationship to cell morphology. J Cell Physiol. Jan. 1996;166(1):33-42.
Hansen et al., Reversible inhibition by histidinol of protein synthesis in human cells at the activation of histidine. J Biol Chem. Jun. 25, 1972;247(12):3854-7.
Hutchings et al., An Antimalarial Alkaloid From Hydrangea. III. Degradation. J Org Chem. 1952;17(1):19-34.
Jarman-Smith et al., Human fibroblast culture on a crosslinked dermal porcine collagen matrix. Biochem Eng J. 2004;20(2-3):217-22.
Kikuchi et al., Potent antimalarial febrifugine analogues against the plasmodium malaria parasite. J Med Chem. Jun. 6, 2002;45(12):2563-70.
Koepfli et al., Alkaloids of Dichroa febrifuga; isolation and degradative studies. J Am Chem Soc. Mar. 1949;71(3):1048-54.
Li et al., Inhibitory effect of pravastatin on transforming growth factor beta1-inducible gene h3 expression in a rat model of chronic cyclosporine nephropathy. Am J Nephrol. Nov.-Dec. 2005;25(6):611-20. Epub Nov. 22, 2005.
Mucida et al., Reciprocal TH17 and regulatory T cell differentiation mediated by retinoic acid. Science. Jul. 13, 2007;317(5835):256-60. Epub Jun. 14, 2007.
Paley et al., Tryptophanyl-tRNA synthetase in cell lines resistant to tryptophan analogs. Exp Cell Res. Jul. 1991;195(1):66-78.
Pines et al., Reduction in dermal fibrosis in the tight-skin (Tsk) mouse after local application of halofuginone. Biochem Pharmacol. Nov. 1, 2001;62(9):1221-7.
Rocchi et al., A unique PPARgamma ligand with potent insulin-sensitizing yet weak adipogenic activity. Mol Cell. Oct. 2001;8(4):737-47.
Taniguchi et al., A diastereocontrolled synthesis of (+)-febrifugine: a potent antimalarial piperidine alkaloid. Org Lett. Oct. 5, 2000;2(20):3193-5.
Viennet et al., Contractile forces generated by striae distensae fibroblasts embedded in collagen lattices. Arch Dermatol Res. Jul. 2005;297(1):10-7. Epub May 10, 2005.
Wang et al., A synthetic triterpenoid, 2-cyano-3,12-dioxooleana-1,9-dien-28-oic acid (CDDO), is a ligand for the peroxisome proliferator-activated receptor gamma. Mol Endocrinol. Oct. 2000;14(10):1550-6.
Wang et al., Concise asymmetric synthesis of antimalarial alkaloid (+)-febrifugine. Synlett. 2009;14:2301-04.
Watson et al., Fibrillin microfibrils are reduced in skin exhibiting striae distensae. Br J Dermatol. Jun. 1998;138(6):931-7.
Weber et al., Statins in the treatment of central nervous system autoimmune disease. J Neuroimmunol. Sep. 2006;178(1-2):140-8. Epub Jul. 24, 2006.
Wee et al., Asymmetric synthesis of (+)-isofebrifugine and (-)-sedacryptine from a common chiral nonracemic building block. Org Lett. Sep. 4, 2008;10(17):3869-72. Epub Aug. 2, 2008.
Wijdeven et al., Complementary chemoenzymatic routes to both enantiomers of febrifugine. Org Biomol Chem. Jul. 21, 2009;7(14):2976-80. Epub Jun. 4, 2009.
International Search Report and Written Opinion for PCT/US2008/009774 mailed Jan. 22, 2009.
International Preliminary Report on Patentability for PCT/US2008/009774 mailed Feb. 25, 2010.
International Search Report and Written Opinion for PCT/US2010/000460, mailed Nov. 9, 2010.
International Search Report and Written Opinion for PCT/US2009/004581 mailed Mar. 29, 2010.
International Preliminary Report on Patentability for PCT/US2009/004581 mailed Feb. 24, 2011.
[No Author Listed] "A new lead for autoimmune disease." EurekAlert. Public release date Jun. 4, 2009. Available at http://www.eurekalert.org/pub_releases/2009-06/chb-an1060109.php. Last accessed Apr. 28, 2010. 3 pages.
[No Author Listed] "Sun Products Formulary." Cosmetics & Toiletries. Mar. 1987;102:117-36.
[No Author Listed] "Sun Products Formulary." Cosmetics & Toiletries. Dec. 1990;105:122-39.
Acosta-Rodriguez et al., Interleukins 1beta and 6 but not transforming growth factor-beta are essential for the differentiation of interleukin 17-producing human T helper cells. Nat Immunol. Sep. 2007;8(9):942-9. Epub Aug. 5, 2007.
Afzali et al., The role of T helper 17 (Th17) and regulatory T cells (Treg) in human organ transplantation and autoimmune disease. Clin Exp Immunol. Apr. 2007;148(1):32-46.
Al-Shaar et al., The Synthesis of Heterocycles via Addition-Elimination Reactions of 4- and 5-Aminoimidazoles. J Chem Soc Perkin 1. 1992;21:2789-811.

(56) References Cited

OTHER PUBLICATIONS

Ashoorzadeh et al., Synthetic evaluation of an enantiopure tetrahydropyridine N-oxide. Synthesis of (+)-febrifugine. Tetrahedron. 2009;65(24):4671-80.

Avram, Cellulite: a review of its physiology and treatment. J Cosmet Laser Ther. Dec. 2004;6(4):181-5.

Banwell et al., Analogues of SB-203207 as inhibitors of tRNA synthetases. Bioorg Med Chem Lett. Oct. 16, 2000;10(20):2263-6.

Barabino et al., The controlled-environment chamber: a new mouse model of dry eye. Invest Ophthalmol Vis Sci. Aug. 2005;46(8):2766-71.

Baumgart et al., Inflammatory bowel disease: cause and immunobiology. Lancet. May 12, 2007;369(9573):1627-40.

Berge et al., Phamaceutical Salts. J Pharma Sciences. 1977;66:1-19.

Berlanga et al., Antiviral effect of the mammalian translation initiation factor 2alpha kinase GCN2 against RNA viruses. EMBO J. Apr. 19, 2006;25(8):1730-40. Epub Apr. 6, 2006.

Bettelli et al., Induction and effector functions of T(H)17 cells. Nature. Jun. 19, 2008;453(7198):1051-7.

Bettelli et al., Reciprocal developmental pathways for the generation of pathogenic effector TH17 and regulatory T cells. Nature. May 11, 2006;441(7090):235-8. Epub Apr. 30, 2006.

Border et al., Transforming growth factor beta in tissue fibrosis. N Engl J Med. Nov. 10, 1994;331(19):1286-92. 9 pages.

Boye et al., S100A4 and metastasis: a small actor playing many roles. Am J Pathol. Feb. 2010;176(2):528-35. Epub Dec. 17, 2009.

Branton et al., TGF-β and fibrosis. Microbes Infect. 1999;1:1349-65.

Bromberg et al., Stat3 as an oncogene. Cell. Aug. 6, 1999;98(3):295-303.

Brunsing et al., B- and T-cell development both involve activity of the unfolded protein response pathway. J Biol Chem. Jun. 27, 2008;283(26):17954-61. Epub Mar. 28, 2008.

Cahn, An Introduction to the Sequence Rule. J Chem, Educ. 1964;41:116-125.

Cahn et al., Specification of Configuration about Quadricovalent Asymmetric Atoms J Chem Soc. 1951:612-22.

Cahn et al., [Spezifikation der molekularen Chiralität] Specification of Molecular Chirality. Angew Chem. 1966;78:413-47. German. Translated copy in Angew Chem Int Ed. 1966;5:385-415.

Cahn et al., The Specification of Asymmetric Configuration in Organic Chemistry. Experientia. 1956;12:81-94.

Carlson et al., The Th17-ELR+ CXC chemokine pathway is essential for the development of central nervous system autoimmune disease. J Exp Med. Apr. 14, 2008;205(4):811-23. Epub Mar. 17, 2008.

Carrell et al., A Novel Procedure for the Synthesis of Libraries Containing Small Organic Molecules. Angew Chem Int Ed Engl. 1994;33:2059-61.

Chang et al., Coactivator TIF1beta interacts with transcription factor C/EBPbeta and glucocorticoid receptor to induce alpha1-acid glycoprotein gene expression. Mol Cell Biol. Oct. 1998;18(10):5880-7.

Chauhan et al., Autoimmunity in dry eye is due to resistance of Th17 to Treg suppression. J Immunol. Feb. 1, 2009;182(3):1247-52.

Cho et al., An unnatural biopolymer. Science. Sep. 3, 1993;261(5126):1303-5.

Corry et al., Primarily vascularized allografts of hearts in mice. The role of H-2D, H-2K, and non-H-2 antigens in rejection. Transplantation. Oct. 1973; 16(4):343-50.

Critchley et al., Antibacterial activity of REP8839, a new antibiotic for topical use. Antimicrob Agents Chemother. Oct. 2005;49(10):4247-52.

Cull et al., Screening for receptor ligands using large libraries of peptides linked to the C terminus of the lac repressor. Proc Natl Acad Sci U S A. Mar. 1, 1992;89(5):1865-9.

Cwirla et al., Peptides on phage: a vast library of peptides for identifying ligands. Proc Natl Acad Sci U S A. Aug. 1990;87(16):6378-82.

De Jonge et al., Phase I and pharmacokinetic study of halofuginone, an oral quinazolinone derivative in patients with advanced solid tumours. Eur J Cancer. Aug. 2006;42(12):1768-74. Epub Jul. 3, 2006.

Desmouliére et al., Tissue repair, contraction, and the myofibroblast. Wound Repair Regen. Jan.-Feb. 2005;13(1):7-12.

Devlin et al., Random peptide libraries: a source of specific protein binding molecules. Science. Jul. 27, 1990;249(4967):404-6.

Dewitt et al., "Diversomers": an approach to nonpeptide, nonoligomeric chemical diversity. Proc Natl Acad Sci U S A. Aug. 1, 1993;90(15):6909-13.

Djuretic et al., Transcription factors T-bet and Runx3 cooperate to activate Ifng and silence I14 in T helper type 1 cells. Nat Immunol. Feb. 2007;8(2):145-53. Epub Dec. 31, 2006.

Dong, $T_H17$ cells in development: an updated view of their molecular identity and genetic programming. Nat Rev Immunol. 2008;8:337-48.

Dong et al., Uncharged tRNA activates GCN2 by displacing the protein kinase moiety from a bipartite tRNA-binding domain. Mol Cell. Aug. 2000;6(2):269-79.

Elkin et al., Inhibition of bladder carcinoma angiogenesis, stromal support, and tumor growth by halofuginone. Cancer Res. Aug. 15, 1999;59(16):4111-8.

Elliot et al., Inflammatory Bowel Disease and Celiac Disease. In: The Autoimmune Diseases, 3rd ed., Rose et al., eds., Academic Press, San Diego, CA. 1998:477-509.

Elson et al., Experimental models of inflammatory bowel disease. Gastroenterology. Oct. 1995;109(4):1344-67.

Emamaullee et al., Caspase inhibitor therapy enhances marginal mass islet graft survival and preserves long-term function in islet transplantation. Diabetes. May 2007;56(5):1289-98. Epub Feb. 15, 2007.

Emmanuvel et al., A concise enantioselective synthesis of (+)-febrifugine. Tetrahedron: Asymmetry. 2009;20(1):84-88.

Erb et al., Recursive deconvolution of combinatorial chemical libraries. Proc Natl Acad Sci U S A. Nov. 22, 1994;91(24):11422-6.

Fafournoux et al., Amino acid regulation of gene expression. Biochem J. Oct. 1, 2000;351(Pt 1):1-12.

Farhanullah et al., Design and synthesis of quinolinones as methionyl-tRNA synthetase inhibitors. Bioorg Med Chem. Nov. 1, 2006;14(21):7154-9. Epub Jul. 18, 2006.

Felici et al., Selection of antibody ligands from a large library of oligopeptides expressed on a multivalent exposition vector. J Mol Biol. Nov. 20, 1991;222(2):301-10.

Fingar et al., Target of rapamycin (TOR): an integrator of nutrient and growth factor signals and coordinator of cell growth and cell cycle progression. Oncogene. Apr. 19, 2004;23(18):3151-71.

Finn et al., Discovery of a potent and selective series of pyrazole bacterial methionyl-tRNA synthetase inhibitors. Bioorg Med Chem Lett. Jul. 7, 2003;13(13):2231-4.

Flanders, Smad3 as a mediator of the fibrotic response. Int J Exp Pathol. Apr. 2004;85(2):47-64.

Fodor et al., Multiplexed biochemical assays with biological chips. Nature. Aug. 5, 1993;364(6437):555-6.

Gallop et al., Applications of combinatorial technologies to drug discovery. 1. Background and peptide combinatorial libraries. J Med Chem. Apr. 29, 1994;37(9):1233-51.

Gavin et al., Foxp3-dependent programme of regulatory T-cell differentiation. Nature. Feb. 15, 2007;445(7129):771-5. Epub Jan. 14, 2007.

Glimcher et al., Recent developments in the transcriptional regulation of cytolytic effector cells. Nat Rev Immunol. Nov. 2004;4(11):900-11.

Gnainsky et al., Gene expression during chemically induced liver fibrosis: effect of halofuginone on TGF-beta signaling. Cell Tissue Res. Apr. 2007;328(1):153-66. Epub Dec. 19, 2006.

Gutcher et al., APC-derived cytokines and T cell polarization in autoimmune inflammation. J Clin Invest. May 2007;117(5):1119-27.

Hanami et al., Synthesis of 8-(2'-deoxy-β-D-ribofuranosyl)-imidazo[1,2,a    ]-s-triazin-4-one. Tetrahedron Lett. 2007;48(22):3801-03.

Harding et al., An integrated stress response regulates amino acid metabolism and resistance to oxidative stress. Mol Cell. Mar. 2003;11(3):619-33.

Harding et al., Regulated translation initiation controls stress-induced gene expression in mammalian cells. Mol Cell. Nov. 2000;6(5):1099-108.

(56) References Cited

OTHER PUBLICATIONS

Heim-Riether et al., A novel method for the synthesis of imidazo[5,1-f][1,2,4]triazin-4(3H)-ones. J Org Chem. Sep. 2, 2005;70(18):7331-7.

Hinz et al., Cell-matrix and cell-cell contacts of myofibroblasts: role in connective tissue remodeling. Thromb Haemost. Dec. 2003;90(6):993-1002.

Hinz et al., Mechanisms of force generation and transmission by myofibroblasts. Curr Opin Biotechnol. Oct. 2003;14(5):538-46.

Houghten et al., The use of synthetic peptide combinatorial libraries for the identification of bioactive peptides. Biotechniques. Sep. 1992;13(3):412-21.

Hsu et al., TRIP-Br: a novel family of PHD zinc finger- and bromodomain-interacting proteins that regulate the transcriptional activity of E2F-1/DP-1. EMBO J. May 1, 2001;20(9):2273-85.

Huebner et al., Functional resolution of fibrosis in mdx mouse dystrophic heart and skeletal muscle by halofuginone. Am J Physiol Heart Circ Physiol. Apr. 2008;294(4):H1550-61. Epub Feb. 8, 2008.

Hurdle et al., Prospects for aminoacyl-tRNA synthetase inhibitors as new antimicrobial agents. Antimicrob Agents Chemother. Dec. 2005;49(12):4821-33.

Inman et al., SB-431542 is a potent and specific inhibitor of transforming growth factor-beta superfamily type I activin receptor-like kinase (ALK) receptors ALK4, ALK5, and ALK7. Mol Pharmacol. Jul. 2002;62(1):65-74.

Ivanov et al., The orphan nuclear receptor RORgammat directs the differentiation program of proinflammatory IL-17+ T helper cells. Cell. Sep. 22, 2006;126(6):1121-33.

Jarvest et al., Conformational restriction of methionyl tRNA synthetase inhibitors leading to analogues with potent inhibition and excellent gram-positive antibacterial activity. Bioorg Med Chem Lett. Apr. 7, 2003;13(7):1265-8.

Jarvest et al., Definition of the heterocyclic pharmacophore of bacterial methionyl tRNA synthetase inhibitors: potent antibacterially active non-quinolone analogues. Bioorg Med Chem Lett. Aug. 2, 2004;14(15):3937-41.

Jarvest et al., Discovery and optimisation of potent, selective, ethanolamine inhibitors of bacterial phenylalanyl tRNA synthetase. Bioorg Med Chem Lett. May 2, 2005;15(9):2305-9.

Jarvest et al., Inhibitors of bacterial tyrosyl tRNA synthetase: synthesis of carbocyclic analogues of the natural product SB-219383. Bioorg Med Chem Lett. Sep. 17, 2001;11(18):2499-502.

Jiang et al., Antimalarial activities and therapeutic properties of febrifugine analogs. Antimicrob Agents Chemother. Mar. 2005;49(3):1169-76.

Kanamaru et al., In vitro and in vivo antibacterial activities of TAK-083, an agent for treatment of Helicobacter pylori infection. Antimicrob Agents Chemother. Sep. 2001;45(9):2455-9.

Kanemaki et al., TIP49b, a new RuvB-like DNA helicase, is included in a complex together with another RuvB-like DNA helicase, TIP49a. J Biol Chem. Aug. 6, 1999;274(32):22437-44.

Kanitakis, Anatomy, histology and immunohistochemistry of normal human skin. Eur J Dermatol. Jul.-Aug. 2002; 12(4):390-9; quiz 400-1.

Kastelein et al., Discovery and biology of IL-23 and IL-27: related but functionally distinct regulators of inflammation. Annu Rev Immunol. 2007;25:221-42.

Kawamura et al., Anti-angiogenesis effects of borrelidin are mediated through distinct pathways: threonyl-tRNA synthetase and caspases are independently involved in suppression of proliferation and induction of apoptosis in endothelial cells. J Antibiot (Tokyo). Aug. 2003;56(8):709-15.

Kikuchi et al., Exploration of a new type of antimalarial compounds based on febrifugine. J Med Chem. Jul. 27, 2006;49(15):4698-706.

Kim et al., Aminoacyl-tRNA synthetases and their inhibitors as a novel family of antibiotics. Appl Microbiol Biotechnol. May 2003;61(4):278-88. Epub Mar. 1, 2003.

Kim et al., Deoxyribosyl analogues of methionyl and isoleucyl sulfamate adenylates as inhibitors of methionyl-tRNA and isoleucyl-tRNA synthetases. Bioorg Med Chem Lett. Jul. 15, 2005;15(14):3389-93.

Klarmann, Chapter 8. Suntan Prepartions. In: Cosmetics Science and Technology. Sagarin et al., eds. Interscience Publishers, Inc., New York. 1957:189-212.

Kobayashi et al., Catalytic Asymmetric Synthesis of Antimalarial Alkaloids Febrifugine and Isofebrifugine and Their Biological Activity. J Org Chem. Sep. 3, 1999;64(18):6833-6841.

Kolls et al., Interleukin-17 family members and inflammation. Immunity. Oct. 2004;21(4):467-76.

Laan et al., Neutrophil recruitment by human IL-17 via C-X-C chemokine release in the airways. J Immunol. Feb. 15, 1999;162(4):2347-52.

Lam et al., A new type of synthetic peptide library for identifying ligand-binding activity. Nature. Nov. 7, 1991;354(6348):82-4.

Lam, Application of combinatorial library methods in cancer research and drug discovery: Anticancer Drug Des. Apr. 1997;12(3):145-67.

Le Douarin et al., TIF1alpha: a possible link between KRAB zinc finger proteins and nuclear receptors. J Steroid Biochem Mol Biol. Apr. 1998;65(1-6):43-50.

Lee et al., N-Alkoxysulfamide, N-hydroxysulfamide, and sulfamate analogues of methionyl and isoleucyl adenylates as inhibitors of methionyl-tRNA and isoleucyl-tRNA synthetases. Bioorg Med Chem Lett. Mar. 24, 2003;13(6):1087-92.

Lee et al., XBP-1 regulates a subset of endoplasmic reticulum resident chaperone genes in the unfolded protein response. Mol Cell Biol. Nov. 2003;23(21):7448-59.

Leiba et al., Halofuginone inhibits NF-kappaB and p38 MAPK in activated T cells. J Leukoc Biol. Aug. 2006;80(2):399-406. Epub Jun. 12, 2006.

Li et al., Matrix metalloproteinase-2 and tissue inhibitor of metalloproteinase-2 in colorectal carcinoma invasion and metastasis. World J Gastroenterol. May 28, 2005;11(20):3046-50.

Li et al., Transforming growth factor-beta regulation of immune responses. Annu Rev Immunol. 2006;24:99-146.

Lin et al., IRE1 signaling affects cell fate during the unfolded protein response. Science. Nov. 9, 2007;318(5852):944-9.

Lin et al., The integrated stress response prevents demyelination by protecting oligodendrocytes against immune-mediated damage. J Clin Invest. Feb. 2007;117(2):448-56.

Lohr et al., Role of IL-17 and regulatory T lymphocytes in a systemic autoimmune disease. J Exp Med. Dec. 25, 2006;203(13):2785-91. Epub Nov. 27, 2006.

Ludviksson et al., Dysregulated intrathymic development in the IL-2-deficient mouse leads to colitis-inducing thymocytes. J Immunol. Jan. 1, 1997;158(1):104-11.

Manel et al., The differentiation of human T(H)-17 cells requires transforming growth factor-beta and induction of the nuclear receptor RORγt. Nat Immunol. Jun. 2008;9(6):641-9. Epub May 4, 2008.

McGaha et al., Effect of halofuginone on the development of tight skin (TSK) syndrome. Autoimmunity. Jul. 2002;35(4):277-82.

McGaha et al., Halofuginone, an inhibitor of type-I collagen synthesis and skin sclerosis, blocks transforming-growth-factor-beta-mediated Smad3 activation in fibroblasts. J Invest Dermatol. Mar. 2002;118(3):461-70.

McGeachy et al., TGF-beta and IL-6 drive the production of IL-17 and IL-10 by T cells and restrain T(H)-17 cell-mediated pathology. Nat Immunol. Dec. 2007;8(12):1390-7. Epub Nov. 11, 2007.

Mesaros et al., Activation of Stat3 signaling in AgRP neurons promotes locomotor activity. Cell Metab. Mar. 2008;7(3):236-48.

Mirrashed et al., Pilot study of dermal and subcutaneous fat structures by MRI in individuals who differ in gender, BMI, and cellulite grading. Skin Res Technol. Aug. 2004;10(3):161-8.

Miyamoto et al., Identification of *Saccharomyces cerevisiae* isoleucyl-tRNA synthetase as a target of the G1-specific inhibitor Reveromycin A. J Biol Chem. Aug. 9, 2002;277(32):28810-4. Epub Jun. 5, 2002.

Mombaerts et al., Spontaneous development of inflammatory bowel disease in T cell receptor mutant mice. Cell. Oct. 22, 1993;75(2):274-82.

(56) References Cited

OTHER PUBLICATIONS

Munn et al., GCN2 kinase in T cells mediates proliferative arrest and anergy induction in response to indoleamine 2,3-dioxygenase. Immunity. May 2005;22(5):633-42.

Nagler et al., Inhibition of collagen synthesis, smooth muscle cell proliferation, and injury-induced intimal hyperplasia by halofuginone. Arterioscler Thromb Vasc Biol. Jan. 1997;17(1):194-202.

Nagler et al., Reduction in pulmonary fibrosis in vivo by halofuginone. Am J Respir Crit Care Med. Oct. 1996;154(4 Pt 1):1082-6.

Nagler et al., Suppression of hepatocellular carcinoma growth in mice by the alkaloid coccidiostat halofuginone. Eur J Cancer. Jun. 2004;40(9):1397-403.

Nagler et al., Topical Treatment of Cutaneous Chronic Graft Versus Host Disease with Halofuginone: A Novel Inhibitor of Collagen Type 1 Synthesis. Transplantation. 1999;68(11):1806-09.

Nomura et al., Oncogenic activation of c-Myb correlates with a loss of negative regulation by TIF1beta and Ski. J Biol Chem. Apr. 16, 2004;279(16):16715-26. Epub Feb. 3, 2004.

Nurieva et al., Essential autocrine regulation by IL-21 in the generation of inflammatory T cells. Nature. Jul. 26, 2007;448(7152):480-3. Epub Jun. 20, 2007.

Nürnberger et al., So-called cellulite: an invented disease. J Dermatol Surg Oncol. Mar. 1978;4(3):221-9.

Ono et al., Improved technique of heart transplantation in rats. J Thorac Cardiovasc Surg. Feb. 1969;57(2):225-9.

Ooi et al., A concise enantioselective synthesis of antimalarial febrifugine alkaloids. Org Lett. Mar. 22, 2001;3(6):953-5.

Oslejskova et al., Metastasis-inducing S100A4 protein is associated with the disease activity of rheumatoid arthritis. Rheumatology (Oxford). Dec. 2009;48(12):1590-4. Epub Oct. 14, 2009.

Oslejskova et al., The metastasis associated protein S100A4: a potential novel link to inflammation and consequent aggressive behaviour of rheumatoid arthritis synovial fibroblasts. Ann Rheum Dis. Nov. 2008;67(11):1499-504. Epub Dec. 4, 2007.

Ozcelik et al., The effect of halofuginone, a specific inhibitor of collagen type 1 synthesis, in the prevention of esophageal strictures related to caustic injury. Am J Surg. Feb. 2004;187(2):257-60.

Park et al., A distinct lineage of CD4 T cells regulates tissue inflammation by producing interleukin 17. Nat Immunol. Nov. 2005;6(11):1133-41. Epub Oct. 2, 2005.

Park et al., Indoleamine 2,3-dioxygenase-expressing dendritic cells are involved in the generation of CD4+CD25+ regulatory T cells in Peyer's patches in an orally tolerized, collagen-induced arthritis mouse model. Arthritis Res Ther. 2008;10(1):R11. Epub Jan. 25, 2008.

Patani et al., Bioisosterism: A Rational Approach in Drug Design. Chem Rev. Dec. 19, 1996;96(8):3147-3176.

Patil et al., Synthesis of Pyrrolo[2,1-*f*][1,2,4]triazine Congeners of Nucleic Acid Purines via the *N*-Amination of 2-Substituted Pyrroles [1]. J Heterocycl Chem. 1994;31(4):781-86.

Peitz at al., Ability of the hydrophobic FGF and basic TAT peptides to promote cellular uptake of recombinant Cre recombinase: a tool for efficient genetic engineering of mammalian genomes. Proc Natl Acad Sci U S A. Apr. 2, 2002;99(7):4489-94. Epub Mar. 19, 2002.

Peng et al., Preparation of a 7-arylthieno[3,2-d]pyrimidin-4-amine library. J Comb Chem. May-Jun. 2007;9(3):431-6. Epub Mar. 8, 2007.

Peng et al., The immunosuppressant rapamycin mimics a starvation-like signal distinct from amino acid and glucose deprivation. Mol Cell Biol. Aug. 2002;22(15):5575-84.

Petraitiene et al., Efficacy, plasma pharmacokinetics, and safety of icofungipen, an inhibitor of Candida isoleucyl-tRNA synthetase, in treatment of experimental disseminated candidiasis in persistently neutropenic rabbits. Antimicrob Agents Chemother. May 2005;49(5):2084-92.

Petraitis et al., Efficacy of PLD-118, a novel inhibitor of candida isoleucyl-tRNA synthetase, against experimental oropharyngeal and esophageal candidiasis caused by fluconazole-resistant C. albicans. Antimicrob Agents Chemother. Oct. 2004;48(10):3959-67.

Piérard et al., Cellulite: from standing fat herniation to hypodermal stretch marks. Am J Dermatopathol. Feb. 2000;22(1):34-7.

Pines et al., Halofuginone: a novel antifibrotic therapy. Gen Pharmacol. Apr. 1998;30(4):445-50.

Pines at al., Halofuginone to treat fibrosis in chronic graft-versus-host disease and scleroderma. Biol Blood Marrow Transplant. Jul. 2003;9(7):417-25.

Pohlmann et al., New aminoacyl-tRNA synthetase inhibitors as antibacterial agents. Curr Drug Targets Infect Disord. Dec. 2004;4(4):261-72.

Puccetti et al., IDO and regulatory T cells: a role for reverse signalling and non-canonical NF-kappaB activation. Nat Rev Immunol. Oct. 2007;7(10):817-23.

Qiu et al., Crystal structure of *Staphylococcus aureus* tyrosyl-tRNA synthetase in complex with a class of potent and specific inhibitors. Protein Sci. Oct. 2001;10(10):2008-16.

Querleux et al., Anatomy and physiology of subcutaneous adipose tissue by in vivo magnetic resonance imaging and spectroscopy: relationships with sex and presence of cellulite. Skin Res Technol. May 2002;8(2):118-24.

Rashid et al., Topical omega-3 and omega-6 fatty acids for treatment of dry eye. Arch Ophthalmol. Feb. 2008;126(2):219-25.

Rathmell et al., Activated AKT promotes increased resting T cell size, CD28-independent T cell growth, and development of autoimmunity and lymphoma. Eur J Immunol. Aug. 2003;33(8):2223-32.

Reich et al., GenePattern 2.0. Nat Genet. May 2006;38(5):500-1.

Reigan et al., Synthesis and enzymatic evaluation of xanthine oxidase-activated prodrugs based on inhibitors of thymidine phosphorylase. Bioorg Med Chem Lett. Nov. 1, 2004;14(21):5247-50.

Reiner, Development in motion: helper T cells at work. Cell. Apr. 6, 2007;129(1):33-6.

Romani et al., IL-17 and therapeutic kynurenines in pathogenic inflammation to fungi. J Immunol. Apr. 15, 2008;180(8):5157-62.

Ron et al., Signal integration in the endoplasmic reticulum unfolded protein response. Nat Rev Mol Cell Biol. Jul. 2007;8(7):519-29.

Rosenbaum et al., An exploratory investigation of the morphology and biochemistry of cellulite. Plast Reconstr Surg. Jun. 1998;101(7):1934-9.

Ruan et al., A unique hydrophobic cluster near the active site contributes to differences in borrelidin inhibition among threonyl-tRNA synthetases. J Biol Chem. Jan. 7, 2005;280(1):571-7. Epub Oct. 26, 2004.

Sato et al., Halofuginone prevents extracellular matrix deposition in diabetic nephropathy. Biochem Biophys Res Commun. Feb. 6, 2009;379(2):411-6. Epub Dec. 27, 2008.

Scheuner et al., The unfolded protein response: a pathway that links insulin demand with beta-cell failure and diabetes. Endocr Rev. May 2008;29(3):317-33. Epub Apr. 24, 2008.

Schimmel et al., Aminoacyl tRNA synthetases as targets for new anti-infectives. FASEB J. Dec. 1998;12(15):1599-609.

Schneider et al., S100A4: a common mediator of epithelial-mesenchymal transition, fibrosis and regeneration in diseases? J Mol Med. May 2008;86(5):507-22. Epub Mar. 6, 2008.

Scott et al., Searching for peptide ligands with an epitope library. Science. Jul. 27, 1990;249(4967):386-90.

Smalls et al., Quantitative model of cellulite: three-dimensional skin surface topography, biophysical characterization, and relationship to human perception. J Cosmet Sci. Mar.-Apr. 2005;56(2):105-20.

Song, A facile synthesis of new 4-(phenylamino)thieno[3,2,*d*]pyrimidines using 3-aminothiophene-2-carboxamide. Heterocyclic Communications. 2007;13(1):33-34.

Srinivas et al., Cre reporter strains produced by targeted insertion of EYFP and ECFP into the ROSA26 locus. BMC Dev Biol. 2001;1:4. Epub Mar. 27, 2001.

Stefanska et al., A potent seryl tRNA synthetase inhibitor SB-217452 isolated from a Streptomyces species. J Antibiot (Tokyo). Dec. 2000;53(12):1346-53.

Stefanska et al., SB-203207 and SB-203208, two novel isoleucyl tRNA synthetase inhibitors from a *Streptomyces* sp. I. Fermentation, isolation and properties. J Antibiot (Tokyo). Apr. 2000;53(4):357-63.

(56) References Cited

OTHER PUBLICATIONS

Steinman et al., How to successfully apply animal studies in experimental allergic encephalomyelitis to research on multiple sclerosis. Ann Neurol. Jul. 2006;60(1):12-21.
Steinman, A brief history of T(H)17, the first major revision in the T(H)1/T(H)2 hypothesis of T cell-mediated tissue damage. Nat Med. Feb. 2007;13(2):139-45. Erratum in: Nat Med. Mar. 2007;13(3):385.
Stockinger et al., Differentiation and function of Th17 T cells. Curr Opin Immunol. Jun. 2007;19(3):281-6. Epub Apr. 12, 2007.
Sukemoto et al., Concise asymmetric synthesis of (+)-febrifugine utilizing trans-selective intramolecular conjugate addition. Synthesis. 2008;19:3081-87.
Sukuru et al., Discovering new classes of Brugia malayi asparaginyl-tRNA synthetase inhibitors and relating specificity to conformational change. J Comput Aided Mol Des. Mar. 2006;20(3):159-78. Epub Apr. 28, 2006.
Sundrud et al., Halofuginone inhibits TH17 cell differentiation by activating the amino acid starvation response. Science. Jun. 5, 2009;324(5932):1334-8.
Sundrud et al., Transcription factor GATA-1 potently represses the expression of the HIV-1 coreceptor CCR5 in human T cells and dendritic cells. Blood. Nov. 15, 2005;106(10):3440-8. Epub Aug. 9, 2005.
Szymanski et al., The new aspects of aminoacyl-tRNA synthetases. Acta Biochim Pol. 2000;47(3):821-34.
Takaya et al., New type of febrifugine analogues, bearing a quinolizidine moiety, show potent antimalarial activity against Plasmodium malaria parasite. J Med Chem. Aug. 12, 1999;42(16):31636.
Tandon et al., Potent and selective inhibitors of bacterial methionyl tRNA synthetase derived from an oxazolone-dipeptide scaffold. Bioorg Med Chem Lett. Apr. 19, 2004;14(8):1909-11.
Ting et al., Isolation of prolyl-tRNA synthetase as a free form and as a form associated with glutamyl-tRNA synthetase. J Biol Chem. Sep. 5, 1992;267(25):17701-9.
Toh et al., The role of T cells in rheumatoid arthritis: new subsets and new targets. Curr Opin Rheumatol. May 2007;19(3):284-8.
Tomasek et al., Myofibroblasts and mechano-regulation of connective tissue remodelling. Nat Rev Mol Cell Biol. May 2002;3(5):349-63.
Torchala et al., IA, database of known ligands of aminoacyl-tRNA synthetases. J Comput Aided Mol Des. Sep. 2007;21(9):523-5. Epub Sep. 20, 2007.
Van De Vijver et al., Aminoacyl-tRNA synthetase inhibitors as potent and synergistic immunosuppressants. J Med Chem. May 22, 2008;51(10):3020-9. Epub. Apr 26, 2008.
Van Vlasselaer et al., Transforming growth factor-beta directs IgA switching in human B cells. J Immunol. Apr. 1, 1992;148(7):2062-7.
Veldhoen et al., Signals mediated by transforming growth factor-beta initiate autoimmune encephalomyelitis, but chronic inflammation is needed to sustain disease. Nat Immunol. Nov. 2006;7(11):1151-6. Epub Sep. 24, 2006.
Veldhoen et al., TGFβ in the context of an inflammatory cytokine milieu supports de novo differentiation of IL-17-producing T cells. Immunity. Feb. 2006;24(2):179-89.
Vogel et al., Neue Synthesen von Pyrazolo[1,5-a]-s-triazinen. Helvetica Chimica Acta. 1975;58(3):761-71. German.
Waldner et al., Activation of antigen-presenting cells by microbial products breaks self tolerance and induces autoimmune disease. J Clin Invest. Apr. 2004;113(7):990-7.
Weaver et al., IL-17 family cytokines and the expanding diversity of effector T cell lineages. Annu Rev Immunol. 2007;25:821-52.
Wei et al., IL-21 is produced by Th17 cells and drives IL-17 production in a STAT3-dependent manner. J Biol Chem. Nov. 30, 2007;282(48):34605-10. Epub Sep. 20, 2007.
Wilen et al., Strategies in Optical Resolutions. Tetrahedron. 1977;33:2725-36.
Wilson et al., Development, cytokine profile and function of human interleukin 17-producing helper T cells. Nat Immunol. Sep. 2007;8(9):950-7. Epub Aug. 5, 2007.
Winum et al., Sulfamates and their therapeutic potential. Med Res Rev. Mar. 2005;25(2):186-228.
Wu et al., FOXP3 controls regulatory T cell function through cooperation with NFAT. Cell. Jul. 28, 2006;126(2):375-87.
Xavier et al., Amelioration of radiation-induced fibrosis: inhibition of transforming growth factor-beta signaling by halofuginone. J Biol Chem. Apr. 9, 2004;279(15):15167-76. Epub Jan. 19, 2004.
Yang et al., STAT3 regulates cytokine-mediated generation of inflammatory helper T cells. J Biol Chem. Mar. 30, 2007;282(13):9358-63. Epub Feb. 3, 2007.
Yang et al., T helper 17 lineage differentiation is programmed by orphan nuclear receptors ROR alpha and ROR gamma. Immunity. Jan. 2008;28(1):29-39. Epub Dec. 27, 2007.
Yasumi et al., Interleukin-17 as a new marker of severity of acute hepatic injury. Hepatol Res. Apr. 2007;37(4):248-54.
Yu et al., A series of heterocyclic inhibitors of phenylalanyl-tRNA synthetases with antibacterial activity. Bioorg Med Chem Lett. Mar. 8, 2004;14(5):1343-6.
Yu et al., A series of quinoline analogues as potent inhibitors of C. albicans prolyl tRNA synthetase. Bioorg Med Chem Lett. Feb. 26, 2001;11(4):541-4.
Zhou et al., IL-6 programs T(H)-17 cell differentiation by promoting sequential engagement of the IL-21 and IL-23 pathways. Nat Immunol. Sep. 2007;8(9):967-74. Epub Jun. 20, 2007.
Ziolkowska et al., High levels of IL-17 in rheumatoid arthritis patients: IL-15 triggers in vitro IL-17 production via cyclosporin A-sensitive mechanism. J Immunol. Mar. 1, 2000;164(5):2832-8.
Zuckermann et al., Discovery of nanomolar ligands for 7-transmembrane G-protein-coupled receptors from a diverse N-(substituted)glycine peptoid library. J Med Chem. Aug. 19, 1994;37(17):2678-85.
International Search Report and Written Opinion for PCT/US2013/021223, mailed Jun. 19, 2013.
Office Communication, mailed Jul. 11, 2013, for U.S. Appl. No. 12/673,119.
[No Author Listed] Goodman and Gilman's The Pharmacological Basis of Therapeutics. 7th ed. 1985:36.
Anderson et al., Metabolic reprogramming, caloric restriction and aging. Trends Endocrinol Metab. Mar. 2010;21(3):134-41. doi: 10.1016/j.tem.2009.11.005. Epub Dec. 7, 2009.
Bronte et al., Regulation of immune responses by L-arginine metabolism. Nat Rev Immunol. Aug. 2005;5(8):641-54.
Caro et al., Effect of 40% restriction of dietary amino acids (except methionine) on mitochondrial oxidative stress and biogenesis, AIF and SIRT1 in rat liver. Biogerontology. Oct. 2009;10(5):579-92. doi: 10.1007/s10522-008-9200-4. Epub Nov. 28, 2008.
Coatney et al., Studies in human malaria. XXV. Trial of febrifugine, an alkaloid obtained from Dichroa febrifuga lour., against the Chesson strain of Plasmodium vivax. J Natl Malar Soc. Jun. 1950;9(2):183-6.
Cobbold et al., Infectious tolerance via the consumption of essential amino acids and mTOR signaling. Proc Natl Acad Sci U S A. Jul. 21, 2009;106(29):12055-60. doi: 10.1073/pnas.0903919106. Epub Jun. 30, 2009.
Deval et al., Amino acid limitation regulates the expression of genes involved in several specific biological processes through GCN2-dependent and GCN2-independent pathways. FEBS J. Feb. 2009;276(3):707-18. doi: 10.1111/j.1742-4658.2008.06818.x. Epub Dec. 19, 2008.
Esposito et al., Rapamycin inhibits relapsing experimental autoimmune encephalomyelitis by both effector and regulatory T cells modulation. J Neuroimmunol. Mar. 30, 2010;220(1-2):52-63. doi: 10.1016/j.jneuroim.2010.01.001. Epub Feb. 11, 2010.
Finlay et al., Metabolism, migration and memory in cytotoxic T cells. Nat Rev Immunol. Feb. 2011;11(2):109-17. doi: 10.1038/nri2888. Epub Jan. 14, 2011.
Fontana et al., Extending healthy life span—from yeast to humans. Science. Apr. 16, 2010;328(5976):321-6. doi: 10.1126/science.1172539.
Grohmann et al., Control of immune response by amino acid metabolism. Immunol Rev. Jul. 2010;236:243-64. doi: 10.1111/j.1600-065X.2010.00915.x.

(56) References Cited

OTHER PUBLICATIONS

Haigis et al., The aging stress response. Mol Cell. Oct. 22, 2010;40(2):333-44. doi: 10.1016/j.molcel.2010.10.002.

Heacock et al., Synthesis and Aminoacyl-tRNA Synthetase Inhibitory Activity of Prolyl Adenylate Analogs. Bioorganic Chemistry. 1996;24(3):273-89.

Hotamisligil et al., Nutrient sensing and inflammation in metabolic diseases. Nat Rev Immunol. Dec. 2008;8(12):923-34. doi: 10.1038/nri2449.

Howitz et al., Xenohormesis: sensing the chemical cues of other species. Cell. May 2, 2008;133(3):387-91. doi: 10.1016/j.cell.2008.04.019.

Huang et al., Dendritic cells, indoleamine 2,3 dioxygenase and acquired immune privilege. Int Rev Immunol. Apr. 2010;29(2):133-55. doi: 10.3109/08830180903349669.

Ibba et al., Aminoacyl-tRNA synthesis. Annu Rev Biochem. 2000;69:617-50.

Jahn et al., Mono Q chromatography permits recycling of DNA template and purification of RNA transcripts after T7 RNA polymerase reaction. Nucleic Acids Res. May 25, 1991;19(10):2786.

Keller et al., Halofuginone and other febrifugine derivatives inhibit prolyl-tRNA synthetase. Nat Chem Biol. Feb. 12, 2012;8(3):311-7. doi: 10.1038/nchembio.790.

Kilberg et al., Nutritional control of gene expression: how mammalian cells respond to amino acid limitation. Annu Rev Nutr. 2005;25:59-85.

Koon et al., Phase II AIDS Malignancy Consortium Trial of Topical Halofuginone in AIDS-Related Kaposi Sarcoma. J Acquir Immune Defic Syndr. 2011;56:64-68.

Mukhopadhyay et al., The GAIT system: a gatekeeper of inflammatory gene expression. Trends Biochem Sci. Jul. 2009;34(7):324-31. doi: 10.1016/j.tibs.2009.03.004. Epub Jun. 15, 2009.

Nath et al., Metformin attenuated the autoimmune disease of the central nervous system in animal models of multiple sclerosis. J Immunol. Jun. 15, 2009;182(12):8005-14. doi: 10.4049/jimmunol.0803563.

Palii et al., Specificity of amino acid regulated gene expression: analysis of genes subjected to either complete or single amino acid deprivation. Amino Acids. May 2009;37(1):79-88. doi: 10.1007/s00726-008-0199-2. Epub Nov. 14, 2008.

Pleiss et al., Rapid, transcript-specific changes in splicing in response to environmental stress. Mol Cell. Sep. 21, 2007;27(6):928-37.

Plouffe et al., In silico activity profiling reveals the mechanism of action of antimalarials discovered in a high-throughput screen. Proc Natl Acad Sci U S A. Jul. 1, 2008;105(26):9059-64. doi: 10.1073/pnas.0802982105. Epub Jun. 25, 2008.

Powell et al., The mammalian target of rapamycin: linking T cell differentiation, function, and metabolism. Immunity. Sep. 24, 2010;33(3):301-11. doi: 10.1016/j.immuni.2010.09.002.

Sancak et al., The Rag GTPases bind raptor and mediate amino acid signaling to mTORC1. Science. Jun. 13, 2008;320(5882):1496-501. doi: 10.1126/science.1157535. Epub May 22, 2008.

Splan et al., Transfer RNA modulates the editing mechanism used by class II prolyl-tRNA synthetase. J Biol Chem. Mar. 14, 2008;283(11):7128-34. doi: 10.1074/jbc.M709902200. Epub Jan. 7, 2008.

Von Bubnoff et al., Indoleamine 2,3-dioxygenase-expressing myeloid dendritic cells and macrophages in infectious and noninfectious cutaneous granulomas. J Am Acad Dermatol. Oct. 2011;65(4):819-32. doi: 10.1016/j.jaad.2010.07.050. Epub Apr. 17, 2011.

Xiao et al., Leucine deprivation increases hepatic insulin sensitivity via GCN2/mTOR/S6K1 and AMPK pathways. Diabetes. Mar. 2011;60(3):746-56. doi: 10.2337/db10-1246. Epub Jan. 31, 2011.

Yaremchuk et al., A succession of substrate induced conformational changes ensures the amino acid specificity of Thermus thermophiles prolyl-tRNA synthetase: comparison with histidyl-tRNA synthetase. J Mol Biol. Jun. 15, 2001;309(4):989-1002.

Zelante et al., IL-23 and the Th17 pathway promote inflammation and impair antifungal immune resistance. Eur J Immunol. Oct. 2007;37(10):2695-706.

Zhu et al., Synthesis and biological evaluation of febrifugine analogues as potential antimalarial agents. Bioorg Med Chem. Jul. 1, 2009;17(13):4496-502. doi: 10.1016/j.bmc.2009.05.011. Epub May 9, 2009.

Zhu et al., Synthesis and evaluation of 4-quinazolinone compounds as potential antimalarial agents. Eur J Med Chem. Sep. 2010;45(9):3864-9. doi: 10.1016/j.ejmech.2010.05.040. Epub May 24, 2010.

Zoncu et al., mTOR: from growth signal integration to cancer, diabetes and ageing. Nat Rev Mol Cell Biol. Jan. 2011;12(1):21-35. doi: 10.1038/nrm3025. Epub Dec. 15, 2010.

International Preliminary Report on Patentability for PCT/US2013/021223, mailed Jul. 24, 2014.

\* cited by examiner

| Proliferation | 15.7nM +/- 1.2 |
|---|---|
| CD25 Express | 34.4nM +/- 2.6 |
| Th1 | 18.4nM +/- 0.5 |
| Th2 | > 20nM |
| *Th17* | 3.6nM +/- 0.4 |
Fig. 5B
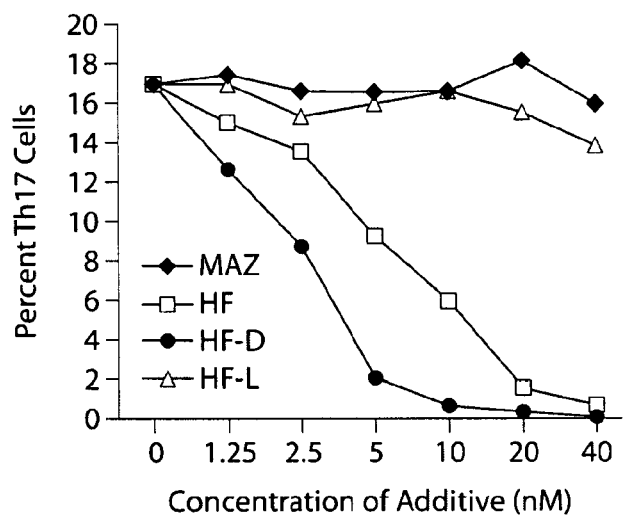
Fig. 5C
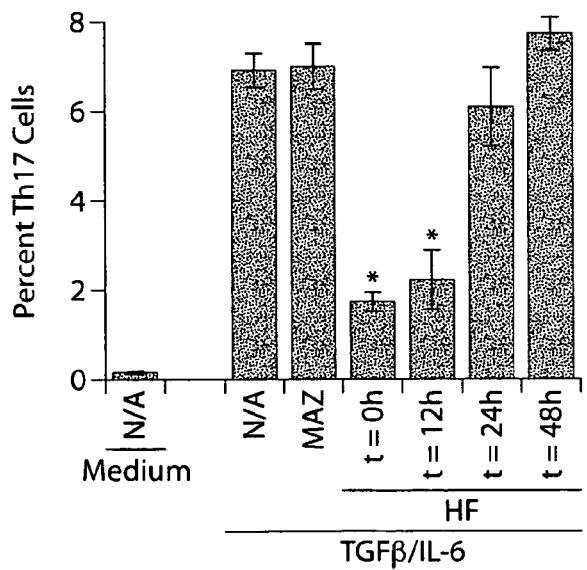
Fig. 5D

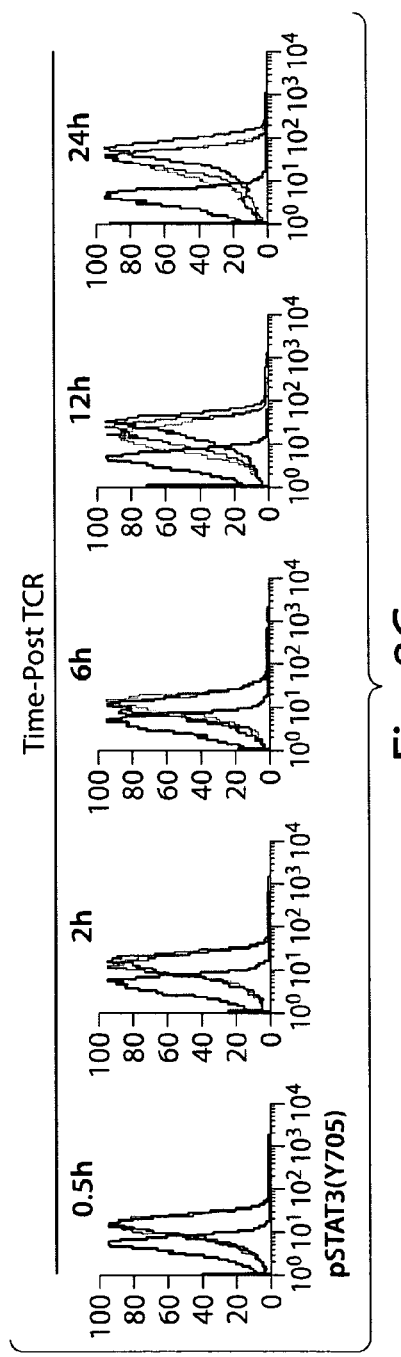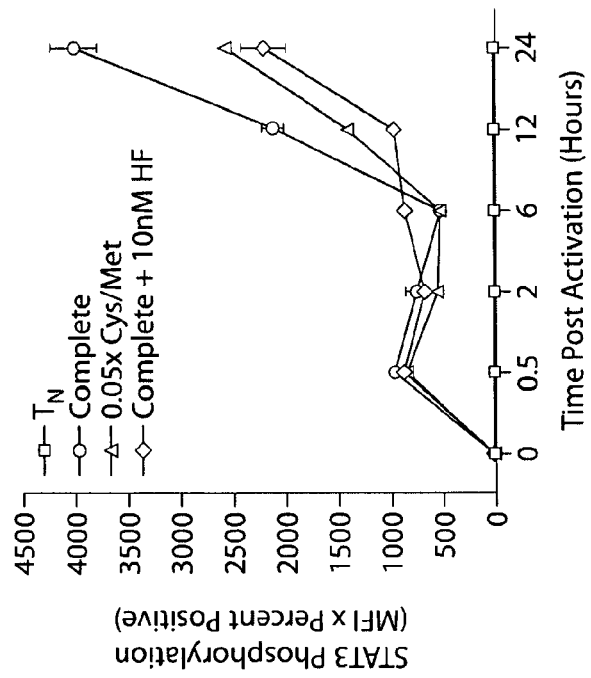
Fig. 8C
Fig. 8D

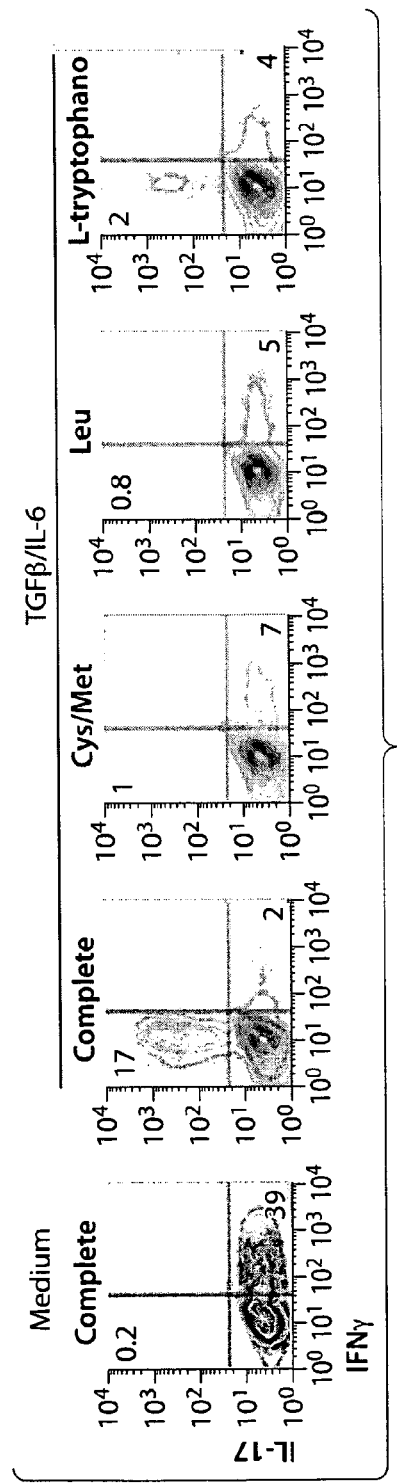
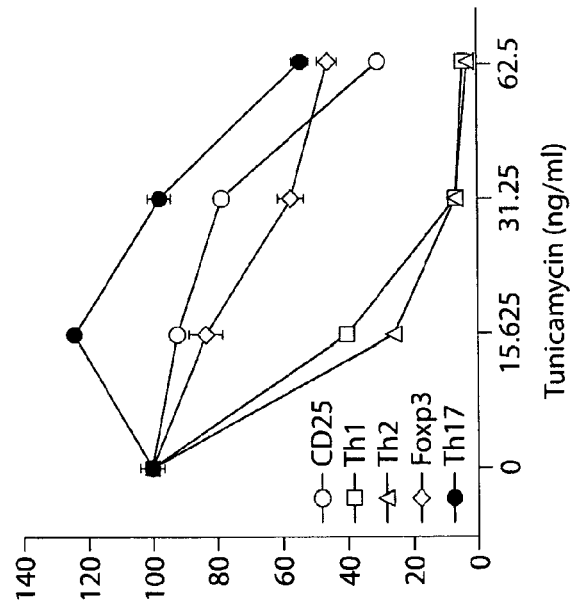
Fig. 8E
Fig. 8F

Fig. 15

| Gene symbol | Gene title | HF vs. MAZ1310-3hr | HF vs. MAZ1310-6hr |
|---|---|---|---|
| Gpt2 | Glutamic pyruvate transaminase (alanine aminotransferase) | 10.0 ± 1.2 | 16.7 ± 2.2 |
| Trib3 | Tribbles homolog 3 (Drosophila) | 7.1 ± 2.0 | 18.5 ± 8.5 |
| Eif4Ebp1 | Eukaryotic translation initiation factor 4E binding protein 1 | 6.8 ± 1.8 | 5.3 ± 0.3 |
| Asns | Asparagine synthetase | 6.1 ± 1.2 | 7.1 ± 0.5 |
| Ddit3 | DNA-damage inducible transcript 3 | 5.6 ± 1.1 | 5.0 ± 0.7 |
| Pck2 | Phosphoenolpyruvate carboxykinase 2 (mitochondrial) | 4.9 ± 0.8 | 7.4 ± 0.9 |
| Pycr1 | Pyrroline-5-carboxylate reductase 1 | 4.6 ± 0.7 | 6.6 ± 0.4 |
| Cebpb | CCAAT/enhancer binding protein (C/EBP), beta | 3.9 ± 0.5 | 8.0 ± 0.2 |
| Phgdh | 3-phosphoglycerate dehydrogenase | 3.8 ± 0.9 | 4.2 ± 0.3 |
| Psph | Phosphoserine phosphatase | 3.5 ± 0.4 | 3.4 ± 0.3 |
| Xist | Inactive X specific transcripts | 3.5 ± 1.7 | 2.1 ± 0.7 |
| Pdcd1lg2 | Programmed cell death 1 ligand 2 | 3.2 ± 0.7 | 2.5 ± 0.3 |
| Vegfa | Vascular endothelial growth factor A | 3.2 ± 0.7 | 5.8 ± 0.5 |
| Cldn12 | Claudin 12 | 3.2 ± 0.9 | 4.6 ± 0.4 |
| Slc1a4 | Solute carrier family 1 (glutamate/neutral amino acid transporter), member 4 | 3.0 ± 0.1 | 3.2 ± 0.5 |
| Atf3 | Activating transcription factor 3 | 3.0 ± 0.3 | 3.2 ± 0.5 |
| Ncoa7 | Nuclear receptor coactivator 7 | 2.7 ± 0.4 | 2.6 ± 0.2 |
| Aars | Alanyl-tRNA synthetase | 2.6 ± 0.3 | 2.3 ± 0.5 |
| Sesn2 | Sestrin 2 | 2.5 ± 0.5 | 3.1 ± 0.5 |
| Cebpg | CCAAT/enhancer binding protein (C/EBP), gamma | 2.4 ± 0.3 | 5.7 ± 0.6 |
| Slc6a9 | Solute carrier family 6 (neurotransmitter transporter, glycine), member 9 | 2.4 ± 0.1 | 2.7 ± 0.1 |
| Herpud1 | Homocysteine-inducible, endoplasmic reticulum stress-inducible, ubiquitin-like domain member 1 | 2.4 ± 0.1 | 4.9 ± 0.7 |
| Trim12 | Tripartite motif protein 12 | 2.4 ± 0.2 | 2.8 ± 0.2 |
| Clic4 | Chloride intracellular channel 4 (mitochondrial) | 2.4 ± 0.1 | 8.9 ± 1.0 |
| Atf5 | Activating transcription factor 5 | 2.3 ± 0.4 | 7.3 ± 1.7 |
| Mpa2l | Macrophage activation 2 like | 2.3 ± 0.4 | 2.6 ± 0.3 |
| Aff1 | AF4/FMR2 family member 1 | 2.3 ± 0.1 | 2.1 ± 0.0 |
| Lars | Leucyl-tRNA synthetase | 2.2 ± 0.7 | 16.0 ± 1.6 |
| Cth | Cystathionase (cystathionine gamma-lyase) | 2.2 ± 0.3 | 2.5 ± 0.5 |
| Chd2 | Chromodomain helicase DNA binding protein 2 | 2.2 ± 0.3 | 2.2 ± 0.3 |
| Cars | Cysteinyl-tRNA synthetase | 2.2 ± 0.4 | 2.1 ± 0.2 |
| Slamf7 | SLAM family member 7 | 2.1 ± 0.3 | 2.1 ± 0.1 |
| Cxcl10 | Chemokine (C-X-C motif) ligand 10 | 2.1 ± 0.5 | 2.6 ± 0.0 |
| Psat1 | Phosphoserine aminotransferase 1 | 2.1 ± 0.5 | 2.7 ± 0.2 |
| Aldh18a1 | Aldehyde dehydrogenase 18 family, member A1 | 2.1 ± 0.2 | 2.3 ± 0.1 |
| Pycs | 1-@pyrroline-5-carboxylate synthetase | 2.1 ± 0.3 | 2.0 ± 0.1 |
| Cd274 | CD274 antigen | 2.1 ± 0.2 | 3.1 ± 0.8 |
| D8Errd56e | DNA segment, Chr 8, ERATO Doi 56, expressed | 2.0 ± 0.3 | 2.6 ± 0.2 |
| Irf1 | Interferon regulatory factor 1 | 2.0 ± 0.3 | 2.0 ± 0.1 |
| Pvr | Poliovirus receptor | 2.0 ± 0.1 | 1.9 ± 0.3 |
| Nfkbiz | Nuclear factor of kappa light polypeptide gene enhancer in B-cells inhibitor, zeta | 2.0 ± 0.2 | 2.8 ± 0.3 |
| Icam1 | Intercellular adhesion molecule | 2.0 ± 0.1 | 6.6 ± 0.4 |
| Slc14af | Solute carrier family 14 (urea transporter), member 1 | 2.0 ± 0.3 | 2.3 ± 0.1 |
| Sars1 | Seryl-aminoacyl-tRNA synthetase | 2.0 ± 0.3 | 6.5 ± 0.9 |
| Slc7a3 | Solute carrier family 7 (cationic amino acid transporter, y+ system), member 3 | 2.0 ± 0.2 | |

Fig. 16A

| Affymetrix probe ID | Gene Name |
|---|---|
| 1433966_x_at | Asparagine synthetase |
| 1451095_a_at | Asparagine synthetase |
| 1451083_s_at | Alanyl-tRNA synthetase |
| 1432685_at | Alanyl-tRNA synthetase |
| 1435154_at | Similar to solute carrier family 7 (cationic amino acid transporter, y+ system), member 3 |
| 1454991_at | Solute carrier family 7 (cationic amino acid transporter, y+ system), member 1 |
| 1454992_at | Solute carrier family 7 (cationic amino acid transporter, y+ system), member 1 |
| 1421533_at | Solute carrier family 7 (cationic amino acid transporter, y+ system), member 1 |
| 1421093_at | Solute carrier family 7 (cationic amino acid transporter, y+ system), member 10 |
| 1420413_at | Solute carrier family 7 (cationic amino acid transporter, y+ system), member 11 |
| 1443536_at | Solute carrier family 7 (cationic amino acid transporter, y+ system), member 11 |
| 1419579_at | Solute carrier family 7 (cationic amino acid transporter, y+ system), member 12 |
| 1422648_at | Solute carrier family 7 (cationic amino acid transporter, y+ system), member 2 |
| 1426008_a_at | Solute carrier family 7 (cationic amino acid transporter, y+ system), member 2 |
| 1440506_at | Solute carrier family 7 (cationic amino acid transporter, y+ system), member 3 |
| 1417022_at | Solute carrier family 7 (cationic amino acid transporter, y+ system), member 4 |
| 1426069_s_at | Solute carrier family 7 (cationic amino acid transporter, y+ system), member 4 |
| 1426068_at | Solute carrier family 7 (cationic amino acid transporter, y+ system), member 4 |
| 1435776_x_at | Solute carrier family 7 (cationic amino acid transporter, y+ system), member 5 |
| 1418326_at | Solute carrier family 7 (cationic amino acid transporter, y+ system), member 6 |
| 1460541_at | Solute carrier family 7 (cationic amino acid transporter, y+ system), member 7 |
| 1433467_at | Solute carrier family 7 (cationic amino acid transporter, y+ system), member 7 |
| 1417392_a_at | Solute carrier family 7 (cationic amino acid transporter, y+ system), member 8 |
| 1447181_s_at | Solute carrier family 7 (cationic amino acid transporter, y+ system), member 9 |
| 1417929_at | Solute carrier family 7 (cationic amino acid transporter, y+ system), member 13 |
| 1448783_at | Solute carrier family 7 (cationic amino acid transporter, y+ system), member 13 |
| 1431740_at | Solute carrier family 7 (cationic amino acid transporter, y+ system), member 13 |
| 1449301_at | Solute carrier family 1 (glutamate/neutral amino acid transporter), member 4 |
| 1456003_a_at | Solute carrier family 1 (glutamate/neutral amino acid transporter), member 4 |
| 1423550_at | Solute carrier family 1 (glutamate/neutral amino acid transporter), member 4 |
| 1423549_at | Solute carrier family 1 (neutral amino acid transporter), member 5 |
| 1440379_at | Solute carrier family 1 (neutral amino acid transporter), member 5 |
| 1416629_at | Solute carrier family 5 (neutral amino acid transporter, system A), member 4b |
| 1422757_at | Methylenetetrahydrofolate dehydrogenase (NAD+ dependent), methenyltetrahydrofolate cyclohydrolase |
| 1419253_at | Methylenetetrahydrofolate dehydrogenase (NAD+ dependent), methenyltetrahydrofolate cyclohydrolase |
| 1419254_at | Methylenetetrahydrofolate dehydrogenase (NAD+ dependent), methenyltetrahydrofolate cyclohydrolase 1-like |
| 1456653_a_at | Methylenetetrahydrofolate dehydrogenase (NADP+ dependent), methenyltetrahydrofolate cyclohydrolase, formyltetrahydrofolate synthase |
| 1415917_at | Methylenetetrahydrofolate dehydrogenase (NADP+ dependent), methenyltetrahydrofolate cyclohydrolase, formyltetrahydrofolate synthase |
| 1415916_a_at | Methylenetetrahydrofolate dehydrogenase (NADP+ dependent), methenyltetrahydrofolate cyclohydrolase, formyltetrahydrofolate synthase |
| 1436704_x_at | Methylenetetrahydrofolate dehydrogenase (NADP+ dependent), methenyltetrahydrofolate cyclohydrolase, formyltetrahydrofolate synthase |
| 1451064_a_at | Phosphoserine aminotransferase 1 |
| 1454607_s_at | Phosphoserine aminotransferase 1 |
| 1415673_at | Phosphoserine phosphatase |
| 1417562_at | Eukaryotic translation initiation factor 4E binding protein 1 |
| 1417563_at | Eukaryotic translation initiation factor 4E binding protein 1 |
| 1434976_x_at | Eukaryotic translation initiation factor 4E binding protein 1 |

| | |
|---|---|
| 1443672_at | Leucyl-tRNA synthetase, mitochondrial |
| 1435682_at | Leucyl-tRNA synthetase, mitochondrial |
| 1439225_at | Leucyl-tRNA synthetase, mitochondrial |
| 1425364_a_at | Solute carrier family 3 (activators of dibasic and neutral amino acid transport), member 2 |
| 1452154_at | Isoleucine-tRNA synthetase |
| 1426705_s_at | Isoleucine-tRNA synthetase |
| 1426735_at | Isoleucine-tRNA synthetase 2, mitochondrial |
| 1441665_at | Isoleucine-tRNA synthetase 2, mitochondrial |
| 1418901_at | CCAAT/enhancer binding protein (C/EBP), beta |
| 1427844_a_at | CCAAT/enhancer binding protein (C/EBP), beta |
| 1425262_at | CCAAT/enhancer binding protein (C/EBP), gamma |
| 1425261_at | CCAAT/enhancer binding protein (C/EBP), gamma |
| 1451639_at | CCAAT/enhancer binding protein (C/EBP), gamma |
| 1432331_a_at | Paired related homeobox 2 |
| 1456903_at | Pentraxin related gene |
| 1418666_at | Pentraxin related gene |
| 1426808_at | Lectin, galactose binding, soluble 3 |
| 1445626_at | Lectin, galactose binding, soluble 3 (Lgals3), mRNA |
| 1448929_at | Coagulation factor XIII, A1 subunit |
| 1416182_at | Amyloid beta (A4) precursor protein-binding, family A, member 3 |
| 1454720_at | Amyloid beta (A4) precursor protein-binding, family A, member 3 |
| 1417133_at | Peripheral myelin protein |
| 1458193_at | Peripheral myelin protein 2 /// similar to myelin P2 protein - mouse |
| 1423516_a_at | Nidogen 2 |
| 1454159_a_at | Insulin-like growth factor binding protein 2 |
| 1418675_at | Oncostatin M receptor |
| 1418674_at | Oncostatin M receptor |
| 1459217_at | Oncostatin M receptor |
| 1426063_a_at | GTP binding protein (gene overexpressed in skeletal muscle) |
| 1450023_at | GTP binding protein 1 |
| 1450022_at | GTP binding protein 1 |
| 1448437_a_at | GTP binding protein 2 |
| 1416691_at | GTP binding protein 2 |
| 1416690_at | GTP binding protein 2 |
| 1442305_at | GTP binding protein 3 |
| 1457975_at | GTP binding protein 3 |
| 1450980_at | GTP binding protein 4 |
| 1423143_at | GTP binding protein 4 |
| 1450873_at | GTP binding protein 5 |
| 1423142_a_at | GTP binding protein 5 |
| 1451467_s_at | GTP binding protein 5 |
| 1452636_x_at | GTP binding protein 5 |
| 1460029_at | GTP binding protein 6 (putative) |
| 1427350_a_at | GTP binding protein 6 (putative) |
| 1424519_at | GTP binding protein 7 (putative) |
| 1418309_at | Tumor necrosis factor receptor superfamily, member 11b (osteoprotegerin) |
| 1449033_at | Tumor necrosis factor receptor superfamily, member 11b (osteoprotegerin) |

Fig. 16B

| | |
|---|---|
| 1428666_at | Asparaginyl-tRNA synthetase |
| 1452866_at | Asparaginyl-tRNA synthetase |
| 1415694_at | Tryptophanyl-tRNA synthetase |
| 1437832_x_at | Tryptophanyl-tRNA synthetase |
| 1434813_x_at | Tryptophanyl-tRNA synthetase |
| 1425106_a_at | Tryptophanyl-tRNA synthetase |
| 1430111_a_at | Branched chain aminotransferase 1, cytosolic |
| 1450871_a_at | Branched chain aminotransferase 1, cytosolic |
| 1425764_a_at | Branched chain aminotransferase 2, mitochondrial |
| 1460323_at | Threonyl-tRNA synthetase |
| 1436856_x_at | Threonyl-tRNA synthetase-like 1 |
| 1431125_a_at | Threonyl-tRNA synthetase-like 1 |
| 1434738_at | Threonyl-tRNA synthetase-like 2 |
| 1448403_at | Leucyl-tRNA synthetase |
| 1418892_at | Ras homolog gene family, member J |
| 1448594_at | WNT1 inducible signaling pathway protein 1 |
| 1448593_at | WNT1 inducible signaling pathway protein 1 |
| 1425458_a_at | Growth factor receptor bound protein 10 |
| 1425457_a_at | Growth factor receptor bound protein 10 |
| 1430164_a_at | Growth factor receptor bound protein 10 |
| 1440935_at | Growth factor receptor bound protein 10, mRNA (cDNA clone MGC:28740 IMAGE:4481345) |
| 1428365_a_at | Protease, serine, 15 |
| 1416168_at | Serine (or cysteine) peptidase inhibitor, clade F, member 1 |
| 1453724_a_at | Serine (or cysteine) peptidase inhibitor, clade F, member 1 |
| 1450196_s_at | Glycogen synthase 1, muscle III glycogen synthase 3, brain |
| 1438606_a_at | Chloride intracellular channel 4 (mitochondrial) |
| 1423393_at | Chloride intracellular channel 4 (mitochondrial) |
| 1423392_at | Chloride intracellular channel 4 (mitochondrial) |
| 1422018_at | Human immunodeficiency virus type 1 enhancer binding protein 2 |
| 1434904_at | Human immunodeficiency virus type 1 enhancer binding protein 2 (Hivep2), mRNA |
| 1444990_at | Human immunodeficiency virus type 1 enhancer binding protein 2 (Hivep2), mRNA |

Fig. 16C

```
                              SEQUENCE LISTING

<160> NUMBER OF SEQ ID NOS: 8

<210> SEQ ID NO 1
<211> LENGTH: 27
<212> TYPE: DNA
<213> ORGANISM: Artificial sequence
<220> FEATURE:
<223> OTHER INFORMATION: Synthetic Polynucleotide

<400> SEQUENCE: 1
tgactgcctt tccgtgcagt gtctgag                                              27

<210> SEQ ID NO 2
<211> LENGTH: 28
<212> TYPE: DNA
<213> ORGANISM: Artificial sequence
<220> FEATURE:
<223> OTHER INFORMATION: Synthetic Polynucleotide

<400> SEQUENCE: 2
acagccaagc ggtgaaagcc aaagcagc                                             28

<210> SEQ ID NO 3
<211> LENGTH: 27
<212> TYPE: DNA
<213> ORGANISM: Artificial sequence
<220> FEATURE:
<223> OTHER INFORMATION: Synthetic Polynucleotide

<400> SEQUENCE: 3
tagtcacagc agcgctgcag ccgaagc                                              27

<210> SEQ ID NO 4
<211> LENGTH: 27
<212> TYPE: DNA
<213> ORGANISM: Artificial sequence
<220> FEATURE:
<223> OTHER INFORMATION: Synthetic Polynucleotide

<400> SEQUENCE: 4
tactccaccg ccttcacctg cgggttc                                              27

<210> SEQ ID NO 5
<211> LENGTH: 28
<212> TYPE: DNA
<213> ORGANISM: Artificial sequence
<220> FEATURE:
<223> OTHER INFORMATION: Synthetic Polynucleotide

<400> SEQUENCE: 5
accaggatta tctatgaccg gaaatttc                                             28

<210> SEQ ID NO 6
<211> LENGTH: 27
<212> TYPE: DNA
<213> ORGANISM: Artificial sequence
<220> FEATURE:
<223> OTHER INFORMATION: Synthetic Polynucleotide

<400> SEQUENCE: 6
tgggaggctc atcgctggta gggctag                                              27
```

```
<210> SEQ ID NO 7
<211> LENGTH: 25
<212> TYPE: DNA
<213> ORGANISM: Artificial sequence
<220> FEATURE:
<223> OTHER INFORMATION: Synthetic Polynucleotide

<400> SEQUENCE: 7
gggggctata agttctttgc tgacc                                     25

<210> SEQ ID NO 8
<211> LENGTH: 27
<212> TYPE: DNA
<213> ORGANISM: Artificial sequence
<220> FEATURE:
<223> OTHER INFORMATION: Synthetic Polynucleotide

<400> SEQUENCE: 8
tccaacactt cgagaggtcc ttttcac                                   27
```

HALOFUGINONE ANALOGS FOR INHIBITION OF TRNA SYNTHETASES AND USES THEREOF

RELATED APPLICATIONS

The present application is a national stage filing under 35 U.S.C. §371 of international PCT application, PCT/US2009/004581, filed Aug. 11, 2009, which claims priority under 35 U.S.C. §119(e) to U.S. provisional patent applications, U.S. Ser. No. 61/188,740, filed Aug. 11, 2008, and U.S. Ser. No. 61/153,866, filed Feb. 19, 2009, each of which is incorporated herein by reference.

GOVERNMENT SUPPORT

This invention was made with U.S. Government support under HD029468 and CA078048 awarded by National Institutes of Health. The U.S. Government has certain rights in the invention.

BACKGROUND OF THE INVENTION

Halofuginone (1) is a halogenated derivative of febrifugine (3), a natural product extracted from the roots of the hydrangea *Dichroa febrifuga*. *Dichroa febrifuga* is one of the "fifty fundamental herbs" of traditional Chinese medicine, originally used as an anti-malarial remedy (Jiang et al., *Antimicrob. Agents Chemother.* (2005) 49:1169-1176). Halofuginone, otherwise known as 7-bromo-6-chloro-3-[3-(3-hydroxy-2-piperidinyl)-2-oxopropyl]-4(3H)-quinazolinone, and halofuginone derivatives were first described in U.S. Pat. No. 2,694,711, incorporated herein by reference. Febrifugine has been shown to be the active ingredient in *Dichroa febrifuga* extracts; halofuginone was originally synthesized in search of less toxic anti-malarial derivatives of febrifugine. In addition to its anti-malarial properties, however, halofuginone has striking anti-fibrotic properties in vivo (Pines, et al., *Biol. Blood Marrow Transplant* (2003) 9: 417-425; U.S. Pat. No. 6,028,075, incorporated herein by reference). Halofuginone shows some toxicity in humans, such as nausea, vomiting, and fatigue, and possibly bleeding complications (de Jonge et al., *Eur. J. Cancer* (2006) 42: 1768-1774).

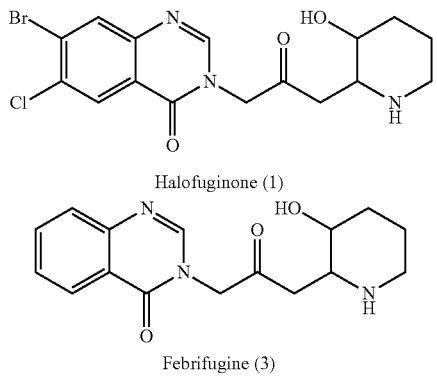

Halofuginone (1)

Febrifugine (3)

Since halofuginone has shown promising biological activities, there remains a need for identifying further related compounds with useful biological activities, especially those that may be less toxic than halofuginone or febrifugine.

SUMMARY OF THE INVENTION

The present invention stems from the recognition that analogs of the quinazolinone alkaloid halofuginone are inhibitors of metazoan glutamyl-prolyl tRNA synthetase (EPRS), particularly mammalian EPRS (FIGS. 21 and 22), and/or non-metazoan prolyl tRNA synthetase, particularly protozoan tRNA synthetase. Inhibitors of EPRS such as halofuginone and halofuginone analogs can inhibit the pro-fibrotic behavior of fibroblasts (FIG. 1 and Table 1) and therefore may be useful in treating disorders associated with fibrosis. In addition, halofuginone and analogs of halofuginone are useful in the modification of effector T-cell differentiation (FIG. 2 and Table 2) and therefore may be useful in treating diseases such as inflammatory diseases and autoimmune diseases. Furthermore, halofuginone and halofuginone analogs can inhibit angiogenesis and may be useful in treating tumor neovascularization and ocular diseases involving choroidal neovascularization and retinal edema. Halofuginone and halofuginone analogs may also be useful as antiprotozoal agents given their ability to inhibit protozoal prolyl tRNA synthetase. The present invention provides novel classes of quinazolinones, quinolinones, and heteroaryl derivatives of halofuginone and analogs thereof. The inventive compounds may have more desirable properties than halofuginone. For example, the inventive compounds may be less toxic than halofuginone or febrifugine and/or the inventive compounds may be more potent than halofuginone or febrifugine.

In one aspect, the inventive compounds are generally of the formula:

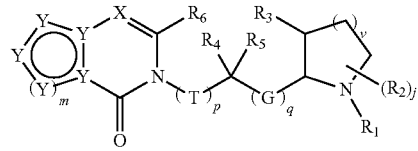

wherein:
  j is an integer between 0 and 10, inclusive;
  p is an integer between 0 and 6, inclusive;
  q is an integer between 0 and 6, inclusive;
  m is 1 or 2;
  v is an integer between 1 and 3, inclusive;
  X is N or $CR_X$, wherein $R_X$ is hydrogen; halogen; substituted or unsubstituted aliphatic; substituted or unsubstituted heteroaliphatic; substituted or unsubstituted aryl; substituted or unsubstituted heteroaryl; —$OR_F$; —$SR_F$; —$N(R_F)_2$; and —$C(R_F)_3$; wherein each occurrence of $R_F$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  each occurrence of Y is independently S, O, N, $NR_Y$, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of T and G is independently —S—, —O—, —NR$_E$—, or C(R$_E$)$_2$—, wherein R$_E$ is selected from the group consisting of hydrogen, halogen, substituted or unsubstituted aliphatic, substituted or unsubstituted heteroaliphatic, substituted or unsubstituted aryl, substituted or unsubstituted heteroaryl, —OR$_G$, —SR$_G$, —N(R$_G$)$_2$, and —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$_A$; —C(=O)OR$_A$; —C(=O)N(R$_A$)$_2$; or —C(R$_A$)$_3$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of R$_2$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO$_2$R$_B$; —C(=O)N(R$_B$)$_2$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —C(=O)N(R$_C$)$_2$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_4$ and R$_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO$_2$R$_D$; —C(=O)N(R$_D$)$_2$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; or R$_4$ and R$_5$ may optionally be taken together to form =O, =S, =NR$_D$, =N—OR$_D$, =N—NHR$_D$, =N—N(R$_D$)$_2$, or =C(R$_D$)$_2$; or R$_4$ and R$_5$ may optionally be taken together with the intervening atom to form a saturated or unsaturated, substituted or unsubstituted cyclic or heterocyclic structure; and R$_6$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety, or a salt thereof.

In certain embodiments, the inventive compound is of the stereochemistry shown in formula:

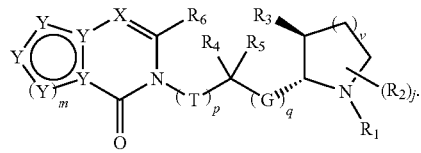

In other embodiments, the inventive compound is of the stereochemistry shown in formula:

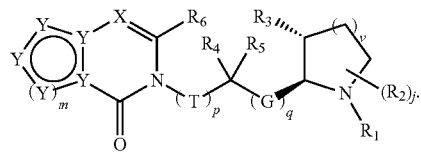

Without wishing to be bound by any particular theory, these compounds are thought to act by binding in the active site of the tRNA synthetase, thereby inhibiting the incorporation of proline into tRNA. The invention also provides methods of preparing the inventive compounds. The inventive compounds may be prepared via a total synthesis from commercially available starting materials or may be prepared via a semi-synthetic process starting from a compound such as halofuginone or febrifugine.

In another aspect, the present invention provides methods of treatment comprising administering an inventive compound to a subject. Without wishing to be bound by a particular theory, the compounds of the invention are thought to act by inhibiting glutamyl-prolyl tRNA synthetase (EPRS) or prolyl tRNA synthetase. See FIGS. 21 and 22. The compounds of the invention or pharmaceutical compositions thereof may be used to treat any disease including autoimmune diseases, such as multiple sclerosis, rheumatoid arthritis, lupus, psoriasis, scleroderma, or dry eye syndrome, inflammatory diseases, cardiovascular diseases, neurodegenerative diseases, protein aggregation disorders, and disorders involving angiogenesis, such as cancer, restenosis, macular degeneration, and choroidal neovascularization. The compounds of the invention may also be used to promote wound healing and/or prevent scarring and may be useful cosmetically, such as for the treatment of cellulite or stretch marks. Therefore, the inventive compounds may be used in cosmetic as well as pharmaceutical treatments. The compounds of the invention may be used to treat or prevent disease in humans and other animals including domesticated animals. In certain embodiments, the compounds of the invention may be used to inhibit pro-fibrotic behavior in fibroblasts or inhibit the differentiation of Th17 cells. Therefore, the inventive compounds may be useful in preventing fibrosis. The inventive compounds may also be used as probes of biological pathways. The inventive compounds may also be used in studying the differentiation of T cells.

In some embodiments of the method, a second agent which inhibits the expression or activity of a proinflammatory cytokine is administered to the subject. In some embodiments, the proinflammatory cytokine is selected from one or more of TNFα, IFNγ, GM-CSF, MIP-2, IL-12, IL-1α, IL-1β, and IL-23. In some embodiments of the method, a second agent which is an agent that inhibits expression or activity of IL-6 or IL-21 is administered to the subject. In some embodiments, a second agent which is an agent that inhibits TNFα is administered to the subject. In some embodiments, the agent that inhibits TNFα is an anti-TNFα antibody. In some embodiments, the agent that inhibits TNFα is a soluble TNF receptor. In other embodiments of the method, a second agent which is an immunomodulatory agent (e.g., steroids, non-steroidal anti-inflammatory agent, rapamycin, FK506, cyclosporine, HDAC inhibitors) is administered to the subject.

In another aspect, the present invention provides pharmaceutical and cosmetic compositions comprising the inventive compounds. The compositions may comprise an inventive compound in a therapeutically effective amount to suppress Th17 differentiation and/or treat or prevent autoimmune diseases, inflammatory diseases, cardiovascular diseases, neurodegenerative diseases, protein aggregation disorders, fibrosis, cellulite, stretch marks, or disorders involving angiogenesis, such as cancer, restenosis, macular degeneration, and choroidal neovascularization. The pharmaceutical compositions may optionally include a pharmaceutically acceptable excipient. The cosmetic compositions may optionally include a cosmetically acceptable excipient. In some embodiments, the pharmaceutical composition further comprises a second agent that inhibits expression or activity of a proinflammatory cytokine. In some embodiments, the proinflammatory cytokine is selected from one or more of IL-6, I-21, TNFα, IFNγ, GM-CSF, MIP-2, IL-12, IL-1α, IL-1β, and IL-23. Any mode of administration including oral, parenteral, and topical administration of the inventive compound or a pharmaceutical composition thereof may be used.

References, scientific articles, patent applications, and patents cited in this application are incorporated herein by reference.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, Some *Modern Methods of Organic Synthesis*, $3^{rd}$ Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substituent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- or 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-bentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl- 2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula ($—NH_2$). A "substituted amino" refers either to a mono-substituted amine ($—NHR^h$) of a disubstituted amine ($—NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the disubstituted amino group ($—NR^h_2$) form a 5- to 6-membered heterocyclic ring.

The term "alkoxy" refers to a "substituted hydroxyl" of the formula ($—OR^i$), wherein $R^i$ is an optionally substituted alkyl group, as defined herein, and the oxygen moiety is directly attached to the parent molecule.

The term "alkylthioxy" refers to a "substituted thiol" of the formula ($—SR^r$), wherein $R^r$ is an optionally substituted alkyl group, as defined herein, and the sulfur moiety is directly attached to the parent molecule.

The term "alkylamino" refers to a "substituted amino" of the formula ($—NR^h_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula ($—OR^i$), wherein $R^i$ is an optionally substituted aryl group, as defined herein, and the oxygen moiety is directly attached to the parent molecule.

The term "arylamino," refers to a "substituted amino" of the formula ($—NR^h_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula ($—SR^r$), wherein $R^r$ is an optionally substituted aryl group, as defined herein, and the sulfur moiety is directly attached to the parent molecule.

The term "azido," as used herein, refers to a group of the formula ($—N_3$).

The term "cyano," as used herein, refers to a group of the formula ($—CN$).

The terms "halo" and "halogen" as used herein refer to an atom selected from fluorine (fluoro, $—F$), chlorine (chloro, $—Cl$), bromine (bromo, $—Br$), and iodine (iodo, $—I$).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula ($-NR^h_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula ($-OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula ($-SR^r$), wherein $R^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 12-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—NR$^h_2$), wherein R$^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "heteroarylthioxy" refers to a "substituted thiol" of the formula (—SR$^r$), wherein R$^r$ is an optionally substituted heteroaryl group, as defined herein, and the sulfur moiety is directly attached to the parent molecule.

The term "hydroxy," or "hydroxyl," as used herein, refers to a group of the formula (—OH). A "substituted hydroxyl" refers to a group of the formula (—OR$^i$), wherein R$^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula (═NR$^r$), wherein R$^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to ═NH wherein R$^r$ is hydrogen.

The term "isocyano," as used herein, refers to a group of the formula (—NC).

The term "nitro," as used herein, refers to a group of the formula (—NO$_2$).

The term "oxo," as used herein, refers to a group of the formula (═O).

The term "stable moiety," as used herein, preferably refers to a moiety which possess stability sufficient to allow manufacture, and which maintains its integrity for a sufficient period of time to be useful for the purposes detailed herein.

A "suitable amino-protecting group," as used herein, is well known in the art and include those described in detail in *Greene's Protective Groups in Organic Synthesis*, P. G. M. Wuts and T. W. Greene, 4$^{th}$ edition, Wiley-Interscience, 2006, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group" as used herein, is well known in the art and includes those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiofuranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, is well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio," or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein refers to implanting, absorbing, ingesting, injecting, or inhaling the inventive compound.

As used herein, the terms "treatment," "treat," and "treating" refer to reversing, alleviating, delaying the onset of, or inhibiting the progress of a disease or disorder, or one or more symptoms thereof, described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to delay or prevent recurrence.

The terms "effective amount" and "therapeutically effective amount," as used herein, refer to the amount or concentration of an inventive compound, that, when administered to a subject, is effective to at least partially treat a condition from which the subject is suffering (e.g., a neurodegenerative disease).

BRIEF DESCRIPTION OF THE DRAWINGS

FIG. 5A, right, is a graph showing dose-response analyses of HF effects on CD8+ T cell or B cell function. Cells were activated in the presence of DMSO, 40 nM compound 9 (MAZ1310), or increasing concentrations of HF (1.25-40 nM). CFSE dilution, cell surface CD25 expression, and intracellular cytokine production were determined as above 2-5 days after activation. CFSE dilution and percentages of CD8+ T cells expressing CD25, IFNγ+ granzyme B+ (cytotoxic T lymphocytes) or IL-6+ B cells are displayed and the values are normalized to cells treated with 40 nM MAZ1310±SD.

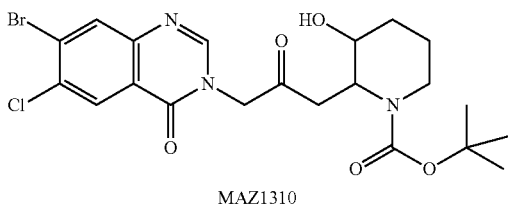 [SMILES: CC(C)(C)OC(=O)N1CCCC(O)C1CC(=O)Cn1cnc2cc(Br)c(Cl)cc2c1=O]

MAZ1310

FIG. 5B is a table showing IC$_{50}$ values calculated for the effects of halofuginone on CD4+ CD25− T cell functions as indicated.

FIG. 5C is a graph showing data for experiments in which a racemic mixture of halofuginone (HF) or HPLC-purified D- or L-enantiomers of halofuginone (HF-D, or HF-L) were added to CD4+ CD25− T cells activated in the presence of TGFβ plus IL-6 and the percent of Th17 cells (IL-17+ IFNγ−) was determined by intracellular cytokine staining on day 4. Values are normalized to cells treated with 40 nM compound 9 (MAZ1310)±SD.

FIG. 5D is a graph showing the percent of Th17 cells (IL-17+ IFNγ−) determined by intracellular staining 4 days after activation as above and values are presented as mean percent of Th17 cells±SD. CD4+ CD25− T cells were activated in the indicated cytokine conditions, and 10 nM halofuginone was added at the indicated times following activation. Asterisks indicate statistical significance (p<0.005) relative to T cells treated with 10 nM compound 9 (MAZ1310) at the time of activation.

Figure 5A:
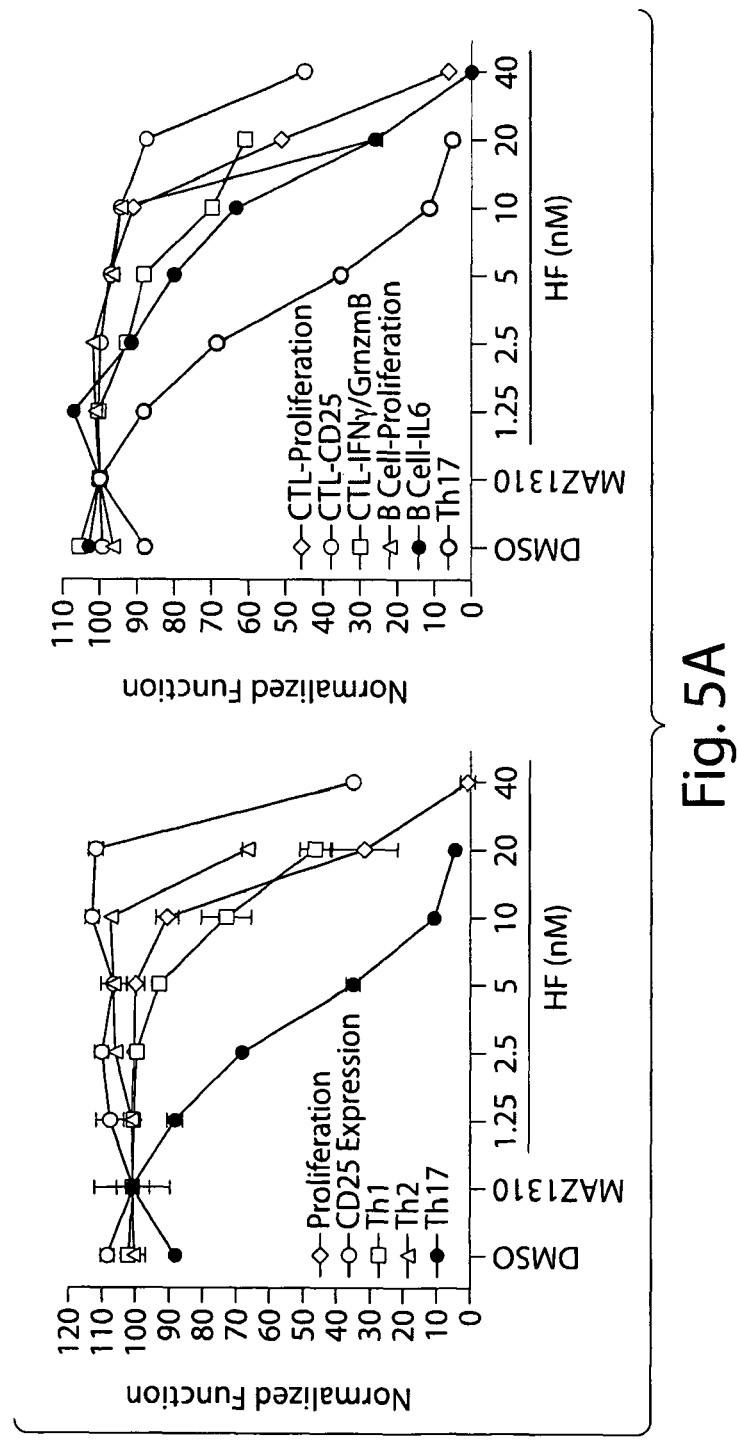
FIG. 5A, left, is a graph showing dose response analyses performed on activated carboxyfluorescein succinimidyl ester (CFSE)-labeled CD4$^+$ CD25$^-$ T cells in the presence of DMSO, 40 nM compound 9 (MAZ1310), or increasing concentrations of halofuginone (HF) (1.25-40 nM). CFSE dilution and cell surface CD25 expression were determined 48 hours after activation. Intracellular cytokine production was determined on day 4 or 5 following restimulation with phorbol myristate acetate (PMA) and ionomycin. CFSE dilution and percentages of cells expressing CD25, IFNγ$^+$ IL4$^-$ (Th1 cells), IL-4$^+$ IFNγ$^-$ (Th2 cells) or IL-17$^+$ IFNγ$^-$ (Th17 cells) cells are displayed and the values are normalized to T cells treated with 40 nM MAZ1310±SD.
Figure 5E:
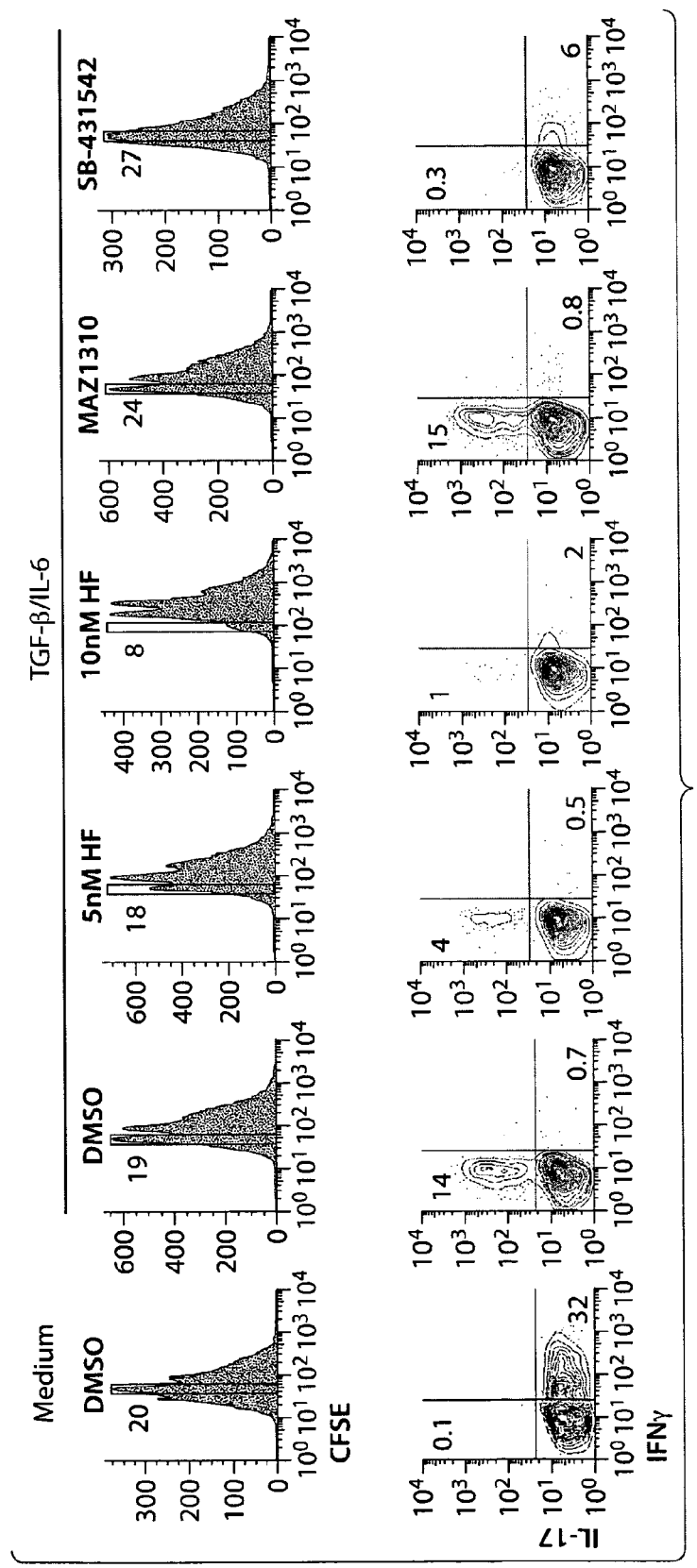
FIG. 5. Selective inhibition of Th17 cell development by halofuginone.

FIG. 5E is a set of FACS analyses of CFSE-labeled T cells activated in the indicated cytokine conditions in the presence of DMSO, 5 nM halofuginone (HF), 10 nM HF, 10 nM compound 9 (MAZ1310), or 10 μM SB-431542. Foxp3 intracellular staining was performed 3 days after T cell activation and intracellular cytokine staining was performed on day 4. Cells with equivalent CFSE fluorescence are gated on as indicated and intracellular Foxp3 or cytokine expression is shown within each gated population.

Figure 5F:
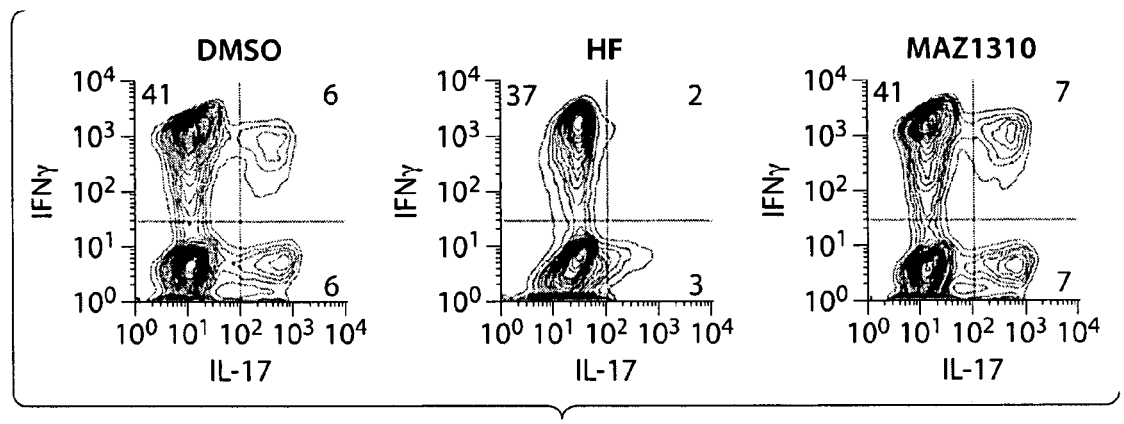

FIG. 5F is a set of FACS analyses of purified primary human memory T cells (CD4+ CD45RO+) activated in co-culture with CD14+ monocytes and treated with DMSO, 100 nM HF or 100 nM MAZ1310. T cells were expanded for 6 days and intracellular cytokine expression was determined following restimulation with PMA plus ionomycin.

Figure 5G:
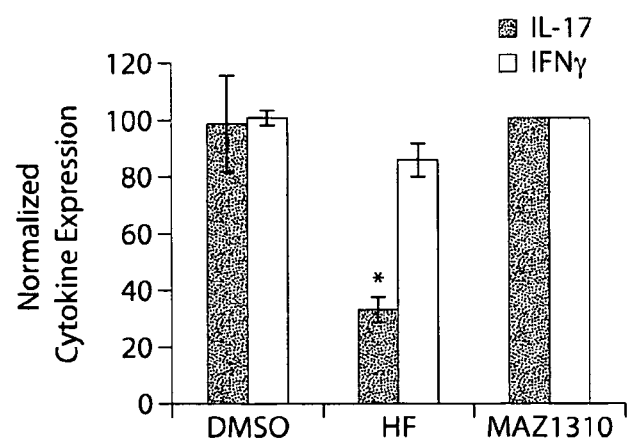

FIG. 5G is a graph depicting the percent of IL-17− (black bars) or IFNγ− (white bars) expressing T cells upon treatment with the indicated additives. The data were normalized to T cells treated with MAZ1310 and are displayed as mean values±SD. Asterisk indicates statistical significance (p<0.05). All data represent at least three similar experiments.

FIG. 6. HF inhibits Th17 differentiation through effects on STAT3 phosphorylation. FIG. 6A is a set of representative histograms displaying the kinetics of STAT3 phosphorylation in developing Th17 cells treated with or without halofuginone. Resting naïve T cells (grey, shaded peak), T cells activated in the presence of TGFβ plus IL-6 (TGFβ/IL-6) treated with 10 nM MAZ1310 (light gray trace), 5 nM HF (medium gray trace), or 10 nM HF (dark gray trace). T cells were fixed at the indicated times and intracellular phospho-STAT3 staining was performed.

Figure 6A:
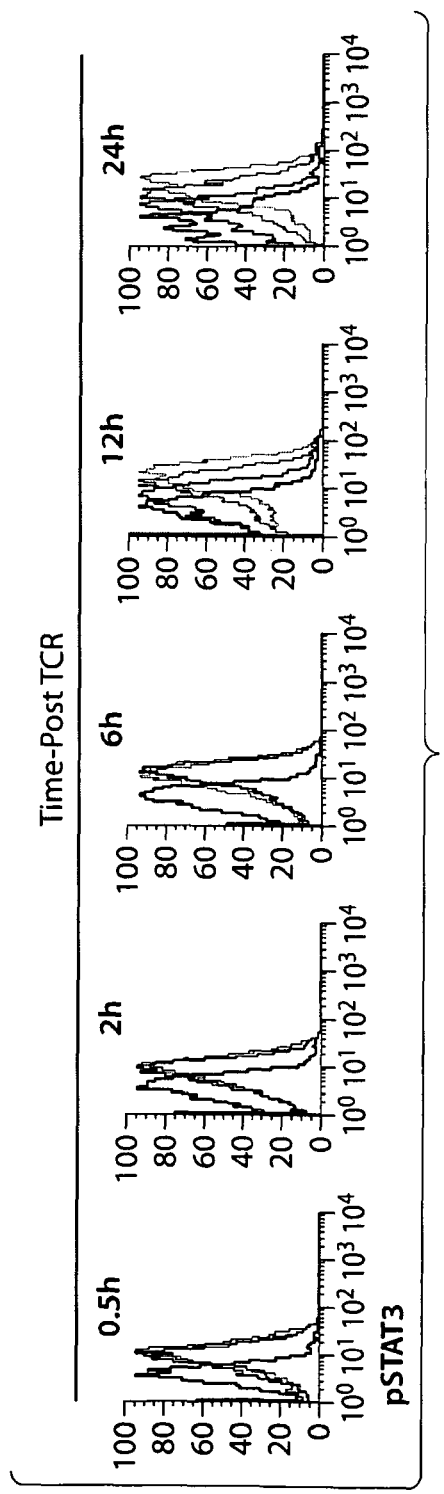
Figure 6B:
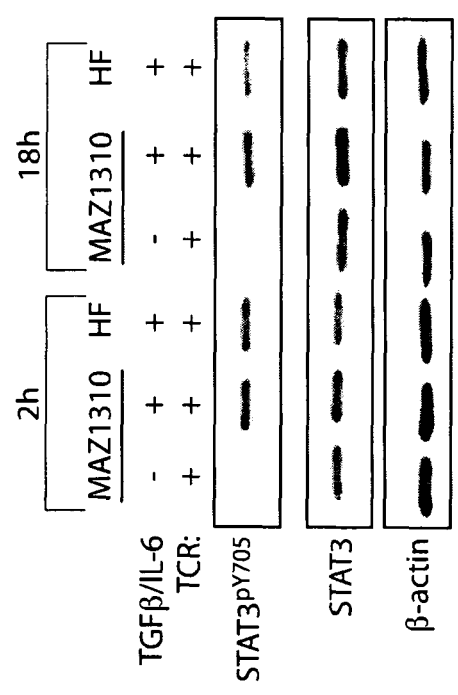

FIG. 6B depicts western blot analysis of CD4+ CD25− T cells treated with 10 nM HF or 10 nM MAZ1310 and activated in the presence or absence of TGFβ plus IL-6. Whole cell lysates were generated at the indicated times following activation.

Figure 6C:
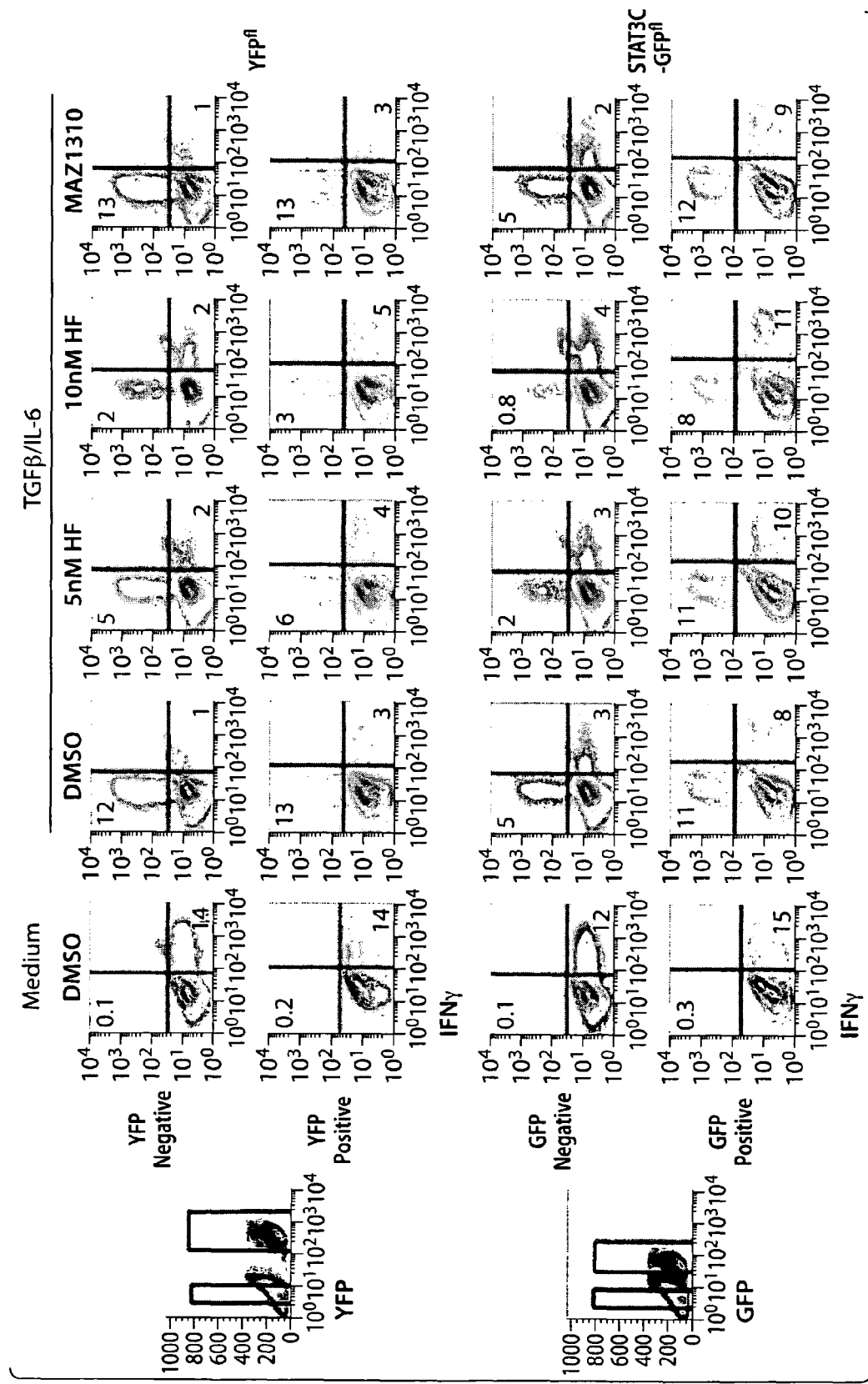

FIG. 6C is a set of FACS analyses of CD4+ CD25− T cells from YFPfl/fl or STAT3C-GFPfl/fl mice treated with recombinant TAT-Cre which were activated in the presence or absence of TGFβ plus IL-6 and treated with DMSO, 5 nM HF, 10 nM HF, or 10 nM MAZ1310 as indicated. T cells were restimulated after 4 days and intracellular cytokine staining was performed. T cells expressing YFP or GFP are gated on as shown.

Figure 6D:
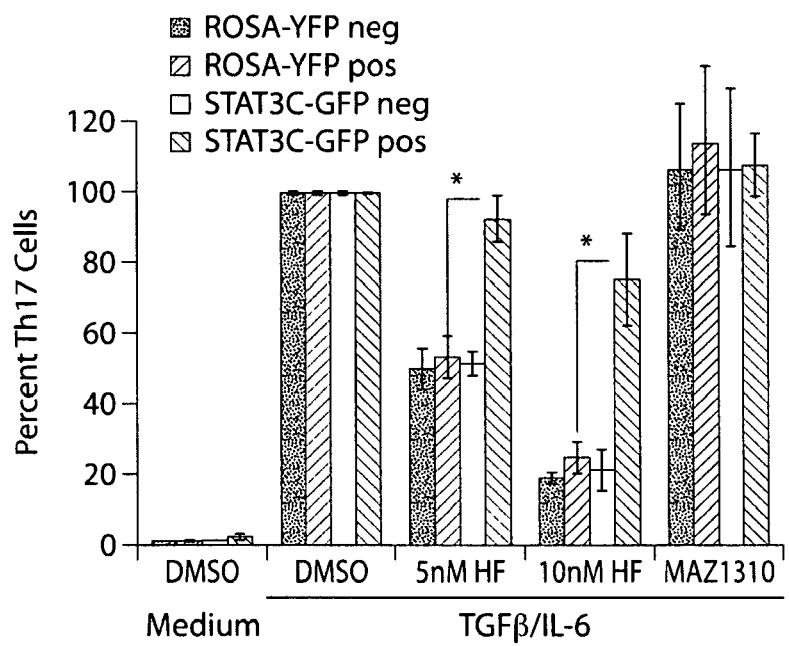

FIG. 6D is a bar graph displaying the percent of Th17 cells (IL-17+ IFNγ−) within YFP− cells (black bars), YFP+ cells (grey bars), STAT3CGFP− cells (white bars) or STAT3C− GFP+ (etched bars). The data are normalized to DMSO-treated cultures and are presented as mean values±SD on duplicate samples. Asterisks indicate statistical differences between STAT3C-GFP+ cells and YFP+ cells (p<0.05).

Figure 6E:
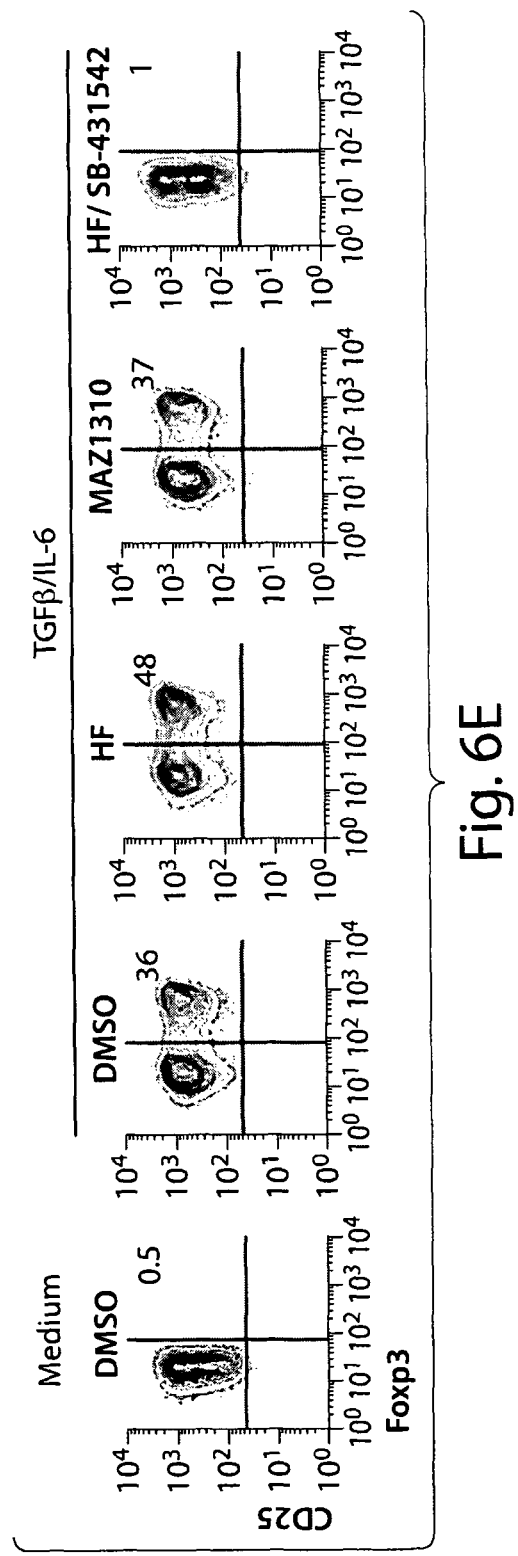

FIG. 6E is a set of FACS analyses of CD4+ CD25− T cells activated in medium or TGFβ plus IL-6, treated with DMSO, 10 nM HF, 10 nM MAZ1310, or 10 nM HF plus 10 μM SB-431542. Foxp3 expression was determined on day 3 by intracellular staining. All experiments were performed at least three times with similar results.

FIG. 7. Halofuginone activates the amino acid starvation response pathway in T cells. FIG. 7A shows dot plot analyses of microarray data from CD4+ CD25− T cells treated with 10 nM HF or 10 nM MAZ1310 and activated in Th17 polarizing cytokine conditions for 3 or 6 hours. Gray dots indicate transcripts increased at least 2-fold by HF treatment at both 3 and 6 hours. Hallmark amino acid starvation response genes are identified by text and arrowheads.

Figure 4A:
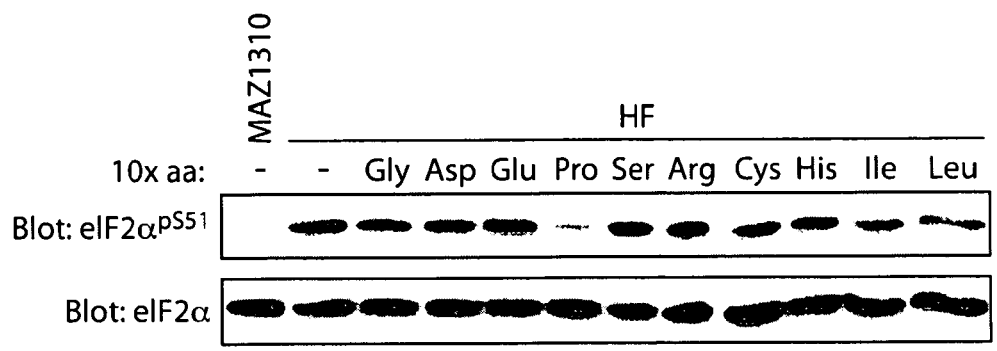
FIG. 4A depicts western blot analysis showing that halofuginone induced eIF2alpha phosphorylation.
Figure 7A:
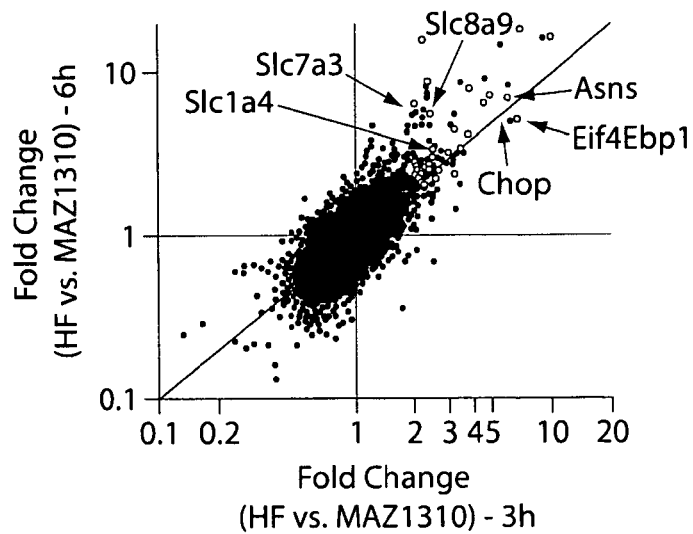
Figure 7B:
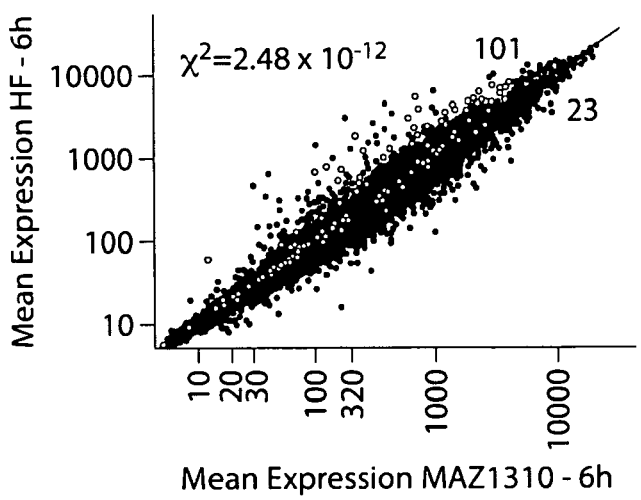

FIG. 7B is a graph showing chi-squared analysis of microarray data from FIG. 4A, which shows the expression distribution of genes previously found to be regulated by ATF4 in tunicamycin-treated mouse embryonic fibroblasts (dark dots—see the table in FIG. 14).

Figure 7C:
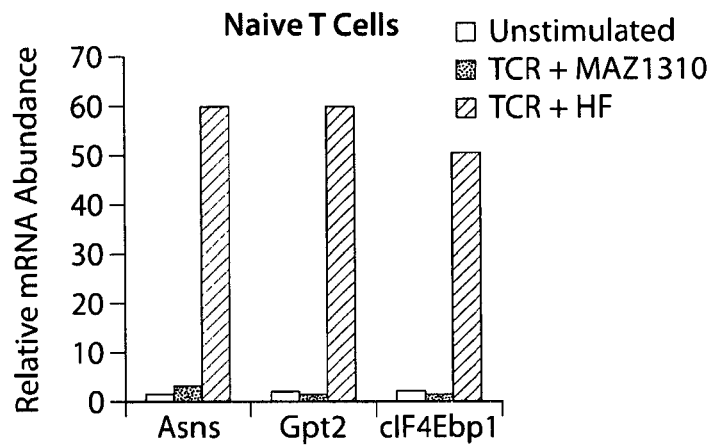

FIG. 7C is a graph depicting results of quantitative real-time PCR performed on cDNA generated from unstimulated naïve T cells or those activated for 4 hours in the presence of 10 nM MAZ1310 or 10 nM HF. Asns, Gpt2 or eIF4Ebp1 mRNA expression was normalized to Hprt levels and data are presented as mean values±SD in duplicate samples.

Figure 7D:
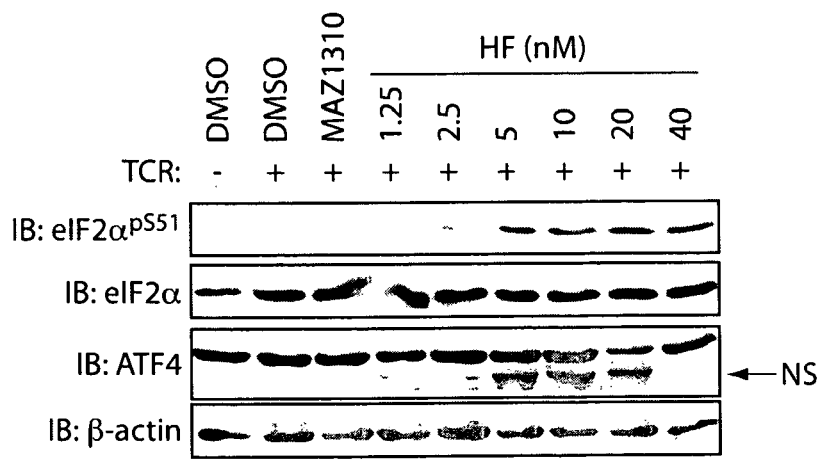

FIG. 7D depicts western blot analysis of purified CD4+ CD25− T cells either unstimulated, or TCR-activated without exogenous cytokines in the presence of DMSO, 40 nM MAZ1310 or titrating concentrations of HF (1.25-40 nM). Whole cell lysates were prepared 4 hours-post TCR activation and immunoblotting was performed with the indicated antibodies. ATF4 protein is indicated by arrowhead. NS—non-specific band.

Figure 7E:
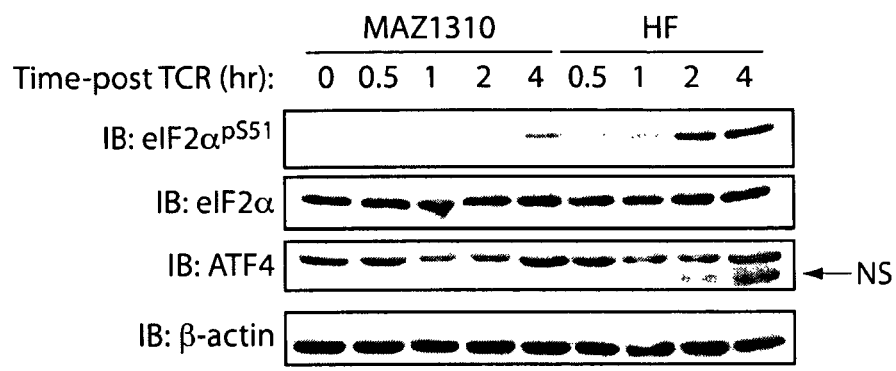

FIG. 7E depicts western blot analysis of purified CD4+ CD25− T cells activated through the TCR for the indicated times without exogenous cytokines in the presence of either 10 nM MAZ1310 or 10 nM HF as indicated. Whole cell lysates were prepared during the timecourse and immunoblotting was performed.

Figure 7F:
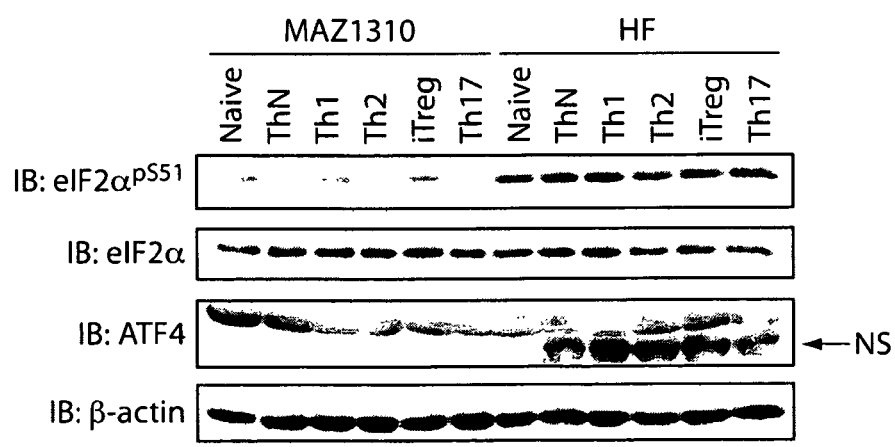

FIG. 7F depicts western blot analysis of CD4+ CD25− T cells either left unstimulated or were TCR-activated in the absence or presence of the indicated polarizing cytokine conditions and 10 nM MAZ1310 or 10 nM HF as indicated. Whole cell lysates were generated 4 hours after activation and immunoblotting was performed. Microarray data were generated from three independent experiments and all other data are representative of at least two similar experiments.

Figure 8A:
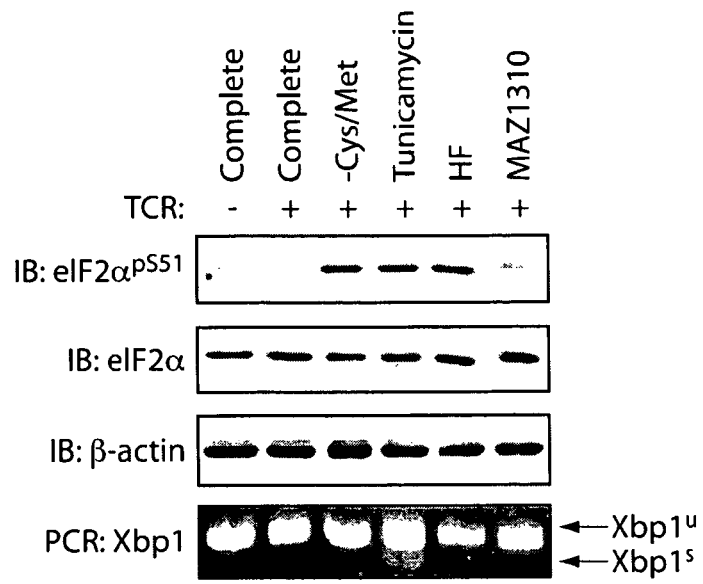

FIG. 8. Amino acid deprivation inhibits Th17 differentiation. FIG. 8A depicts western blot and Xbp1 splicing analysis of CD4+ CD25− T cells left unstimulated, or activated through the TCR for 4 hours in complete medium (complete—200 μM Cys/100 μM Met), medium lacking Cys/Met (-Cys/Met) or complete medium containing 1 μg/ml tunicamycin, 10 nM HF, or 10 nM MAZ1310. Western blotting was performed on whole cell extracts with the indicated antibodies. Xbp-1 splicing assay was performed on cDNA synthesized from T cell cultures.

Figure 8B:
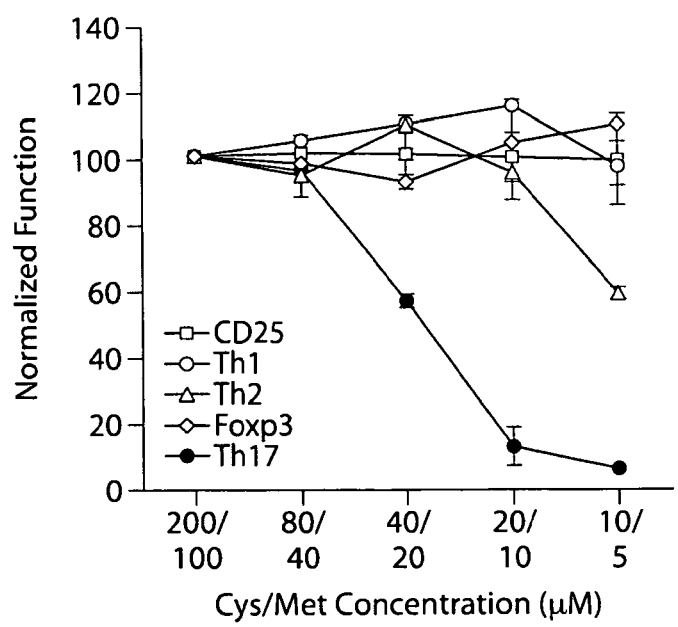

FIG. 8B is a graph depicting dose-response analyses of the effects of limiting Cys/Met concentrations on T cell activation and differentiation. Activated CD4+ CD25− T cells were cultured in the absence or presence of polarizing cytokines to induce Th1, Th2, iTreg or Th17 differentiation. Titrating concentrations of Cys/Met are indicated. CD25 and Foxp3 expression was determined 3 days post activation, cytokine production determined by intracellular staining on day 4 or 5. Percentages of cells expressing CD25, Foxp3, IFNγ+ IL4− (Th1 cells), IL-4+ IFNγ− (Th2 cells), or IL-17+ IFNγ− (Th17 cells) are displayed, and the values are normalized to T cells cultured in complete medium (200 μM Cys/100 μM Met).

FIG. 8C is a set of representative histograms show the kinetics of STAT3 phosphorylation in CD4+ CD25− T cells activated in the presence of TGFβ plus IL-6. Resting naïve T cells (grey, shaded peak), T cells cultured in complete medium (200 μM Cys/100 μM Met—dark grey trace), low Cys/Met concentrations (10 μM Cys/5 μM Met—medium gray trace) or complete medium with 10 nM HF (light gray trace). T cells were fixed at the indicated times and intracellular phospho-STAT3 staining was performed.

FIG. 8D is a graph depicting quantification of the intracellular phospho-STAT3 data. Data are presented as the percent of phospho-STAT3+ T cells in each condition multiplied by mean fluorescence intensity (MFI). Mean values from duplicate samples are displayed ±SD.

FIG. 8E is a set of FACS analyses of activated T cells cultured in the indicated cytokine condition in complete medium (complete—200 μM Cys/100 μM Met/4 mM Leucine), medium containing 0.1× cysteine and methionine (Cys/Met), medium containing 0.1× leucine (Leu) or complete medium plus 0.2 mM L-tryptophanol. Cells were expanded for 4 days and restimulated with PMA and ionomycin for intracellular cytokine staining.

FIG. 8F is a graph depicting analyses of CD4+ CD25− T cells cultured in the presence of titrating concentrations of tunicamycin as indicated. These cells were analyzed for CD25 upregulation or differentiation into Th1, Th2, iTreg, or Th17 cells. All experiments were performed 3 times with similar results.

Figure 9A:
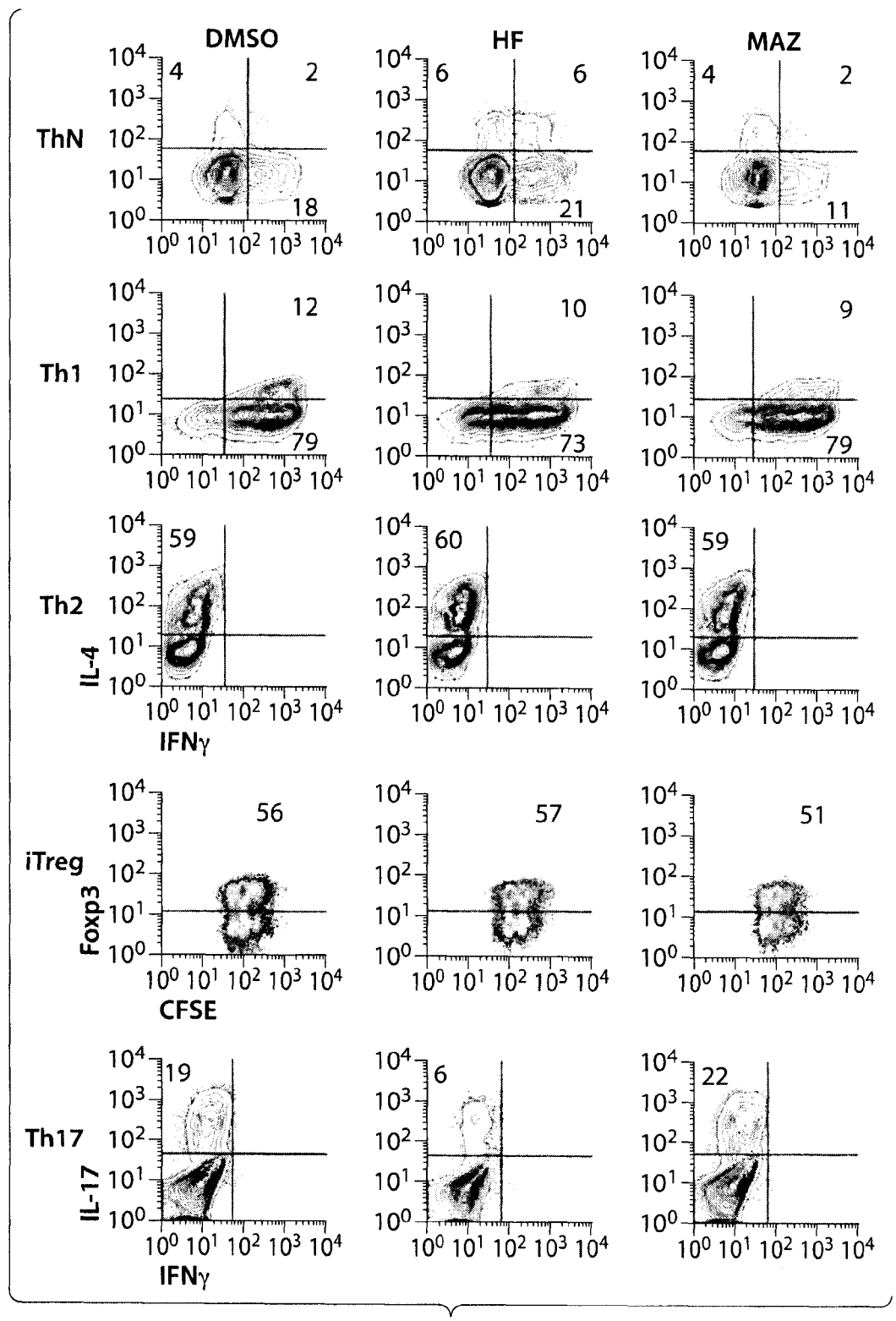

FIG. 9. Effects of halofuginone on T cell activation and effector function. FIG. 9A is a set of FACS analyses of CFSE labeled CD4+ CD25− T cells activated in the absence or presence of polarizing cytokines. DMSO, 5 nM HF, or 5 nM MAZ1310 was added to the cells at the time of T cell activation. Intracellular Foxp3 staining was performed on expanded cells 3 days after activation. Cytokine expression was determined by intracellular staining after PMA and ionomycin restimulation on day 4-5.

Figure 9B:
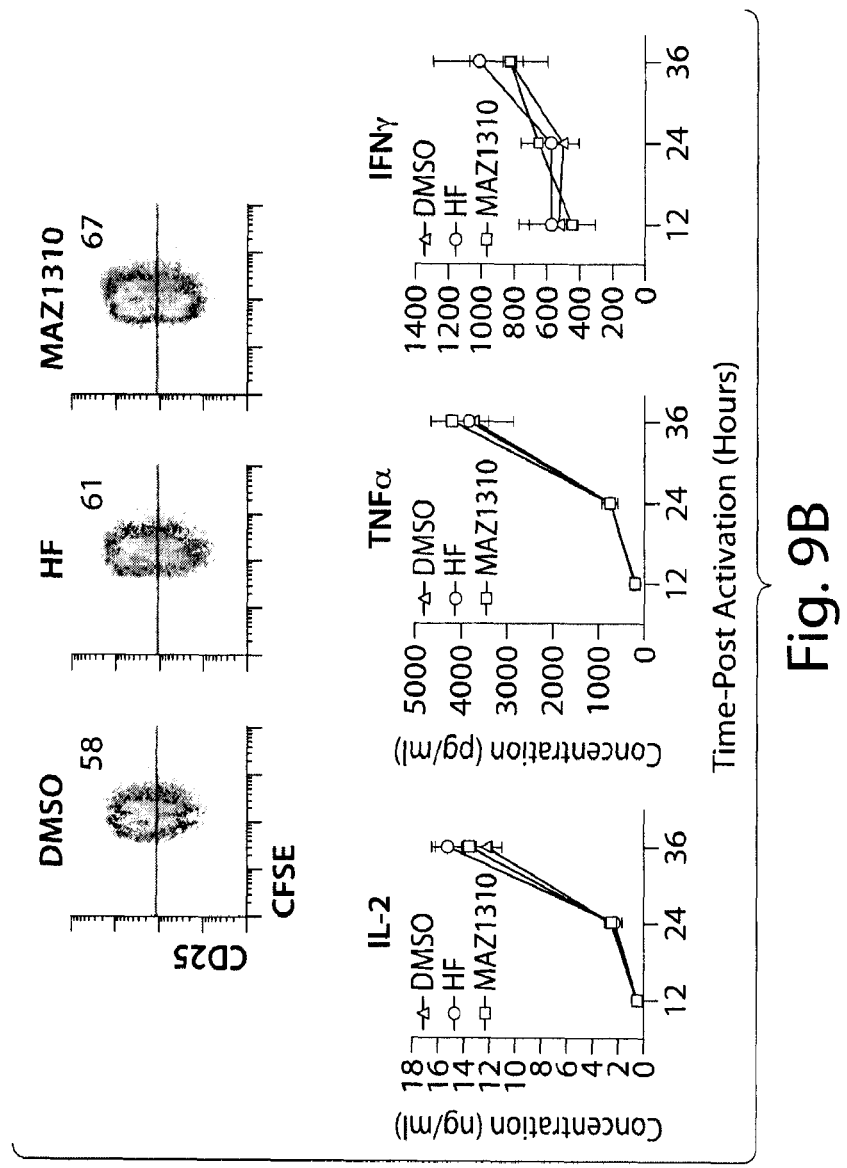

FIG. 9B is a set of FACS and graphical analyses of CFSE labeled CD4+ CD25− T cells treated with DMSO, 5 nM HF, or 5 nM MAZ1310 activated in the absence of polarizing cytokines. CFSE dilution and CD25 cell surface expression was determined on day 2 by FACS analyses. T cells were activated as above without exogenous cytokines and supernatants were harvested at the indicated time-points following activation. Cytokine secretion was determined using a cytometric bead array (CBA) on duplicate samples. Cytokine concentrations were determined by comparison to standard curves and data are presented as the mean cytokine concentrations±SD.

Figure 9C:
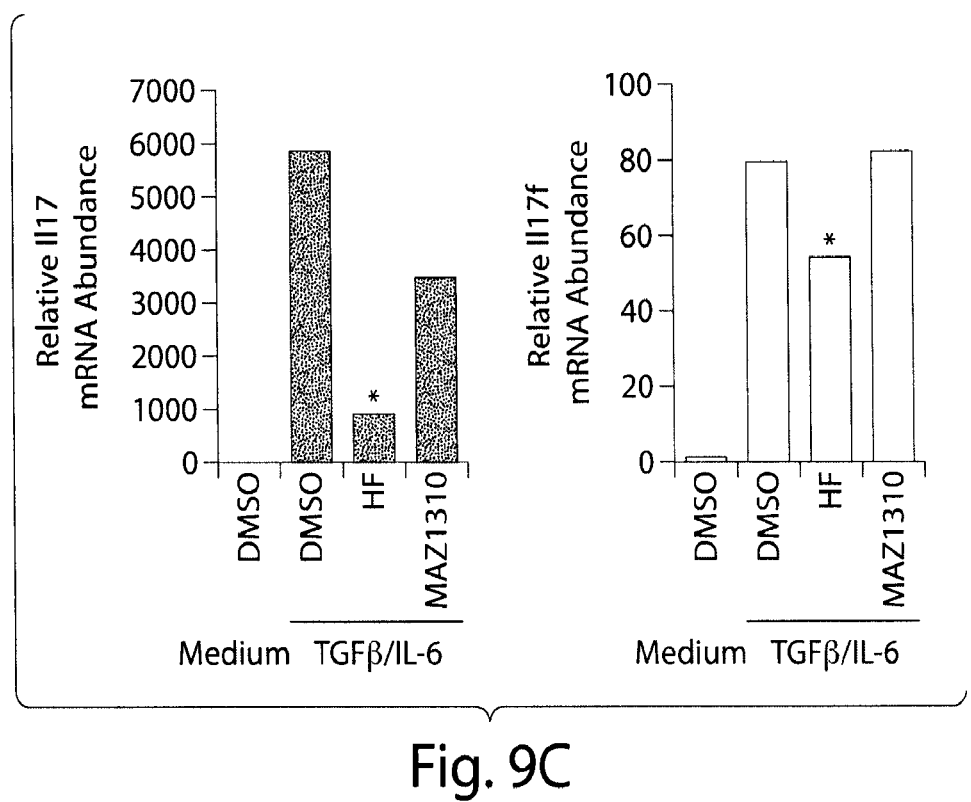

FIG. 9C is a set of graphs depicting HF effects on IL-17 and IL-17f mRNA expression in Th17 cells. CD4+ CD25− T cells were differentiated under Th17 cytokine conditions in the presence of DMSO, 10 nM HF, or 10 nM MAZ1310 for 4 days as above. Cells were harvested and restimulated with PMA and ionomycin as above, and cDNA was generated for Sybrgreen real-time PCR analysis. Data indicate fold changes in mRNA expression normalized to Hprt and are presented as mean expression±SD. Asterisks indicate statistical significance for Il17 mRNA ($p<0.001$) and Il17f mRNA ($p<0.05$) for HF-treated T cells relative to those treated with MAZ1310. All data are representative of at least three independent experiments.

FIG. 10. Halofuginone does not regulate TGFβ signaling in T and B cells. FIG. 10A is a set of FACS analyses of CD4+ CD25− T cells activated in Th1 or Th2 polarizing conditions, either in the presence or absence of TGFβ. DMSO, 10 nM HF, 10 nM MAZ1310, or 10 μM SB-431542 added as indicated at the time of activation. Intracellular cytokine staining was performed on expanded T cells on day 5.

Figure 10A:
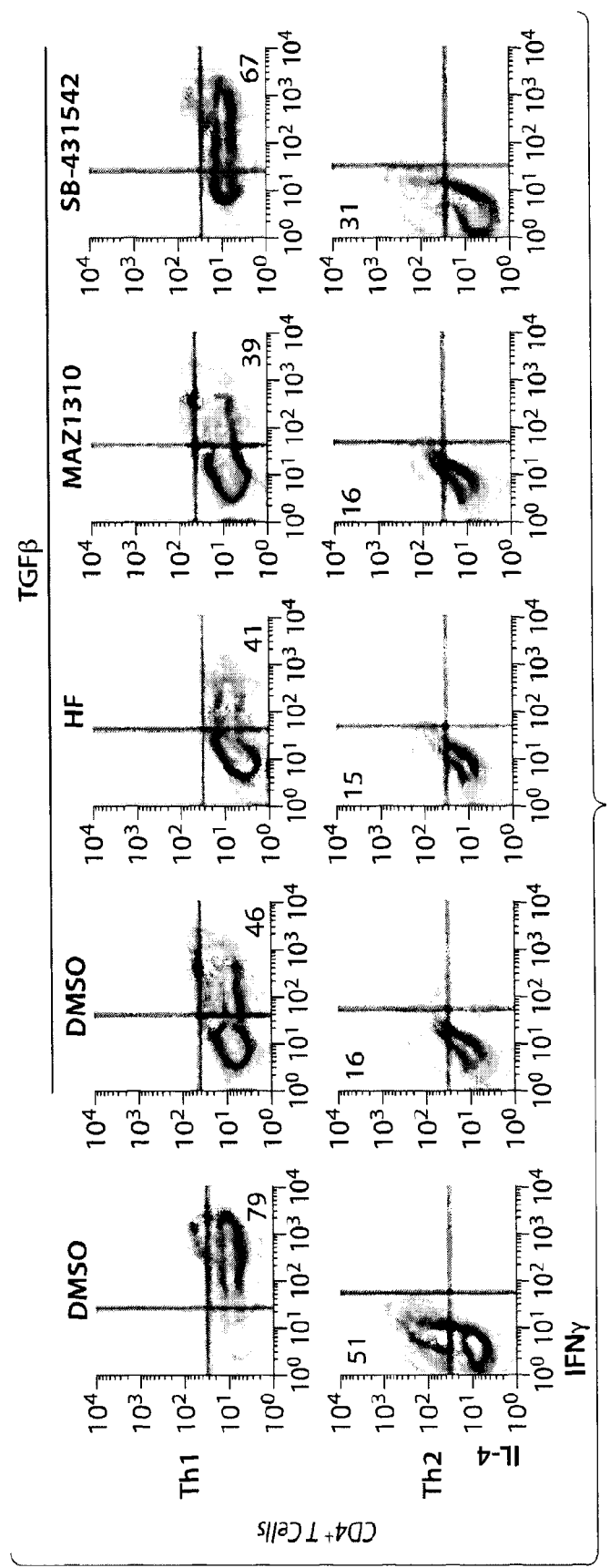
Figure 10B:
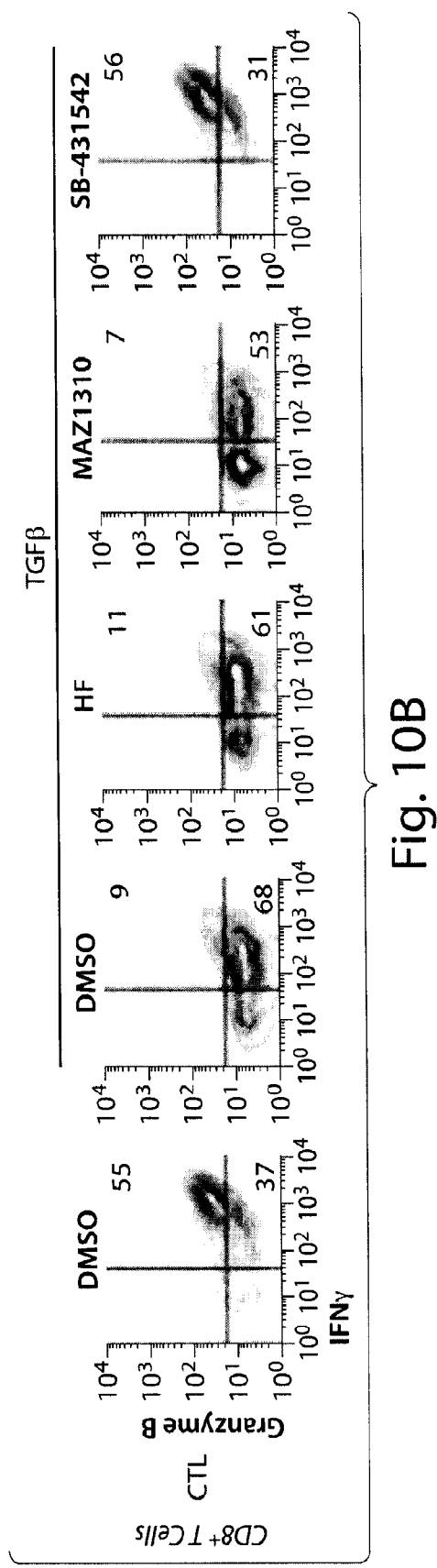

FIG. 10B is a set of FACS analyses of CD8+ T cells activated in the presence or absence of TGFβ and cultured with DMSO, 10 nM HF, 10 nM MAZ1310, or 10 μM SB-431542. Expanded cells were restimulated on day 5 and intracellular staining was performed.

Figure 10C:
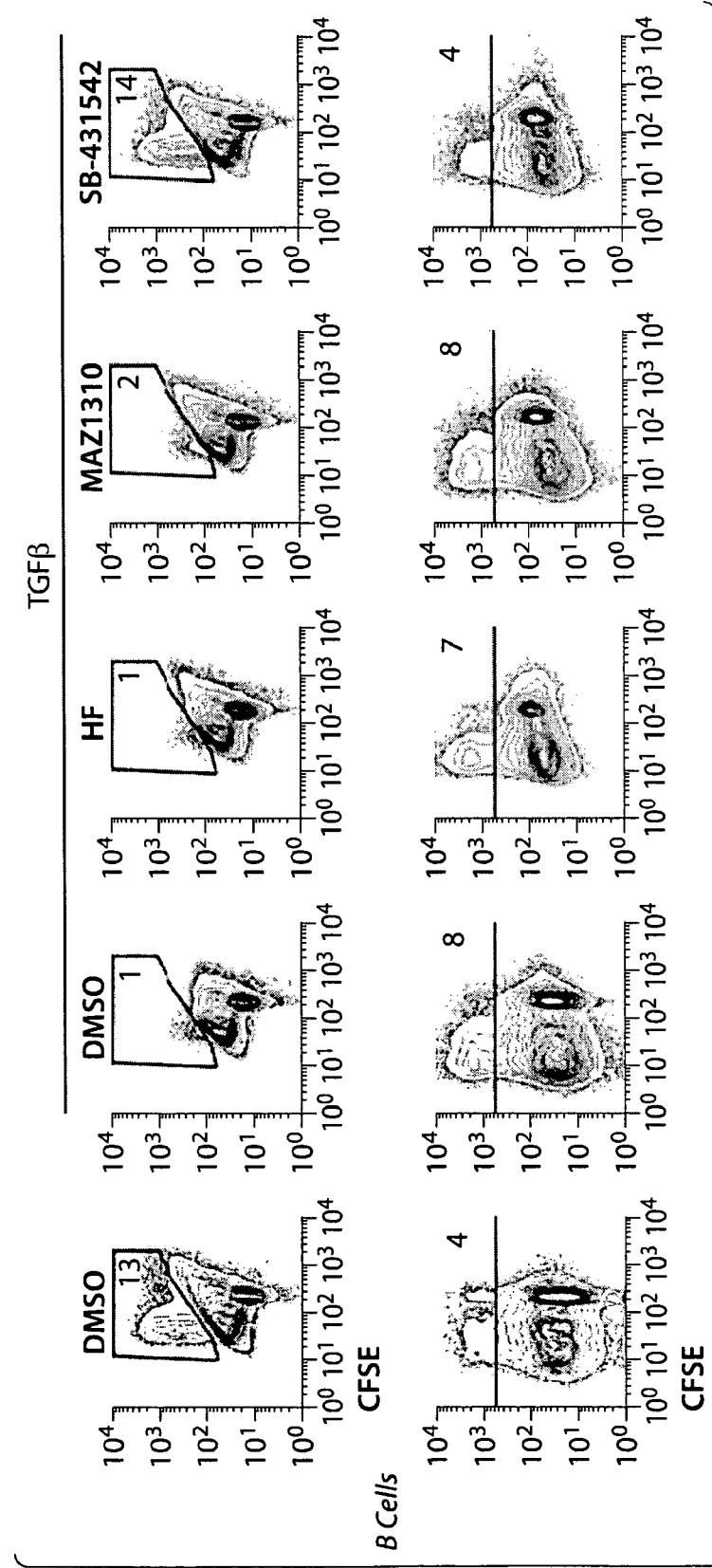

FIG. 10C is a set of FACS analyses of CFSE-labeled B cells activated by LPS stimulation in the presence or absence of TGFβ plus DMSO, 10 nM HF, 10 nM MAZ1310, or 10 μM SB-431542. Intracellular IL-6 production in B cells restimulated with PMA plus ionomycin, or cell-surface IgA expression was determined 4 days after activation.

Figure 10D:
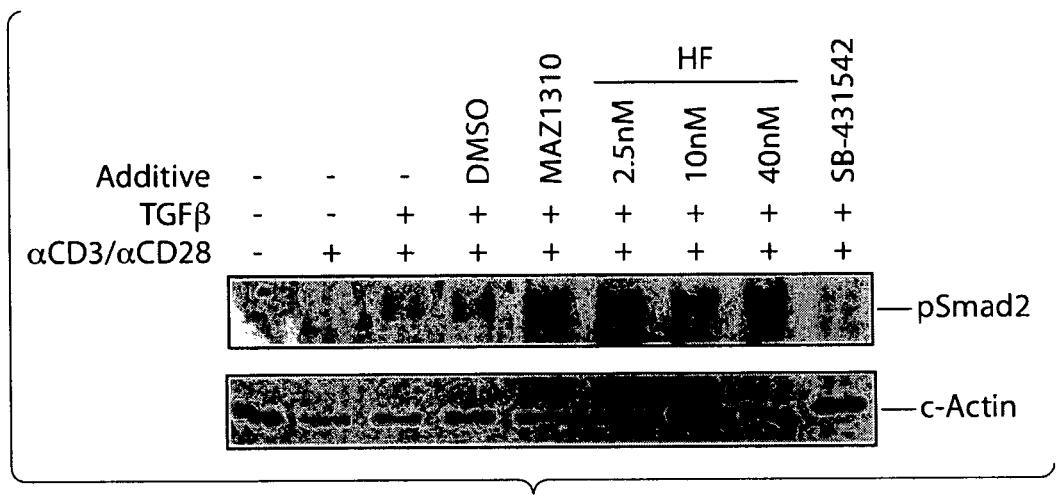

FIG. 10D depicts western blot analyses of purified CD4+ CD25− T cells treated with DMSO, 40 nM MAZ1310, titrating concentrations of HF (2.5-40 nM) or 10 μM SB-431542 for 30 minutes in complete medium supplemented with 0.1% fetal calf serum. T cells were then activated in the presence or absence of 3 ng/ml TGFβ. Whole cell extracts were prepared after 1 hour of stimulation and western blot analyses were performed using the indicated antibodies. These data are representative of three similar experiments.

Figure 11A:
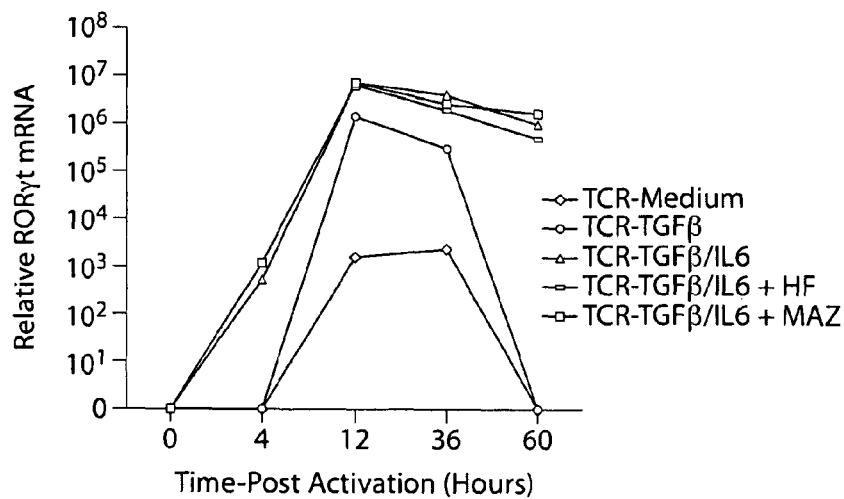

FIG. 11. Halofuginone inhibits RORγt function, not expression. FIG. 11A is a graph depicting analyses of CD4+ CD25− T cells treated with DMSO (if no indication), 10 nM HF, or 10 nM MAZ1310 as indicated and activated in the presence of cytokines as noted. T cells were harvested at the indicated times following activation, RNA was isolated and quantitative real-time PCR was performed on cDNA. RORγt expression was normalized to Gapdh levels and the data are presented as fold changes relative to unstimulated T cells.

Figure 11B:
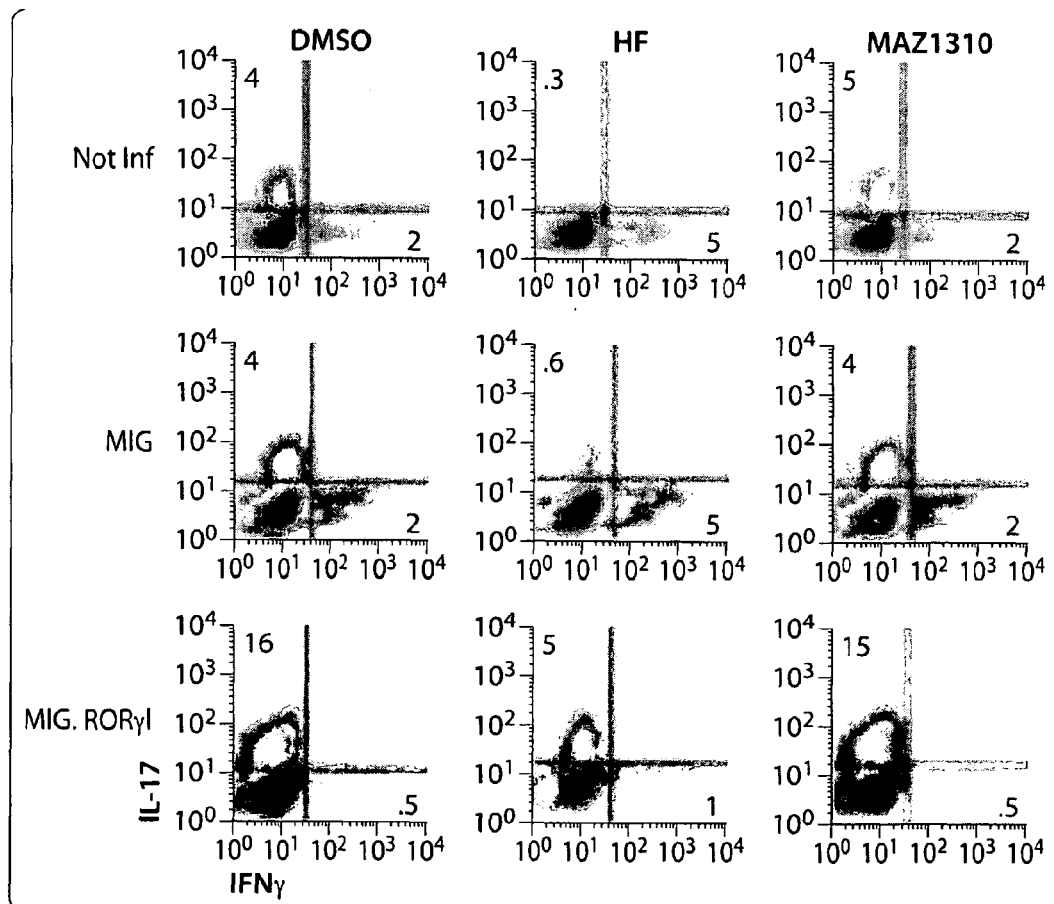

FIG. 11B is a set of FACS analyses of CD4+ CD25− T cells activated in the presence or absence of TGFβ plus IL-6, which were transduced with empty (MIG) or RORγt-expressing (MIG.RORγt) retroviruses 12 hours-post activation. Infected T cells were expanded and restimulated on day 4 for intracellular staining. MIG and MIG.RORγt-transduced cells were gated based on GFP fluorescence.

Figure 11C:
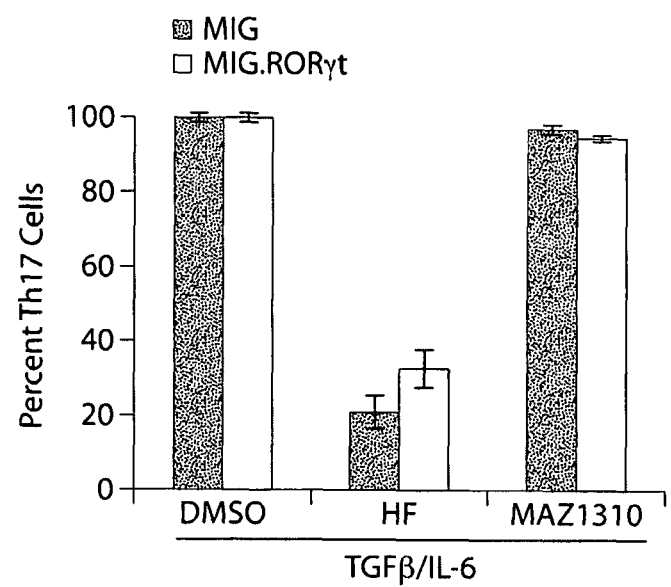

FIG. 11C is a graph depicting the percent of Th17 cells (IL-17+ IFNγ−) in cultures of MIG-transduced (black bars) or MIG.RORγt-transduced (white bars) T cells as determined by intracellular cytokine staining were normalized to DMSO-treated cultures. The data were presented as mean values±SD on duplicate samples. These data are representative of three similar experiments.

Figure 12A:
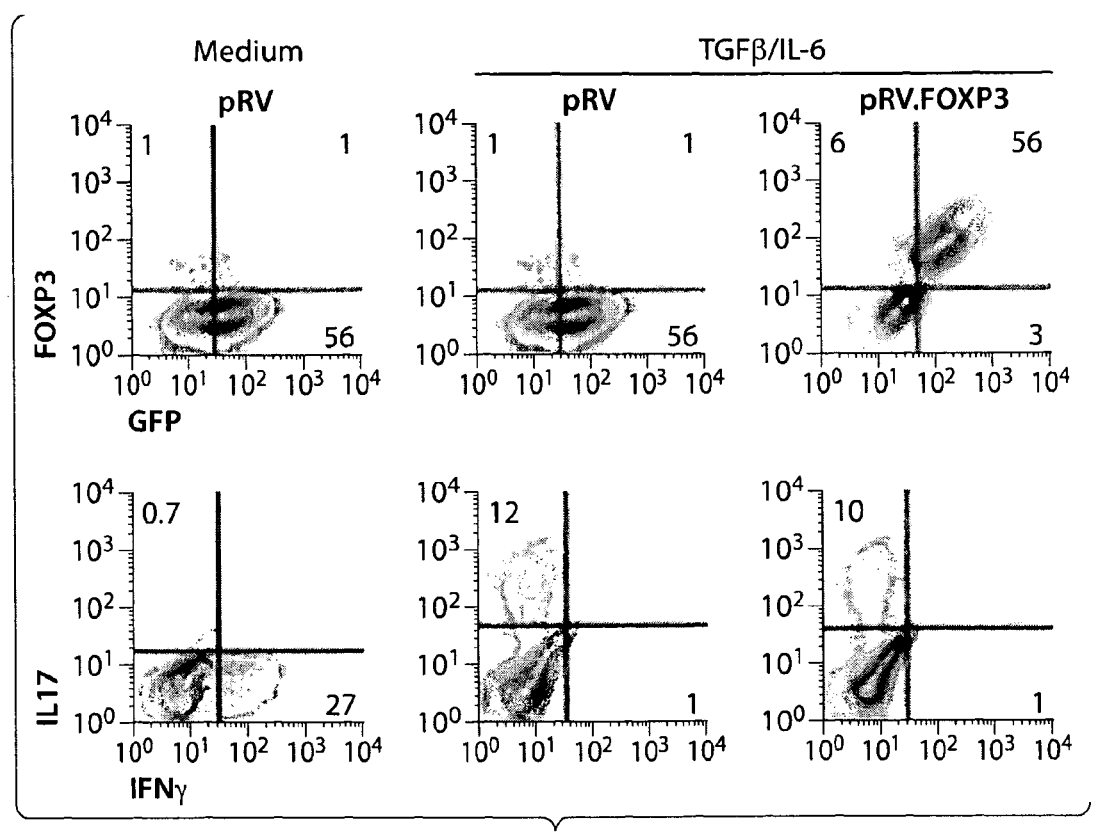

FIG. 12. Halofuginone-enforced Foxp3 expression is not necessary or sufficient for the inhibition of Th17 differentiation. FIG. 12A is a set of FACS analyses of CD4+ CD25− T cells activated in the presence or absence of TGFβ plus IL-6 which were transduced with empty (pRV) or FOXP3-expressing (pRV.FOXP3) retroviruses 12 hours after activation. Intracellular FOXP3 and cytokine expression was determined 3 days after infection (4 days after activation). IFNγ and IL-17 expression in pRV- and pRV.FOXP3-transduced cells was determined by FACS analyses after gating on GFP+ cells.

Figure 12B:
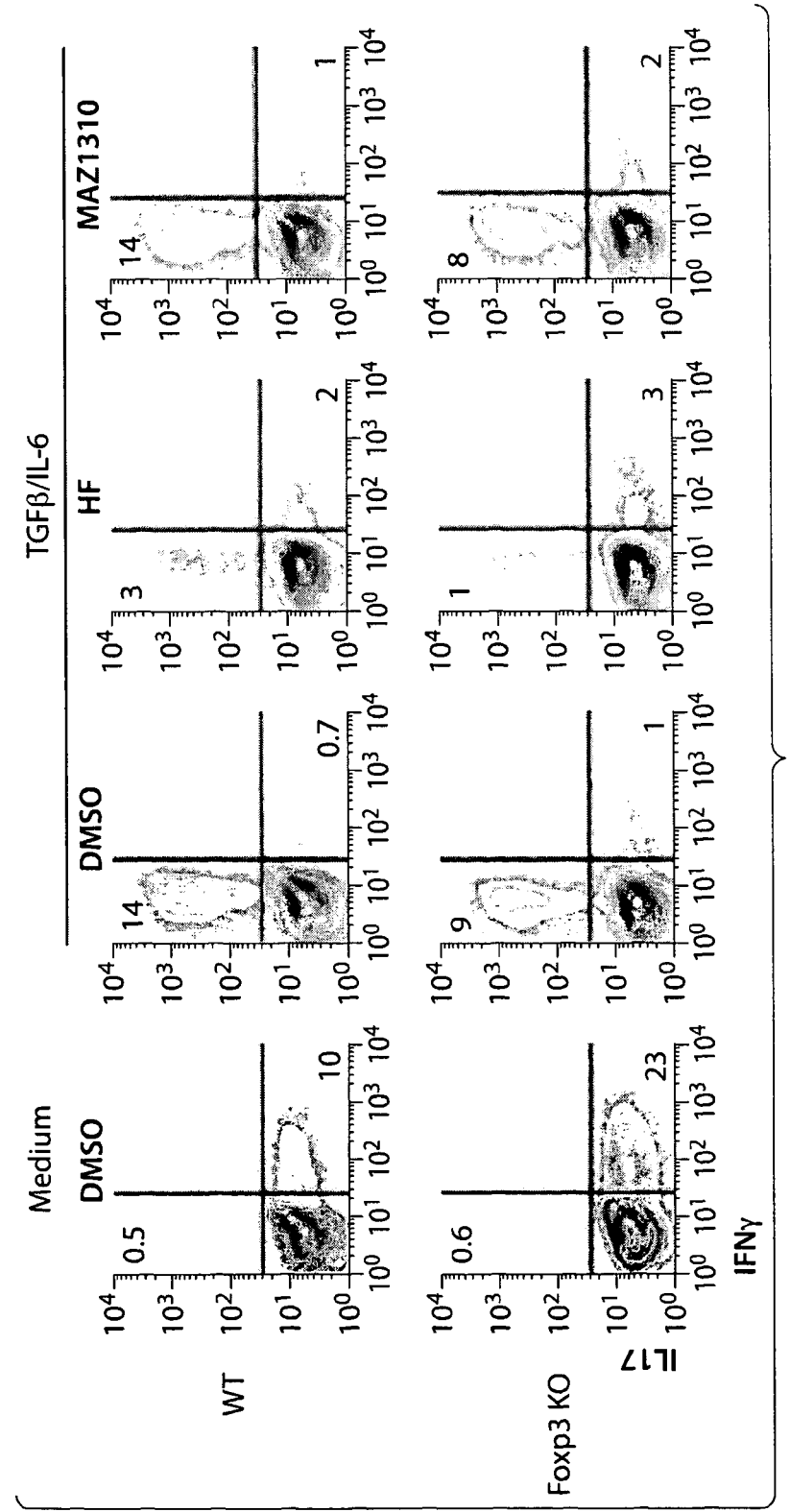

FIG. 12B is a set of FACS analyses of FACS sorted naïve CD4+ T cells from wild-type (WT) or Foxp3-deficient (Foxp3 KO) male mice, treated with DMSO, 10 nM HF, or 10 nM MAZ1310 as indicated and activated in the absence or presence of TGFβ plus IL-6. T cells were expanded and were restimulated on day 4 for intracellular cytokine staining. These results are representative of cells purified from two pairs of WT and Foxp3 KO mice.

Figure 13:
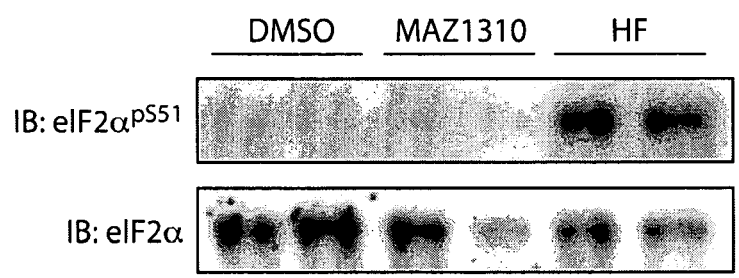

FIG. 13. Halofuginone induces a stress response in fibroblasts. SV-MES mesangial cells were stimulated for 2 hours with DMSO, 20 nM MAZ1310, or 20 nM HF. Whole cell lysates were analyzed for expression of phosphorylated or total eIF2α by western blotting. These data represent at least two similar experiments.

FIG. 14. Amino acid deprivation mimics the effects of halofuginone on T cell differentiation. FIG. 14A depicts western blot analyses of CD4+ CD25− T cells activated through the TCR for the indicated times without polarizing cytokines in the presence or absence of cysteine and methionine (Cys/Met). Whole cell lysates were prepared and immunoblotting was performed.

Figure 14A:
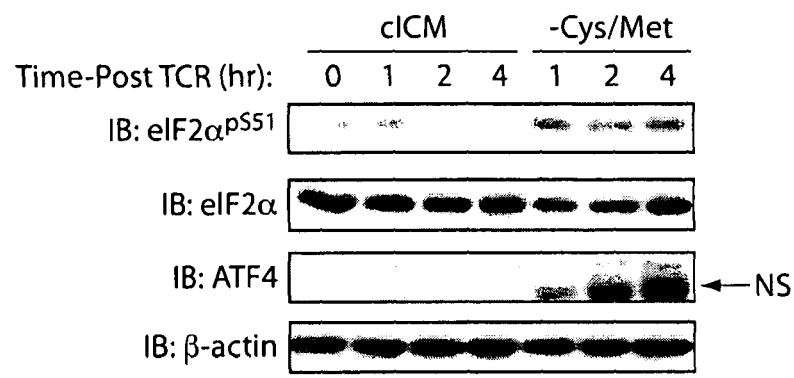
Figure 14B:
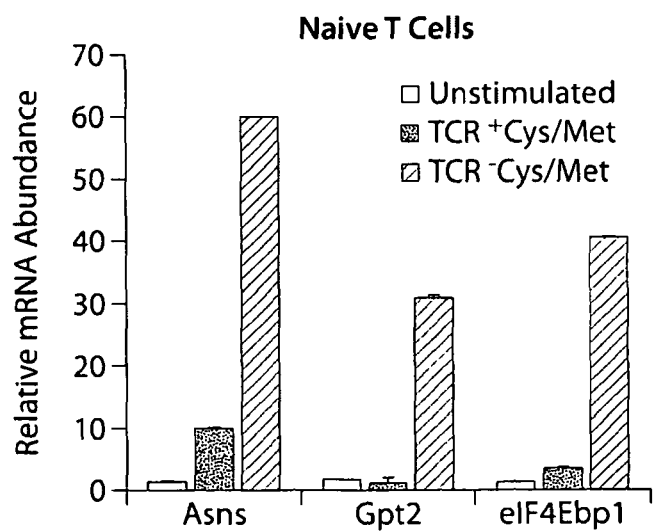

FIG. 14B is a graph depicting results of quantitative real-time PCR performed on cDNA generated from naïve T cells, either left unstimulated or activated through the TCR for 4 hours without exogenous cytokines in the presence or absence of Cys/Met as indicated. Asns, Gpt2 or eIF4Ebp1 mRNA expression was normalized to Hprt levels, and data are presented as mean expression values±SD in duplicate samples.

Figure 14C:
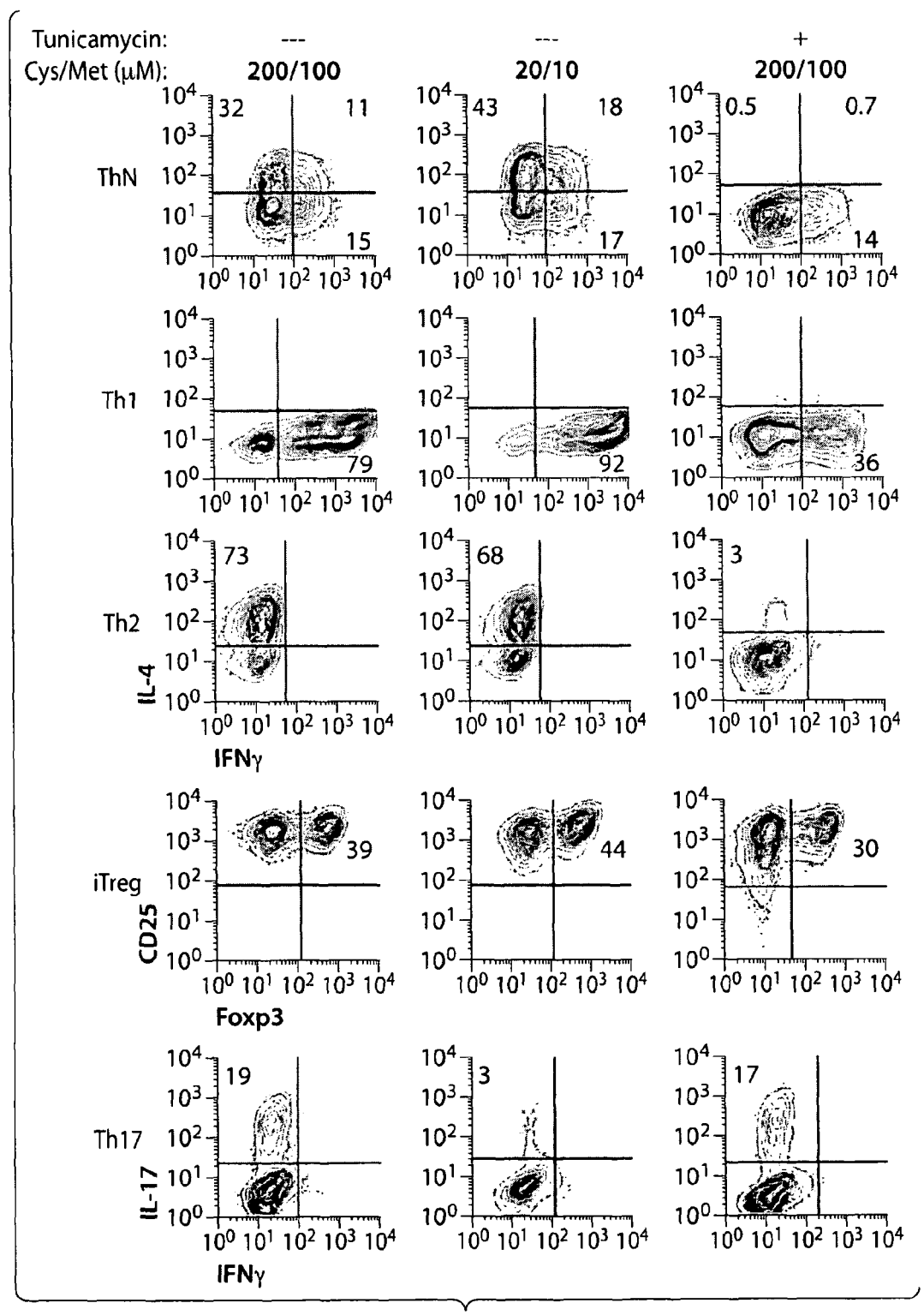

FIG. 14C is a set of FACS analyses of CD4+ CD25− T cells cultured in complete medium (200 μM Cys/100 μM Met), medium containing limiting concentrations of Cys/Met (0.1×-20 μM Cys/10 μM Met), or complete medium plus 31.25 ng/ml tunicamycin. Cells were activated through the TCR in the absence or presence of polarizing cytokines to induce Th1, Th2, iTreg, or Th17 differentiation. Foxp3 intracellular staining was performed on day 3-post activation, and intracellular cytokine expression was determined on cells restimulated with PMA plus ionomycin on day 4-5.

Figure 14D:
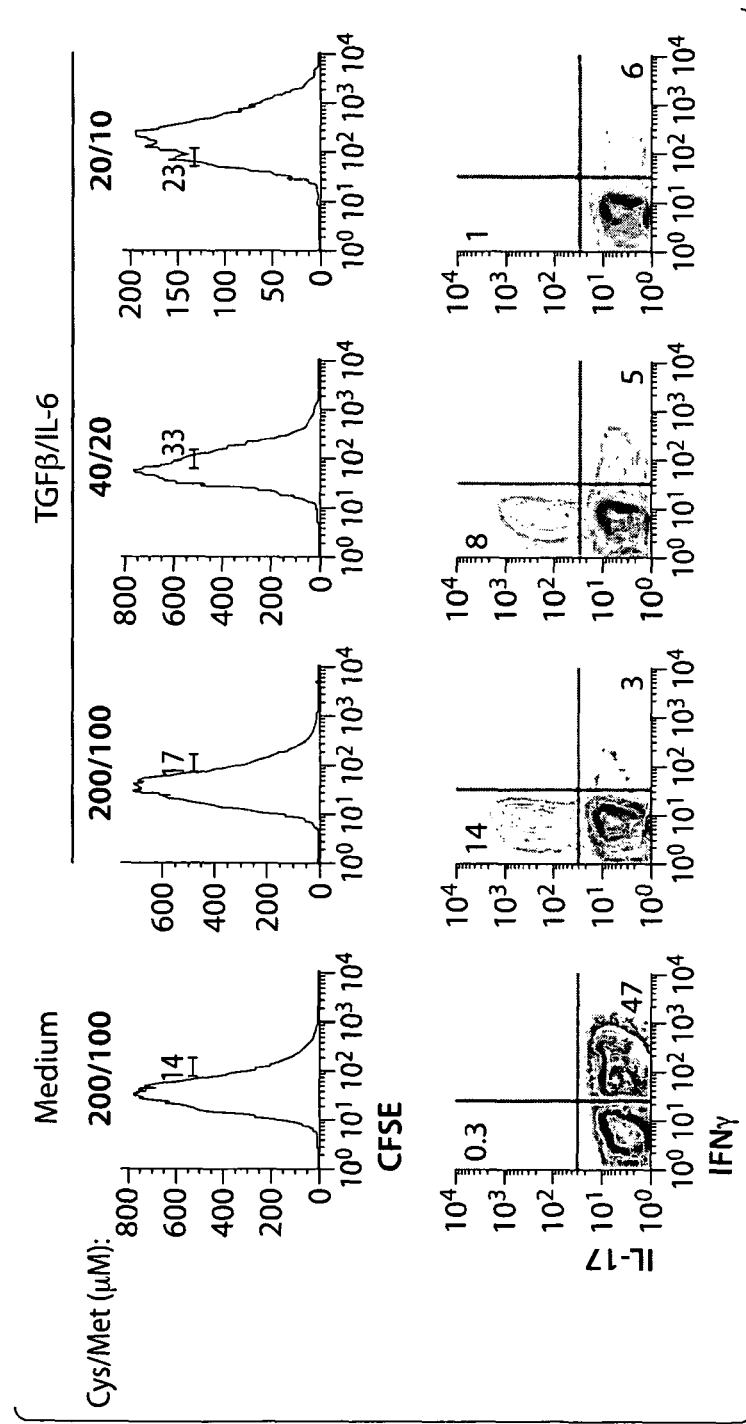

FIG. 14D is a set of FACS analyses of CD4+ CD25− T cells labeled with CFSE, cultured in medium containing the indicated concentrations of Cys/Met and activated in the absence or presence of TGFβ plus IL-6. Cells were expanded until day 4 when CFSE dilution and intracellular cytokine production was determined on restimulated cells. Cells with equivalent CFSE fluorescence are gated on as indicated, and intracellular cytokine expression is shown within each gated population.

FIG. 15. Genes induced by halofuginone treatment in T cells. Gene symbols and names of transcripts increased at least 2-fold by HF treatment at both 3 and 6 hours. Mean fold increases±SD from triplicate samples of HF- versus MAZ1310-treated T cells is shown at 3 and 6 hours.

FIGS. 16A-C. Probe IDs of known stress response genes. Affymetrix probe IDs and gene names previously identified as ATF4 responsive during tunicamycin-induced ER stress in mouse embryonic fibroblasts.

Figure 17:
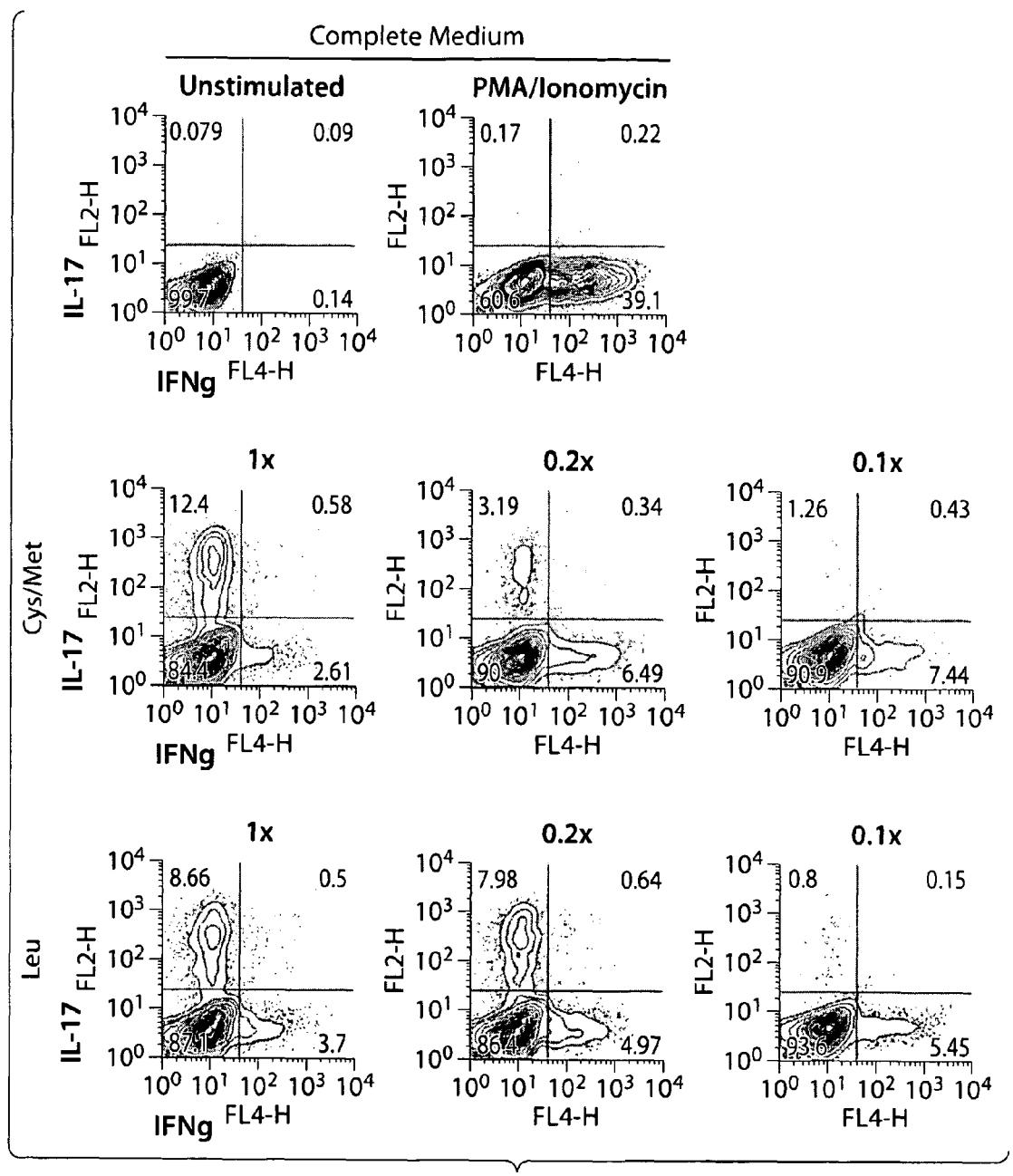
Figure 17:
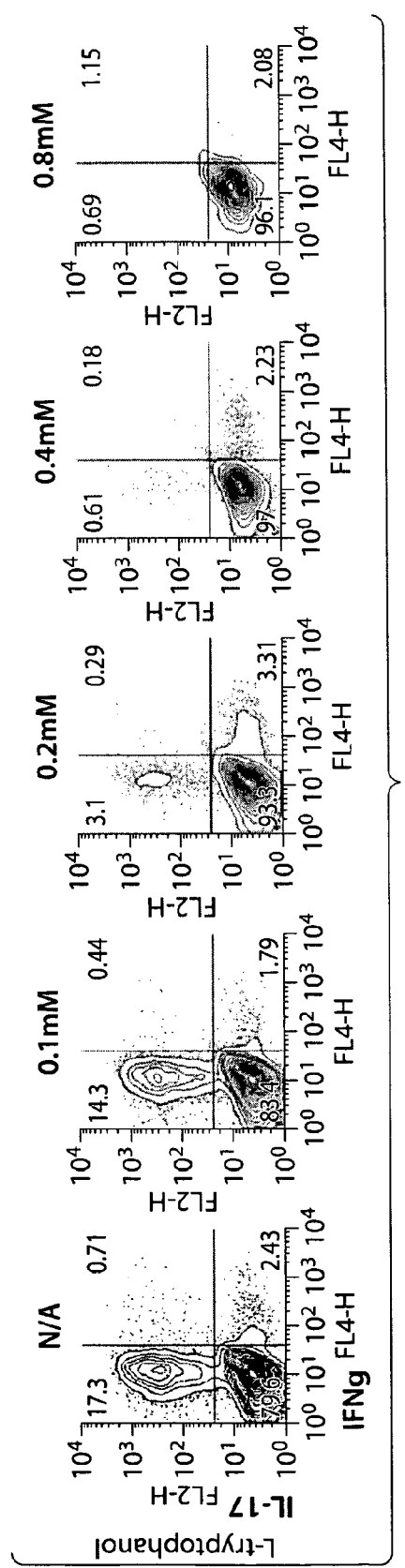

FIG. 17 is a set of FACS analyses showing that depletion of amino acids or tRNA synthetase inhibition with L-tryptophanol inhibits Th17 differentiation. T cells were cultured in the presence of medium containing 0.1×, 0.2×, and 1× cysteine and methionine (Cys/Met), medium containing 0.1×, 0.2×, and 1× leucine (Leu), or complete medium plus 0.1 mM, 0.2 mM, 0.4 mM, or 0.8 mM tryptophanol. Cells were activated and cultured under Th17 differentiating conditions, restimulated, and assayed for IL-17 and IFNγ expression.

FIG. 18. Inhibition of IL-17-associated autoimmune inflammation in vivo. FIG. 18A is a set of FACS analyses of CNS-infiltrating mononuclear cells which were isolated from myelin oligodendrocyte glycoprotein (MOG)-immunized mice during active disease (day 19—clinical score=2) and stimulated ex vivo with PMA and ionomycin. Expression of IFNγ (left panel) and IL-17 (right panel) was determined in CD4+ TCRβ+ T cells.

Figure 18A:
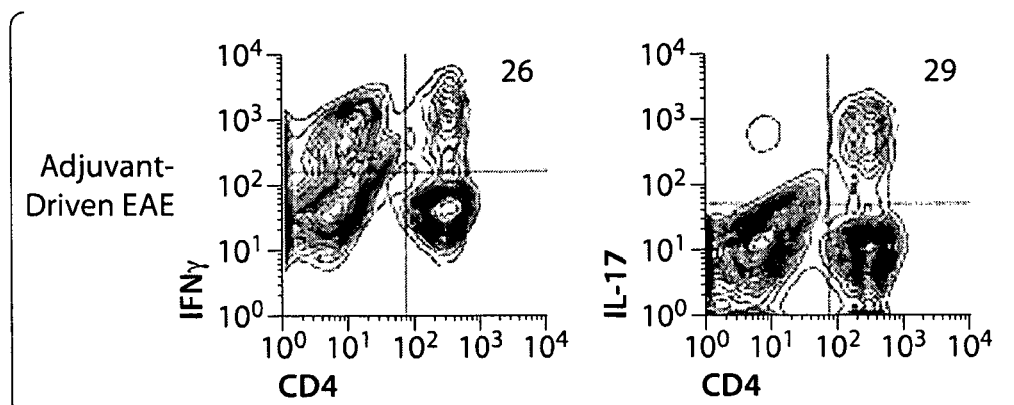
Figure 18B:
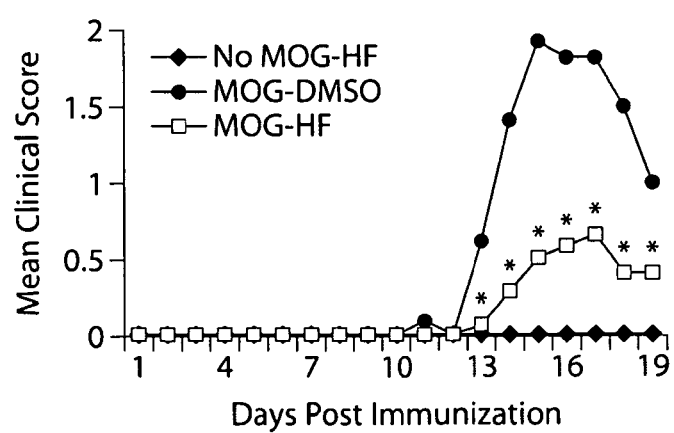

FIG. 18B is a graph depicting the effect of systemic HF administration on adjuvant-driven experimental autoimmune encephalomyelitis (EAE). Control mice were immunized with an emulsion of PBS in Complete Freund's Adjuvant (CFA) and treated with 2 mg HF daily (no MOG+HF (n=10)). Other mice were immunized with MOG$_{33-55}$ in CFA and treated daily with either DMSO (MOG+DMSO (n=12)), or 2 mg HF (MOG+HF (n=14)). Disease was monitored daily.

Figure 18C:
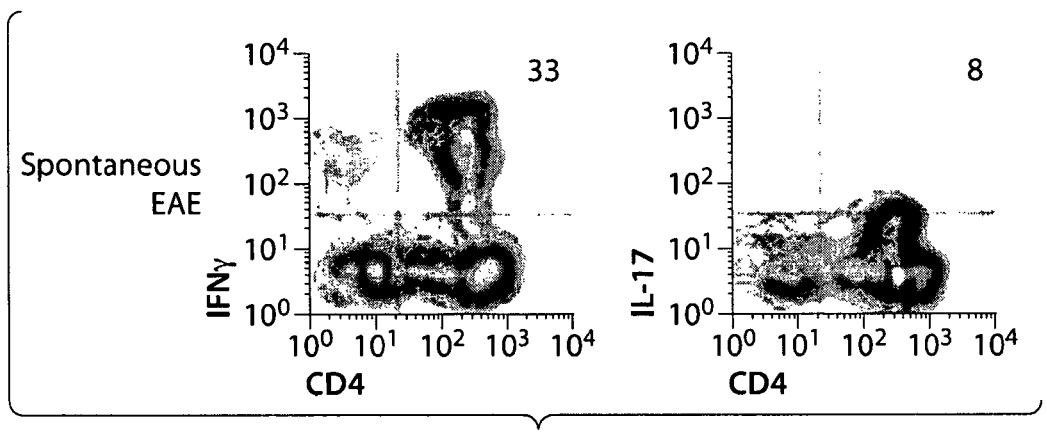

FIG. 18C is a set of FACS analyses of leukocytes isolated from CNS tissue of mice with active EAE following transfer of PLP-specific T cells. Cells were stimulated ex vivo with PMA and ionomycin and expression of IFNγ (left panel) or IL-17 (right panel) was determined in PLP-reactive (TCRVβ6 gated) CD4+ T cells by intracellular staining.

Figure 18D:
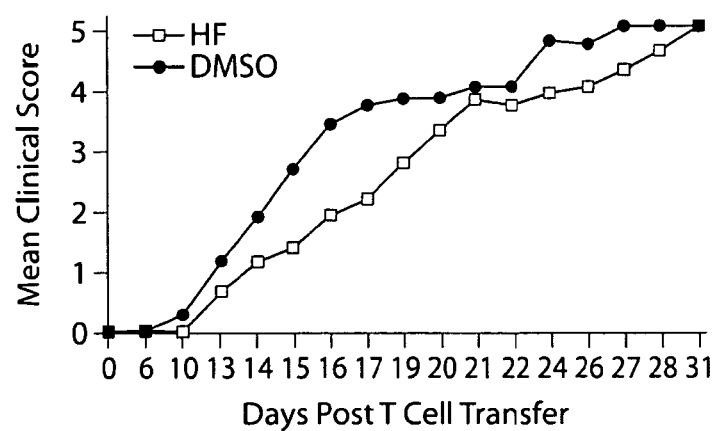

FIG. 18D is a graph depicting the effect of HF in a passive EAE model. Following the transfer of PLP-specific T cells, recipient mice were treated daily either with 2 mg HF (n=6) or vehicle control (n=5) and disease was monitored daily. Data are shown as mean EAE scores.

Figure 18E:
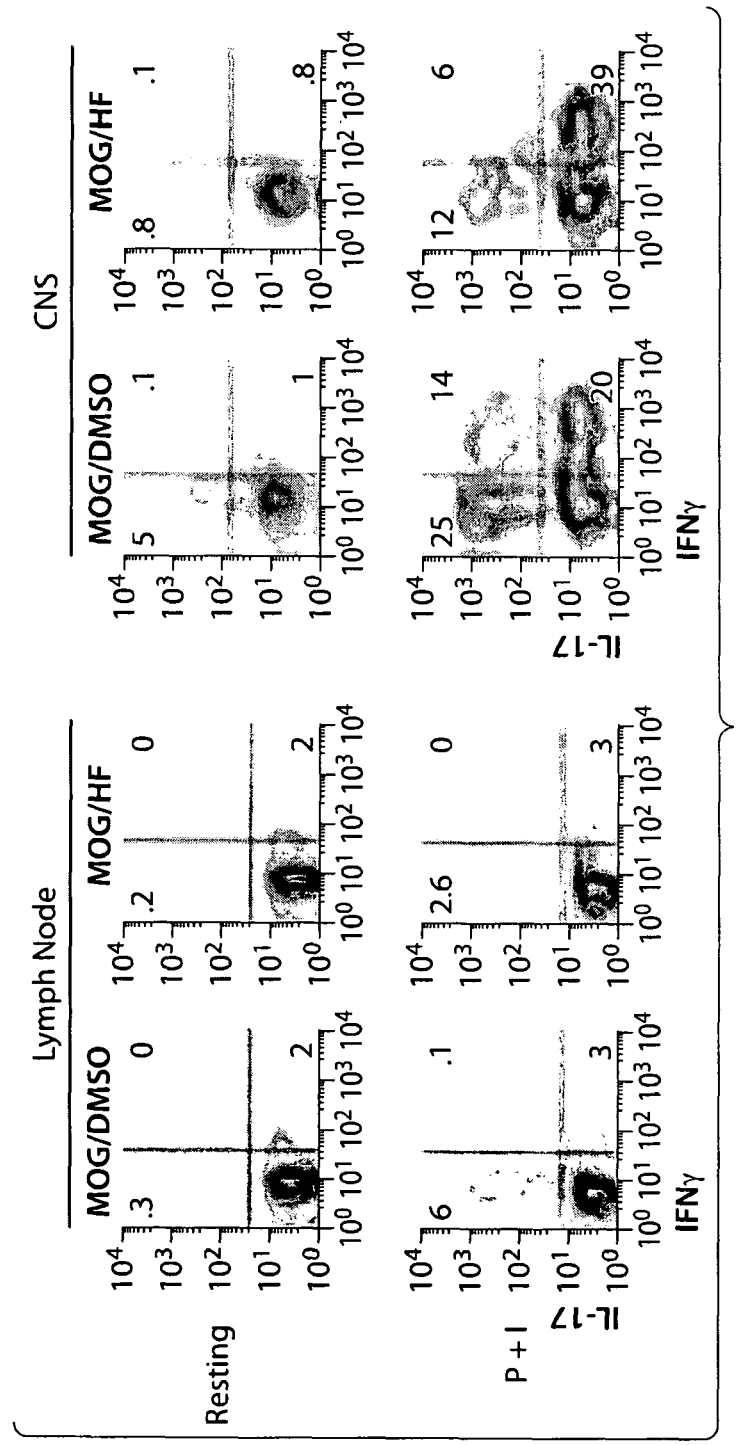

FIG. 18E is a set of FACS analyses of cells from lymph node or CNS of HF treated animals or control animals in an adjuvant-driven EAE model. For FIG. 18E, left panels, paraaortic lymph nodes were harvested from MOG-immunized mice treated with DMSO or HF after 6 days. Cells were cultured in the absence (resting—top panels) or presence (P+I—bottom panels) of PMA and ionomycin and stained for intracellular cytokine expression. For FIG. 18E, right panels, mononuclear cells were isolated from CNS tissue of DMSO-treated (clinical score=2) or HF-treated (clinical score=0) mice 17 days after immunization with MOG. Intracellular staining was performed on cells following PMA and ionomycin stimulation as above. Cytokine production is shown in TCRβ+ CD4+ gated cells and the percentages of IL-17-expressing cells are indicated.

Figure 18F:
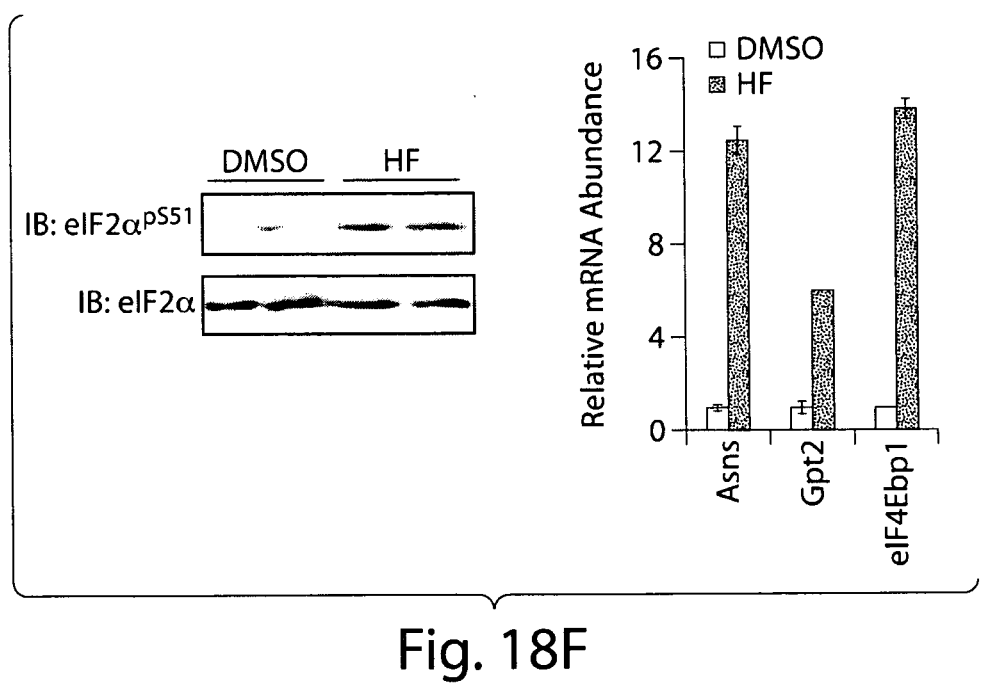

FIG. 18F, left panel, depicts western blot analysis of protein from cells of wild-type mice injected i.p. with vehicle (DMSO) or 2.5 mg HF. Spleens were harvested 6 hours post injection, red blood cells were removed by NH$_4$Cl lysis buffer and immunoblotting for phosphorylated or total eIF2a was performed on whole cell extracts. FIG. 20F, right panel is a graph depicting levels of AAR-associated gene expression (Asns, Gpt2, eIF4Ebp1) analyzed by quantitative real-time PCR using cDNA from splenocytes of mice treated with DMSO or HF as above. Expression of AAR-associated transcripts were normalized to Hprt levels and data are presented as mean relative expression from duplicate samples±SD. All data represent 2-3 similar experiments.

Figure 19A:
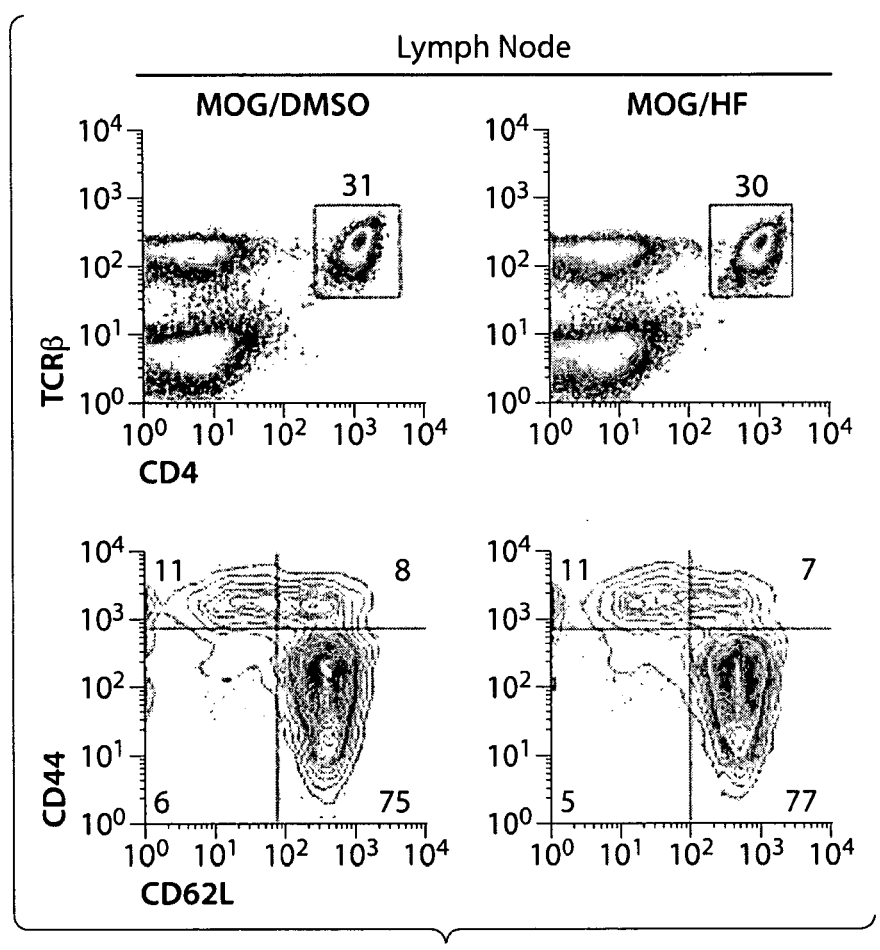
Figure 19B:
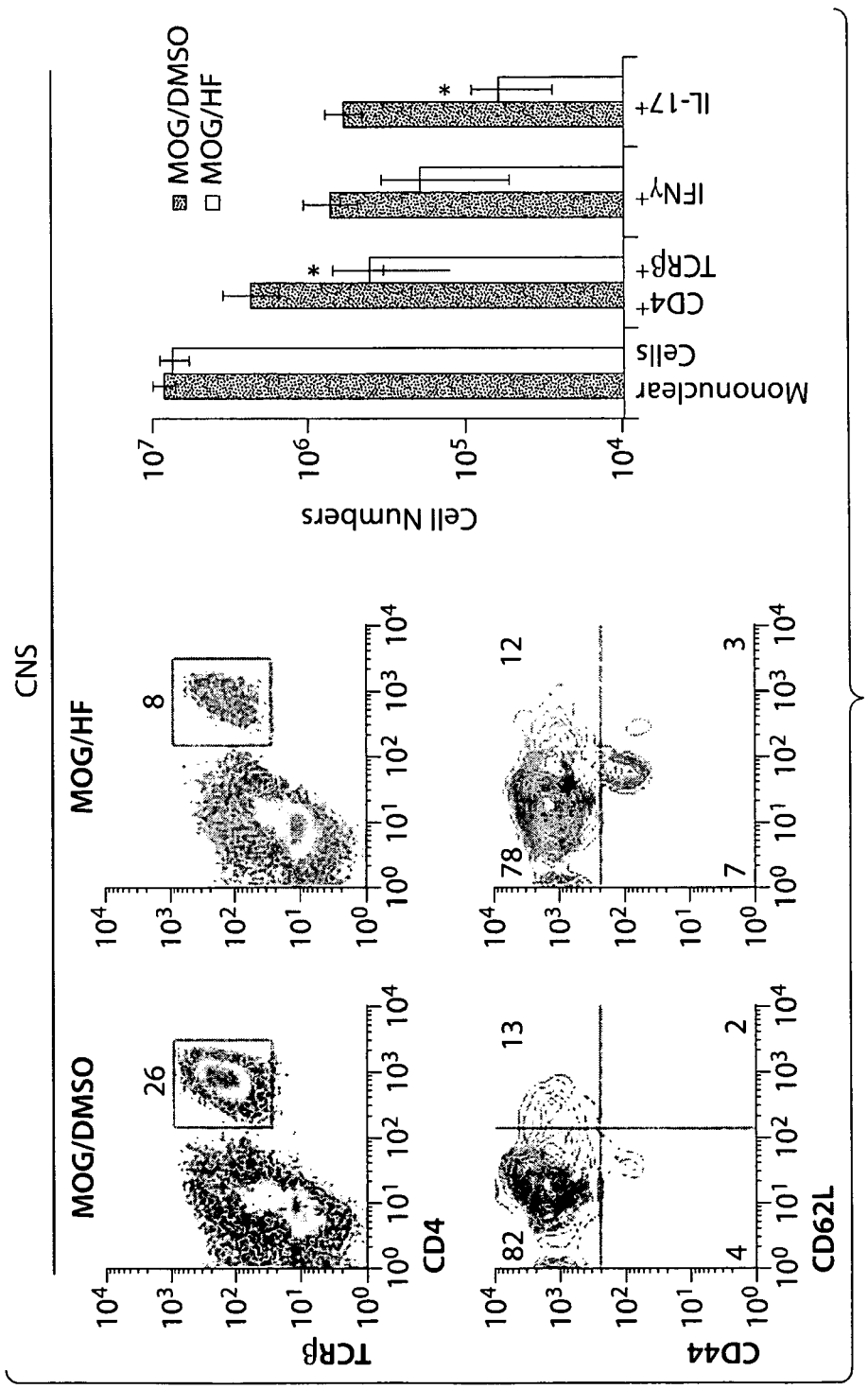

FIG. 19. Regulation of T cell differentiation by halofuginone during adjuvant-driven EAE. FIG. 19A is a set of FACS analyses of T cells from paraaortic lymph nodes (day 6). FIG. 19B, left panel, is a set of FACS analyses of T cells from CNS tissue (day 18). T cells analyzed in FIGS. 21A and 21B were from control- or HF-treated mice analyzed for CD44 and CD62L expression following induction of EAE. CD44 and CD62L expression in shown on cells gated for CD4 and TCRβ expression as shown. FIG. 21B, right panel, is a graph depicting cell numbers of CNS infiltrates in DMSO-treated mice (clinical score=2) or HF-treated mice (clinical score=0), which were determined during active EAE disease (day 18). Total mononuclear cells, CD4$^+$ TCRβ$^+$ T cells, Th1 cells (IFNγ$^+$) or Th17 cells (IL-17$^+$) present within CNS preparations were quantified following FACS analyses and are displayed as mean numbers±SD. Asterisks indicate statistical significance. These data are representative of at least 2 independent experiments analyzing at least 3 mice per group.

Figure 20:
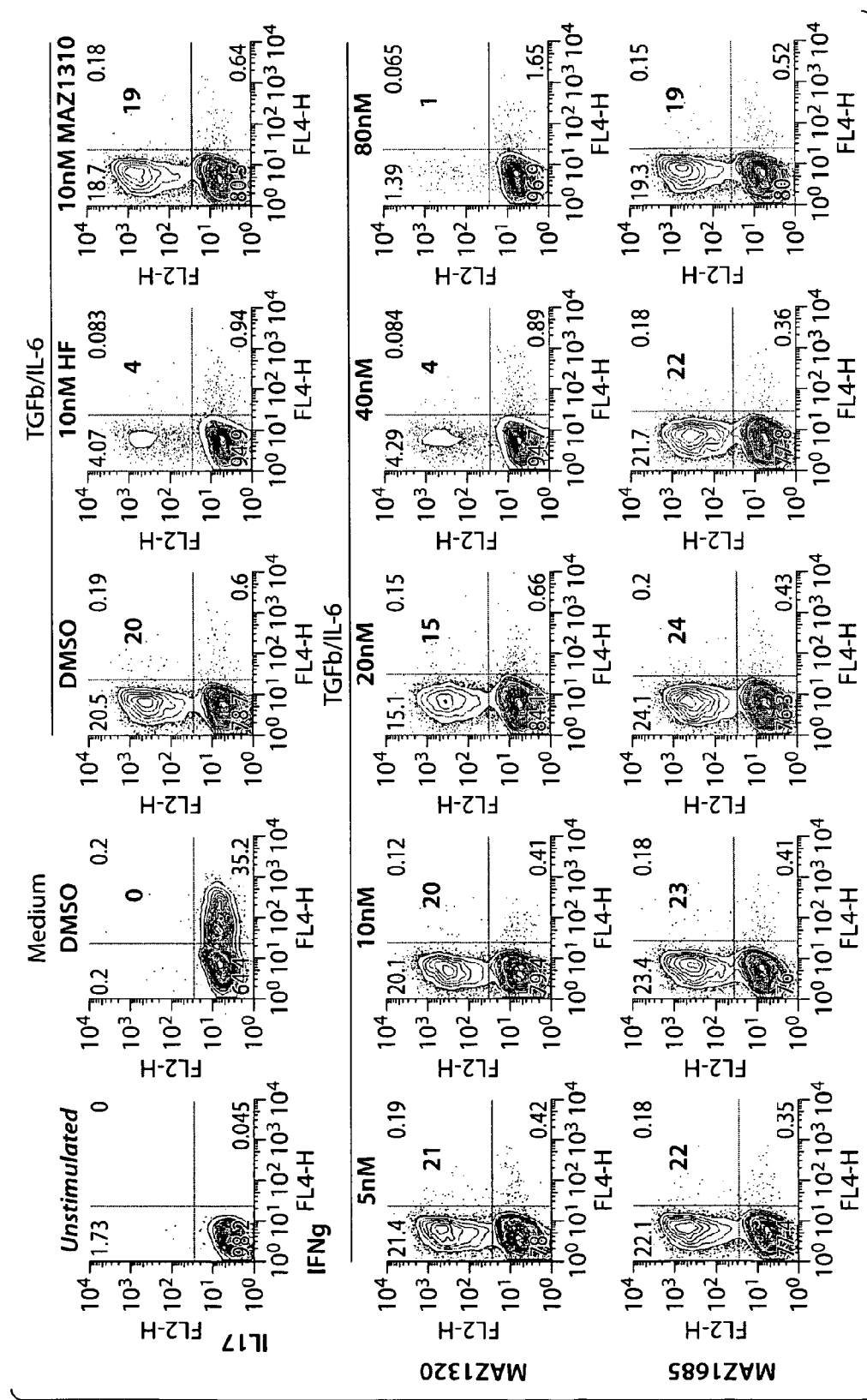
Figure 20:
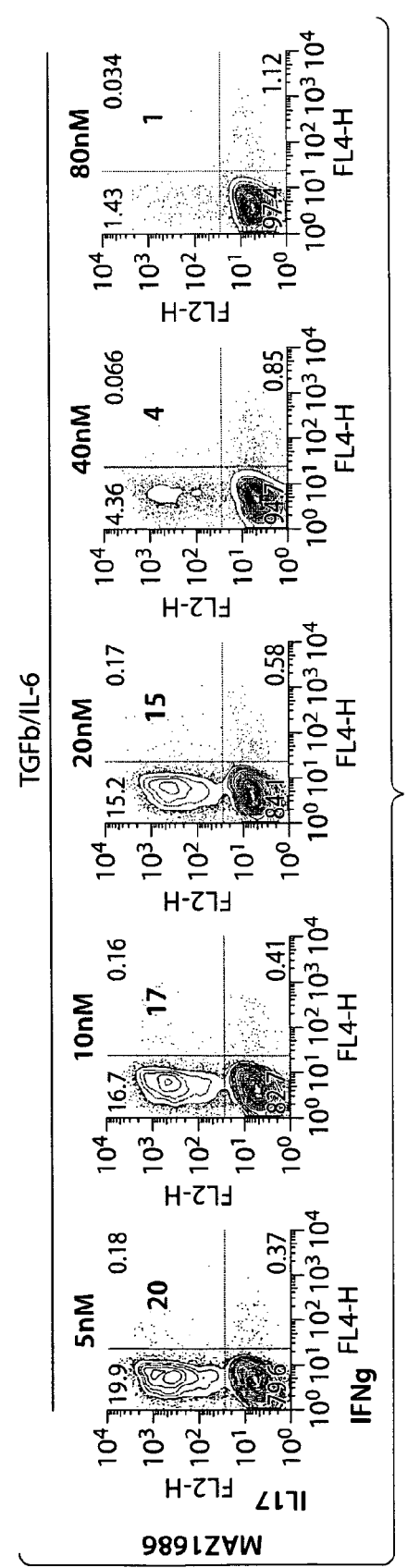

FIG. 20. Novel derivatives of HF selectively inhibit Th17 differentiation. Two novel active derivatives of HF (MAZ1320 and MAZ1686) selectively inhibit differentiation of Th17 cells without inhibiting Th1 differentiation.

Figure 21:
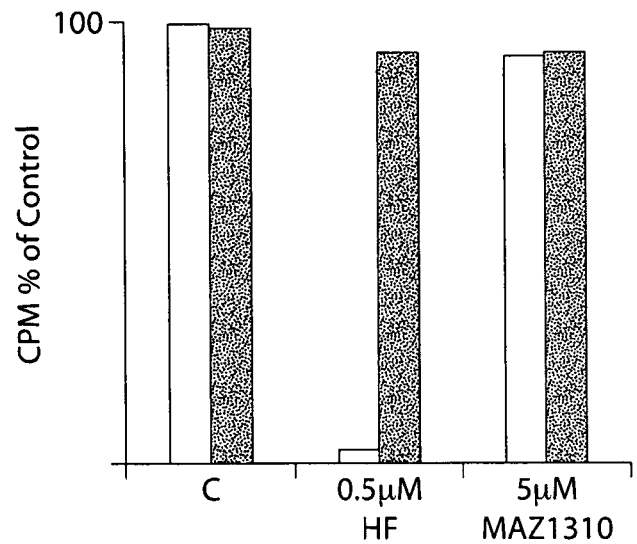

FIG. 21. HF inhibits the incorporation of $^{14}$C proline but not $^{35}$S methionine into tRNA. This figure establishes the specificity of HF as an inhibitor of prolyl-tRNA synthetase (EPRS) but not a different tRNA synthetase (methionyl tRNA synthetase) in a crude in vitro translation system.

Figure 22:
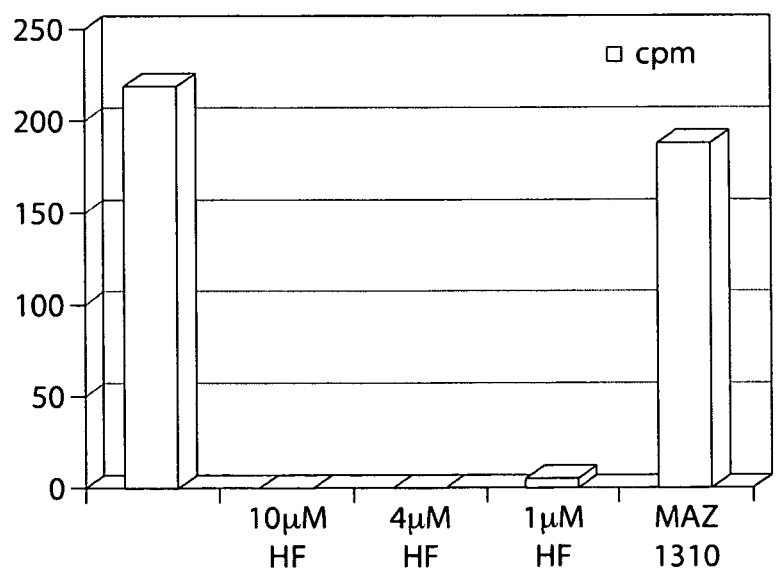

FIG. 22. HF inhibits purified EPRS. These data establish that HF directly inhibits purified mammalian EPRS.

Figure 23:
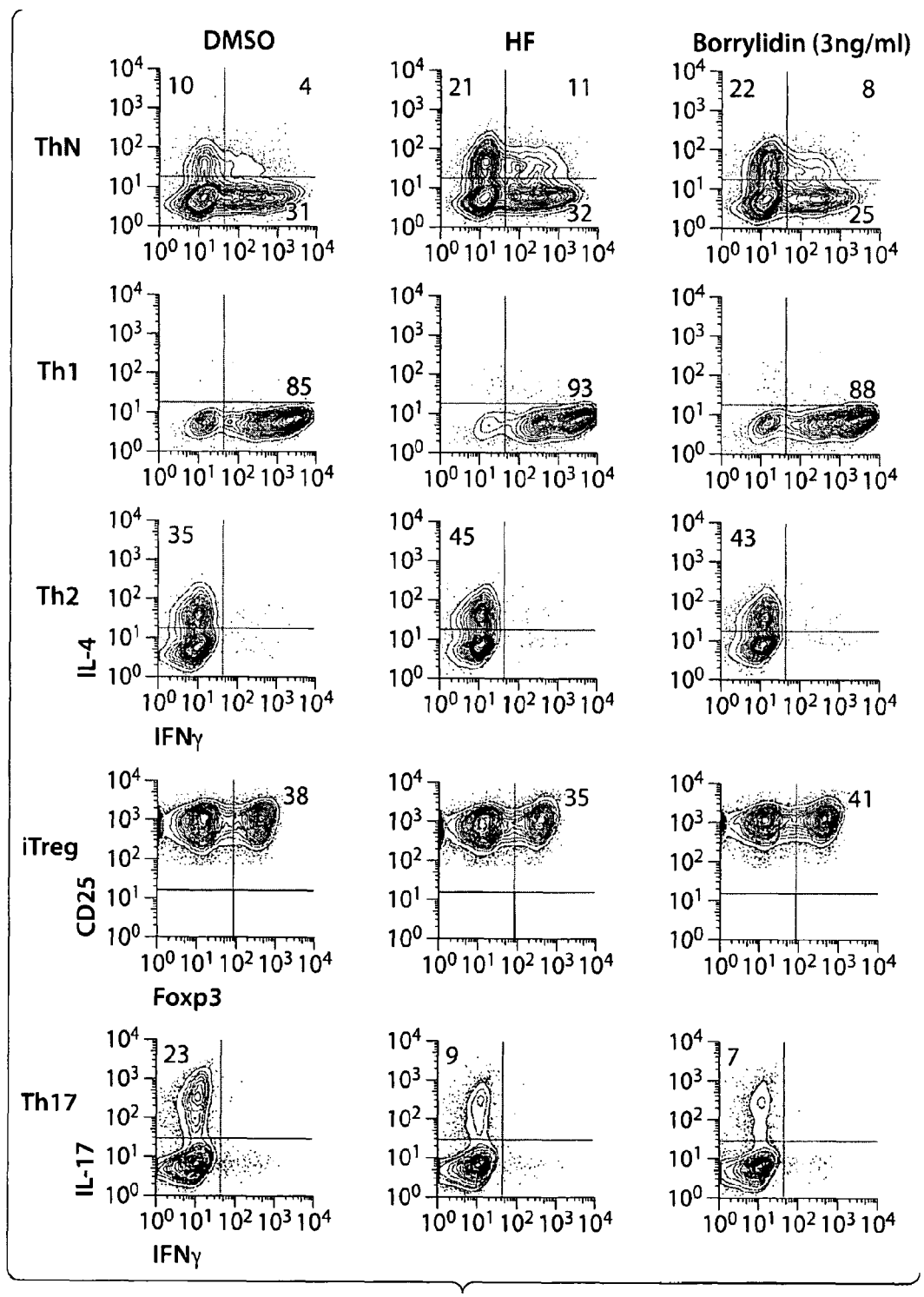

FIG. 23. A tRNA synthetase inhibitor structurally unrelated to HF selectively inhibits Th17 differentiation. Borrelidin, a threonyl tRNA synthetase inhibitor structurally unrelated to HF was tested for its ability to alter T-cell differentiation. Borrelidin inhibits Th17 differentiation without affecting Th1, Th2, or Treg differentiation or cell number, a selectivity identical to that of HF. tRNA synthetase inhibition therefore provides a general approach to the selective inhibition of Th17 differentiation without generalized immunosuppression.

Figure 24:
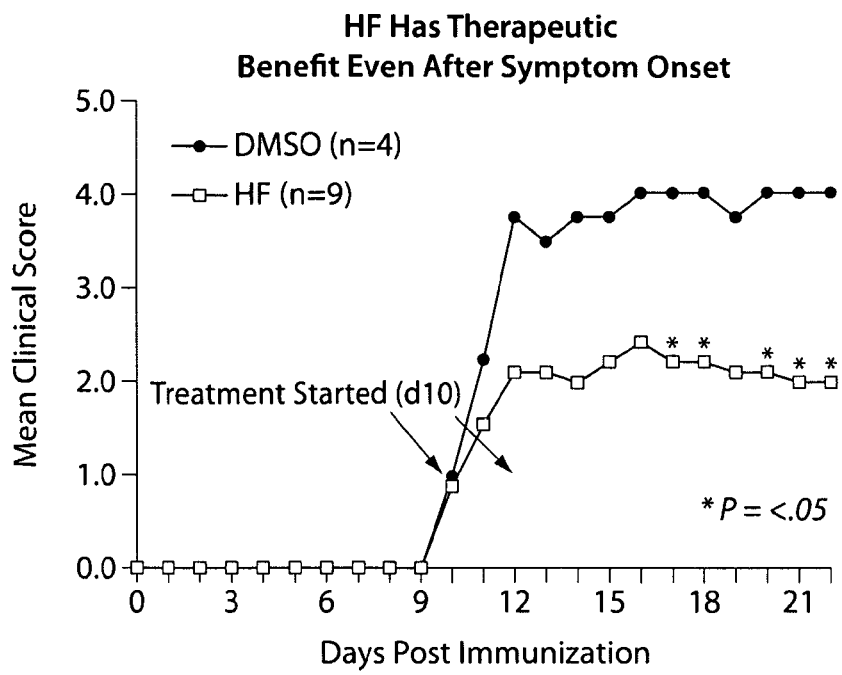

FIG. 24. HF Has Therapeutic Benefit Even After Symptom Onset. HF was injected into mice immunized to produce experimental autoimmune encephalomyelitis (EAE) as described in FIG. 18, with the exception that HF was not introduced into the animals until day 10 following immunization. These data demonstrate that HF controls autoimmune inflammation even after inflammatory pathogenesis is evident, providing a more accurate representation of autoimmune disease in humans.

Figure 25:
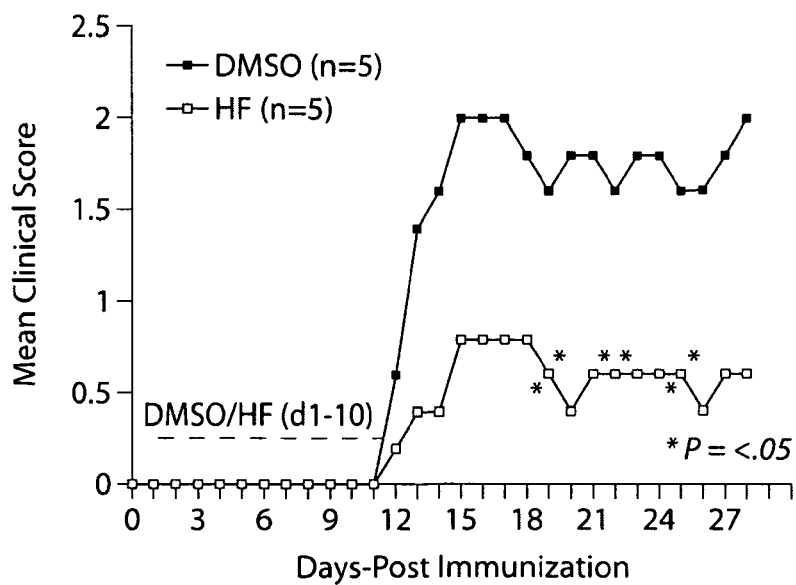

FIG. 25. Transient treatment with HF prevents the development of EAE symptoms. HF was injected into mice immunized to produce EAE as described in FIG. 18, with the exception that HF injection was terminated at day 10 following immunization. These data demonstrate that HF exerts a protective effect that extends well beyond the time of treatment, consistent with its proposed role in preventing the differentiation of pro-inflammatory Th17 cells.

DETAILED DESCRIPTION OF CERTAIN EMBODIMENTS OF THE INVENTION

The present invention provides novel analogs of halofuginone. In some embodiments, the inventive compounds include a quinazolinone moiety connected via a linker to a piperidine, pyrrolidine, or other heterocycle as shown herein. The compounds of the present invention are useful in the treatment of disorders associated with glutamyl-prolyl tRNA synthetase (EPRS) inhibition, Th17 differentiation, and amino acid starvation response (AAR) induction, such as chronic inflammation, fibrosis, autoimmune diseases, scarring, angiogenesis, transplant, implant, or device rejection, ischemic damage, viral infections, and neurodegenerative disorders. The compounds may also be used in treating protozoal infections by inhibiting the prolyl tRNA synthetase of protozoa. The present invention also provides pharmaceutical compositions and methods of using the inventive compounds for the treatment of various diseases (e.g., neurodegenerative diseases), as well as methods for synthesizing halofuginone analogs.

Compounds

Compounds of the present invention include quinazolinones, quinolinones, and analogs and derivatives of halofuginone. Particularly useful compounds of the present invention include those with biological activity. The inventive compounds have been found to have a variety of biological activities. In some embodiments, the compounds of the invention inhibit tRNA synthetase. In particular, the compounds of the invention inhibit glutamyl-prolyl tRNA synthetase (EPRS) (e.g., mammalian EPRS, human EPRS). In certain embodiments, the compounds of the invention inhibit non-metazoan prolyl tRNA synthetase (e.g., protozoal prolyl tRNA synthease). In certain embodiments, the compounds of the invention suppress the differentiation of a subset of effector T-cells (i.e., Th17 cells). In certain embodiments, the compounds of the invention suppress IL-17 production. In certain embodiments, the compounds of the invention activate the amino acid starvation response (AAR). In some embodiments, the compounds of the inventions are useful in the treatment of a disease associated with IL-17 production, such as arthritis, inflammatory bowel disease, psoriasis, multiple sclerosis, lupus, asthma, dry eye syndrome, and other autoimmune and/or inflammatory diseases. In certain other embodiments, the compounds of the invention suppress pro-fibrotic gene expression; therefore, they are useful in treating or preventing fibrosis. In some embodiments, the compounds inhibit viral gene expression, replication, and maturation. In other embodiments, the compounds protect organs from stress. In certain embodiments, the compounds suppress the synthesis of toxic proteins such as polyglutamine-containing proteins that cause neurodegenerative diseases such as Huntington's disease. In some embodiments, the compounds promote autophagy. In certain embodiments, the compounds inhibit the synthesis of proline-rich proteins such as collagen. In certain other embodiments, the compounds inhibit angiogenesis. In certain embodiments, the compounds are used to treat protozoal infections. In certain embodiments, the compound have an IC$_{50}$ of less than approximately 10 µM, e.g., less than approximately 1 µM, e.g., less than approximately 0.1 µM, or e.g., less than approximately 0.01 µM. The inventive compounds are useful in the treatment of a variety of diseases. Certain compounds of the invention are useful in treating inflammatory diseases or autoimmune diseases, such as inflammatory bowel disease, multiple sclerosis, rheumatoid arthritis, lupus, psoriasis, scleroderma, or dry eye syndrome. In certain embodiments, the compounds are useful in the treatment of cardiovascular diseases, diseases involving angiogenesis, neurodegenerative diseases, or protein aggregation disorders. Certain compounds of the invention are also useful as anti-scarring agents. In some embodiments, inventive compounds are useful in treating viral infections. In other embodiments, the compounds are useful in the treatment or prevention of restenosis. In certain embodiments, an inventive compound is less toxic than halofuginone, febrifuginone, or other related natural products. In certain other embodiments, an inventive compound is more potent than halofuginone, febrifuginone, or other related natural products.

It will be noted that structures of some of the compounds of the invention include asymmetric centers. It is to be understood accordingly that the isomers arising from such asymmetry are included within the scope of the invention, unless indicated otherwise. Such isomers can be obtained in substantially pure form by purification techniques and/or by stereochemically controlled synthesis. The compounds of this invention may exist in stereoisomeric form, and therefore can be produced as individual stereoisomers or as mixtures thereof.

In certain embodiments, the invention provides a compound of formula (I) or a pharmaceutically acceptable salt thereof:

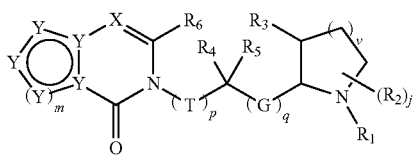

(I)

wherein
  j is an integer between 0 and 10, inclusive;
  p is an integer between 0 and 6, inclusive;
  q is an integer between 0 and 6, inclusive;
  m is 1 or 2;
  v is an integer between 1 and 3, inclusive;
  X is N or $CR_X$, wherein $R_X$ is hydrogen; halogen; substituted or unsubstituted aliphatic; substituted or unsubstituted heteroaliphatic; substituted or unsubstituted aryl; substituted or unsubstituted heteroaryl; —$OR_F$; —$SR_F$; —$N(R_F)_2$; and —$C(R_F)_3$; wherein each occurrence of $R_F$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  each occurrence of Y is independently S, O, N, $NR_Y$, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  each occurrence of T and G is independently —S—, —O—, —$NR_E$—, or $C(R_E)_2$—, wherein each occurrence of $R_E$ is independently hydrogen; halogen; substituted or unsubstituted aliphatic; substituted or unsubstituted heteroaliphatic; substituted or unsubstituted aryl; substituted or unsubstituted heteroaryl; —$OR_G$; —$SR_G$; —$N(R_G)_2$; and —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  $R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  $R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
  $R_4$ and $R_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —$C(=O)N(R_D)_2$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; or $R_4$ and $R_5$ may optionally be taken together to form =O, =S, =$NR_D$, =N—$OR_D$, =N—$NHR_D$, =N—$N(R_D)_2$, =$C(R_D)_2$; or $R_4$ and $R_5$ may optionally be taken together with the intervening atom to form a saturated or unsaturated, substituted or unsubstituted cyclic or heterocyclic structure; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In some embodiments, when T and G are each —$CH_2$—, p and q are each 1, X is N, and v is 2, $R_4$ and $R_5$ are not taken together to form =O or =N—$NHR_D$.

In some embodiments, when T and G are each —$CH_2$—, p and q are each 1, X is N, m is 2, and v is 1, $R_4$ and $R_5$ are not —OH and —H, and $R_4$ and $R_5$ are not taken together to form =O.

In certain embodiments, the compound is of the stereochemistry of formula (Ia):

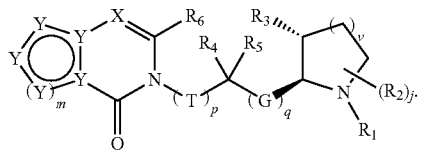

(Ia)

In certain embodiments, the compound is of the stereochemistry of formula (Ib):

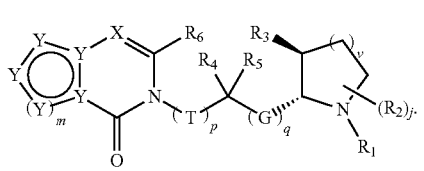

(Ib)

In certain embodiments, the compound is of one of the formulae:

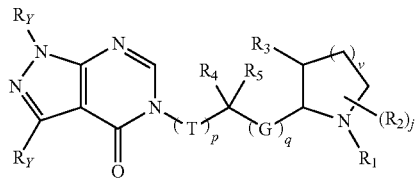

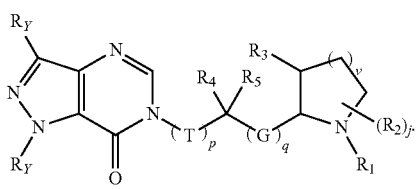

In certain embodiments, the compound is of one of the formulae:

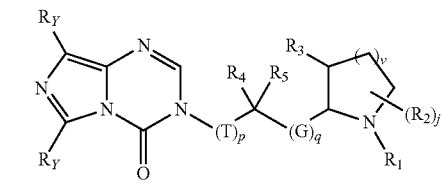

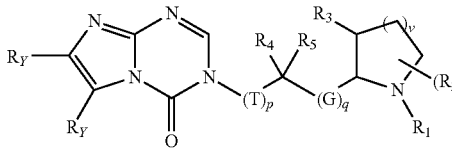

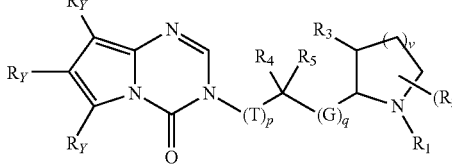

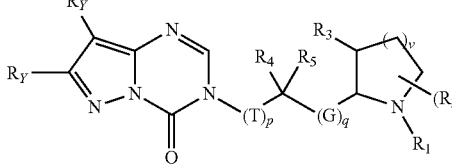

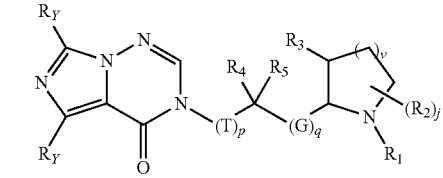

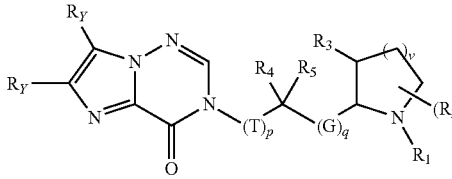

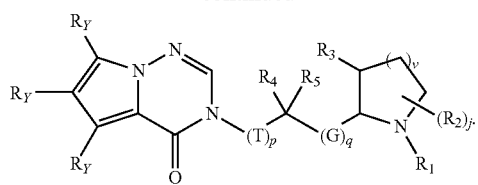

In certain embodiments, the compound is of one of the formulae:

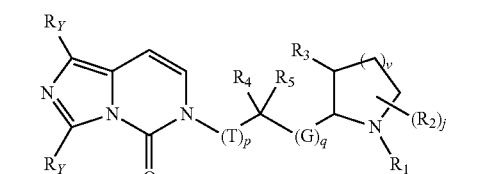

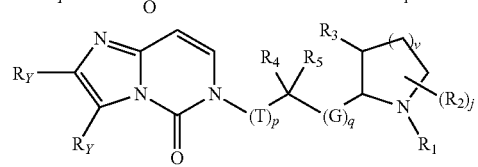

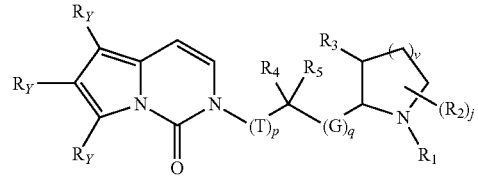

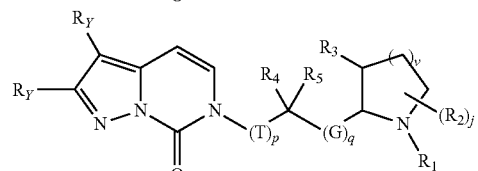

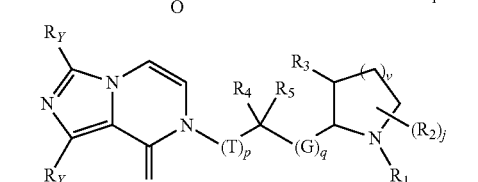

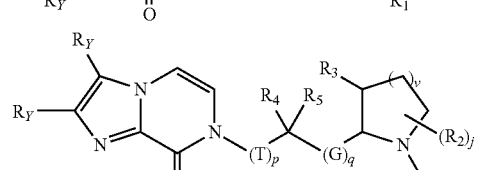

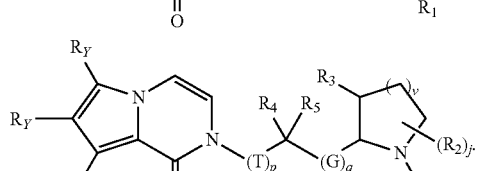

In certain embodiments, the compound is of one of the formulae:

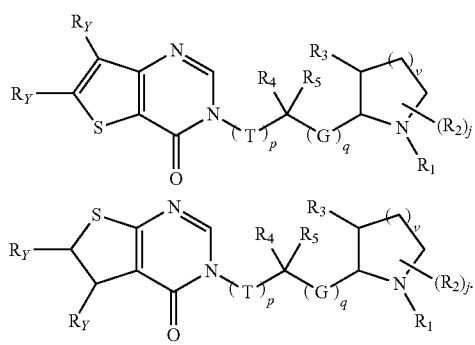

In certain embodiments, the compound is of one of the formulae:

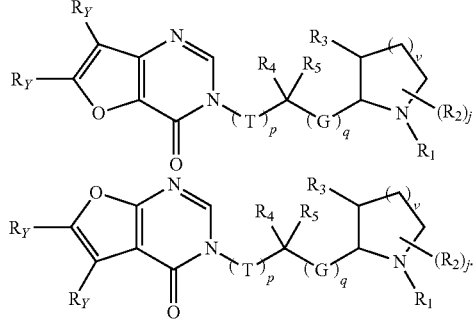

In certain embodiments, the compound is of one of the formulae:

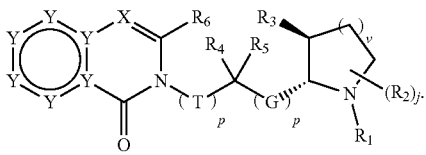

In certain embodiments, the compound is of one of the formulae:

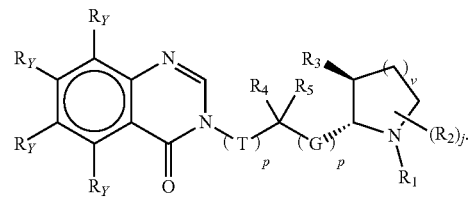

In certain embodiments, the compound is of one of the formulae:

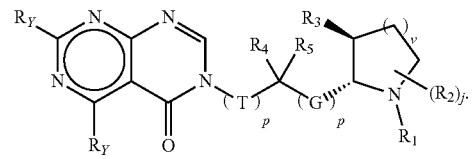

In certain embodiments, the compound is of one of the formulae:

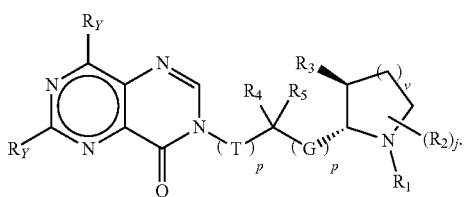

In certain embodiments, $R_1$ of formula I, Ia, or Ib is hydrogen. In some embodiments, $R_1$ of formula I, Ia, or Ib is $C_{1-6}$ alkyl. In certain other embodiments, $R_1$ of formula I, Ia, or Ib is a suitable amino protecting group, as defined herein.

In some embodiments, $R_2$ of formula I, Ia, or Ib is hydrogen. In certain embodiments, all instances of $R_2$ of formula I, Ia, or Ib are hydrogen. In other embodiments, $R_2$ of formula I, Ia, or Ib is a halogen. In certain embodiments, $R_2$ of formula I, Ia, or Ib is chloro, bromo, or iodo. In certain embodiments, $R_2$ of formula I, Ia, or Ib is a hydroxyl or alkoxyl group. In some embodiments, $R_2$ of formula I, Ia, or Ib is a substituted or unsubstituted aliphatic group. In certain embodiments, $R_2$ of formula I, Ia, or Ib is a substituted or unsubstituted aryl group. In certain embodiments, $R_2$ of formula I, Ia, or Ib is an amino group. In certain other embodiments, $R_2$ of formula I, Ia, or Ib is a cyano group. In some embodiments, $R_2$ of formula I, Ia, or Ib is a carboxylic acid or ester group.

In certain embodiments, $R_3$ of formula I, Ia, or Ib is hydrogen. In certain other embodiments, $R_3$ of formula I, Ia, or Ib is hydroxyl. In certain embodiments, $R_3$ of formulae I, Ia, or Ib is alkoxy. In certain embodiments, $R_3$ of formula I, Ia, or Ib is a protected hydroxyl group. In certain embodiments, $R_3$ of formula I, Ia, or Ib is phosphate. In certain embodiments, $R_3$ of formula I, Ia, or Ib is sulfate. In certain other embodiments, $R_3$ of formula I, Ia, or Ib is acetate (—OAc). In some embodiments, $R_3$ of formula I, Ia, or Ib is a thioxy group. In some embodiments, $R_3$ of formula I, Ia, or Ib is an amino group. In some embodiments, $R_3$ of formula I, Ia, or Ib is a protected amino group.

In certain embodiments, $R_4$ of formula I, Ia, or Ib is hydrogen. In certain other embodiments, $R_4$ of formula I, Ia, or Ib is hydroxyl. In certain embodiments, $R_4$ of formula I, Ia, or Ib is alkoxy. In certain embodiments, $R_4$ of formula I, Ia, or Ib is a protected hydroxyl group. In certain embodiments, $R_4$ of formula I, Ia, or Ib is a substituted or unsubstituted aliphatic or heteroaliphatic group. In some embodiments, $R_4$ of formula I, Ia, or Ib is an amino group. In some embodiments, $R_4$ of formula I, Ia, or Ib is a protected amino group.

In certain embodiments, $R_5$ of formula I, Ia, or Ib is hydrogen. In certain other embodiments, $R_5$ of formula I, Ia, or Ib is hydroxyl. In certain embodiments, $R_5$ of formula I, Ia, or Ib is alkoxy. In certain embodiments, $R_5$ of formulae I, Ia, or Ib is a protected hydroxyl group. In certain embodiments, $R_5$ of formula I, Ia, or Ib is a substituted or unsubstituted aliphatic or heteroaliphatic group. In some embodiments, $R_5$ of formula I, Ia, or Ib is an amino group. In some embodiments, $R_5$ of formula I, Ia, or Ib is a protected amino group.

In certain embodiments, $R_4$ and $R_5$ of formula I, Ia, or Ib are taken together to form =O. In some embodiments, $R_4$ and $R_5$ of formula I, Ia, or Ib are taken together to form =S. In other embodiments, $R_4$ and $R_5$ of formula I, Ia, or Ib are taken together to form =$NR_D$, and $R_D$ is as described herein. In certain embodiments, $R_4$ and $R_5$ of formula I, Ia, or Ib are taken together to form =N—$OR_D$. In certain other embodiments, $R_4$ and $R_5$ of formula I, Ia, or Ib are taken together to form =N—$NHR_D$. In certain other embodiments, $R_4$ and $R_5$ of formula I, Ia, or Ib are taken together to form =N—$N(R_D)_2$. In some embodiments, $R_4$ and $R_5$ of formula I, Ia, or Ib are taken together to form =$C(R_D)_2$. In certain embodiments, $R_4$ and $R_5$ of formula I, Ia, or Ib are taken together to form =$CH_2$.

In some embodiments, $R_4$ and $R_5$ of formula I, Ia, or Ib are taken together with the intervening carbon to form a ring. In some embodiments, the ring formed is an oxetane ring. In certain embodiments, the ring formed is an aziridine ring. In certain embodiments, the ring formed is an azetidine ring. In certain embodiments, the ring formed is an epoxide ring. In certain other embodiments, the ring formed is a cyclopropyl ring. In some embodiments, the ring formed is a cyclic acetal. In other embodiments, the ring formed is a 5-membered cyclic acetal. In yet other embodiments, the ring formed is a 6-membered cyclic acetal.

In certain embodiments, $R_6$ of formula I, Ia, or Ib is hydrogen. In certain other embodiments, $R_6$ of formula I, Ia, or Ib is aliphatic. In certain embodiments, $R_6$ of formula I, Ia, or Ib is alkyl.

In certain embodiments, j of formula I, Ia, or Ib is 0. In certain embodiments, j of formula I, Ia, or Ib is 1. In certain embodiments, j of formula I, Ia, or Ib is 2. In certain embodiments, j of formula I, Ia, or Ib is 3, 4, 5, 6, 7, 8, 9, or 10.

In some embodiments, m of formula I, Ia, or Ib is 1. In other embodiments, m of formula I, Ia, or Ib is 2.

In some embodiments, X of formula I, Ia, or Ib is N. In other embodiments, X of formula I, Ia, or Ib is $CR_x$, wherein $R_x$ is as defined herein. In certain embodiments, X of formula I, Ia, or Ib is CH.

In some embodiments, at least one instance of Y of formula I, Ia, or Ib is CH. In some embodiments, Y of formula I, Ia, or Ib is $CR_Y$, where $R_Y$ is as defined herein. In other embodiments, Y of formula I, Ia, or Ib is S. In certain embodiments, Y of formula I, Ia, or Ib is N. In certain other embodiments, Y is $NR_Y$. In other embodiments, Y of formula I, Ia, or Ib is O. In yet other embodiments, Y of formula I, Ia, or Ib is S. In some embodiments, all instances of Y of formula I, Ia, or Ib are $CR_Y$. In other embodiments, at least one instance of Y of formula I, Ia, or Ib is not $CR_Y$. In yet other embodiments, at least two instances of Y of formula I, Ia, or Ib are not $CR_Y$.

In some embodiments, $R_Y$ of formula I, Ia, or Ib is hydrogen. In other embodiments, $R_Y$ of formula I, Ia, or Ib is a halogen. In certain embodiments, $R_Y$ of formula I, Ia, or Ib is chloro, bromo, or iodo. In certain embodiments, $R_Y$ of formula I, Ia, or Ib is a hydroxyl or alkoxy group. In some embodiments, $R_Y$ of formula I, Ia, or Ib is a substituted or unsubstituted aliphatic group. In certain embodiments, $R_Y$ of formula I, Ia, or Ib is a substituted or unsubstituted alkyl group. In certain embodiments, $R_Y$ of formula I, Ia, or Ib is a substituted or unsubstituted aryl group. In certain embodiments, $R_Y$ of formula I, Ia, or Ib is a substituted or unsubstituted alkenyl group. In certain other embodiments, $R_Y$ of formula I, Ia, or Ib is a substituted or unsubstituted alkynyl group. In some embodiments, $R_Y$ of formula I, Ia, or Ib is an acyl group. In other embodiments, $R_Y$ of formula I, Ia, or Ib is an amino group. In certain embodiments, $R_Y$ of formula I, Ia, or Ib is a protected amino group.

In certain embodiments, Y of formula I, Ia, or Ib is $CR_Y$ and $R_Y$ is hydrogen. In certain embodiments, Y of formula I, Ia, or Ib is $CR_Y$ and $R_Y$ is bromo. In other embodiments, Y of formula I, Ia, or Ib is $CR_Y$ and $R_Y$ is chloro. In certain embodiments, Y of formula I, Ia, or Ib is $CR_Y$ and $R_Y$ is —CN. In certain embodiments, Y of formula I, Ia, or Ib is $CR_Y$ and $R_Y$ is alkyl. In certain embodiments, Y of formula I, Ia, or Ib is $CR_Y$ and $R_Y$ is alkenyl. In certain embodiments, Y of formula I, Ia, or Ib is $CR_Y$ and $R_Y$ is alkynyl. In certain embodiments, Y of formula I, Ia, or Ib is $CR_Y$ and $R_Y$ is aryl. In certain embodiments, Y of formula I, Ia, or Ib is $CR_Y$ and $R_Y$ is phenyl. In certain embodiments, Y of formula I, Ia, or Ib is $CR_Y$ and $R_Y$ is benzylic. In certain embodiments, Y of formula I, Ia, or Ib is $CR_Y$ and $R_Y$ is heteroaryl. In certain embodiments, Y of formula I, Ia, or Ib is $CR_Y$ and $R_Y$ is pyridinyl. In certain embodiments, Y of formula I, Ia, or Ib is $CR_Y$ and $R_Y$ is carbocyclic. In certain embodiments, Y of formula I, Ia, or Ib is $CR_Y$ and $R_Y$ is heterocyclic. In certain embodiments, Y of formula I, Ia, or Ib is $CR_Y$ and $R_Y$ is morpholinyl. In certain embodiments, Y of formula I, Ia, or Ib is $CR_Y$ and $R_Y$ is piperidinyl.

In certain embodiments, T of formula I, Ia, or Ib is —$C(R_E)_2$—, where $R_E$ is as defined herein. In certain other embodiments, T of formula I, Ia, or Ib is —$CH_2$—. In some embodiments, T of formula I, Ia, or Ib is —O—. In other embodiments, T of formula I, Ia, or Ib is —S—. In certain embodiments, T of formula I, Ia, or Ib is —$NR_E$—.

In certain embodiments, p of formula I, Ia, or Ib is 1. In some embodiments, p of formula I, Ia, or Ib is 2. In other embodiments, p of formula I, Ia, or Ib is 3, 4, 5, or 6.

In certain embodiments, G of formula I, Ia, or Ib is —$C(R_E)_2$—, where $R_E$ is as defined herein. In certain other embodiments, G of formula I, Ia, or Ib is —$CH_2$—. In some embodiments, G of formula I, Ia, or Ib is —O—. In other embodiments, G of formula I, Ia, or Ib is —S—. In certain embodiments, G of formula I, Ia, or Ib is —$NR_E$—.

In certain embodiments, q of formula I, Ia, or Ib is 1. In some embodiments, q of formula I, Ia, or Ib is 2. In other embodiments, q of formula I, Ia, or Ib is 3, 4, 5, or 6.

In certain embodiments, at least one of T and G of formula I, Ia, or Ib is —$CH_2$—. In other embodiments, both T and G of formula I, Ia, or Ib are —$CH_2$—. In certain other embodiments, only one of T and G of formula I, Ia, or Ib is —$CH_2$—. In certain embodiments, at least one of T and G of formula I, Ia, or Ib is —$NR_E$—. In certain embodiments, at least one of T and G of formula I, Ia, or Ib is —O—.

In certain embodiments, v of formula I, Ia, or Ib is 2 to form a piperidine ring. In certain embodiments, v of formula I, Ia, or Ib is 1 to form a pyrrolidine ring. In other embodiments, v of formula I, Ia, or Ib is 3 to form a homopiperidine ring.

In some embodiments, compounds of formula I, Ia, or Ib are of the following formulae:

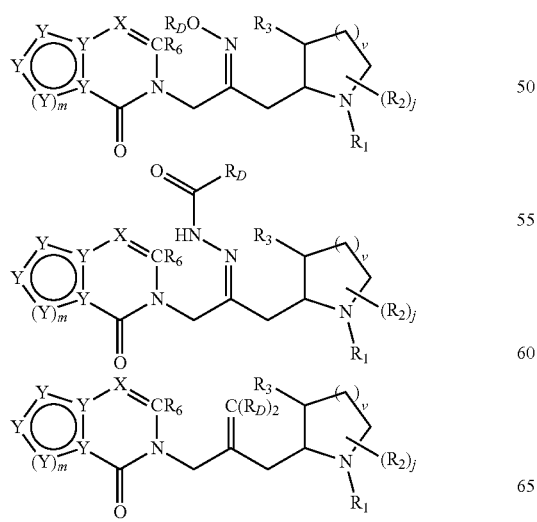

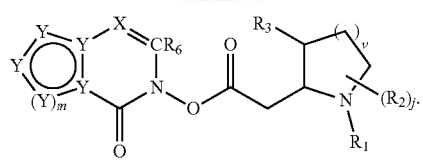
In some embodiments, compounds of formula I, Ia, or Ib are of the following formulae:
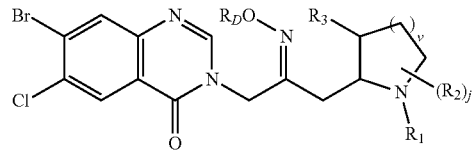
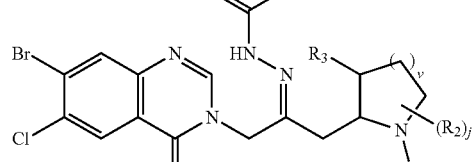
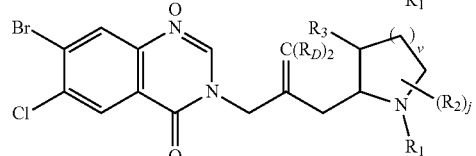
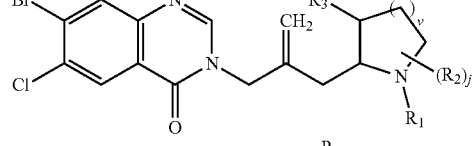
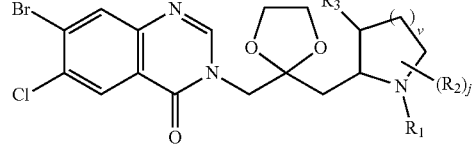
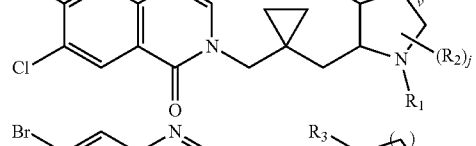
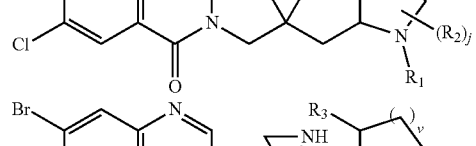
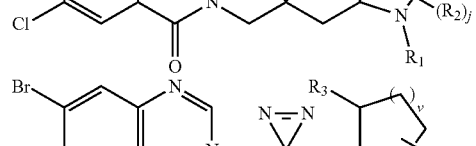
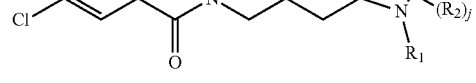
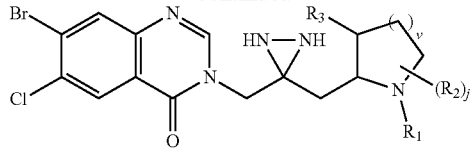
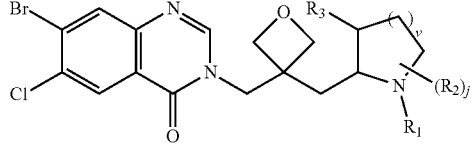
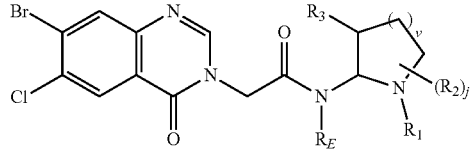
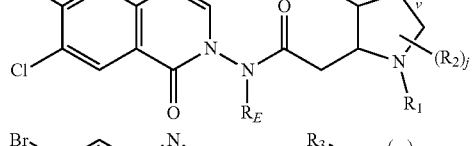
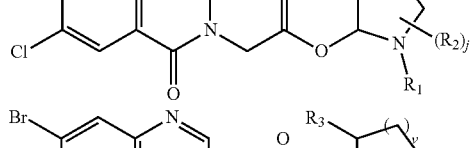
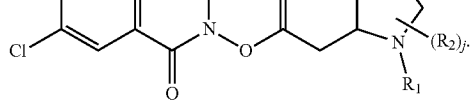
In some embodiments, compounds of formula I, Ia, or Ib are of the following formulae:
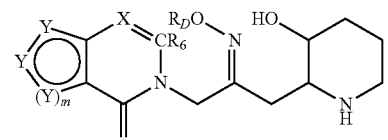
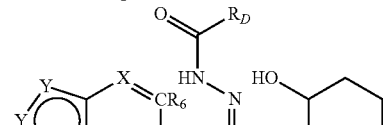
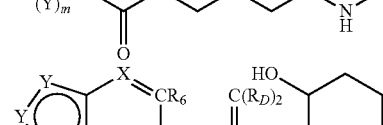
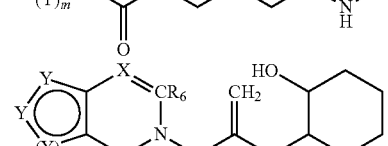

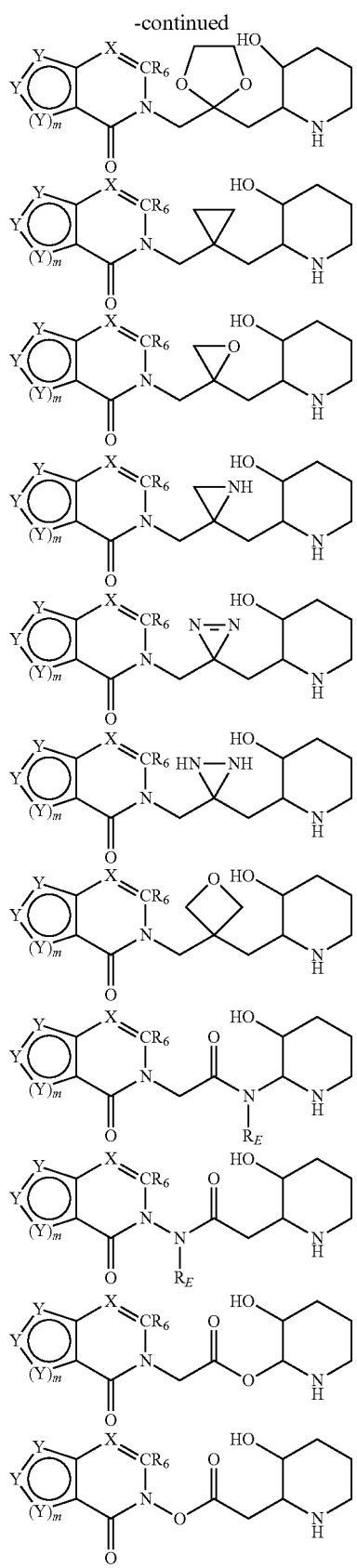
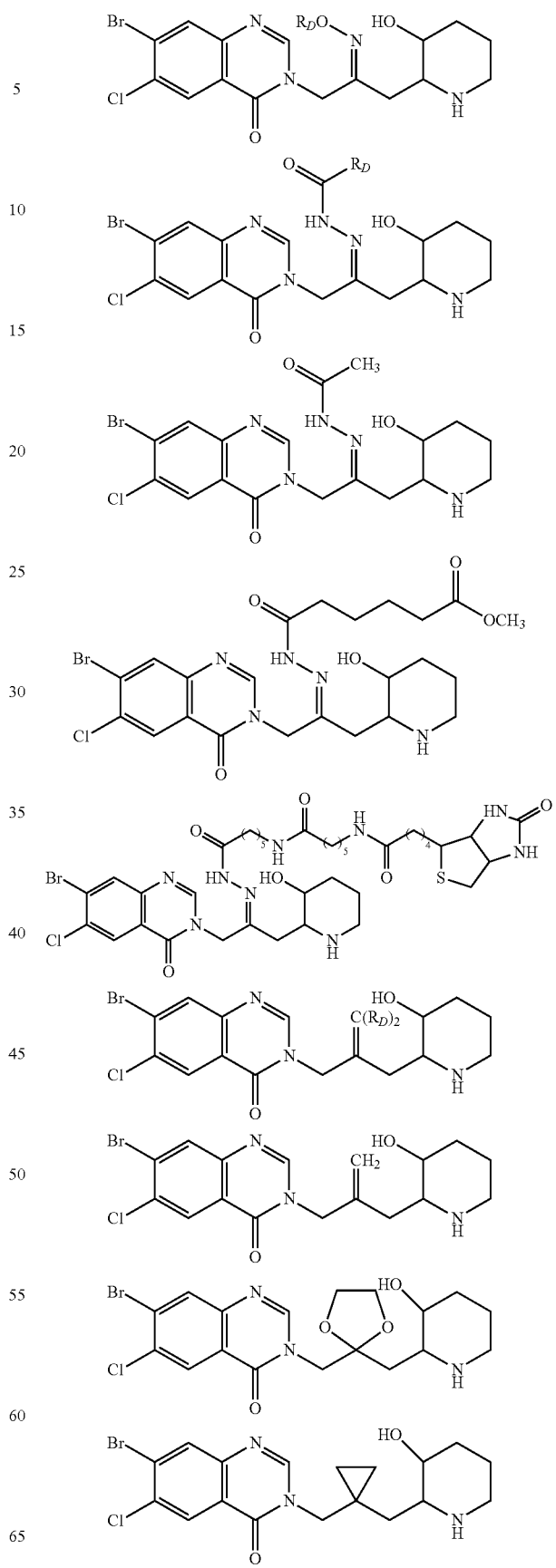
In certain embodiments, compounds of formula I, Ia, or Ib are of the following formulae:

-continued
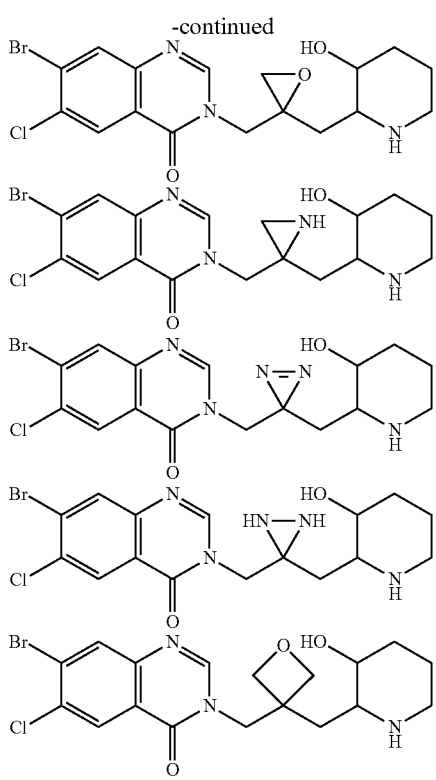
In certain embodiments, compounds of formula I or Ia are of the following formulae:
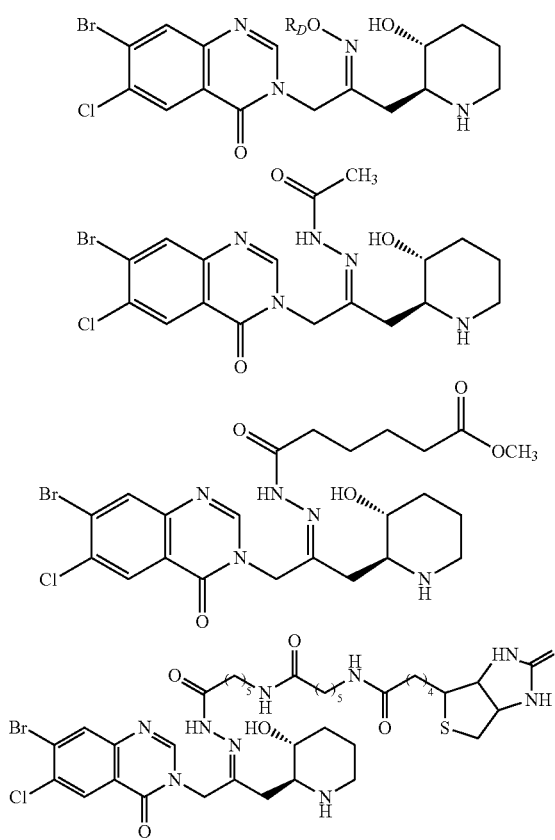
-continued
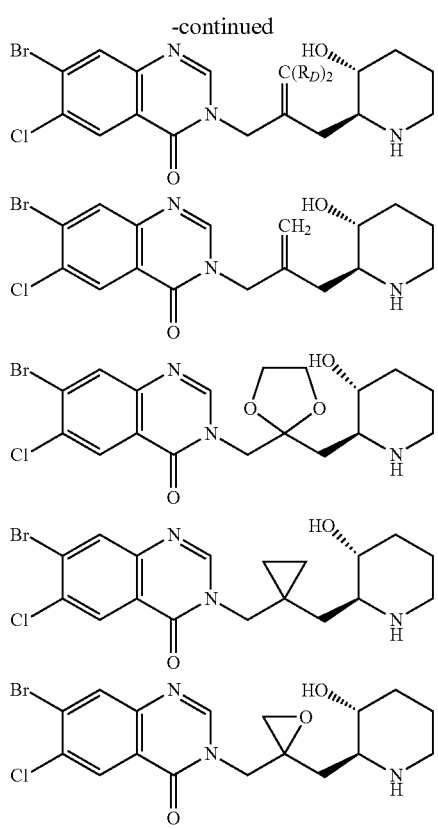
In certain embodiments, compounds of formula I or Ib are of the following formulae:
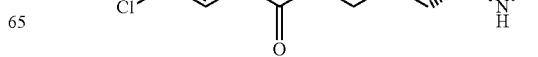

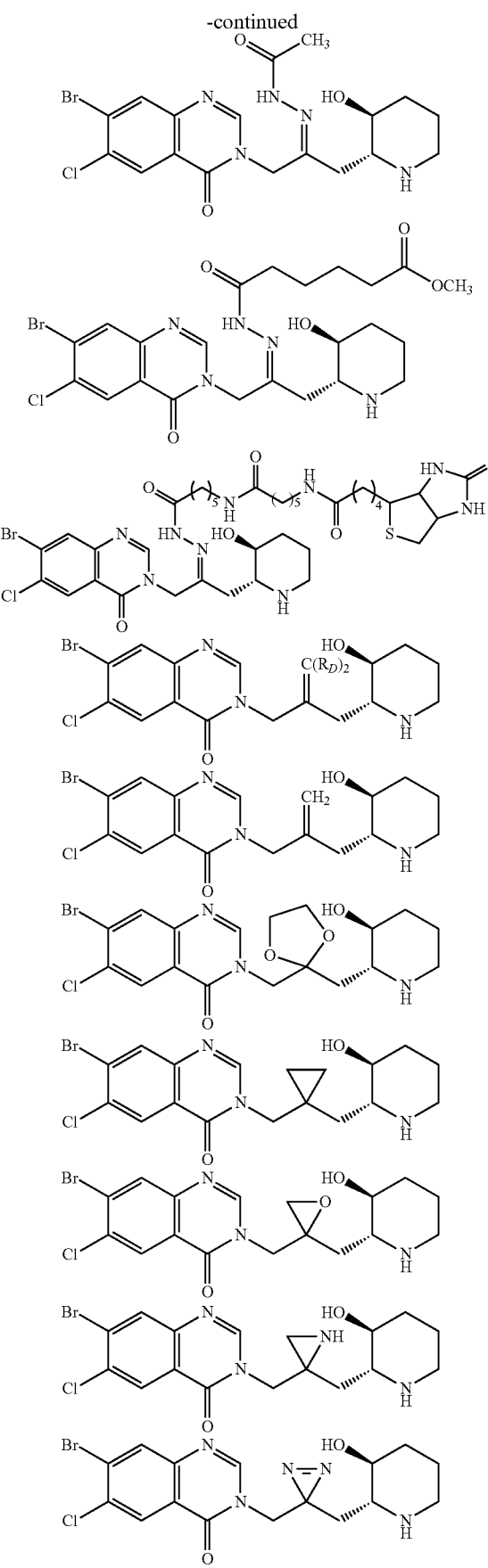

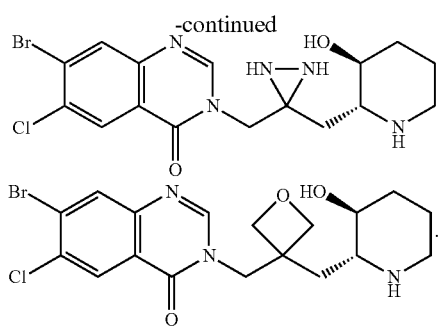

In certain embodiments, the invention provides a compound of formula (II) or a pharmaceutically acceptable salt thereof:

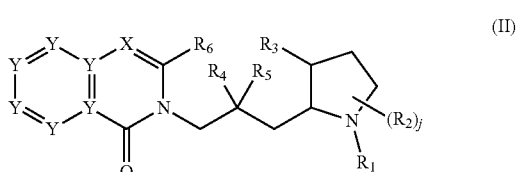

(II)

wherein j is an integer between 0 and 6, inclusive;

each occurrence of Y is independently S, O, N, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; provided that $R_1$ is not a tert-butoxycarbonyl group;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —C(=O)R$_B$; —CO$_2$R$_B$; —C(=O)N(R$_B$)$_2$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —C(=O)N(R$_C$)$_2$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino, alkylamino, dialkylamino, heteroaryloxy; or heteroarylthioxy moiety; provided that R$_3$ is not —OCH$_2$Ph;

R$_4$ and R$_5$ are independently hydrogen or —OH; or

R$_4$ and R$_5$ may be taken together to form =O; and

R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In some embodiments, R$_1$ of formula II is not a tert-butoxycarbonyl group.

In some embodiments, R$_3$ of formula II is not —OCH$_2$Ph.

In some embodiments, the compound of formula II is not of the formula:

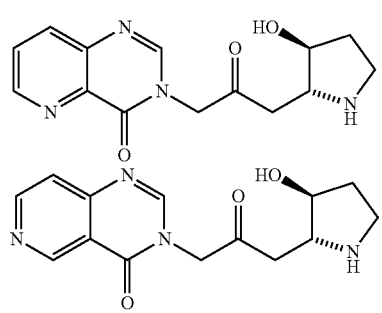

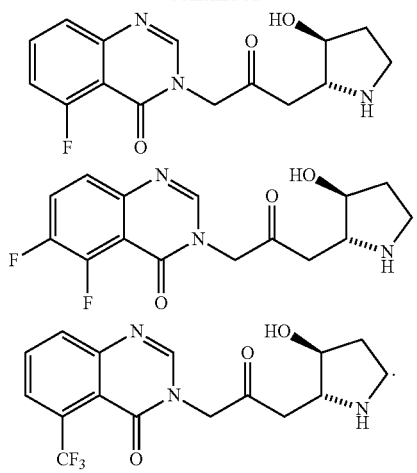

In certain embodiments, the compound has the stereochemistry shown in formula (IIa):

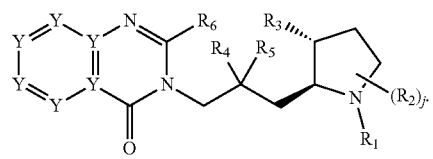

(IIa)

In certain embodiments, the compound has the stereochemistry shown in formula (IIb):

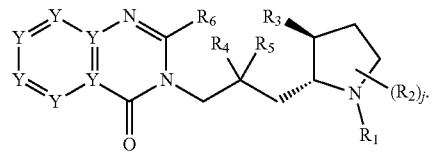

(IIb)

In certain embodiments, the compound of formula II is of the formula:

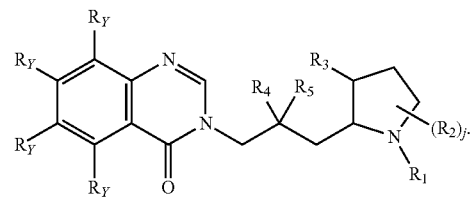

In certain embodiments, the compound of formula II is of the formula:

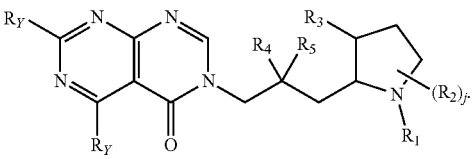

In certain embodiments, the compound of formula II is of the formula:

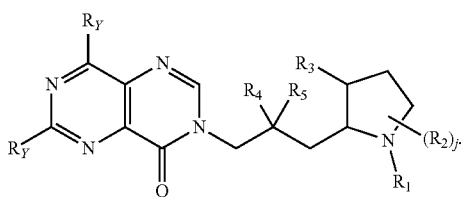

In certain embodiments, $R_1$ of formula II, IIa, or IIb is hydrogen. In certain other embodiments, $R_1$ of formula II, IIa, or IIb is a suitable amino protecting group, as defined herein.

In some embodiments, $R_2$ of formula II, IIa, or IIb is hydrogen. In other embodiments, $R_2$ of formula II, IIa, or IIb is a halogen. In certain embodiments, $R_2$ of formula II, IIa, or IIb is chloro, bromo, or iodo. In certain embodiments, $R_2$ of formula II, IIa, or IIb is a hydroxyl or alkoxyl group. In some embodiments, $R_2$ of formula II, IIa, or IIb is a substituted or unsubstituted aliphatic group. In certain embodiments, $R_2$ of formula II, IIa, or IIb is a substituted or unsubstituted aryl group. In certain embodiments, $R_2$ of formula II, IIa, or IIb is an amino group. In certain other embodiments, $R_2$ of formula II, IIa, or IIb is a cyano group. In some embodiments, $R_2$ of formula II, IIa, or IIb is a carboxylic acid or ester group.

In certain embodiments, $R_3$ of formula II, IIa, or IIb is hydrogen. In certain other embodiments, $R_3$ of formula II, IIa, or IIb is hydroxyl. In certain embodiments, $R_3$ of formula II, IIa, or IIb is alkoxy. In certain embodiments, $R_3$ of formula II, IIa, or IIb is a protected hydroxyl group. In certain embodiments, $R_3$ of formula II, IIa, or IIb is phosphate. In certain embodiments, $R_3$ of formula II, IIa, or IIb is sulfate. In certain other embodiments, $R_3$ of formula II, IIa, or IIb is acetate (—OAc). In some embodiments, $R_3$ of formula II, IIa, or IIb is a thioxy group. In some embodiments, $R_3$ of formula II, IIa, or IIb is an amino group. In some embodiments, $R_3$ of formula II, IIa, or IIb is a protected amino group.

In certain embodiments, $R_4$ of formula II, IIa, or IIb is hydrogen. In certain other embodiments, $R_4$ of formula II, IIa, or IIb is hydroxyl. In certain embodiments, $R_5$ of formula II, IIa, or IIb is hydrogen. In certain other embodiments, $R_5$ of formula II, IIa, or IIb is hydroxyl. In certain embodiments, $R_4$ and $R_5$ of formula II, IIa, or IIb are taken together to form =O.

In certain embodiments, $R_6$ of formula II, IIa, or IIb is hydrogen. In certain other embodiments, $R_6$ of formula II, IIa, or IIb is aliphatic. In certain embodiments, $R_6$ of formula II, IIa, or IIb is alkyl.

In certain embodiments, j of formula II, IIa, or IIb is 0. In certain embodiments, j is 1. In certain embodiments, j is 2. In certain embodiments, j is 3, 4, 5, or 6.

In some embodiments, at least one instance of Y of formula II, IIa, or IIb is CH. In some embodiments, Y of formula II, IIa, or IIb is $CR_Y$, where $R_Y$ is as defined herein. In other embodiments, Y is S. In certain embodiments, Y is N. In certain other embodiments, Y is $NR_Y$. In other embodiments, Y is O. In some embodiments, all instances of Y are $CR_Y$. In other embodiments, at least one instance of Y is not $CR_Y$. In yet other embodiments, at least two instances of Y are not $CR_Y$.

In some embodiments, $R_Y$ of formula II, IIa, or IIb is hydrogen. In other embodiments, $R_Y$ of formula II, IIa, or IIb is a halogen. In certain embodiments, $R_Y$ of formula II, IIa, or IIb is chloro, bromo, or iodo. In certain embodiments, $R_Y$ of formula II, IIa, or IIb is a hydroxyl or alkoxy group. In some embodiments, $R_Y$ of formula II, IIa, or IIb is a substituted or unsubstituted aliphatic group. In certain embodiments, $R_Y$ of formula II, IIa, or IIb is a substituted or unsubstituted alkyl group. In certain embodiments, $R_Y$ of formula II, IIa, or IIb is a substituted or unsubstituted aryl group. In certain embodiments, $R_Y$ of formula II, IIa, or IIb is a substituted or unsubstituted alkenyl group. In certain other embodiments, $R_Y$ of formula II, IIa, or IIb is a substituted or unsubstituted alkynyl group. In some embodiments, $R_Y$ of formula II, IIa, or IIb is an acyl group. In other embodiments, $R_Y$ of formula II, IIa, or IIb is an amino group. In certain embodiments, $R_Y$ of formula II, IIa, or IIb is a protected amino group.

In certain embodiments, Y of formula II, IIa, or IIb is $CR_Y$ and $R_Y$ is hydrogen. In some embodiments, Y of formula II, IIa, or IIb is $CR_Y$ and $R_Y$ is bromo. In other embodiments, Y of formula II, IIa, or IIb is $CR_Y$ and $R_Y$ is chloro. In certain embodiments, Y of formula II, IIa, or IIb is $CR_Y$ and $R_Y$ is —CN. In certain embodiments, Y of formula II, IIa, or IIb is $CR_Y$ and $R_Y$ is alkyl. In certain embodiments, Y of formula II, IIa, or IIb is $CR_Y$ and $R_Y$ is alkenyl. In certain embodiments, Y of formula II, IIa, or IIb is $CR_Y$ and $R_Y$ is alkynyl. In certain embodiments, Y of formula II, IIa, or IIb is $CR_Y$ and $R_Y$ is aryl. In certain embodiments, Y of formula II, IIa, or IIb is $CR_Y$ and $R_Y$ is phenyl. In certain embodiments, Y of formula II, IIa, or IIb is $CR_Y$ and $R_Y$ is benzylic. In certain embodiments, Y of formula II, IIa, or IIb is $CR_Y$ and $R_Y$ is heteroaryl. In certain embodiments, Y of formula II, IIa, or IIb is $CR_Y$ and $R_Y$ is pyridinyl. In certain embodiments, Y of formula II, IIa, or IIb is $CR_Y$ and $R_Y$ is carbocyclic. In certain embodiments, Y of formula II, IIa, or IIb is $CR_Y$ and $R_Y$ is heterocyclic. In certain embodiments, Y of formula II, IIa, or IIb is $CR_Y$ and $R_Y$ is morpholinyl. In certain embodiments, Y of formula II, IIa, or IIb is $CR_Y$ and $R_Y$ is piperidinyl.

In certain embodiments, compounds of formula II, IIa, or IIb are of the formula:

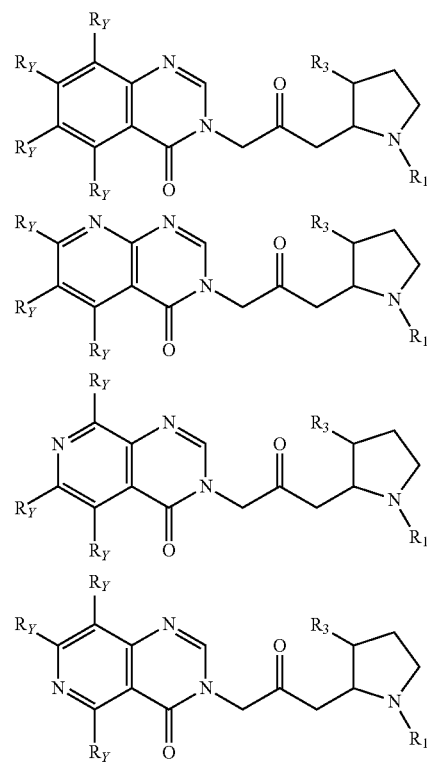

-continued

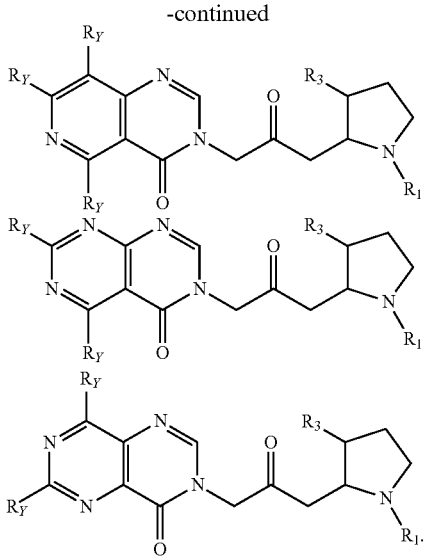

In certain embodiments, compounds of formula II, IIa, or IIb are of the formula:

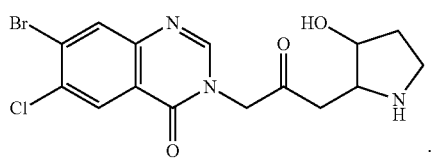 [SMILES: O=C(CC1NCCC1O)Cn1cnc2cc(Br)c(Cl)cc2c1=O]

In certain embodiments, a compound of formula II or IIa is of the formula:

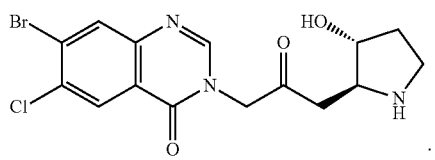 [SMILES: O=C(C[C@@H]1NCC[C@H]1O)Cn1cnc2cc(Br)c(Cl)cc2c1=O]

In certain embodiments, a compound of formula II or IIb is of the formula:

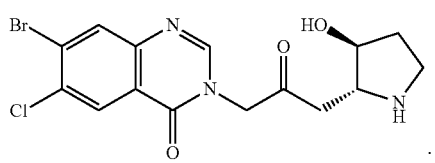

In certain embodiments, compounds of formula II, IIa, or IIb are of the formula:

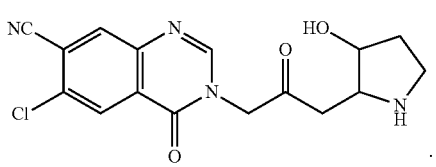 [SMILES: N#Cc1cc2ncn(CC(=O)CC3NCCC3O)c(=O)c2cc1Cl]

In certain embodiments, a compound of formula II or IIa is of the formula:

In certain embodiments, a compound of formula II or IIb is of the formula:

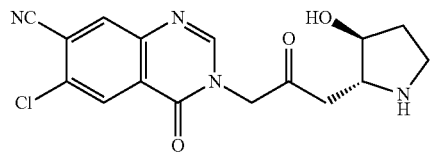

In certain embodiments, compounds of formula II, IIa, or IIb are of the formula:

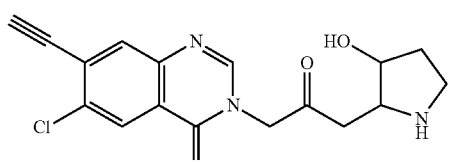

In certain embodiments, a compound of formula II or IIa is of the formula:

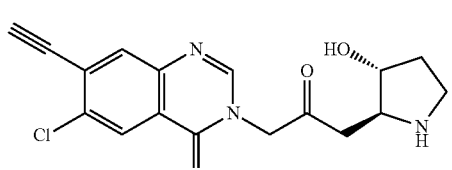

In certain embodiments, a compound of formula II or IIb is of the formula:

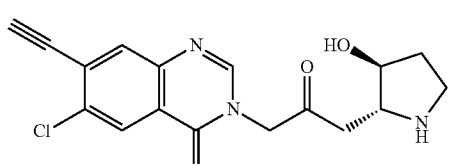

In certain embodiments, compounds of formula II, IIa, or IIb are of the formula:

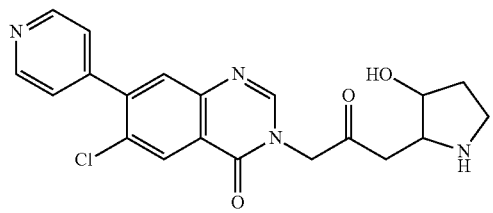

In certain embodiments, a compound of formula II or IIa is of the formula:

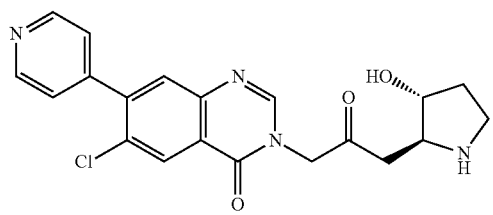

In certain embodiments, a compound of formula II or IIb is of the formula:

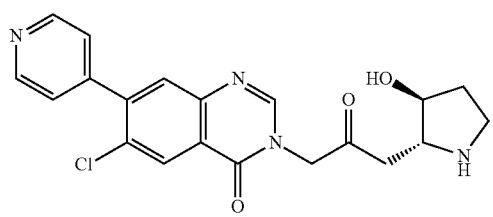

In certain embodiments, compounds of formula II, IIa, or IIb are of the formula:

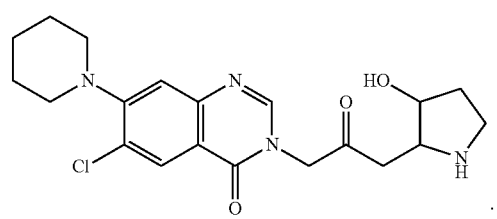 [SMILES: O=C(CC1NCCC1O)Cn1cnc2cc(N3CCCCC3)c(Cl)cc2c1=O]

In certain embodiments, a compound of formula II or IIa is of the formula:

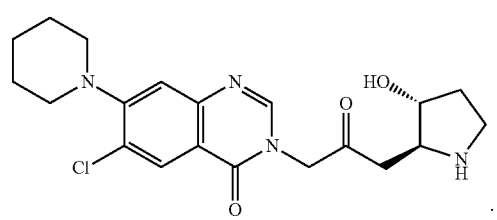 [SMILES: O=C(C[C@@H]1NCC[C@H]1O)Cn1cnc2cc(N3CCCCC3)c(Cl)cc2c1=O]

In certain embodiments, a compound of formula II or IIb is of the formula:

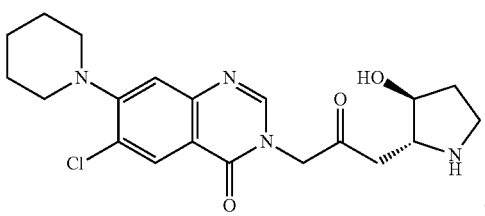

In certain embodiments, compounds of formula II, IIa, or IIb are of the formula:

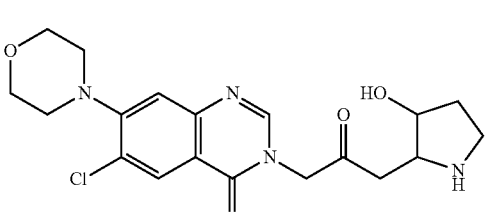

In certain embodiments, a compound of formula II or IIa is of the formula:

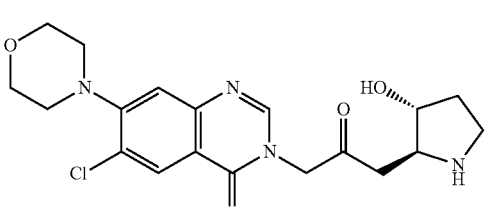

In certain embodiments, a compound of formula II or IIb is of the formula:

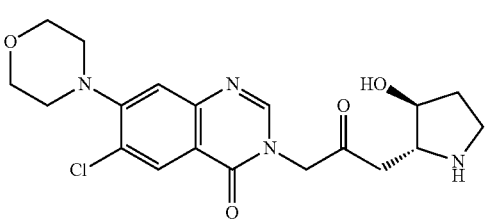

In certain embodiments, compounds of formula II, IIa, or IIb are of the formula:

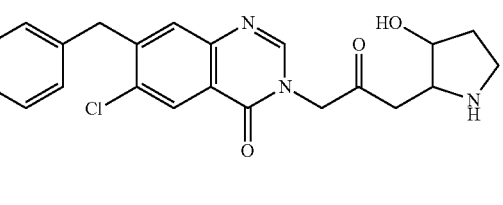

In certain embodiments, a compound of formula II or IIa is of the formula:

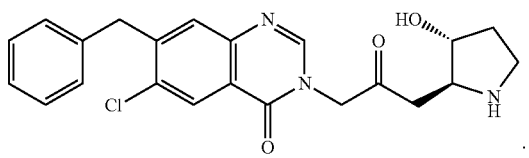 [SMILES: O=C(C[C@@H]1NCC[C@H]1O)Cn1cnc2cc(Cc3ccccc3)c(Cl)cc2c1=O]

In certain embodiments, a compound of formula II or IIb is of the formula:

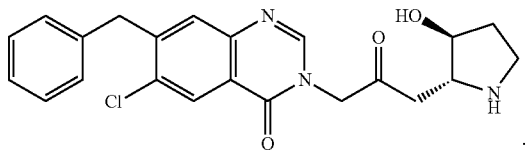 [SMILES: O=C(C[C@H]1NCC[C@@H]1O)Cn1cnc2cc(Cc3ccccc3)c(Cl)cc2c1=O]

In certain embodiments, compounds of formula II, IIa, or IIb are of the formula:

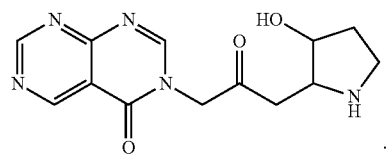 [SMILES: O=C(CC1NCCC1O)Cn1cnc2ncncc2c1=O]

In certain embodiments, a compound of formula II or IIa is of the formula:

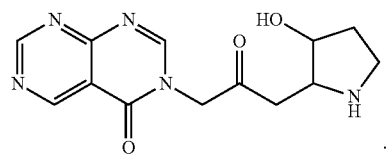 [SMILES: O=C(CC1NCCC1O)Cn1cnc2ncncc2c1=O]

In certain embodiments, a compound of formula II or IIb is of the formula:

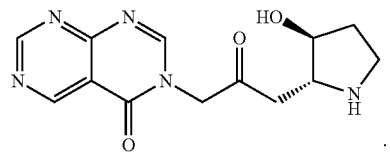 [SMILES: O=C(C[C@H]1NCC[C@@H]1O)Cn1cnc2ncncc2c1=O]

In certain embodiments, compounds of formula II, IIa, or IIb are of the formula:

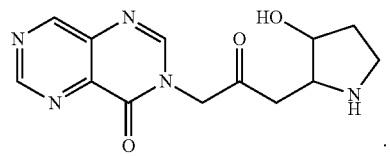 [SMILES: O=C(CC1NCCC1O)Cn1cnc2cncnc2c1=O]

In certain embodiments, a compound of formula II or IIa is of the formula:

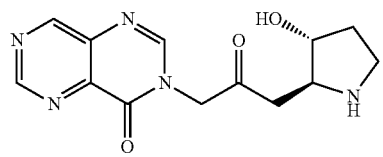

In certain embodiments, a compound of formula II or IIb is of the formula:

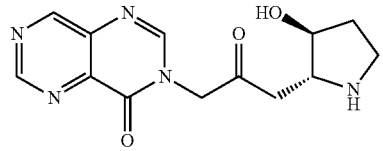

In certain embodiments, compounds of formula II, IIa, or IIb are of the formula:

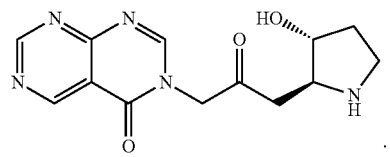

In certain embodiments, a compound of formula II or IIa is of the formula:

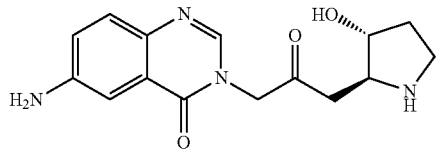

In certain embodiments, a compound of formula II or IIb is of the formula:

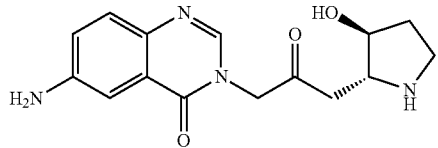

In certain embodiments, the invention provides a compound of formula (III) or a pharmaceutically acceptable salt thereof:

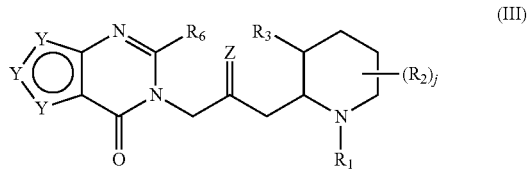

wherein
j is an integer between 0 and 8, inclusive;
each occurrence of Y is independently S, O, N, $NR_Y$, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

Z is =O or =N—$NHR_D$, wherein $R_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In some embodiments, the compound of formula III is not of formula

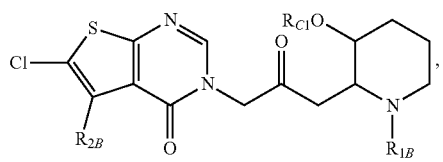

wherein $R_{2B}$ is hydrogen, chlorine, or bromine; $R_{C1}$ is hydrogen or methyl; and $R_{1B}$ is hydrogen, —$CO_2CH_3$, or —$CO_2CH_2CH=CH_2$.

In certain embodiments, the compound is of the stereochemistry of formula (IIIa):

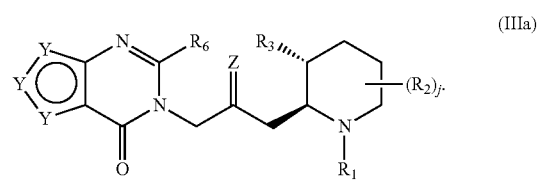

In certain embodiments, the compound is of the stereochemistry of formula (IIIb):

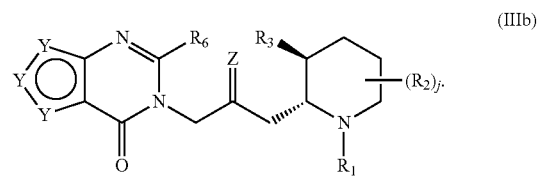

In certain embodiments, $R_1$ of formula III, IIIa, or IIIb is hydrogen. In certain other embodiments, $R_1$ of formula III, IIIa, or IIIb is a suitable amino protecting group, as defined herein.

In some embodiments, $R_2$ of formula III, IIIa, or IIIb is hydrogen. In other embodiments, $R_2$ of formula III, IIIa, or IIIb is a halogen. In certain embodiments, $R_2$ of formula III, IIIa, or IIIb is chloro, bromo, or iodo. In certain embodiments, $R_2$ of formula III, IIIa, or IIIb is a hydroxyl or alkoxyl group. In some embodiments, $R_2$ of formula III, IIIa, or IIIb is a substituted or unsubstituted aliphatic group. In certain embodiments, $R_2$ of formula III, IIIa, or IIIb is a substituted or unsubstituted aryl group. In certain embodiments, $R_2$ of formula III, IIIa, or IIIb is an amino group. In certain other embodiments, $R_2$ of formula III, IIIa, or IIIb is a cyano group. In some embodiments, $R_2$ of formula III, IIIa, or IIIb is a carboxylic acid or ester group.

In certain embodiments, $R_3$ of formula III, IIIa, or IIIb is hydrogen. In certain other embodiments, $R_3$ of formula III, IIIa, or IIIb is hydroxyl. In certain embodiments, $R_3$ of formula III, IIIa, or IIIb is alkoxy. In certain embodiments, $R_3$ of formula III, IIIa, or IIIb is a protected hydroxyl group. In certain embodiments, $R_3$ of formula III, IIIa, or IIIb is phosphate. In certain embodiments, $R_3$ of formula III, IIIa, or IIIb is sulfate. In certain other embodiments, $R_3$ of formula III, IIIa, or IIIb is acetate (—OAc). In some embodiments, $R_3$ of formula III, IIIa, or IIIb is a thioxy group. In some embodiments, $R_3$ of formula III, IIIa, or IIIb is an amino group. In some embodiments, $R_3$ of formula III, IIIa, or IIIb is a protected amino group.

In certain embodiments, $R_6$ of formula III, IIIa, or IIIb is hydrogen. In certain other embodiments, $R_6$ of formula III, IIIa, or IIIb is aliphatic. In certain embodiments, $R_6$ of formula III, IIIa, or IIIb is alkyl.

In certain embodiments, Z of formula III, IIIa, or IIIb is =O. In certain other embodiments, Z of formula III, IIIa, or IIIb is =N—NHR$_D$, wherein R$_D$ is as defined herein.

In certain embodiments, j of formula III, IIIa, or IIIb is 0. In certain embodiments, j is 1. In certain embodiments, j is 2. In certain embodiments, j is 3, 4, 5, 6, 7, or 8.

In some embodiments, at least one instance of Y of formula III, IIIa, or IIIb is CH. In some embodiments, Y of formula III, IIIa, or IIIb is CR$_Y$, where R$_Y$ is as defined herein. In other embodiments, Y is S. In certain embodiments, Y is N. In certain other embodiments, Y is NR$_Y$. In other embodiments, Y is O. In some embodiments, all instances of Y are CR$_Y$. In other embodiments, at least one instance of Y is not CR$_Y$. In yet other embodiments, at least two instances of Y are not CR$_Y$.

In some embodiments, R$_Y$ of formula III, IIIa, or IIIb is hydrogen. In other embodiments, R$_Y$ of formula III, IIIa, or IIIb is a halogen. In certain embodiments, R$_Y$ of formula III, IIIa, or IIIb is chloro, bromo, or iodo. In certain embodiments, R$_Y$ of formula III, IIIa, or IIIb is a hydroxyl or alkoxyl group. In some embodiments, R$_Y$ of formula III, IIIa, or IIIb is a substituted or unsubstituted aliphatic group. In certain embodiments, R$_Y$ of formula III, IIIa, or IIIb is a substituted or unsubstituted alkyl group. In certain embodiments, R$_Y$ of formula III, IIIa, or IIIb is a substituted or unsubstituted aryl group. In certain embodiments, R$_Y$ of formula III, IIIa, or IIIb is a substituted or unsubstituted alkenyl group. In certain other embodiments, R$_Y$ of formula III, IIIa, or IIIb is a substituted or unsubstituted alkynyl group. In some embodiments, R$_Y$ of formula III, IIIa, or IIIb is an acyl group. In other embodiments, R$_Y$ of formula III, IIIa, or IIIb is an amino group. In certain embodiments, R$_Y$ of formula III, IIIa, or IIIb is a protected amino group.

In certain embodiments, Y of formula III, IIIa, or IIIb is CR$_Y$ and R$_Y$ is hydrogen. In some embodiments, Y of formula III, IIIa, or IIIb is CR$_Y$ and R$_Y$ is bromo. In other embodiments, Y of formula III, IIIa, or IIIb is CR$_Y$ and R$_Y$ is chloro.

In some embodiments, compounds of formula III, IIIa, or IIIb are of the following formulae:

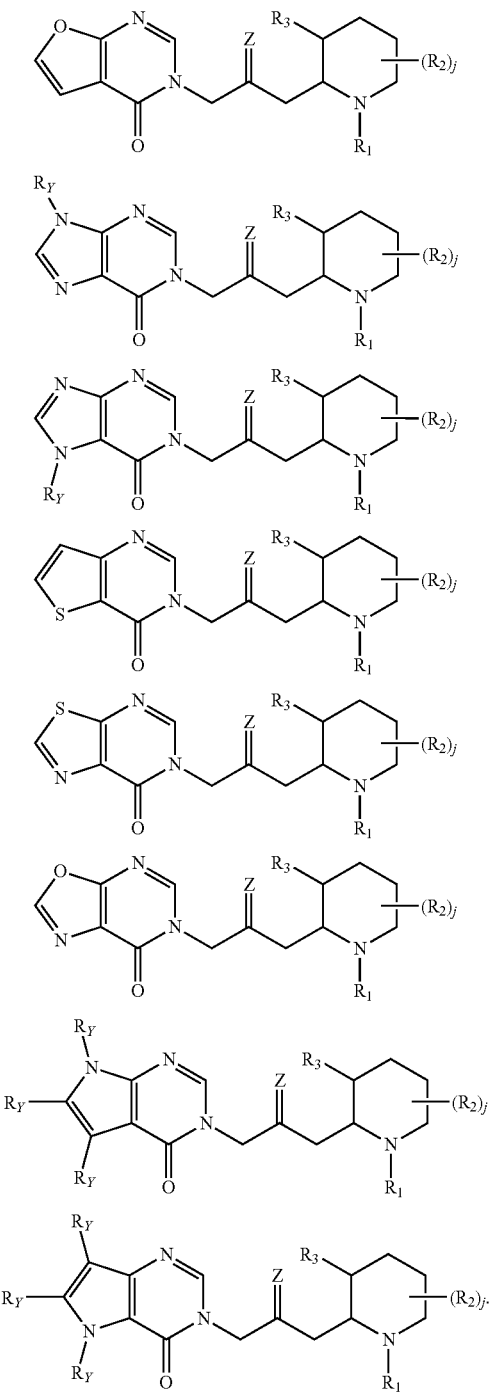

In some embodiments, compounds of formula III, IIIa, or IIIb are of the following formulae:

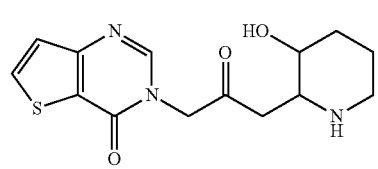

-continued

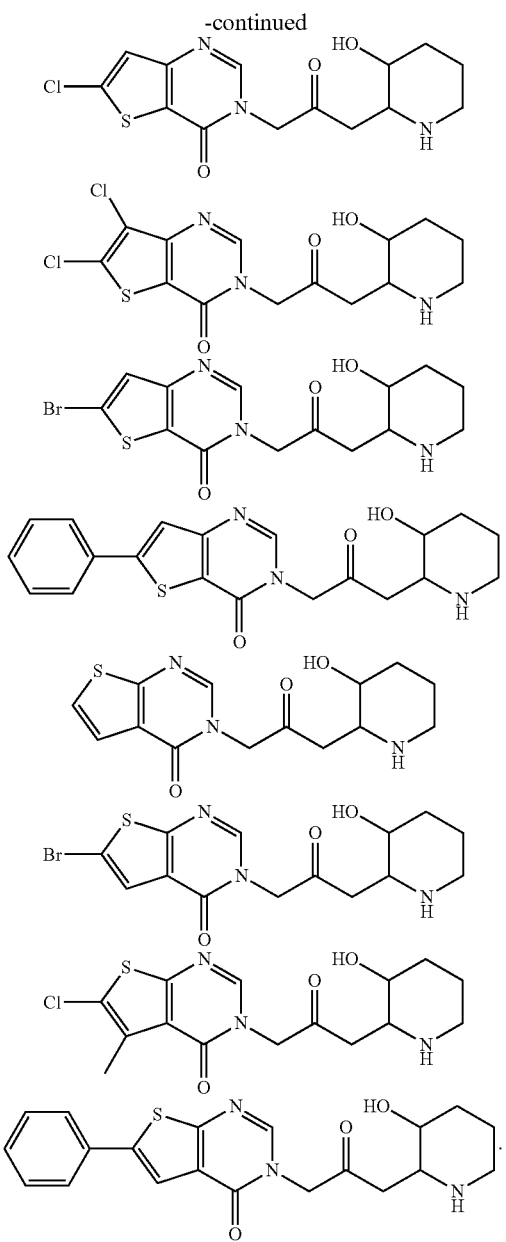

In certain embodiments, the invention provides a compound of formula (IV) or a pharmaceutically acceptable salt thereof:

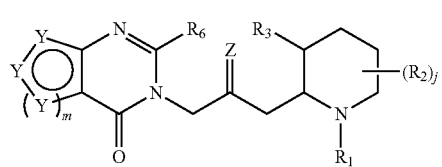

(IV)

wherein
j is an integer between 0 and 8, inclusive;
m is an integer between 1 and 2, inclusive;
each occurrence of Y is independently S, O, N, $NR_Y$, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_G$; $-C(=O)R_G$; $-CO_2R_G$; $-C(=O)N(R_G)_2$; $-CN$; $-SCN$; $-SR_G$; $-SOR_G$; $-SO_2R_G$; $-NO_2$; $-N(R_G)_2$; $-NHC(O)R_G$; or $-C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

Z is $=O$ or $=N-NHR_D$, wherein $R_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R_A$; $-C(=O)OR_A$; $-C(=O)N(R_A)_2$; or $-C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR_B$; $-C(=O)R_B$; $-CO_2R_B$; $-C(=O)N(R_B)_2$; $-CN$; $-SCN$; $-SR_B$; $-SOR_B$; $-SO_2R_B$; $-NO_2$; $-N(R_B)_2$; $-NHC(O)R_B$; or $-C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R_C$; $-CO_2R_C$; $-C(=O)N(R_C)_2$; $-CN$; $-SCN$; $-SR_C$; $-SOR_C$; $-SO_2R_C$; $-NO_2$; $-N(R_C)_2$; $-NHC(O)R_C$; or $-C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (IVa):

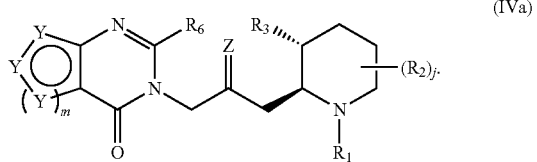

(IVa)

In certain embodiments, the compound is of the stereochemistry of formula (IVb):

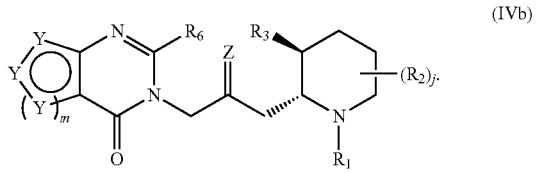

(IVb)

In certain embodiments, $R_1$ of formula IV, IVa, or IVb is hydrogen. In certain other embodiments, $R_1$ of formula IV, IVa, or IVb is a suitable amino protecting group, as defined herein.

In some embodiments, $R_2$ of formula IV, IVa, or IVb is hydrogen. In other embodiments, $R_2$ of formula IV, IVa, or IVb is a halogen. In certain embodiments, $R_2$ of formula IV, IVa, or IVb is chloro, bromo, or iodo. In certain embodiments, $R_2$ of formula IV, IVa, or IVb is a hydroxyl or alkoxyl group. In some embodiments, $R_2$ of formula IV, IVa, or IVb is a substituted or unsubstituted aliphatic group. In certain embodiments, $R_2$ of formula IV, IVa, or IVb is a substituted or unsubstituted aryl group. In certain embodiments, $R_2$ of formula IV, IVa, or IVb is an amino group. In certain other embodiments, $R_2$ of formula IV, IVa, or IVb is a cyano group. In some embodiments, $R_2$ of formula IV, IVa, or IVb is a carboxylic acid or ester group.

In certain embodiments, $R_3$ of formula IV, IVa, or IVb is halogen. In certain other embodiments, $R_3$ of formula IV, IVa, or IVb is hydroxymethyl. In certain embodiments, $R_3$ of formula IV, IVa, or IVb is alkoxymethyl. In certain embodiments, $R_3$ of formula IV, IVa, or IVb is an acyl group. In certain embodiments, $R_3$ of formula IV, IVa, or IVb is cyano. In some embodiments, $R_3$ of formula IV, IVa, or IVb is a thioxy group. In some embodiments, $R_3$ of formula IV, IVa, or IVb is an amino group. In some embodiments, $R_3$ of formula IV, IVa, or IVb is a protected amino group.

In certain embodiments, $R_6$ of formula IV, IVa, or IVb is hydrogen. In certain other embodiments, $R_6$ of formula IV, IVa, or IVb is aliphatic. In certain embodiments, $R_6$ of formula IV, IVa, or IVb is alkyl.

In certain embodiments, Z of formula IV, IVa, or IVb is =O. In certain other embodiments, Z of formula IV, IVa, or IVb is =N—$NHR_D$, where $R_D$ is as defined herein.

In certain embodiments, j of formula IV, IVa, or IVb is 0. In certain embodiments, j is 1. In certain embodiments, j is 2, 3, 4, 5, 6, 7, or 8.

In some embodiments, m of formula IV, IVa, or IVb is 1. In other embodiments, m of formula IV, IVa, or IVb is 2.

In some embodiments, at least one instance of Y of formula IV, IVa, or IVb is CH. In some embodiments, Y of formula IV, IVa, or IVb is $CR_Y$, where $R_Y$ is as defined herein. In other embodiments, Y is S. In certain embodiments, Y is N. In certain other embodiments, Y is $NR_Y$. In other embodiments, Y is O. In some embodiments, all instances of Y are $CR_Y$. In other embodiments, at least one instance of Y is not $CR_Y$. In yet other embodiments, at least two instances of Y are not $CR_Y$.

In some embodiments, $R_Y$ of formula IV, IVa, or IVb is hydrogen. In other embodiments, $R_Y$ of formula IV, IVa, or IVb is a halogen. In certain embodiments, $R_Y$ of formula IV, IVa, or IVb is chloro, bromo, or iodo. In certain embodiments, $R_Y$ of formula IV, IVa, or IVb is a hydroxyl or alkoxyl group. In some embodiments, $R_Y$ of formula IV, IVa, or IVb is a substituted or unsubstituted aliphatic group. In certain embodiments, $R_Y$ of formula IV, IVa, or IVb is a substituted or unsubstituted alkyl group. In certain embodiments, $R_Y$ of formula IV, IVa, or IVb is a substituted or unsubstituted aryl group. In certain embodiments, $R_Y$ of formula IV, IVa, or IVb is a substituted or unsubstituted alkenyl group. In certain other embodiments, $R_Y$ of formula IV, IVa, or IVb is a substituted or unsubstituted alkynyl group. In some embodiments, $R_Y$ of formula IV, IVa, or IVb is an acyl group. In other embodiments, $R_Y$ of formula IV, IVa, or IVb is an amino group. In certain embodiments, $R_Y$ of formula IV, IVa, or IVb is a protected amino group.

In certain embodiments, Y of formula IV, IVa, or IVb is $CR_Y$ and $R_Y$ is hydrogen. In some embodiments, Y of formula IV, IVa, or IVb is $CR_Y$ and $R_Y$ is bromo. In other embodiments, Y of formula IV, IVa, or IVb is $CR_Y$ and $R_Y$ is chloro.

In some embodiments, compounds of formula IV, IVa, or IVb are of the formula:

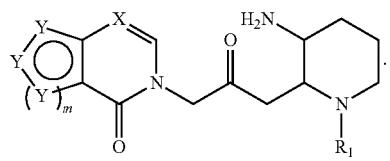

In some embodiments, compounds of formula IV, IVa, or IVb are of the formula:

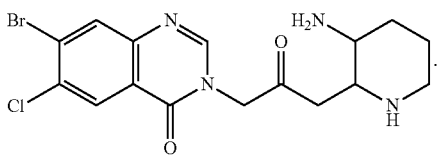 [SMILES: NC1CCCNC1CC(=O)Cn1cnc2cc(Br)c(Cl)cc2c1=O]

In some embodiments, a compound of formula IV or IVa is of the formula:

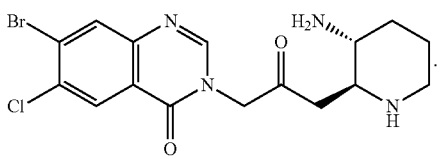 [SMILES: N[C@@H]1CCCN[C@H]1CC(=O)Cn1cnc2cc(Br)c(Cl)cc2c1=O]

In some embodiments, a compound of formula IV or IVb is of the formula:

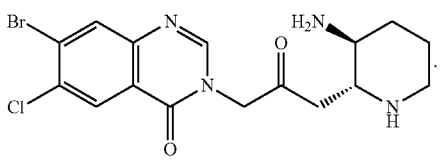 [SMILES: N[C@H]1CCCN[C@@H]1CC(=O)Cn1cnc2cc(Br)c(Cl)cc2c1=O]

In some embodiments, compounds of formula IV, IVa, or IVb are of the formula:

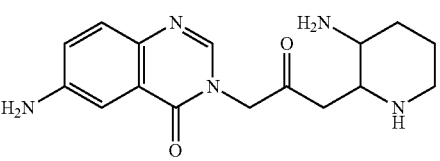

In some embodiments, a compound of formula IV or IVa is of the formula:

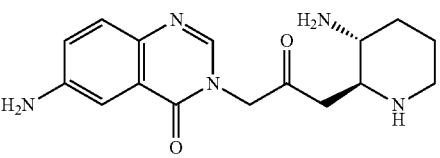

In some embodiments, a compound of formula IV or IVb is of the formula:

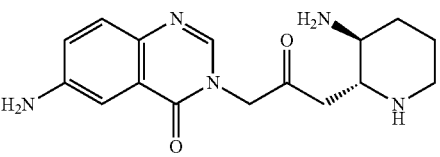

In certain embodiments, the invention provides a compound of formula (V) or a pharmaceutically acceptable salt thereof:

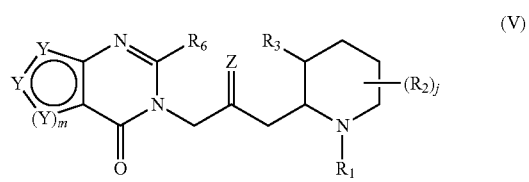

(V)

wherein j is an integer between 1 and 8, inclusive;

m is an integer between 1 and 2, inclusive;

each occurrence of Y is independently S, O, N, $NR_Y$, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

Z is =O or =N—$NHR_D$, wherein $R_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —C(=O)N(R$_C$)$_2$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (Va):

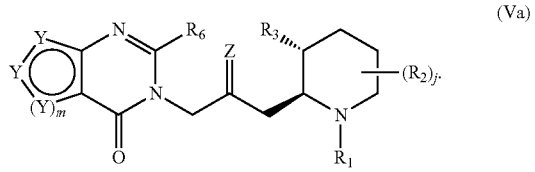

(Va)

In certain embodiments, the compound is of the stereochemistry of formula (Vb):

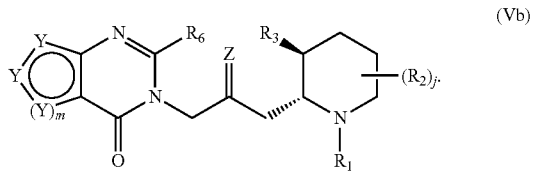

(Vb)

In certain embodiments, R$_1$ of formula V, Va, or Vb is hydrogen. In certain other embodiments, R$_1$ of formula V, Va, or Vb is a suitable amino protecting group, as defined herein.

In other embodiments, R$_2$ of formula V, Va, or Vb is a halogen. In certain embodiments, R$_2$ of formula V, Va, or Vb is chloro, bromo, or iodo. In certain embodiments, R$_2$ of formula V, Va, or Vb is a hydroxyl or alkoxyl group. In some embodiments, R$_2$ of formula V, Va, or Vb is a substituted or unsubstituted aliphatic group. In certain embodiments, R$_2$ of formula V, Va, or Vb is a substituted or unsubstituted aryl group. In certain embodiments, R$_2$ of formula V, Va, or Vb is an amino group. In certain other embodiments, R$_2$ of formula V, Va, or Vb is a cyano group. In some embodiments, R$_2$ of formula V, Va, or Vb is a carboxylic acid or ester group.

In certain embodiments, R$_3$ of formula V, Va, or Vb is hydrogen. In certain other embodiments, R$_3$ of formula V, Va, or Vb is hydroxyl. In certain embodiments, R$_3$ of formula V, Va, or Vb is alkoxy. In certain embodiments, R$_3$ of formula V, Va, or Vb is a protected hydroxyl group. In certain embodiments, R$_3$ of formula V, Va, or Vb is phosphate. In certain embodiments, R$_3$ of formula V, Va, or Vb is sulfate. In certain other embodiments, R$_3$ of formula V, Va, or Vb is acetate (—OAc). In some embodiments, R$_3$ of formula V, Va, or Vb is a thioxy group. In some embodiments, R$_3$ of formula V, Va, or Vb is an amino group. In some embodiments, R$_3$ of formula V, Va, or Vb is a protected amino group.

In certain embodiments, R$_6$ of formula V, Va, or Vb is hydrogen. In certain other embodiments, R$_6$ of formula V, Va, or Vb is aliphatic. In certain embodiments, R$_6$ of formula V, Va, or Vb is alkyl.

In certain embodiments, Z of formula V, Va, or Vb is =O. In certain other embodiments, Z of formula V, Va, or Vb is =N—NHR$_D$.

In certain embodiments, j of formula V, Va, or Vb is 1. In certain embodiments, j of formula V, Va, or Vb is 2. In certain embodiments, j is 3, 4, 5, 6, 7, or 8.

In some embodiments, m of formula V, Va, or Vb is 1. In other embodiments, m of formula V, Va, or Vb is 2.

In some embodiments, at least one instance of Y of formula V, Va, or Vb is CH. In some embodiments, Y of formula V, Va, or Vb is CR$_Y$, where R$_Y$ is as defined herein. In other embodiments, Y is S. In certain embodiments, Y is N. In certain other embodiments, Y is NR$_Y$. In other embodiments, Y is O. In some embodiments, all instances of Y are CR$_Y$. In other embodiments, at least one instance of Y is not CR$_Y$. In yet other embodiments, at least two instances of Y are not CR$_Y$.

In some embodiments, R$_Y$ of formula V, Va, or Vb is hydrogen. In other embodiments, R$_Y$ of formula V, Va, or Vb is a halogen. In certain embodiments, R$_Y$ of formula V, Va, or Vb is chloro, bromo, or iodo. In certain embodiments, R$_Y$ of formula V, Va, or Vb is a hydroxyl or alkoxy group. In some embodiments, R$_Y$ of formula V, Va, or Vb is a substituted or unsubstituted aliphatic group. In certain embodiments, R$_Y$ of formula V, Va, or Vb is a substituted or unsubstituted alkyl group. In certain embodiments, R$_Y$ of formula V, Va, or Vb is a substituted or unsubstituted aryl group. In certain embodiments, R$_Y$ of formula V, Va, or Vb is a substituted or unsubstituted alkenyl group. In certain other embodiments, R$_Y$ of formula V, Va, or Vb is a substituted or unsubstituted alkynyl group. In some embodiments, R$_Y$ of formula V, Va, or Vb is an acyl group. In other embodiments, R$_Y$ of formula V, Va, or Vb is an amino group. In certain embodiments, R$_Y$ of formula V, Va, or Vb is a protected amino group.

In certain embodiments, Y of formula V, Va, or Vb is CR$_Y$ and R$_Y$ is hydrogen. In some embodiments, Y of formula V, Va, or Vb is CR$_Y$ and R$_Y$ is bromo. In other embodiments, Y of formula V, Va, or Vb is CR$_Y$ and R$_Y$ is chloro.

In some embodiments, compounds of formula V, Va, or Vb are of the following formula:

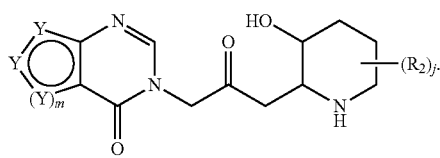

In some embodiments, compounds of formula V, Va, or Vb are of the following formula:

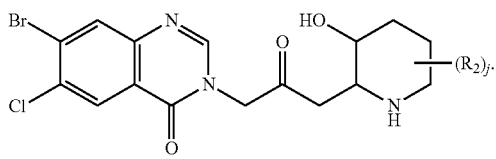

In some embodiments, compounds of formula V or Va are of the following formula:

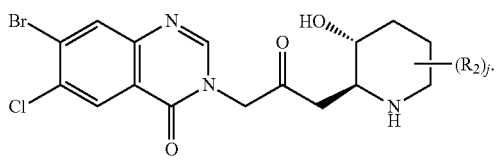

In some embodiments, compounds of formula V or Vb are of the following formula:

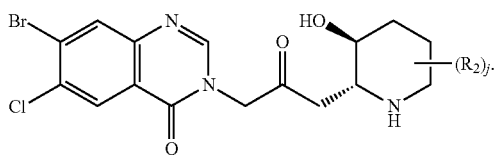

In certain embodiments, the invention provides a compound of formula (VI) or a pharmaceutically acceptable salt thereof:

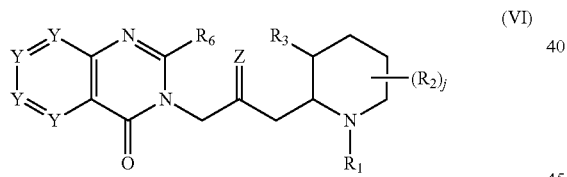

wherein j is an integer between 0 and 8, inclusive;

each occurrence of Y is S, O, N, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

Z is =O or =N—$NHR_D$, wherein $R_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, at least one instance of Y of formula VI is not $CR_Y$.

In certain embodiments, the compound is of the stereochemistry of formula (VIa):

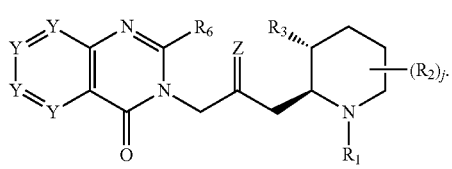
(VIa)

In certain embodiments, the compound is of the stereochemistry of formula (VIb):

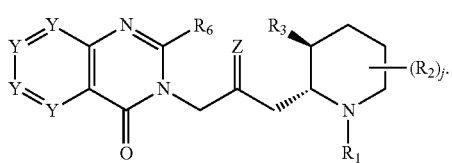
(VIb)

In certain embodiments, $R_1$ of formula VI, VIa, or VIb is hydrogen. In certain other embodiments, $R_1$ of formula VI, VIa, or VIb is a suitable amino protecting group, as defined herein.

In some embodiments, $R_2$ of formula VI, VIa, or VIb is hydrogen. In other embodiments, $R_2$ of formula VI, VIa, or VIb is a halogen. In certain embodiments, $R_2$ of formula VI, VIa, or VIb is chloro, bromo, or iodo. In certain embodiments, $R_2$ of formula VI, VIa, or VIb is a hydroxyl or alkoxyl group. In some embodiments, $R_2$ of formula VI, VIa, or VIb is a substituted or unsubstituted aliphatic group. In certain embodiments, $R_2$ of formula VI, VIa, or VIb is a substituted or unsubstituted aryl group. In certain embodiments, $R_2$ of formula VI, VIa, or VIb is an amino group. In certain other embodiments, $R_2$ of formula VI, VIa, or VIb is a cyano group. In some embodiments, $R_2$ of formula VI, VIa, or VIb is a carboxylic acid or ester group.

In certain embodiments, $R_3$ of formula VI, VIa, or VIb is hydrogen. In certain other embodiments, $R_3$ of formula VI, VIa, or VIb is hydroxyl. In certain embodiments, $R_3$ of formula VI, VIa, or VIb is alkoxy. In certain embodiments, $R_3$ of formula VI, VIa, or VIb is a protected hydroxyl group. In certain embodiments, $R_3$ of formula VI, VIa, or VIb is phosphate. In certain embodiments, $R_3$ of formula VI, VIa, or VIb is sulfate. In certain other embodiments, $R_3$ of formula VI, VIa, or VIb is acetate (—OAc). In some embodiments, $R_3$ of formula VI, VIa, or VIb is a thioxy group. In some embodiments, $R_3$ of formula VI, VIa, or VIb is an amino group. In some embodiments, $R_3$ of formula VI, VIa, or VIb is a protected amino group.

In certain embodiments, $R_6$ of formula VI, VIa, or VIb is hydrogen. In certain other embodiments, $R_6$ of formula VI, VIa, or VIb is aliphatic. In certain embodiments, $R_6$ of formula VI, VIa, or VIb is alkyl.

In certain embodiments, Z of formula VI, VIa, or VIb is =O. In certain other embodiments, Z of formula VI, VIa, or VIb is =N—NHR$_D$, where R$_D$ is as defined herein.

In certain embodiments, j of formula VI, VIa, or VIb is 0. In certain embodiments, j is 1. In certain embodiments, j is 2. In certain embodiments, j is 3, 4, 5, 6, 7, or 8.

In some embodiments, at least one instance of Y of formula VI, VIa, or VIb is CH. In some embodiments, Y of formula VI, VIa, or VIb is $CR_Y$, where $R_Y$ is as defined herein. In certain embodiments, Y is N. In other embodiments, at least one instance of Y is not $CR_Y$. In yet other embodiments, at least two instances of Y are not $CR_Y$.

In some embodiments, $R_Y$ of formula VI, VIa, or VIb is hydrogen. In other embodiments, $R_Y$ of formula VI, VIa, or VIb is a halogen. In certain embodiments, $R_Y$ of formula VI, VIa, or VIb is chloro, bromo, or iodo. In certain embodiments, $R_Y$ of formula VI or VIa is a hydroxyl or alkoxyl group. In some embodiments, $R_Y$ of formula VI, VIa, or VIb is a substituted or unsubstituted aliphatic group. In certain embodiments, $R_Y$ of formula VI, VIa, or VIb is a substituted or unsubstituted alkyl group. In certain embodiments, $R_Y$ of formula VI, VIa, or VIb is a substituted or unsubstituted aryl group. In certain embodiments, $R_Y$ of formula VI, VIa, or VIb is a substituted or unsubstituted alkenyl group. In certain other embodiments, $R_Y$ of formula VI, VIa, or VIb is a substituted or unsubstituted alkynyl group. In some embodiments, $R_Y$ of formula VI, VIa, or VIb is an acyl group. In other embodiments, $R_Y$ of formula VI, VIa, or VIb is an amino group. In certain embodiments, $R_Y$ of formula VI, VIa, or VIb is a protected amino group.

In certain embodiments, Y of formula VI, VIa, or VIb is $CR_Y$ and $R_Y$ is hydrogen. In some embodiments, Y of formula VI, VIa, or VIb is $CR_Y$ and $R_Y$ is bromo. In other embodiments, Y of formula VI, VIa, or VIb is $CR_Y$ and $R_Y$ is chloro.

In some embodiments, compounds of formula VI, VIa, or VIb are of the following formulae:

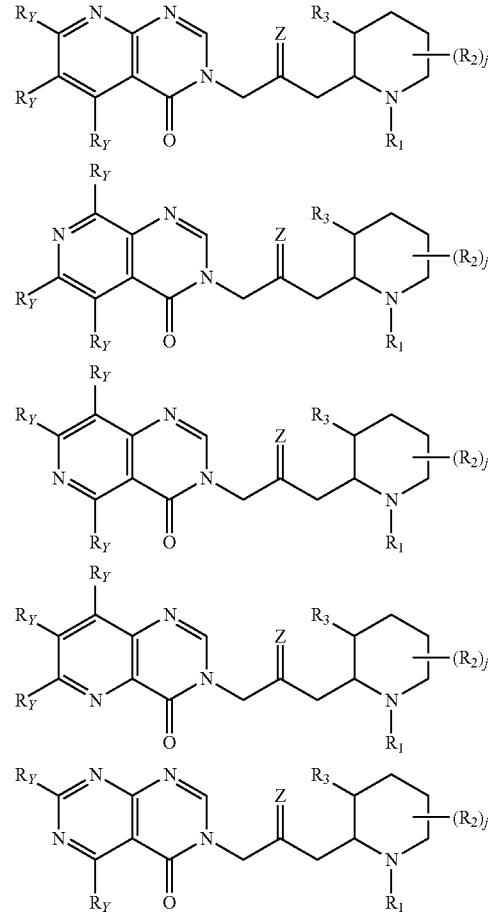

-continued

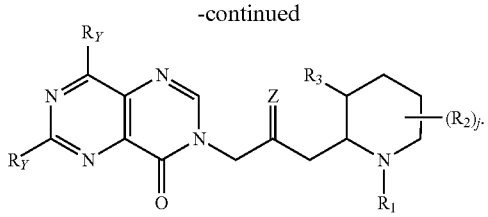

In some embodiments, compounds of formula VI, VIa, or VIb are of the following formulae:

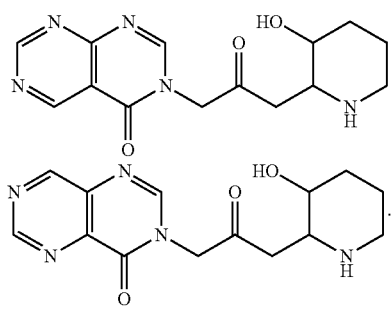

In certain embodiments, the invention provides a compound of formula (VII) or a pharmaceutically acceptable salt thereof:

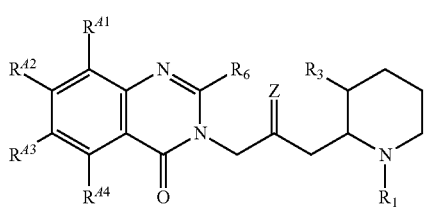

wherein Z is =O or =N—NHR$_D$, wherein R$_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$_A$; —C(=O)OR$_A$; —C(=O)N(R$_A$)$_2$; or —C(R$_A$)$_3$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —C(=O)R$_C$; —CO$_2$R$_C$; —C(=O)N(R$_C$)$_2$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$^{A1}$, R$^{A2}$, and R$^{A3}$ are independently hydrogen; halogen; substituted or unsubstituted aliphatic; substituted or unsubstituted heteroaliphatic; substituted or unsubstituted aryl; substituted or unsubstituted heteroaryl; —OR$_G$; —SR$_G$; —N(R$_G$)$_2$; and —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and R$^{A4}$ is halogen; substituted or unsubstituted aliphatic; substituted or unsubstituted heteroaliphatic; substituted or unsubstituted aryl; substituted or unsubstituted heteroaryl; —OR$_G$; —SR$_G$; —N(R$_G$)$_2$; and —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In some embodiments, the compound of formula VII is not of the formula:

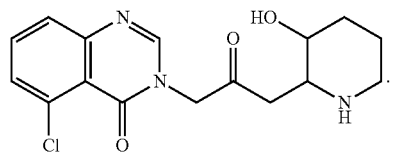 [SMILES: O=C(CC1NCCCC1O)Cn1cnc2cccc(Cl)c2c1=O]

In certain embodiments, the compound is of the stereochemistry of formula (VIIa):

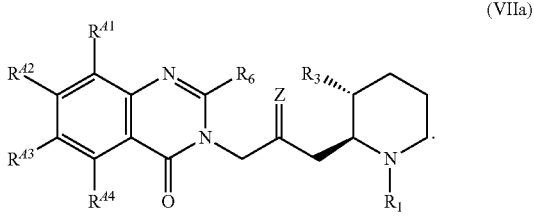

(VIIa)

In certain embodiments, the compound is of the stereochemistry of formula (VIIb):

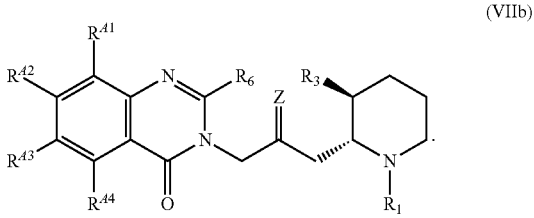

(VIIb)

In certain embodiments, $R_1$ of formula VII, VIIa, or VIIb is hydrogen. In certain other embodiments, $R_1$ of formula VII, VIIa, or VIIb is a suitable amino protecting group, as defined herein.

In some embodiments, $R^{41}$ of formula VII, VIIa, or VIIb is hydrogen. In other embodiments, $R^{41}$ of formula VII, VIIa, or VIIb is a halogen. In certain embodiments, $R^{41}$ of formula VII, VIIa, or VIIb is chloro, bromo, or iodo. In certain embodiments, $R^{41}$ of formula VII, VIIa, or VIIb is a hydroxyl or alkoxy group. In some embodiments, $R^{41}$ of formula VII, VIIa, or VIIb is a substituted or unsubstituted aliphatic group. In certain embodiments, $R^{41}$ of formula VII, VIIa, or VIIb is a substituted or unsubstituted alkyl group. In certain embodiments, $R^{41}$ of formula VII, VIIa, or VIIb is a substituted or unsubstituted aryl group. In certain embodiments, $R^{41}$ of formula VII, VIIa, or VIIb is a substituted or unsubstituted alkenyl group. In certain other embodiments, $R^{41}$ of formula VII, VIIa, or VIIb is a substituted or unsubstituted alkynyl group. In some embodiments, $R^{41}$ of formula VII, VIIa, or VIIb is an acyl group. In some embodiments, $R^{41}$ of formula VII, VIIa, or VIIb is an amino group. In other embodiments, $R^{41}$ of formula VII, VIIa, or VIIb is a protected amino group.

In some embodiments, $R^{42}$ of formula VII, VIIa, or VIIb is hydrogen. In other embodiments, $R^{42}$ of formula VII, VIIa, or VIIb is a halogen. In certain embodiments, $R^{42}$ of formula VII, VIIa, or VIIb is chloro, bromo, or iodo. In certain embodiments, $R^{42}$ of formula VII, VIIa, or VIIb is bromo. In certain embodiments, $R^{42}$ of formula VII, VIIa, or VIIb is a hydroxyl or alkoxy group. In some embodiments, $R^{42}$ of formula VII, VIIa, or VIIb is a substituted or unsubstituted aliphatic group. In certain embodiments, $R^{42}$ of formula VII, VIIa, or VIIb is a substituted or unsubstituted alkyl group. In certain embodiments, $R^{42}$ of formula VII, VIIa, or VIIb is a substituted or unsubstituted aryl group. In certain embodiments, $R^{42}$ of formula VII, VIIa, or VIIb is a substituted or unsubstituted alkenyl group. In certain other embodiments, $R^{42}$ of formula VII, VIIa, or VIIb is a substituted or unsubstituted alkynyl group. In some embodiments, $R^{42}$ of formula VII, VIIa, or VIIb is an acyl group. In some embodiments, $R^{42}$ of formula VII, VIIa, or VIIb is an amino group. In other embodiments, $R^{42}$ of formula VII, VIIa, or VIIb is a protected amino group.

In some embodiments, $R^{43}$ of formula VII, VIIa, or VIIb is hydrogen. In other embodiments, $R^{43}$ of formula VII, VIIa, or VIIb is a halogen. In certain embodiments, $R^{43}$ of formula VII, VIIa, or VIIb is chloro, bromo, or iodo. In certain embodiments, $R^{43}$ of formula VII, VIIa, or VIIb is chloro. In certain embodiments, $R^{43}$ of formula VII, VIIa, or VIIb is a hydroxyl or alkoxy group. In some embodiments, $R^{43}$ of formula VII, VIIa, or VIIb is a substituted or unsubstituted aliphatic group. In certain embodiments, $R^{43}$ of formula VII, VIIa, or VIIb is a substituted or unsubstituted alkyl group. In certain embodiments, $R^{43}$ of formula VII, VIIa, or VIIb is a substituted or unsubstituted aryl group. In certain embodiments, $R^{43}$ of formula VII, VIIa, or VIIb is a substituted or unsubstituted alkenyl group. In certain other embodiments, $R^{43}$ of formula VII, VIIa, or VIIb is a substituted or unsubstituted alkynyl group. In some embodiments, $R^{43}$ of formula VII, VIIa, or VIIb is an acyl group. In some embodiments, $R^{43}$ of formula VII, VIIa, or VIIb is an amino group. In other embodiments, $R^{43}$ of formula VII, VIIa, or VIIb is a protected amino group.

In some embodiments, $R^{44}$ of formula VII, VIIa, or VIIb is a halogen. In certain embodiments, $R^{44}$ of formula VII, VIIa, or VIIb is chloro, bromo, or iodo. In certain embodiments, $R^{44}$ of formula VII, VIIa, or VIIb is chloro. In certain embodiments, $R^{44}$ of formula VII, VIIa, or VIIb is bromo. In certain embodiments, $R^{44}$ of formula VII, VIIa, or VIIb is a hydroxyl or alkoxy group. In some embodiments, $R^{44}$ of formula VII, VIIa, or VIIb is a substituted or unsubstituted aliphatic group. In certain embodiments, $R^{44}$ of formula VII, VIIa, or VIIb is a substituted or unsubstituted alkyl group. In certain embodiments, $R^{44}$ of formula VII, VIIa, or VIIb is a substituted or unsubstituted aryl group. In certain embodiments, $R^{44}$ of formula VII, VIIa, or VIIb is a substituted or unsubstituted alkenyl group. In certain other embodiments, $R^{44}$ of formula VII, VIIa, or VIIb is a substituted or unsubstituted alkynyl group. In some embodiments, $R^{44}$ of formula VII, VIIa, or VIIb is an acyl group. In some embodiments, $R^{44}$ of formula VII, VIIa, or VIIb is an amino group. In other embodiments, $R^{44}$ of formula VII, VIIa, or VIIb is a protected amino group.

In certain embodiments, $R_3$ of formula VII, VIIa, or VIIb is hydrogen. In certain other embodiments, $R_3$ of formula VII, VIIa, or VIIb is hydroxyl. In certain embodiments, $R_3$ of formula VII, VIIa, or VIIb is alkoxy. In certain embodiments, $R_3$ of formula VII, VIIa, or VIIb is a protected hydroxyl group. In certain embodiments, $R_3$ of formula VII, VIIa, or VIIb is phosphate. In certain embodiments, $R_3$ of formula VII, VIIa, or VIIb is sulfate. In certain other embodiments, $R_3$ of formula VII, VIIa, or VIIb is acetate (—OAc). In some embodiments, $R_3$ of formula VII, VIIa, or VIIb is a thioxy group. In some embodiments, $R_3$ of formula VII, VIIa, or VIIb is an amino group. In some embodiments, $R_3$ of formula VII, VIIa, or VIIb is a protected amino group.

In certain embodiments, $R_6$ of formula VII, VIIa, or VIIb is hydrogen. In certain other embodiments, $R_6$ of formula VII, VIIa, or VIIb is aliphatic. In certain embodiments, $R_6$ of formula VII, VIIa, or VIIb is alkyl.

In certain embodiments, Z of formula VII, VIIa, or VIIb is =O. In certain other embodiments, Z of formula VII, VIIa, or VIIb is =N—NHR$_D$, where R$_D$ is as defined herein.

In certain embodiments, the invention provides a compound of formula (VIII) or a pharmaceutically acceptable salt thereof:

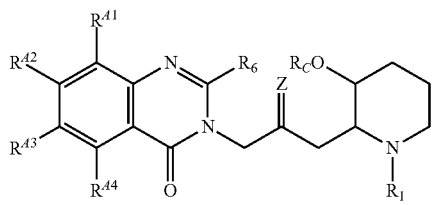

(VIII)

wherein Z is =O or =N—NHR$_D$, wherein R$_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_1$ is hydrogen; a protecting group; an aliphatic moiety; a heteroaliphatic moiety; an acyl moiety; an aryl moiety; a heteroaryl moiety; —C(=O)R$_A$; —C(=O)OR$_A$; —C(=O)N(R$_A$)$_2$; —SO$_2$R$_A$; —S(=O)R$_A$; —C(R$_A$)$_2$NHC(=O)R$_A$; C(=O)OCH$_2$OC(=O)R$_A$; C(=O)OCH$_2$OC(=O)OR$_A$; or —C(R$_A$)$_2$OC(=O)R$_A$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_C$ is a protecting group; an aliphatic moiety; a heteroaliphatic moiety; an acyl moiety; an aryl moiety; a heteroaryl moiety; —C(=O)R$_{C1}$; —C(=O)OR$_{C1}$; —C(=O)N(R$_{C1}$)$_2$; —P(=O)(OR$_{C1}$)$_2$; —S(=O)(OR$_{C1}$)$_2$; or —C(R$_{C1}$)$_2$OC(=O)R$_{C1}$; wherein each occurrence of R$_{C1}$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; provided that R$_C$ is not methyl, ethyl, or acetyl;

R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and R$^{A1}$, R$^{A2}$, R$^{A3}$, and R$^{A4}$ are independently hydrogen; halogen; substituted or unsubstituted aliphatic; substituted or unsubstituted heteroaliphatic; substituted or unsubstituted aryl; substituted or unsubstituted heteroaryl; —OR$_G$; —SR$_G$; —N(R$_G$)$_2$; and —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (VIIIa):

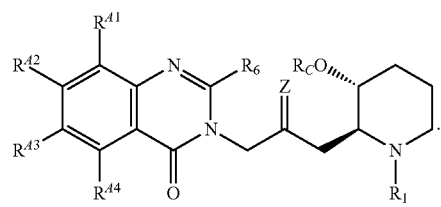

(VIIIa)

In certain embodiments, the compound is of the stereochemistry of formula (VIIIb):

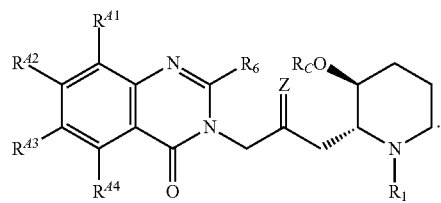

(VIIIb)

In certain embodiments, R$_1$ of formula VIII, VIIIa, or VIIIb is hydrogen. In certain other embodiments, R$_1$ of formula VIII, VIIIa, or VIIIb is a suitable amino protecting group, as defined herein.

In certain embodiments, R$_6$ of formula VIII, VIIIa, or VIIIb is hydrogen. In certain other embodiments, R$_6$ of formula VIII, VIIIa, or VIIIb is aliphatic. In certain embodiments, R$_6$ of formula VIII, VIIIa, or VIIIb is alkyl.

In some embodiments, R$^{A1}$ of formula VIII, VIIIa, or VIIIb is hydrogen. In other embodiments, R$^{A1}$ of formula VIII, VIIIa, or VIIIb is a halogen. In certain embodiments, R$^{A1}$ of formula VIII, VIIIa, or VIIIb is chloro, bromo, or iodo. In certain embodiments, R$^{A1}$ of formula VIII, VIIIa, or VIIIb is a hydroxyl or alkoxyl group. In some embodiments, R$^{A1}$ of formula VIII, VIIIa, or VIIIb is a substituted or unsubstituted aliphatic group. In certain embodiments, R$^{A1}$ of formula VIII, VIIIa, or VIIIb is a substituted or unsubstituted alkyl group. In certain embodiments, R$^{A1}$ of formula VIII, VIIIa, or VIIIb is a substituted or unsubstituted aryl group. In certain embodiments, R$^{A1}$ of formula VIII, VIIIa, or VIIIb is a substituted or unsubstituted alkenyl group. In certain other embodiments, R$^{A1}$ of formula VIII, VIIIa, or VIIIb is a substituted or unsubstituted alkynyl group. In some embodiments, R$^{A1}$ of formula VIII, VIIIa, or VIIIb is an acyl group. In some embodiments, R$^{A1}$ of formula VIII, VIIIa, or VIIIb is an amino group. In other embodiments, R$^{A1}$ of formula VIII, VIIIa, or VIIIb is a protected amino group.

In some embodiments, R$^{A2}$ of formula VIII, VIIIa, or VIIIb is hydrogen. In other embodiments, R$^{A2}$ of formula VIII, VIIIa, or VIIIb is a halogen. In certain embodiments, R$^{A2}$ of formula VIII, VIIIa, or VIIIb is chloro, bromo, or iodo. In certain embodiments, R$^{A2}$ of formula VIII, VIIIa, or VIIIb is bromo. In certain embodiments, R$^{A2}$ of formula VIII, VIIIa, or VIIIb is a hydroxyl or alkoxyl group. In some embodiments, R$^{A2}$ of formula VIII, VIIIa, or VIIIb is a substituted or unsubstituted aliphatic group. In certain embodiments, R$^{A2}$ of formula VIII, VIIIa, or VIIIb is a substituted or unsubstituted alkyl group. In certain embodiments, R$^{A2}$ of formula VIII, VIIIa, or VIIIb is a substituted or unsubstituted aryl group. In certain embodiments, $R^{42}$ of formula VIII, VIIIa, or VIIIb is a substituted or unsubstituted alkenyl group. In certain other embodiments, $R^{42}$ of formula VIII, VIIIa, or VIIIb is a substituted or unsubstituted alkynyl group. In some embodiments, $R^{42}$ of formula VIII, VIIIa, or VIIIb is an acyl group. In some embodiments, $R^{42}$ of formula VIII, VIIIa, or VIIIb is an amino group. In other embodiments, $R^{42}$ of formula VIII, VIIIa, or VIIIb is a protected amino group.

In some embodiments, $R^{43}$ of formula VIII, VIIIa, or VIIIb is hydrogen. In other embodiments, $R^{43}$ of formula VIII, VIIIa, or VIIIb is a halogen. In certain embodiments, $R^{43}$ of formula VIII, VIIIa, or VIIIb is chloro, bromo, or iodo. In certain embodiments, $R^{43}$ of formula VIII, VIIIa, or VIIIb is chloro. In certain embodiments, $R^{43}$ of formula VIII, VIIIa, or VIIIb is a hydroxyl or alkoxyl group. In some embodiments, $R^{43}$ of formula VIII, VIIIa, or VIIIb is a substituted or unsubstituted aliphatic group. In certain embodiments, $R^{43}$ of formula VIII, VIIIa, or VIIIb is a substituted or unsubstituted alkyl group. In certain embodiments, $R^{43}$ of formula VIII, VIIIa, or VIIIb is a substituted or unsubstituted aryl group. In certain embodiments, $R^{43}$ of formula VIII, VIIIa, or VIIIb is a substituted or unsubstituted alkenyl group. In certain other embodiments, $R^{43}$ of formula VIII, VIIIa, or VIIIb is a substituted or unsubstituted alkynyl group. In some embodiments, $R^{43}$ of formula VIII, VIIIa, or VIIIb is an acyl group. In some embodiments, $R^{43}$ of formula VIII, VIIIa, or VIIIb is an amino group. In other embodiments, $R^{43}$ of formula VIII, VIIIa, or VIIIb is a protected amino group.

In some embodiments, $R^{44}$ of formula VIII, VIIIa, or VIIIb is hydrogen. In some embodiments, $R^{44}$ of formula VIII, VIIIa, or VIIIb is a halogen. In certain embodiments, $R^{44}$ of formula VIII, VIIIa, or VIIIb is chloro, bromo, or iodo. In certain embodiments, $R^{44}$ of formula VIII, VIIIa, or VIIIb is chloro. In certain embodiments, $R^{44}$ of formula VIII, VIIIa, or VIIIb is bromo. In certain embodiments, $R^{44}$ of formula VIII, VIIIa, or VIIIb is a hydroxyl or alkoxyl group. In some embodiments, $R^{44}$ of formula VIII, VIIIa, or VIIIb is a substituted or unsubstituted aliphatic group. In certain embodiments, $R^{44}$ of formula VIII, VIIIa, or VIIIb is a substituted or unsubstituted alkyl group. In certain embodiments, $R^{44}$ of formula VIII, VIIIa, or VIIIb is a substituted or unsubstituted aryl group. In certain embodiments, $R^{44}$ of formula VIII, VIIIa, or VIIIb is a substituted or unsubstituted alkenyl group. In certain other embodiments, $R^{44}$ of formula VIII, VIIIa, or VIIIb is a substituted or unsubstituted alkynyl group. In some embodiments, $R^{44}$ of formula VIII, VIIIa, or VIIIb is an acyl group. In some embodiments, $R^{44}$ of formula VIII, VIIIa, or VIIIb is an amino group. In other embodiments, $R^{44}$ of formula VIII, VIIIa, or VIIIb is a protected amino group.

In certain embodiments, $R_C$ of formula VIII, VIIIa, or VIIIb is a suitable hydroxyl protecting group, as defined herein. In certain embodiments, $R_C$ of formula VIII, VIIIa, or VIIIb is an acyl group. In certain embodiments, $R_C$ of formula VIII, VIIIa, or VIIIb is an ester group. In certain embodiments, $R_C$ of formula VIII, VIIIa, or VIIIb is an aliphatic group. In certain embodiments, $R_C$ of formula VIII, VIIIa, or VIIIb is a heteroaliphatic group. In certain embodiments, —$OR_C$ of formula VIII, VIIIa, or VIIIb is a phosphate group. In certain other embodiments, —$OR_C$ of formula VIII, VIIIa, or VIIIb is a sulfate group.

In certain embodiments, Z of formula VIII, VIIIa, or VIIIb is =O. In certain other embodiments, Z of formula VIII, VIIIa, or VIIIb is =N—$NHR_D$, wherein $R_D$ is as defined herein.

In some embodiments, compounds of formula VIII, VIIIa, or VIIIb are of the following formulae:

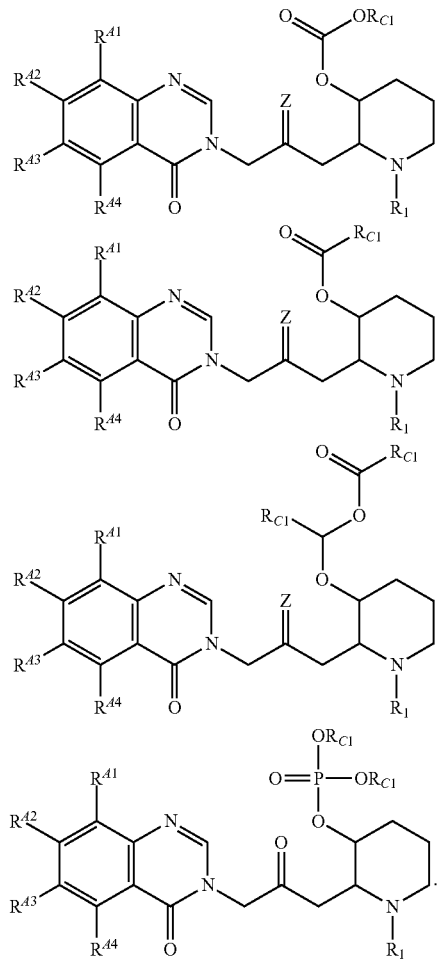

In some embodiments, compounds of formula VIII, VIIIa, or VIIIb are of the following formulae:

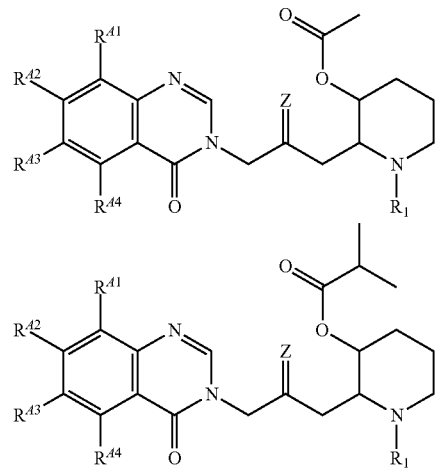

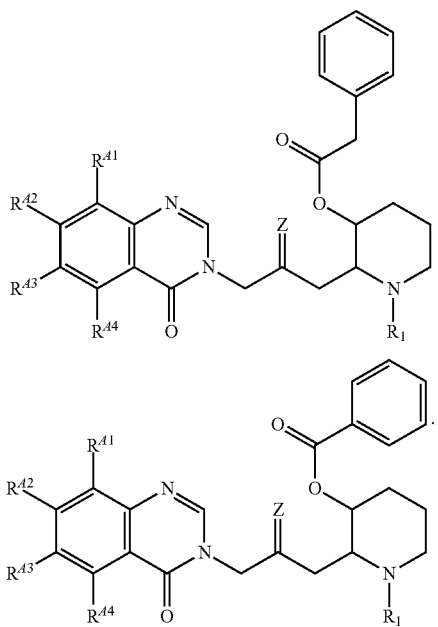
In some embodiments, compounds of formula VIII, VIIIa, or VIIIb are of the following formulae:
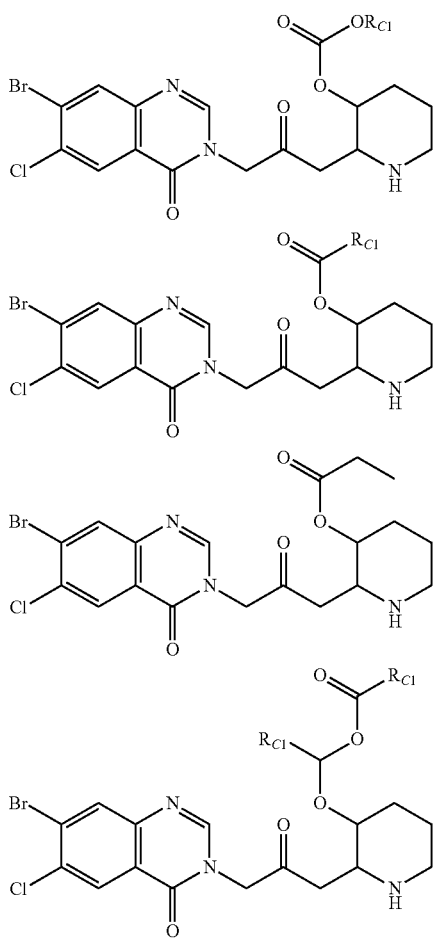
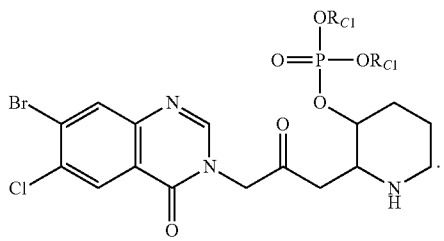
In some embodiments, compounds of formula VIII or VIIIa are of the following formulae:
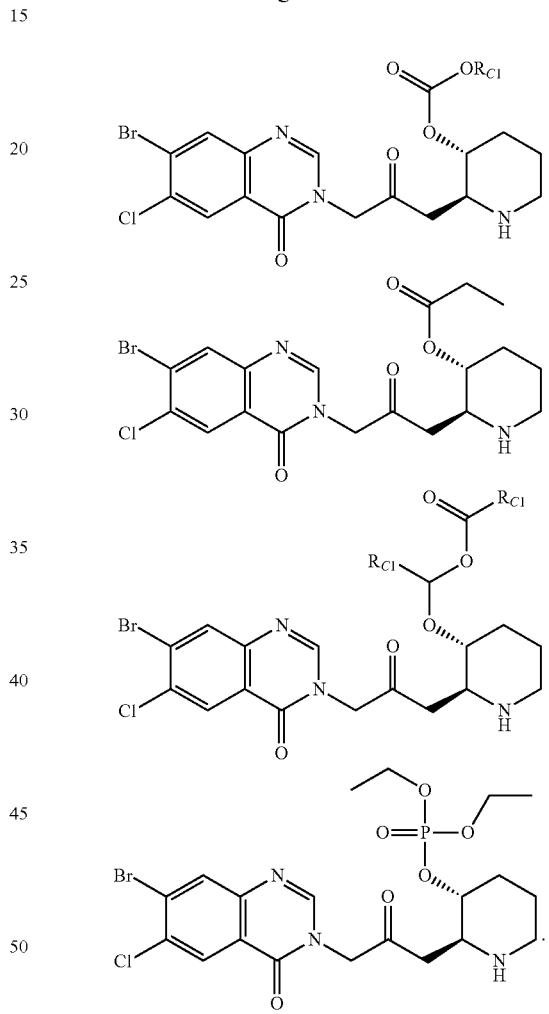
In some embodiments, compounds of formula VIII or VIIIb are of the following formulae:
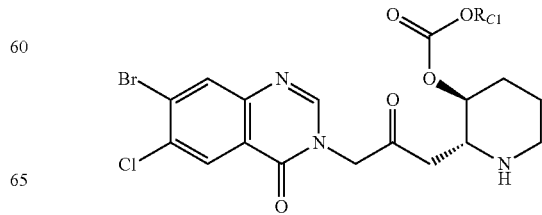

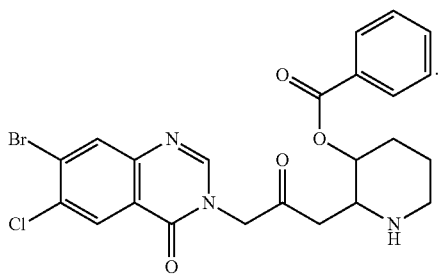
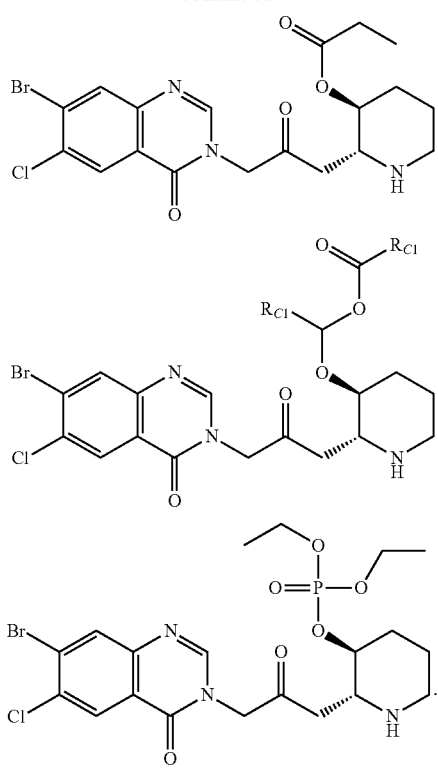
In some embodiments, compounds of formula VIII, VIIIa, or VIIIb are of the following formulae:
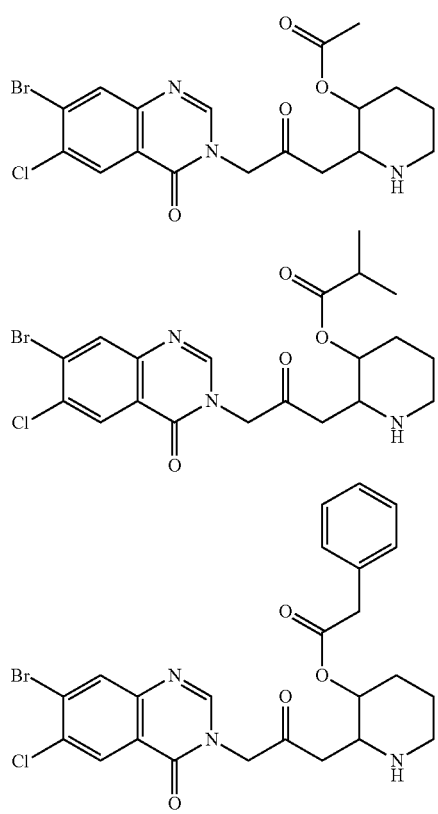
In some embodiments, compounds of formula VIII or VIIIa are of the following formulae:
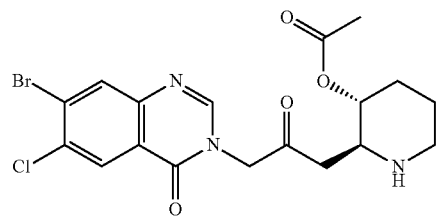
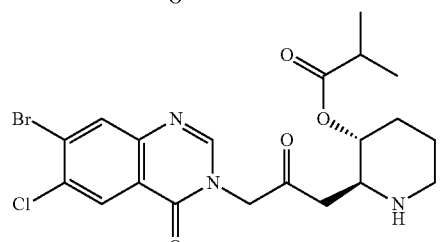
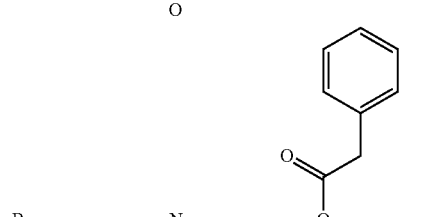
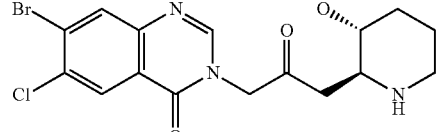
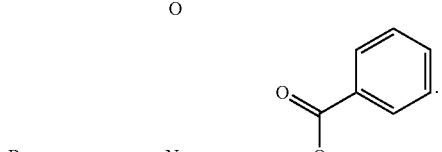
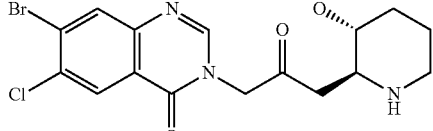
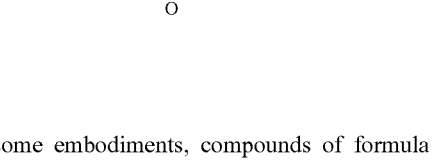
In some embodiments, compounds of formula VIII or VIIIb are of the following formulae:

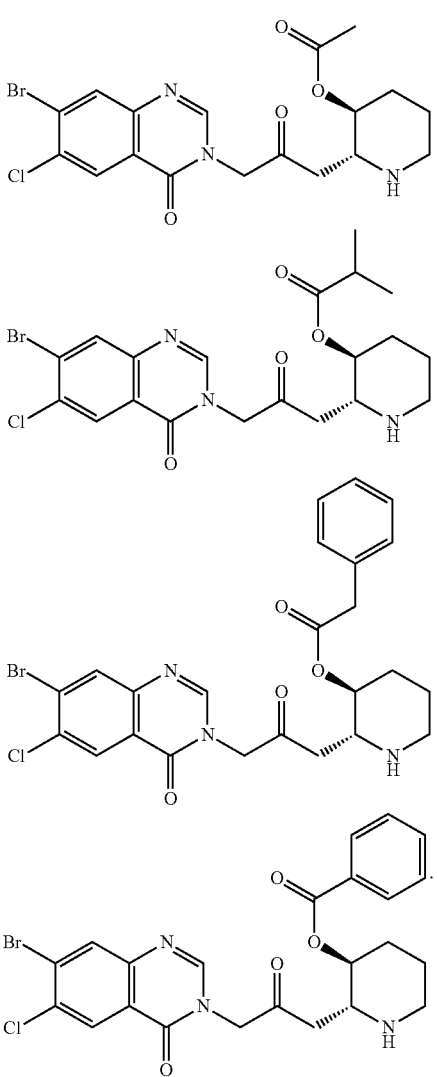

In certain embodiments, the invention provides a compound of formula (IX) or a pharmaceutically acceptable salt thereof:

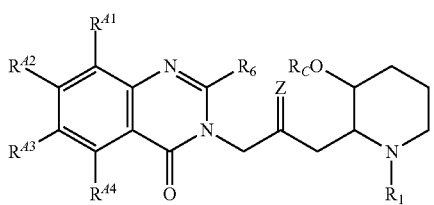

(IX)

wherein Z is =O or =N—NHR$_D$, wherein R$_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_1$ is a protecting group; an aliphatic moiety; a heteroaliphatic moiety; an acyl moiety; an aryl moiety; a heteroaryl moiety; —C(=O)R$_A$; —C(=O)OR$_A$; —C(=O)N(R$_A$)$_2$; —SO$_2$R$_A$; —S(=O)R$_A$; —C(R$_A$)$_2$NHC(=O)R$_A$; C(=O)OCH$_2$OC(=O)R$_A$; C(=O)OCH$_2$OC(=O)OR$_A$; or —C(R$_A$)$_2$OC(=O)R$_A$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; provided that R$_1$ is not —CO$_2$CH$_3$ or —CO$_2$CH$_2$CH=CH$_2$;

R$_C$ is hydrogen; a protecting group; an aliphatic moiety; a heteroaliphatic moiety; an acyl moiety; an aryl moiety; a heteroaryl moiety; —C(=O)R$_{C1}$; —C(=O)OR$_{C1}$; —C(=O)N(R$_{C1}$)$_2$; —P(=O)(OR$_{C1}$)$_2$; —S(=O)(OR$_{C1}$)$_2$; or —C(R$_{C1}$)$_2$OC(=O)R$_{C1}$; wherein each occurrence of R$_{C1}$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and R$^{A1}$, R$^{A2}$, R$^{A3}$, an R$^{A4}$ are independently hydrogen; halogen; substituted or unsubstituted aliphatic; substituted or unsubstituted heteroaliphatic; substituted or unsubstituted aryl; substituted or unsubstituted heteroaryl; —OR$_G$; —SR$_G$; —N(R$_G$)$_2$; and —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (IXa):

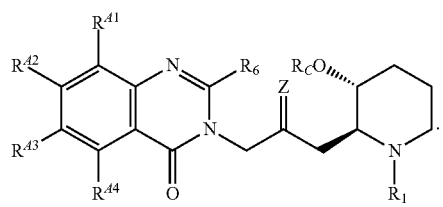

(IXa)

In certain embodiments, the compound is of the stereochemistry of formula (IXb):

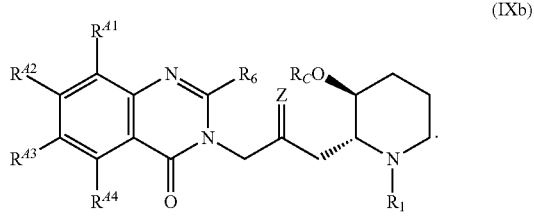

(IXb)

In certain embodiments, $R_1$ of formula IX, IXa, or IXb is a suitable amino protecting group, as defined herein. In certain embodiments, $R_1$ of formula IX, IXa, or IXb is an acyl group. In certain embodiments, $R_1$ of formula IX, IXa, or IXb is an ester group. In certain embodiments, $R_1$ of formula IX, IXa, or IXb is an aliphatic group. In certain embodiments, $R_1$ of formula IX, IXa, or IXb is a heteroaliphatic group.

In certain embodiments, $R_6$ of formula IX, IXa, or IXb is hydrogen. In certain other embodiments, $R_6$ of formula IX, IXa, or IXb is aliphatic. In certain embodiments, $R_6$ of formula IX, IXa, or IXb is alkyl.

In some embodiments, $R^{41}$ of formula IX, IXa, or IXb is hydrogen. In other embodiments, $R^{41}$ of formula IX, IXa, or IXb is a halogen. In certain embodiments, $R^{41}$ of formula IX, IXa, or IXb is chloro, bromo, or iodo. In certain embodiments, $R^{41}$ of formula IX, IXa, or IXb is a hydroxyl or alkoxy group. In some embodiments, $R^{41}$ of formula IX, IXa, or IXb is a substituted or unsubstituted aliphatic group. In certain embodiments, $R^{41}$ of formula IX, IXa, or IXb is a substituted or unsubstituted alkyl group. In certain embodiments, $R^{41}$ of formula IX, IXa, or IXb is a substituted or unsubstituted aryl group. In certain embodiments, $R^{41}$ of formula IX, IXa, or IXb is a substituted or unsubstituted alkenyl group. In certain other embodiments, $R^{41}$ of formula IX, IXa, or IXb is a substituted or unsubstituted alkynyl group. In some embodiments, $R^{41}$ of formula IX, IXa, or IXb is an acyl group. In some embodiments, $R^{41}$ of formula IX, IXa, or IXb is an amino group. In other embodiments, $R^{41}$ of formula IX, IXa, or IXb is a protected amino group.

In some embodiments, $R^{42}$ of formula IX, IXa, or IXb is hydrogen. In other embodiments, $R^{42}$ of formula IX, IXa, or IXb is a halogen. In certain embodiments, $R^{42}$ of formula IX, IXa, or IXb is chloro, bromo, or iodo. In certain embodiments, $R^{42}$ of formula IX, IXa, or IXb is bromo. In certain embodiments, $R^{42}$ of formula IX, IXa, or IXb is a hydroxyl or alkoxy group. In some embodiments, $R^{42}$ of formula IX, IXa, or IXb is a substituted or unsubstituted aliphatic group. In certain embodiments, $R^{42}$ of formula IX, IXa, or IXb is a substituted or unsubstituted alkyl group. In certain embodiments, $R^{42}$ of formula IX, IXa, or IXb is a substituted or unsubstituted aryl group. In certain embodiments, $R^{42}$ of formula IX, IXa, or IXb is a substituted or unsubstituted alkenyl group. In certain other embodiments, $R^{42}$ of formula IX, IXa, or IXb is a substituted or unsubstituted alkynyl group. In some embodiments, $R^{42}$ of formula IX, IXa, or IXb is an acyl group. In some embodiments, $R^{42}$ of formula IX, IXa, or IXb is an amino group. In other embodiments, $R^{42}$ of formula IX, IXa, or IXb is a protected amino group.

In some embodiments, $R^{43}$ of formula IX, IXa, or IXb is hydrogen. In other embodiments, $R^{43}$ of formula IX, IXa, or IXb is a halogen. In certain embodiments, $R^{43}$ of formula IX, IXa, or IXb is chloro, bromo, or iodo. In certain embodiments, $R^{43}$ of formula IX, IXa, or IXb is chloro. In certain embodiments, $R^{43}$ of formula IX, IXa, or IXb is a hydroxyl or alkoxy group. In some embodiments, $R^{43}$ of formula IX, IXa, or IXb is a substituted or unsubstituted aliphatic group. In certain embodiments, $R^{43}$ of formula IX, IXa, or IXb is a substituted or unsubstituted alkyl group. In certain embodiments, $R^{43}$ of formula IX, IXa, or IXb is a substituted or unsubstituted aryl group. In certain embodiments, $R^{43}$ of formula IX, IXa, or IXb is a substituted or unsubstituted alkenyl group. In certain other embodiments, $R^{43}$ of formula IX, IXa, or IXb is a substituted or unsubstituted alkynyl group. In some embodiments, $R^{43}$ of formula IX, IXa, or IXb is an acyl group. In some embodiments, $R^{43}$ of formula IX, IXa, or IXb is an amino group. In other embodiments, $R^{43}$ of formula IX, IXa, or IXb is a protected amino group.

In some embodiments, $R^{44}$ of formula IX, IXa, or IXb is hydrogen. In some embodiments, $R^{44}$ of formula IX, IXa, or IXb is a halogen. In certain embodiments, $R^{44}$ of formula IX, IXa, or IXb is chloro, bromo, or iodo. In certain embodiments, $R^{44}$ of formula IX, IXa, or IXb is chloro. In certain embodiments, $R^{44}$ of formula IX, IXa, or IXb is bromo. In certain embodiments, $R^{44}$ of formula IX, IXa, or IXb is a hydroxyl or alkoxy group. In some embodiments, $R^{44}$ of formula IX, IXa, or IXb is a substituted or unsubstituted aliphatic group. In certain embodiments, $R^{44}$ of formula IX, IXa, or IXb is a substituted or unsubstituted alkyl group. In certain embodiments, $R^{44}$ of formula IX, IXa, or IXb is a substituted or unsubstituted aryl group. In certain embodiments, $R^{44}$ of formula IX, IXa, or IXb is a substituted or unsubstituted alkenyl group. In certain other embodiments, $R^{44}$ of formula IX, IXa, or IXb is a substituted or unsubstituted alkynyl group. In some embodiments, $R^{44}$ of formula IX, IXa, or IXb is an acyl group. In some embodiments, $R^{44}$ of formula IX, IXa, or IXb is an amino group. In other embodiments, $R^{44}$ of formula IX, IXa, or IXb is a protected amino group.

In certain embodiments, $R_C$ of formula IX, IXa, or IXb is hydrogen. In certain embodiments, $R_C$ of formula IX, IXa, or IXb is a suitable hydroxyl protecting group, as defined herein. In certain embodiments, $R_C$ of formula IX, IXa, or IXb is an acyl group. In certain embodiments, $R_C$ of formula IX, IXa, or IXb is an ester group. In certain embodiments, $R_C$ of formula IX, IXa, or IXb is an aliphatic group. In certain embodiments, $R_C$ of formula IX, IXa, or IXb is a heteroaliphatic group. In certain embodiments, —$OR_C$ of formula IX, IXa, or IXb is a phosphate group. In certain other embodiments, —$OR_C$ of formula IX, IXa, or IXb is a sulfate group.

In certain embodiments, Z of formula IX, IXa, or IXb is =O. In certain other embodiments, Z of formula IX, IXa, or IXb is =N—$NHR_D$, where $R_D$ is as defined herein.

In some embodiments, compounds of formula IX, IXa, or IXb are of the following formulae:

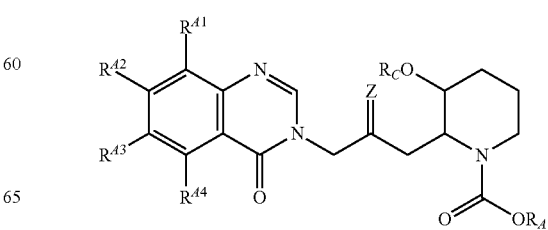

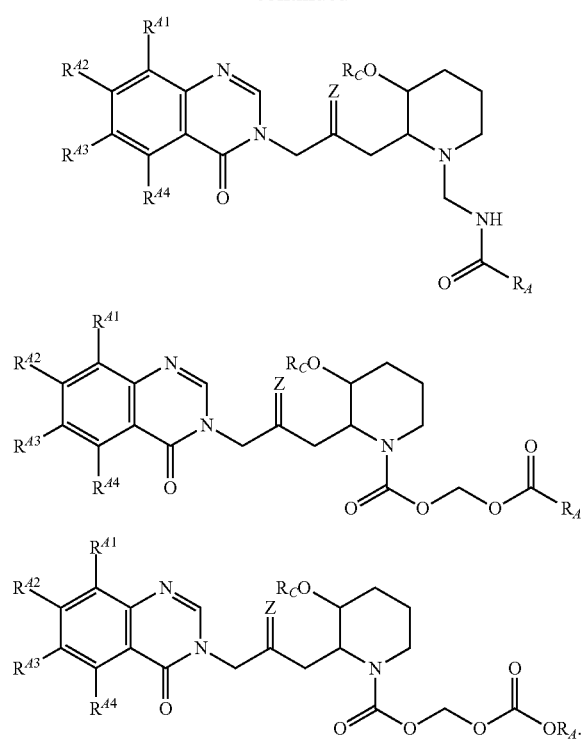

In some embodiments, compounds of formula IX, IXa, or IXb are of the following formulae:

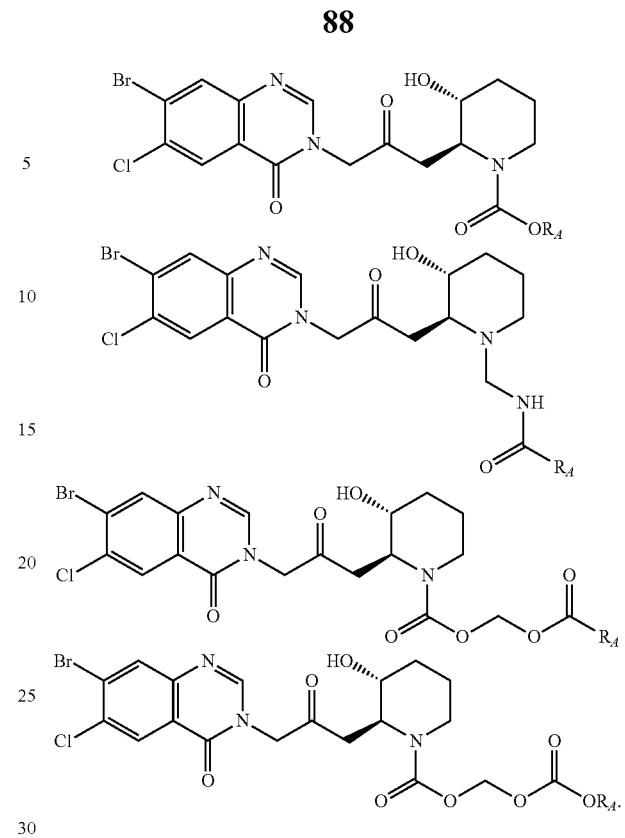

In some embodiments, compounds of formula IX or IXb are of the following formulae:

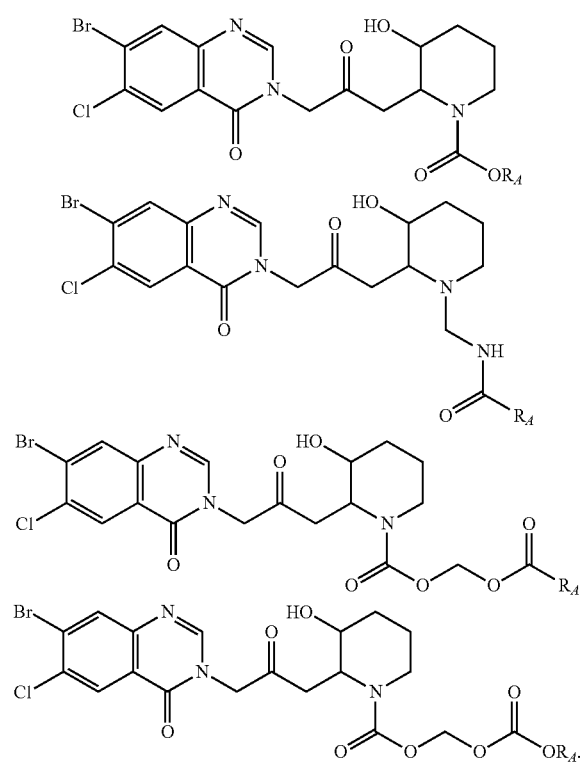

In some embodiments, compounds of formula IX or IXa are of the following formulae:

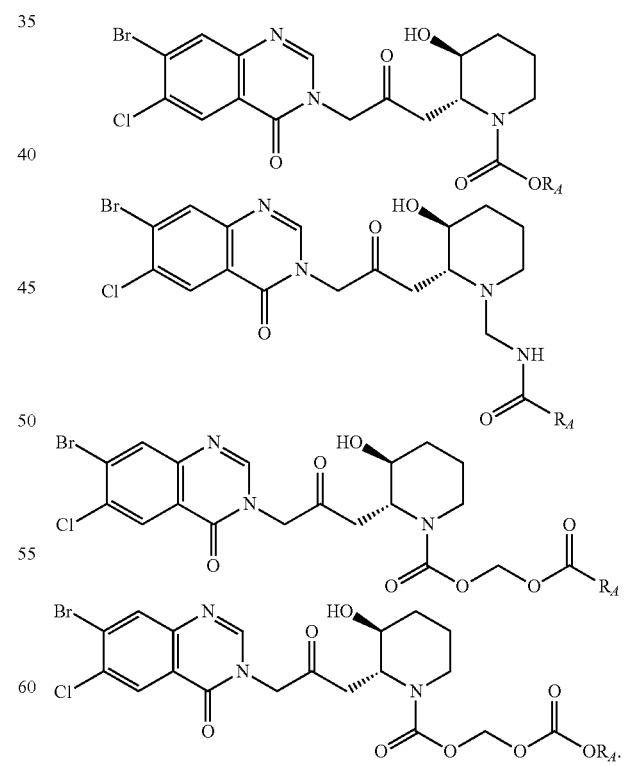

In certain embodiments, the invention provides a compound of formula (X) or a pharmaceutically acceptable salt thereof:

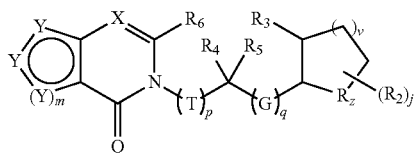

(X)

wherein
j is an integer between 0 and 10, inclusive;
p is an integer between 0 and 6, inclusive;
q is an integer between 0 and 6, inclusive;
m is an integer between 1 and 2, inclusive;
v is an integer between 1 and 3, inclusive;

X is N or $CR_X$, wherein $R_X$ is hydrogen; halogen; substituted or unsubstituted aliphatic; substituted or unsubstituted heteroaliphatic; substituted or unsubstituted aryl; substituted or unsubstituted heteroaryl; —$OR_F$; —$SR_F$; —$N(R_F)_2$; and —$C(R_F)_3$; wherein each occurrence of $R_F$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of Y is S, O, N, $NR_Y$, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of T and G is independently —S—, —O—, —$NR_E$—, or $C(R_E)_2$—, wherein each occurrence of $R_E$ is independently hydrogen; halogen; substituted or unsubstituted aliphatic; substituted or unsubstituted heteroaliphatic; substituted or unsubstituted aryl; substituted or unsubstituted heteroaryl; —$OR_G$; —$SR_G$; —$N(R_G)_2$; and —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_Z$ is —O— or —S—;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_4$ and $R_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —$C(=O)N(R_D)_2$; —CN; —SCN; —$SR_D$; —$SOR_D$; —$SO_2R_D$; —$NO_2$; —$N(R_D)_2$; —$NHC(O)R_D$; or —$C(R_D)_3$; wherein each occurrence of $R_D$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; or $R_4$ and $R_5$ may optionally be taken together to form =O, =S, =$NR_D$, =N—$OR_D$, =N—$NHR_D$, =N—$N(R_D)_2$, =$C(R_D)_2$; or $R_4$ and $R_5$ may optionally be taken together with the intervening atom to form a saturated or unsaturated, substituted or unsubstituted cyclic or heterocyclic structure; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (Xa):

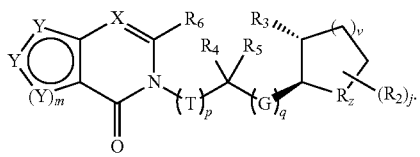

(Xa)

In certain embodiments, the compound is of the stereochemistry of formula (Xb):

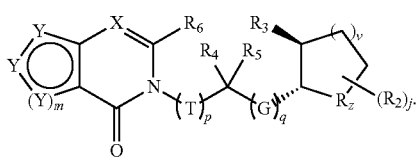

(Xb)

In certain embodiments, $R_z$ of formula X, Xa, or Xb is —O—. In certain other embodiments, $R_z$ of formula X, Xa, or Xb is —S—.

In some embodiments, $R_2$ of formula X, Xa, or Xb is hydrogen. In other embodiments, $R_2$ of formula X, Xa, or Xb is a halogen. In certain embodiments, $R_2$ of formula X, Xa, or Xb is chloro, bromo, or iodo. In certain embodiments, $R_2$ of formula X, Xa, or Xb is a hydroxyl or alkoxyl group. In some embodiments, $R_2$ of formula X, Xa, or Xb is a substituted or unsubstituted aliphatic group. In certain embodiments, $R_2$ of formula X, Xa, or Xb is a substituted or unsubstituted aryl group. In certain embodiments, $R_2$ of formula X, Xa, or Xb is an amino group. In certain other embodiments, $R_2$ of formula X, Xa, or Xb is a cyano group. In some embodiments, $R_2$ of formula X, Xa, or Xb is a carboxylic acid or ester group.

In certain embodiments, $R_3$ of formula X, Xa, or Xb is hydrogen. In certain other embodiments, $R_3$ of formula X, Xa, or Xb is hydroxyl. In certain embodiments, $R_3$ of formula X, Xa, or Xb is alkoxy. In certain embodiments, $R_3$ of formula X, Xa, or Xb is a protected hydroxyl group. In certain embodiments, $R_3$ of formula X, Xa, or Xb is phosphate. In certain embodiments, $R_3$ of formula X, Xa, or Xb is sulfate. In certain other embodiments, $R_3$ of formula X, Xa, or Xb is acetate (—OAc). In some embodiments, $R_3$ of formula X, Xa, or Xb is a thioxy group. In some embodiments, $R_3$ of formula X, Xa, or Xb is an amino group. In some embodiments, $R_3$ of formula X, Xa, or Xb is a protected amino group.

In certain embodiments, $R_4$ of formula X, Xa, or Xb is hydrogen. In certain other embodiments, $R_4$ of formula X, Xa, or Xb is hydroxyl. In certain embodiments, $R_4$ of formula X, Xa, or Xb is alkoxy. In certain embodiments, $R_4$ of formula X, Xa, or Xb is a protected hydroxyl group. In certain embodiments, $R_4$ of formula X, Xa, or Xb is a substituted or unsubstituted aliphatic or heteroaliphatic group. In some embodiments, $R_4$ of formula X, Xa, or Xb is an amino group. In some embodiments, $R_4$ of formula X, Xa, or Xb is a protected amino group.

In certain embodiments, $R_5$ of formula X, Xa, or Xb is hydrogen. In certain other embodiments, $R_5$ of formula X, Xa, or Xb is hydroxyl. In certain embodiments, $R_5$ of formula X, Xa, or Xb is alkoxy. In certain embodiments, $R_5$ of formula X, Xa, or Xb is a protected hydroxyl group. In certain embodiments, $R_5$ of formula X, Xa, or Xb is a substituted or unsubstituted aliphatic or heteroaliphatic group. In some embodiments, $R_5$ of formula X, Xa, or Xb is an amino group. In some embodiments, $R_5$ of formula X, Xa, or Xb is a protected amino group.

In certain embodiments, $R_4$ and $R_5$ of formula X, Xa, or Xb are taken together to form =O. In some embodiments, $R_4$ and $R_5$ of formula X, Xa, or Xb are taken together to form =S. In other embodiments, $R_4$ and $R_5$ of formula X, Xa, or Xb are taken together to form =$NR_D$, and $R_D$ is as described herein. In certain embodiments, $R_4$ and $R_5$ of formula X, Xa, or Xb are taken together to form =N—$OR_D$. In certain other embodiments, $R_4$ and $R_5$ of formula X, Xa, or Xb are taken together to form =N—$NHR_D$. In certain other embodiments, $R_4$ and $R_5$ of formula X, Xa, or Xb are taken together to form =N—$N(R_D)_2$. In some embodiments, $R_4$ and $R_5$ of formula X, Xa, or Xb are taken together to form =$C(R_D)_2$. In certain embodiments, $R_4$ and $R_5$ of formula X, Xa, or Xb are taken together to form =$CH_2$.

In some embodiments, $R_4$ and $R_5$ of formula X, Xa, or Xb are taken together with the intervening carbon to form a ring. In some embodiments, the ring formed is an oxetane ring. In certain embodiments, the ring formed is an aziridine ring. In certain embodiments, the ring formed is an azetidine ring. In certain embodiments, the ring formed is an epoxide ring. In certain other embodiments, the ring formed is a cyclopropyl ring. In some embodiments, the ring formed is a cyclic acetal.

In certain embodiments, $R_6$ of formula X, Xa, or Xb is hydrogen. In certain other embodiments, $R_6$ of formula X, Xa, or Xb is aliphatic. In certain embodiments, $R_6$ of formula X, Xa, or Xb is alkyl.

In certain embodiments, j of formula X, Xa, or Xb is 0. In certain embodiments, j is 1. In certain embodiments, j is 2, 3, 4, 5, 6, 7, 8, 9, or 10.

In some embodiments, m of formula X, Xa, or Xb is 1. In other embodiments, m of formula X, Xa, or Xb is 2.

In some embodiments, at least one instance of Y of formula X, Xa, or Xb is CH. In some embodiments, Y of formula X, Xa, or Xb is $CR_Y$, where $R_Y$ is as defined herein. In other embodiments, Y is S. In certain embodiments, Y is N. In certain other embodiments, Y is $NR_Y$. In other embodiments, Y is O. In some embodiments, all instances of Y are $CR_Y$. In other embodiments, at least one instance of Y is not $CR_Y$. In yet other embodiments, at least two instances of Y are not $CR_Y$.

In some embodiments, $R_Y$ of formula X, Xa, or Xb is hydrogen. In other embodiments, $R_Y$ of formula X, Xa, or Xb is a halogen. In certain embodiments, $R_Y$ of formula X, Xa, or Xb is chloro, bromo, or iodo. In certain embodiments, $R_Y$ of formula X, Xa, or Xb is a hydroxyl or alkoxy group. In some embodiments, $R_Y$ of formula X, Xa, or Xb is a substituted or unsubstituted aliphatic group. In certain embodiments, $R_Y$ of formula X, Xa, or Xb is a substituted or unsubstituted alkyl group. In certain embodiments, $R_Y$ of formula X, Xa, or Xb is a substituted or unsubstituted aryl group. In certain embodiments, $R_Y$ of formula X, Xa, or Xb is a substituted or unsubstituted alkenyl group. In certain other embodiments, $R_Y$ of formula X, Xa, or Xb is a substituted or unsubstituted alkynyl group. In some embodiments, $R_Y$ of formula X, Xa, or Xb is an acyl group. In other embodiments, $R_Y$ of formula X, Xa, or Xb is an amino group. In certain embodiments, $R_Y$ of formula X, Xa, or Xb is a protected amino group.

In certain embodiments, Y of formula X, Xa, or Xb is $CR_Y$ and $R_Y$ is hydrogen. In some embodiments, Y of formula X, Xa, or Xb is $CR_Y$ and $R_Y$ is bromo. In other embodiments, Y of formula X, Xa, or Xb is $CR_Y$ and $R_Y$ is chloro.

In certain embodiments, T of formula X, Xa, or Xb is —$C(R_E)_2$—, where $R_E$ is as defined herein. In some embodiments, T is —O—. In other embodiments, T is —S—. In certain embodiments, T is —NR$_E$—. In certain embodiments, p is 1. In other embodiments, p is 2, 3, 4, 5, or 6.

In certain embodiments, G of formula X, Xa, or Xb is —C(R$_E$)$_2$—, where R$_E$ is as defined herein. In some embodiments, G is —O—. In other embodiments, G is —S—. In certain embodiments, G is —NR$_E$—. In certain embodiments, q is 1. In other embodiments, q is 2, 3, 4, 5, or 6.

In some embodiments, compounds of formula X, Xa, or Xb are of the following formulae:

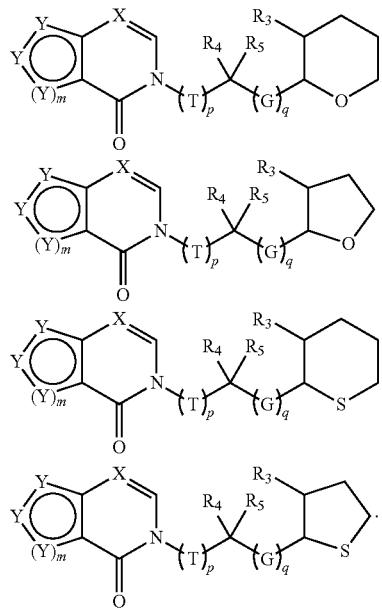

In some embodiments, compounds of formula X, Xa, or Xb are of the following formulae:

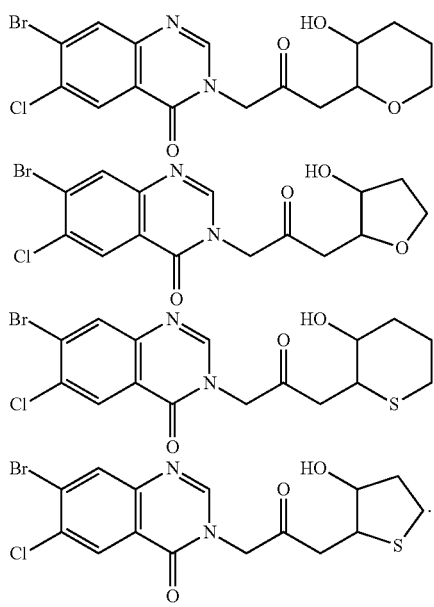

In some embodiments, compounds of formula X or Xa are of the following formulae:

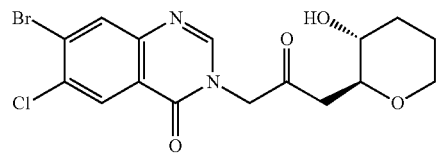

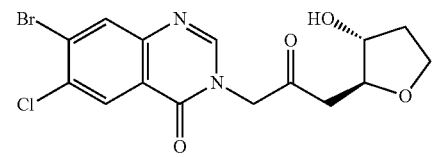

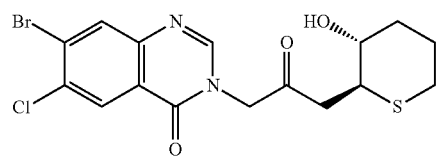

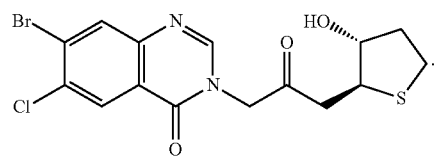

In some embodiments, compounds of formula X or Xb are of the following formulae:

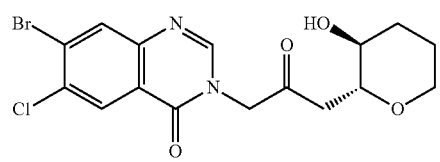

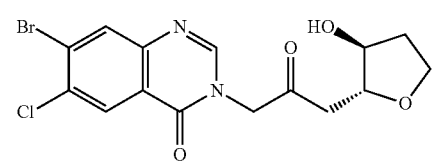

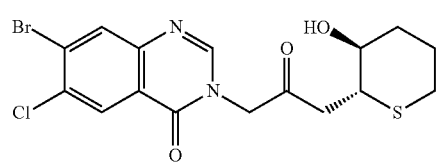

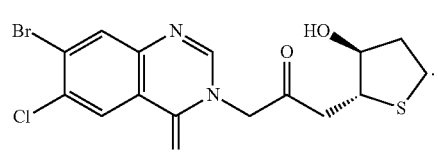

In certain embodiments, the invention provides a compound of formula (XI) or a pharmaceutically acceptable salt thereof:

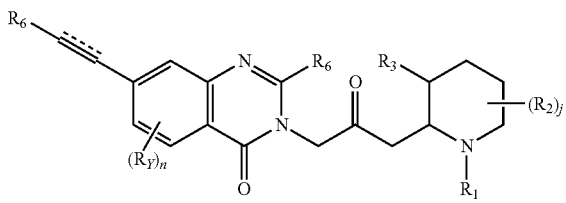

(XI)

wherein

≡≡≡ represents a double or triple bond;

n is an integer between 0 and 3, inclusive;

j is an integer between 0 and 8, inclusive;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_A$; —C(=O)O$R_A$; —C(=O)N($R_A$)$_2$; or —C($R_A$)$_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_G$; —C(=O)$R_G$; —CO$_2R_G$; —C(=O)N($R_G$)$_2$; —CN; —SCN; —S$R_G$; —SO$R_G$; —SO$_2R_G$; —NO$_2$; —N($R_G$)$_2$; —NHC(O)$R_G$; or —C($R_G$)$_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_B$; —C(=O)$R_B$; —CO$_2R_B$; —C(=O)N($R_B$)$_2$; —CN; —SCN; —S$R_B$; —SO$R_B$; —SO$_2R_B$; —NO$_2$; —N($R_B$)$_2$; —NHC(O)$R_B$; or —C($R_B$)$_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$; —CO$_2R_C$; —C(=O)N($R_C$)$_2$; —CN; —SCN; —S$R_C$; —SO$R_C$; —SO$_2R_C$; —NO$_2$; —N($R_C$)$_2$; —NHC(O)$R_C$; or —C($R_C$)$_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_K$; —C(=O)$R_K$; —CO$_2R_K$; —C(=O)N($R_K$)$_2$; —CN; —SCN; —S$R_K$; —SO$R_K$; —SO$_2R_K$; —NO$_2$; —N($R_K$)$_2$; —NHC(O)$R_K$; or —C($R_K$)$_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R_7$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_C$; —C(=O)$R_C$; —CO$_2R_C$; —C(=O)N($R_C$)$_2$; —CN; —SCN; —S$R_C$; —SO$R_C$; —SO$_2R_C$; —NO$_2$; —N($R_C$)$_2$; —NHC(O)$R_C$; —Si($R_C$)$_3$; or —C($R_C$)$_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (XIa):

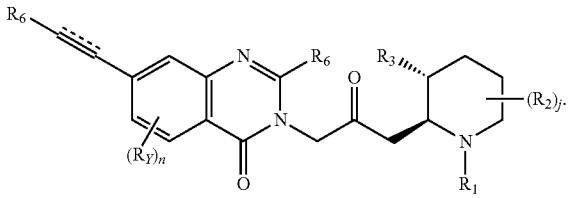

(XIa)

In certain embodiments, the compound is of the stereochemistry of formula (XIb):

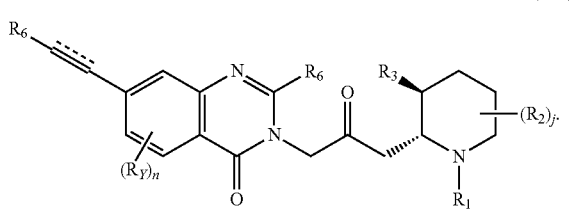

(XIb)

In certain embodiments, ≡ of formula XI, XIa, or XIb represents a triple bond. In certain other embodiments, ≡ of formula XI, XIa, or XIb represents a double bond.

In certain embodiments, $R_1$ of formula XI, XIa, or XIb is hydrogen. In certain other embodiments, $R_1$ of formula XI, XIa, or XIb is a suitable amino protecting group, as defined herein.

In some embodiments, $R_2$ of formula XI, XIa, or XIb is hydrogen. In other embodiments, $R_2$ of formula XI, XIa, or XIb is a halogen. In certain embodiments, $R_2$ of formula XI, XIa, or XIb is chloro, bromo, or iodo. In certain embodiments, $R_2$ of formula XI, XIa, or XIb is a hydroxyl or alkoxyl group. In some embodiments, $R_2$ of formula XI, XIa, or XIb is a substituted or unsubstituted aliphatic group. In certain embodiments, $R_2$ of formula XI, XIa, or XIb is a substituted or unsubstituted aryl group. In certain embodiments, $R_2$ of formula XI, XIa, or XIb is an amino group. In certain other embodiments, $R_2$ of formula XI, XIa, or XIb is a cyano group. In some embodiments, $R_2$ of formula XI, XIa, or XIb is a carboxylic acid or ester group.

In certain embodiments, $R_3$ of formula XI, XIa, or XIb is hydrogen. In certain other embodiments, $R_3$ of formula XI, XIa, or XIb is hydroxyl. In certain embodiments, $R_3$ of formula XI, XIa, or XIb is alkoxy. In certain embodiments, $R_3$ of formula XI, XIa, or XIb is a protected hydroxyl group. In certain embodiments, $R_3$ of formula XI, XIa, or XIb is phosphate. In certain embodiments, $R_3$ of formula XI, XIa, or XIb is sulfate. In certain other embodiments, $R_3$ of formula XI, XIa, or XIb is acetate (—OAc). In some embodiments, $R_3$ of formula XI, XIa, or XIb is a thioxy group. In some embodiments, $R_3$ of formula XI, XIa, or XIb is an amino group. In some embodiments, $R_3$ of formula XI, XIa, or XIb is a protected amino group.

In certain embodiments, $R_6$ of formula XI, XIa, or XIb is hydrogen. In certain other embodiments, $R_6$ of formula XI, XIa, or XIb is aliphatic. In certain embodiments, $R_6$ of formula XI, XIa, or XIb is alkyl.

In certain embodiments, j of formula XI, XIa, or XIb is 0. In certain embodiments, j is 1. In certain embodiments, j is 2. In certain embodiments, j is 3, 4, 5, 6, 7, or 8.

In some embodiments, $R_7$ of formula XI, XIa, or XIb is hydrogen. In other embodiments, $R_7$ of formula XI, XIa, or XIb is a halogen. In some embodiments, $R_7$ of formula XI, XIa, or XIb is a silyl group. In certain embodiments, $R_7$ of formula XI, XIa, or XIb is a trialkylsilyl group. In some embodiments, $R_7$ of formula XI, XIa, or XIb is a substituted or unsubstituted aliphatic group. In some embodiments, $R_7$ of formula XI, XIa, or XIb is a substituted or unsubstituted heteroaliphatic group. In certain embodiments, $R_7$ of formula XI, XIa, or XIb is a substituted or unsubstituted aryl group. In some embodiments, $R_7$ of formula XI, XIa, or XIb is a carboxylic acid or ester group. In other embodiments, $R_7$ of formula XI, XIa, or XIb is an amide group.

In some embodiments, $R_Y$ of formula XI, XIa, or XIb is hydrogen. In other embodiments, $R_Y$ of formula XI, XIa, or XIb is a halogen. In certain embodiments, $R_Y$ of formula XI, XIa, or XIb is chloro, bromo, or iodo. In certain embodiments, $R_Y$ of formula XI, XIa, or XIb is a hydroxyl or alkoxyl group. In some embodiments, $R_Y$ of formula XI, XIa, or XIb is a substituted or unsubstituted aliphatic group. In certain embodiments, $R_Y$ of formula XI, XIa, or XIb is a substituted or unsubstituted alkyl group. In certain embodiments, $R_Y$ of formula XI, XIa, or XIb is a substituted or unsubstituted aryl group. In certain embodiments, $R_Y$ of formula XI, XIa, or XIb is a substituted or unsubstituted alkenyl group. In certain other embodiments, $R_Y$ of formula XI, XIa, or XIb is a substituted or unsubstituted alkynyl group. In some embodiments, $R_Y$ of formula XI, XIa, or XIb is an acyl group. In other embodiments, $R_Y$ of formula XI, XIa, or XIb is an amino group. In certain embodiments, $R_Y$ of formula XI, XIa, or XIb is a protected amino group.

In some embodiments, n of formula XI, XIa, or XIb is 0, 1, 2, or 3. In some embodiments, n is 0. In certain embodiments, n is 1. In certain other embodiments, n is 2. In some embodiments, n is 3.

In some embodiments, compounds of formula XI, XIa, or XIb are of the following formulae:

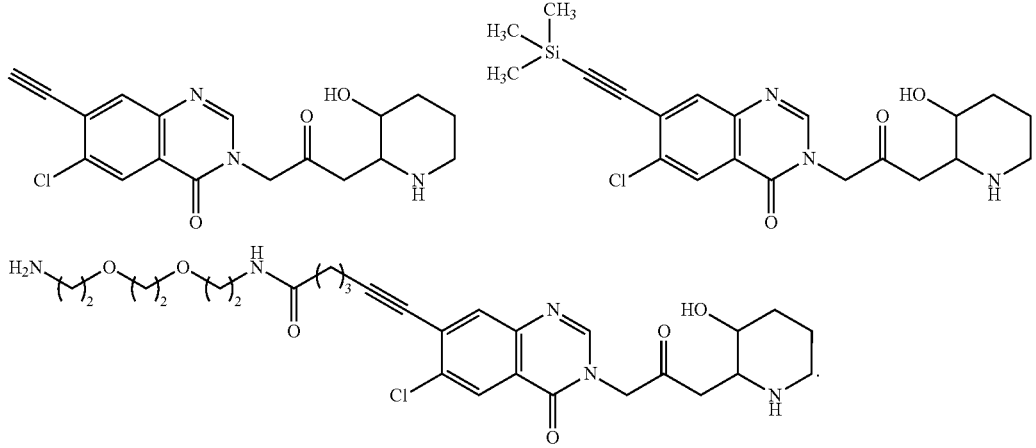

Exemplary compounds of formula XI or XIa include:

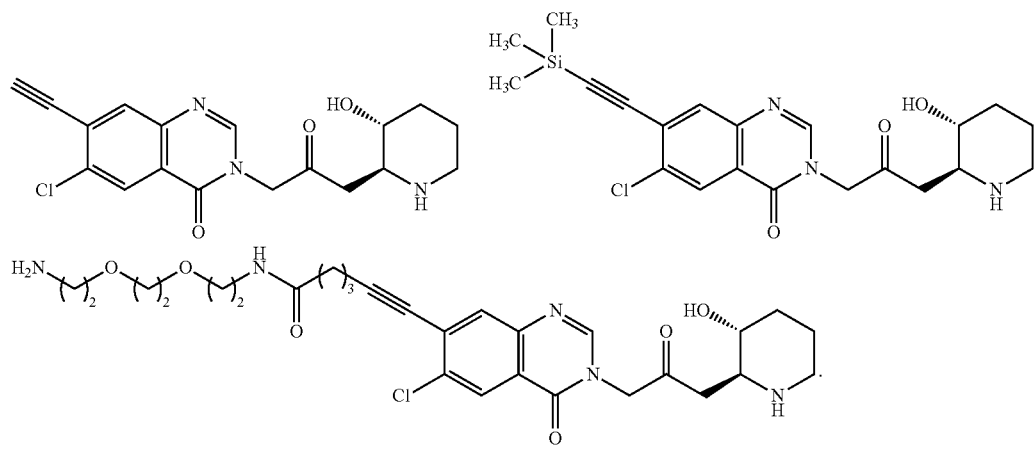

Exemplary compounds of formula XI or XIb include:

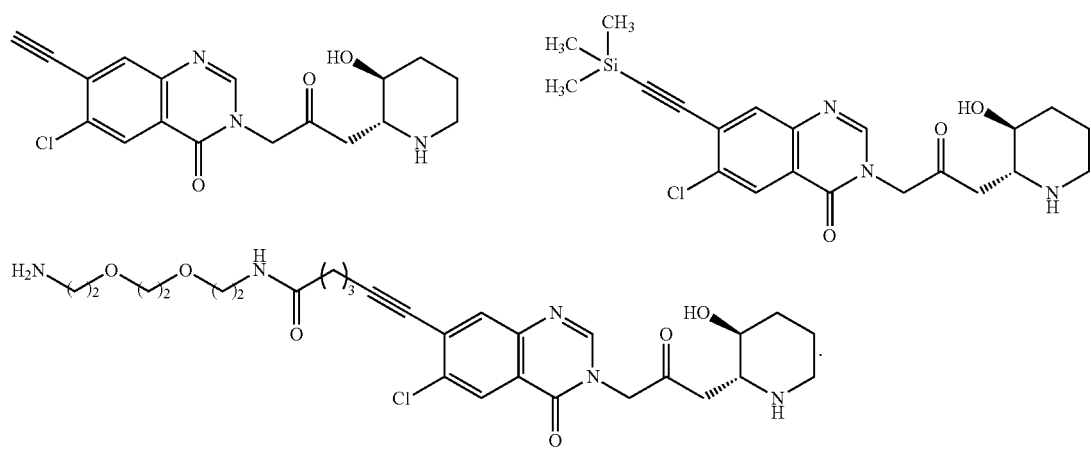

In certain embodiments, the invention provides a compound of formula (XII) or a pharmaceutically acceptable salt thereof:

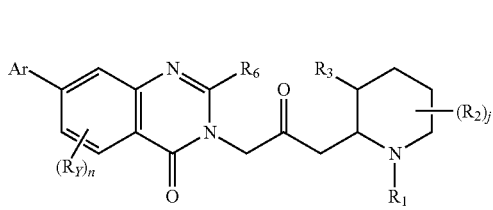

(XII)

wherein
Ar represents a substituted or unsubstituted aryl or heteroaryl group; n is an integer between 0 and 3, inclusive;
j is an integer between 0 and 8, inclusive;
$R_1$ is hydrogen; a protecting group; cyclic or acyclic, substituted or unsubstituted, branched or unbranched aliphatic; cyclic or acyclic, substituted or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R_A$; —C(=O)O$R_A$; —C(=O)N($R_A$)$_2$; or —C($R_A$)$_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —O$R_G$; —C(=O)$R_G$; —CO$_2R_G$; —C(=O)N($R_G$)$_2$; —CN; —SCN; —S$R_G$; —SO$R_G$; —SO$_2R_G$; —NO$_2$; —N($R_G$)$_2$; —NHC(O)$R_G$; or —C($R_G$)$_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (XIIa):

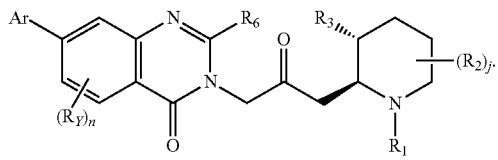

(XIIa)

In certain embodiments, the compound is of the stereochemistry of formula (XIIb):

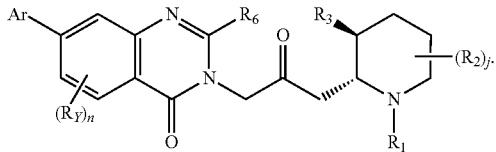

(XIIb)

In certain embodiments, $R_1$ of formula XII, XIIa, or XIIb is hydrogen. In certain other embodiments, $R_1$ of formula XII, XIIa, or XIIb is a suitable amino protecting group, as defined herein.

In some embodiments, $R_2$ of formula XII, XIIa, or XIIb is hydrogen. In other embodiments, $R_2$ of formula XII, XIIa, or XIIb is a halogen. In certain embodiments, $R_2$ of formula XII, XIIa, or XIIb is chloro, bromo, or iodo. In certain embodiments, $R_2$ of formula XII, XIIa, or XIIb is a hydroxyl or alkoxyl group. In some embodiments, $R_2$ of formula XII, XIIa, or XIIb is a substituted or unsubstituted aliphatic group. In certain embodiments, $R_2$ of formula XII, XIIa, or XIIb is a substituted or unsubstituted aryl group. In certain embodiments, $R_2$ of formula XII, XIIa, or XIIb is an amino group. In certain other embodiments, $R_2$ of formula XII, XIIa, or XIIb is a cyano group. In some embodiments, $R_2$ of formula XII, XIIa, or XIIb is a carboxylic acid or ester group.

In certain embodiments, $R_3$ of formula XII, XIIa, or XIIb is hydrogen. In certain other embodiments, $R_3$ of formula XII, XIIa, or XIIb is hydroxyl. In certain embodiments, $R_3$ of formula XII, XIIa, or XIIb is alkoxy. In certain embodiments, $R_3$ of formula XII, XIIa, or XIIb is a protected hydroxyl group. In certain embodiments, $R_3$ of formula XII, XIIa, or XIIb is phosphate. In certain embodiments, $R_3$ of formula XII, XIIa, or XIIb is sulfate. In certain other embodiments, $R_3$ of formula XII, XIIa, or XIIb is acetate (—OAc). In some embodiments, $R_3$ of formula XII, XIIa, or XIIb is a thioxy group. In some embodiments, $R_3$ of formula XII, XIIa, or XIIb is an amino group. In some embodiments, $R_3$ of formula XII, XIIa, or XIIb is a protected amino group.

In certain embodiments, $R_6$ of formula XII, XIIa, or XIIb is hydrogen. In certain other embodiments, $R_6$ of formula XII, XIIa, or XIIb is aliphatic. In certain embodiments, $R_6$ of formula XII, XIIa, or XIIb is alkyl.

In certain embodiments, j of formula XII, XIIa, or XIIb is 0. In certain embodiments, j is 1. In certain embodiments, j is 2. In certain embodiments, j is 3, 4, 5, 6, 7, or 8.

In some embodiments, $R_Y$ of formula XII, XIIa, or XIIb is hydrogen. In other embodiments, $R_Y$ of formula XII, XIIa, or XIIb is a halogen. In certain embodiments, $R_Y$ of formula XII, XIIa, or XIIb is chloro, bromo, or iodo. In certain embodiments, $R_Y$ of formula XII, XIIa, or XIIb is a hydroxyl or alkoxyl group. In some embodiments, $R_Y$ of formula XII, XIIa, or XIIb is a substituted or unsubstituted aliphatic group. In certain embodiments, $R_Y$ of formula XII, XIIa, or XIIb is a substituted or unsubstituted alkyl group. In certain embodiments, $R_Y$ of formula XII, XIIa, or XIIb is a substituted or unsubstituted aryl group. In certain embodiments, $R_Y$ of formula XII, XIIa, or XIIb is a substituted or unsubstituted alkenyl group. In certain other embodiments, $R_Y$ of formula XII, XIIa, or XIIb is a substituted or unsubstituted alkynyl group. In some embodiments, $R_Y$ of formula XII, XIIa, or XIIb is an acyl group. In other embodiments, $R_Y$ of formula XII, XIIa, or XIIb is an amino group. In certain embodiments, $R_Y$ of formula XII, XIIa, or XIIb is a protected amino group.

In certain embodiments, Y of formula XII, XIIa, or XIIb is $CR_Y$ and $R_Y$ is hydrogen. In some embodiments, Y of formula XII, XIIa, or XIIb is $CR_Y$ and $R_Y$ is bromo. In other embodiments, Y of formula XII, XIIa, or XIIb is $CR_Y$ and $R_Y$ is chloro.

In some embodiments, Ar of formula XII, XIIa, or XIIb is phenyl. In other embodiments, Ar of formula XII, XIIa, or XIIb is a nitrogen-containing heterocycle. In some embodiments, Ar of formula XII, XIIa, or XIIb is an oxygen-containing heterocycle. In certain embodiments, Ar of formula XII, XIIa, or XIIb is pyridyl. In some embodiments, Ar of formula XII, XIIa, or XIIb is pyrimidinyl. In some embodiments, Ar of formula XII, XIIa, or XIIb is triazolyl. In certain embodiments, Ar of formula XII, XIIa, or XIIb is thiazolyl. In some embodiments, Ar of formula XII, XIIa, or XIIb is furyl. In other embodiments, Ar of formula XII, XIIa, or XIIb is thienyl.

In some embodiments, n of formula XII, XIIa, or XIIb is 0, 1, 2, or 3. In some embodiments, n is 0. In certain embodiments, n is 1. In certain other embodiments, n is 2. In some embodiments, n is 3.

In certain embodiments, the invention provides a compound of formula (XIII) or a pharmaceutically acceptable salt thereof:

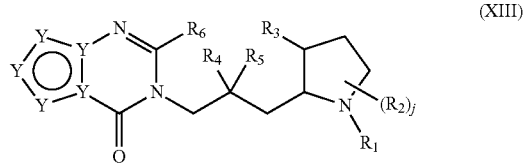

(XIII)

wherein j is an integer between 0 and 6, inclusive;

each occurrence of Y is independently S, O, N, or $CR_Y$, wherein each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; provided that $R_1$ is not a tert-butoxycarbonyl group;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino, alkylamino, dialkylamino, heteroaryloxy; or heteroarylthioxy moiety; provided that $R_3$ is not —$OCH_2Ph$;

$R_4$ and $R_5$ are independently hydrogen or —OH; or $R_4$ and $R_5$ may be taken together to form =O; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound has the stereochemistry shown in formula (XIIIa):

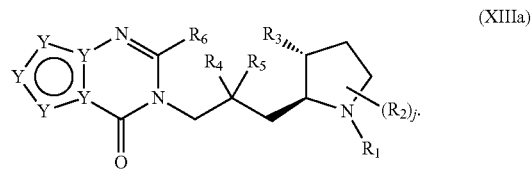

(XIIIa)

In certain embodiments, the compound has the stereochemistry shown in formula (XIIIb):

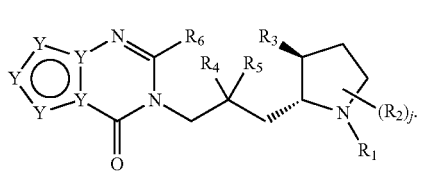

In certain embodiments, the compound of formula XIII is of the formula:

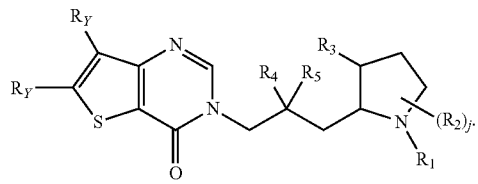

In certain embodiments, the compound of formula XIII is of the formula:

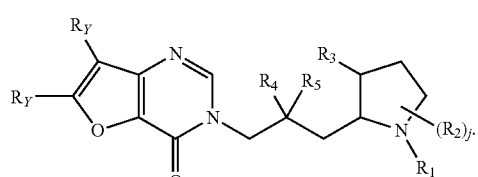

In certain embodiments, the compound of formula XIII is of the formula:

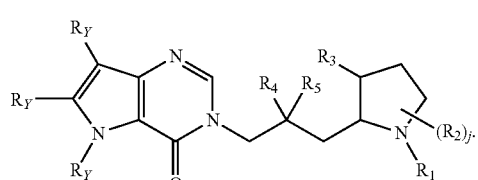

In certain embodiments, the compound of formula XIII is of the formula:

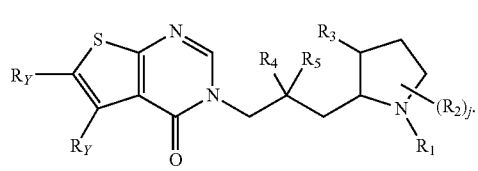

In certain embodiments, the compound of formula XIII is of the formula:

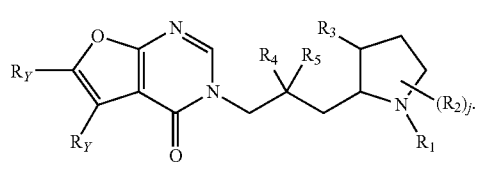

In certain embodiments, the compound of formula XIII is of the formula:

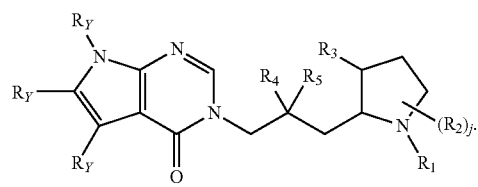

In certain embodiments, the compound of formula XIII is of the formula:

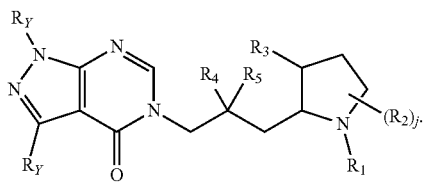

In certain embodiments, the compound of formula XIII is of the formula:

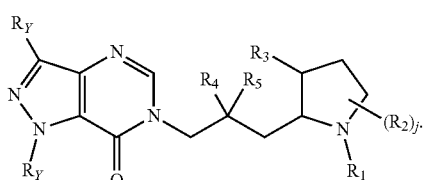

In certain embodiments, the compound of formula XIII is of the formula:

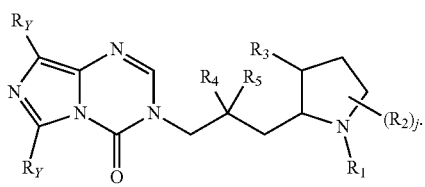

In certain embodiments, the compound of formula XIII is of the formula:

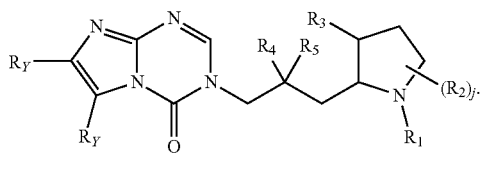

In certain embodiments, the compound of formula XIII is of the formula:

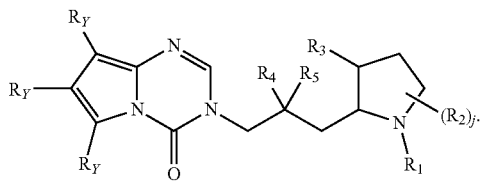

In certain embodiments, the compound of formula XIII is of the formula:

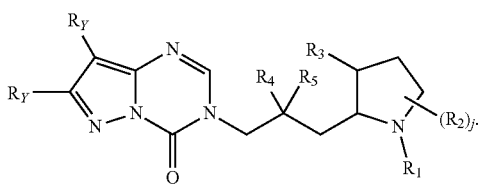

In certain embodiments, the compound of formula XIII is of the formula:

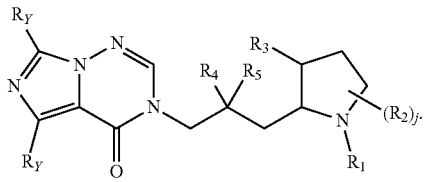

In certain embodiments, the compound of formula XIII is of the formula:

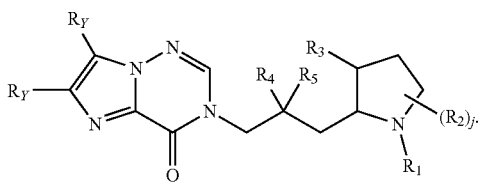

In certain embodiments, the compound of formula XIII is of the formula:

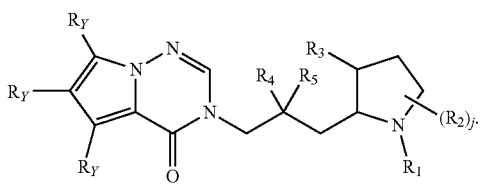

In certain embodiments, $R_1$ of formula XIII, XIIIa, or XIIIb is hydrogen. In certain other embodiments, $R_1$ of formula XIII, XIIIa, or XIIIb is a suitable amino protecting group, as defined herein.

In some embodiments, $R_2$ of formula XIII, XIIIa, or XIIIb is hydrogen. In other embodiments, $R_2$ of formula XIII, XIIIa, or XIIIb is a halogen. In certain embodiments, $R_2$ of formula XIII, XIIIa, or XIIIb is chloro, bromo, or iodo. In certain embodiments, $R_2$ of formula XIII, XIIIa, or XIIIb is a hydroxyl or alkoxyl group. In some embodiments, $R_2$ of formula XIII, XIIIa, or XIIIb is a substituted or unsubstituted aliphatic group. In certain embodiments, $R_2$ of formula XIII, XIIIa, or XIIIb is a substituted or unsubstituted aryl group. In certain embodiments, $R_2$ of formula XIII, XIIIa, or XIIIb is an amino group. In certain other embodiments, $R_2$ of formula XIII, XIIIa, or XIIIb is a cyano group. In some embodiments, $R_2$ of formula XIII, XIIIa, or XIIIb is a carboxylic acid or ester group.

In certain embodiments, $R_3$ of formula XIII, XIIIa, or XIIIb is hydrogen. In certain other embodiments, $R_3$ of formula XIII, XIIIa, or XIIIb is hydroxyl. In certain embodiments, $R_3$ of formula XIII, XIIIa, or XIIIb is alkoxy. In certain embodiments, $R_3$ of formula XIII, XIIIa, or XIIIb is a protected hydroxyl group. In certain embodiments, $R_3$ of formula XIII, XIIIa, or XIIIb is phosphate. In certain embodiments, $R_3$ of formula XIII, XIIIa, or XIIIb is sulfate. In certain other embodiments, $R_3$ of formula XIII, XIIIa, or XIIIb is acetate (—OAc). In some embodiments, $R_3$ of formula XIII, XIIIa, or XIIIb is a thioxy group. In some embodiments, $R_3$ of formula XIII, XIIIa, or XIIIb is an amino group. In some embodiments, $R_3$ of formula XIII, XIIIa, or XIIIb is a protected amino group.

In certain embodiments, $R_4$ of formula XIII, XIIIa, or XIIIb is hydrogen. In certain other embodiments, $R_4$ of formula XIII, XIIIa, or XIIIb is hydroxyl. In certain embodiments, $R_5$ of formula XIII, XIIIa, or XIIIb is hydrogen. In certain other embodiments, $R_5$ of formula XIII, XIIIa, or XIIIb is hydroxyl. In certain embodiments, $R_4$ and $R_5$ of formula XIII, XIIIa, or XIIIb are taken together to form =O.

In certain embodiments, $R_6$ of formula XIII, XIIIa, or XIIIb is hydrogen. In certain other embodiments, $R_6$ of formula XIII, XIIIa, or XIIIb is aliphatic. In certain embodiments, $R_6$ of formula XIII, XIIIa, or XIIIb is alkyl.

In certain embodiments, j of formula XIII, XIIIa, or XIIIb is 0. In certain embodiments, j is 1. In certain embodiments, j is 2. In certain embodiments, j is 3, 4, 5, or 6.

In some embodiments, at least one instance of Y of formula XIII, XIIIa, or XIIIb is CH. In some embodiments, Y of formula XIII, XIIIa, or XIIIb is $CR_Y$, where $R_Y$ is as defined herein. In other embodiments, Y is S. In certain embodiments, Y is N. In certain other embodiments, Y is $NR_Y$. In other embodiments, Y is O. In some embodiments, all instances of Y are $CR_Y$. In other embodiments, at least one instance of Y is not $CR_Y$. In yet other embodiments, at least two instances of Y are not $CR_Y$.

In some embodiments, $R_Y$ of formula XIII, XIIIa, or XIIIb is hydrogen. In other embodiments, $R_Y$ of formula XIII, XIIIa, or XIIIb is a halogen. In certain embodiments, $R_Y$ of formula XIII, XIIIa, or XIIIb is chloro, bromo, or iodo. In certain embodiments, $R_Y$ of formula XIII, XIIIa, or XIIIb is a hydroxyl or alkoxy group. In some embodiments, $R_Y$ of formula XIII, XIIIa, or XIIIb is a substituted or unsubstituted aliphatic group. In certain embodiments, $R_Y$ of formula XIII, XIIIa, or XIIIb is a substituted or unsubstituted alkyl group. In certain embodiments, $R_Y$ of formula XIII, XIIIa, or XIIIb is a substituted or unsubstituted aryl group. In certain embodiments, $R_Y$ of formula XIII, XIIIa, or XIIIb is a substituted or unsubstituted alkenyl group. In certain other embodiments, $R_Y$ of formula XIII, XIIIa, or XIIIb is a substituted or unsubstituted alkynyl group. In some embodiments, $R_Y$ of formula XIII, XIIIa, or XIIIb is an acyl group. In other embodiments, $R_Y$ of formula XIII, XIIIa, or XIIIb is an amino group. In certain embodiments, $R_Y$ of formula XIII, XIIIa, or XIIIb is a protected amino group.

In certain embodiments, Y of formula XIII, XIIIa, or XIIIb is $CR_Y$ and $R_Y$ is hydrogen. In some embodiments, Y of formula XIII, XIIIa, or XIIIb is $CR_Y$ and $R_Y$ is bromo. In other embodiments, Y of formula XIII, XIIIa, or XIIIb is $CR_Y$ and $R_Y$ is chloro. In certain embodiments, Y of formula XIII, XIIIa, or XIIIb is $CR_Y$ and $R_Y$ is —CN. In certain embodiments, Y of formula XIII, XIIIa, or XIIIb is $CR_Y$ and $R_Y$ is alkyl. In certain embodiments, Y of formula XIII, XIIIa, or XIIIb is $CR_Y$ and $R_Y$ is alkenyl. In certain embodiments, Y of formula XIII, XIIIa, or XIIIb is $CR_Y$ and $R_Y$ is alkynyl. In certain embodiments, Y of formula XIII, XIIIa, or XIIIb is $CR_Y$ and $R_Y$ is aryl. In certain embodiments, Y of formula XIII, XIIIa, or XIIIb is $CR_Y$ and $R_Y$ is phenyl. In certain embodiments, Y of formula XIII, XIIIa, or XIIIb is $CR_Y$ and $R_Y$ is benzylic. In certain embodiments, Y of formula XIII, XIIIa, or XIIIb is $CR_Y$ and $R_Y$ is heteroaryl. In certain embodiments, Y of formula XIII, XIIIa, or XIIIb is $CR_Y$ and $R_Y$ is pyridinyl. In certain embodiments, Y of formula XIII, XIIIa, or XIIIb is $CR_Y$ and $R_Y$ is carbocyclic. In certain embodiments, Y of formula XIII, XIIIa, or XIIIb is $CR_Y$ and $R_Y$ is heterocyclic. In certain embodiments, Y of formula XIII, XIIIa, or XIIIb is $CR_Y$ and $R_Y$ is morpholinyl. In certain embodiments, Y of formula XIII, XIIIa, or XIIIb is $CR_Y$ and $R_Y$ is piperidinyl.

In some embodiments, compounds of formula XIII, XIIIa, or XIIIb are of the following formulae:

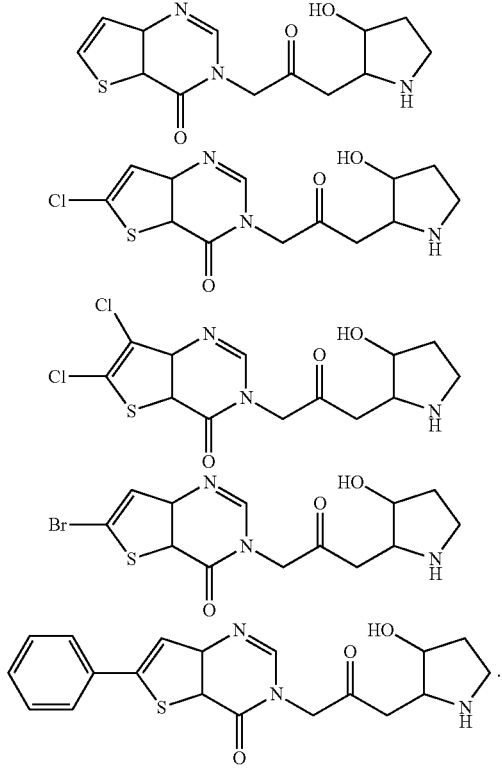

In some embodiments, compounds of formula XIII, XIIIa, or XIIIb are of the following formulae:

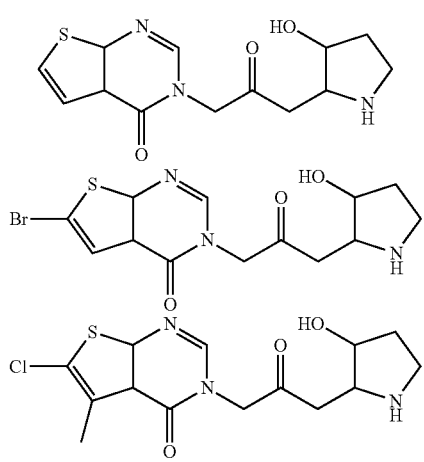

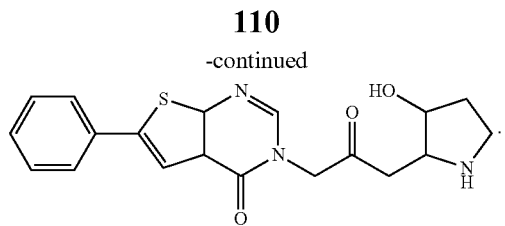

In some embodiments, compounds of formula XIII or XIIIa are of the following formulae:

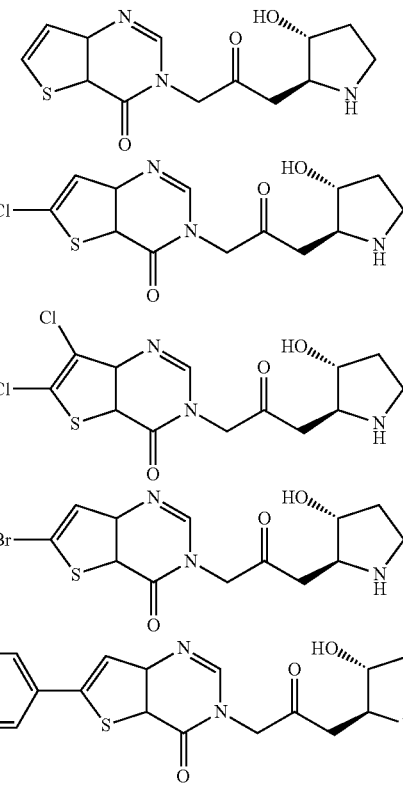

In some embodiments, compounds of formula XIII or XIIIb are of the following formulae:

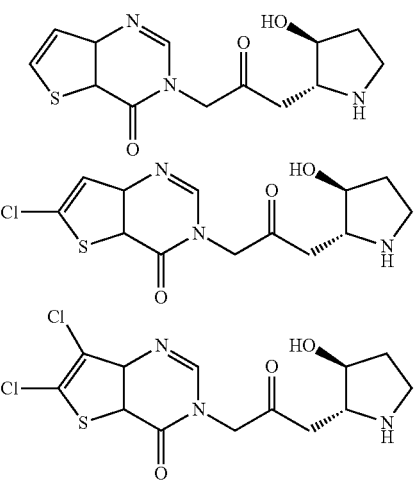

-continued

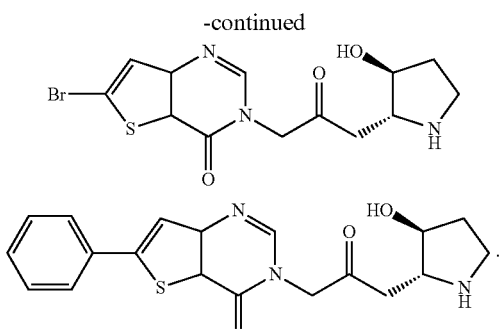

In some embodiments, compounds of formula XIII or XIIIa are of the following formulae:

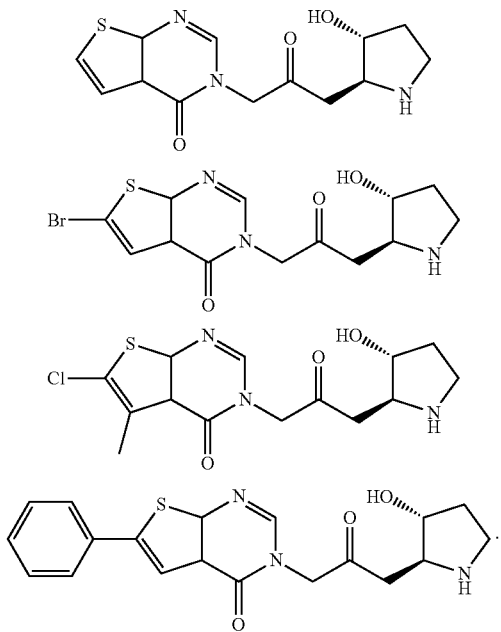

In some embodiments, compounds of formula XIII or XIIIb are of the following formulae:

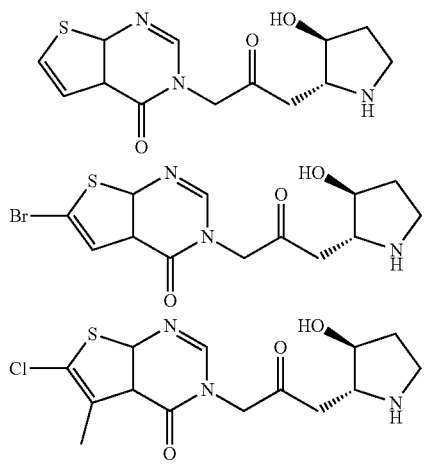

-continued

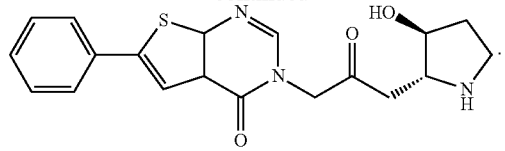

In certain embodiments, the invention provides a compound of formula (XIV) or a pharmaceutically acceptable salt thereof:

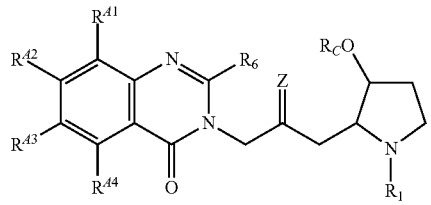

(XIV)

wherein Z is =O or =N—NHR$_D$, wherein R$_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_1$ is hydrogen; a protecting group; an aliphatic moiety; a heteroaliphatic moiety; an acyl moiety; an aryl moiety; a heteroaryl moiety; —C(=O)R$_A$; —C(=O)OR$_A$; —C(=O)N(R$_A$)$_2$; —SO$_2$R$_A$; —S(=O)R$_A$; —C(R$_A$)$_2$NHC(=O)R$_A$; C(=O)OCH$_2$OC(=O)R$_A$; C(=O)OCH$_2$OC(=O)OR$_A$; or —C(R$_A$)$_2$OC(=O)R$_A$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_C$ is a protecting group; an aliphatic moiety; a heteroaliphatic moiety; an acyl moiety; an aryl moiety; a heteroaryl moiety; —C(=O)R$_{C1}$; —C(=O)OR$_{C1}$; —C(=O)N(R$_{C1}$)$_2$; —P(=O)(OR$_{C1}$)$_2$; —S(=O)(OR$_{C1}$)$_2$; or —C(R$_{C1}$)$_2$OC(=O)R$_{C1}$; wherein each occurrence of R$_{C1}$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; provided that R$_C$ is not methyl, ethyl, or acetyl;

R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R^{A1}$, $R^{A2}$, $R^{A3}$, and $R^{A4}$ are independently hydrogen; halogen; substituted or unsubstituted aliphatic; substituted or unsubstituted heteroaliphatic; substituted or unsubstituted aryl; substituted or unsubstituted heteroaryl; —$OR_G$; —$SR_G$; —$N(R_G)_2$; and —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety.

In certain embodiments, the compound is of the stereochemistry of formula (XIVa):

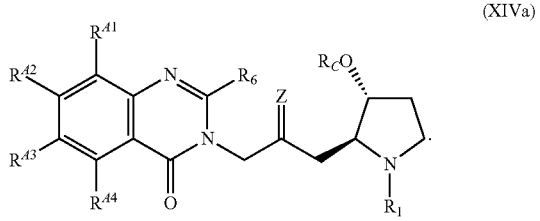

(XIVa)

In certain embodiments, the compound is of the stereochemistry of formula (XIVb):

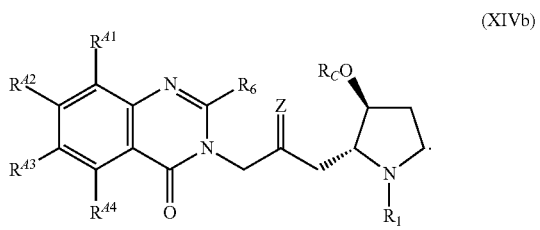

(XIVb)

In certain embodiments, $R_1$ of formula XIV, XIVa, or XIVb is hydrogen. In certain other embodiments, $R_1$ of formula XIV, XIVa, or XIVb is a suitable amino protecting group, as defined herein.

In certain embodiments, $R_6$ of formula XIV, XIVa, or XIVb is hydrogen. In certain other embodiments, $R_6$ of formula XIV, XIVa, or XIVb is aliphatic. In certain embodiments, $R_6$ of formula XIV, XIVa, or XIVb is alkyl.

In some embodiments, $R^{A1}$ of formula XIV, XIVa, or XIVb is hydrogen. In other embodiments, $R^{A1}$ of formula XIV, XIVa, or XIVb is a halogen. In certain embodiments, $R^{A1}$ of formula XIV, XIVa, or XIVb is chloro, bromo, or iodo. In certain embodiments, $R^{A1}$ of formula XIV, XIVa, or XIVb is a hydroxyl or alkoxyl group. In some embodiments, $R^{A1}$ of formula XIV, XIVa, or XIVb is a substituted or unsubstituted aliphatic group. In certain embodiments, $R^{A1}$ of formula XIV, XIVa, or XIVb is a substituted or unsubstituted alkyl group. In certain embodiments, $R^{A1}$ of formula XIV, XIVa, or XIVb is a substituted or unsubstituted aryl group. In certain embodiments, $R^{A1}$ of formula XIV, XIVa, or XIVb is a substituted or unsubstituted alkenyl group. In certain other embodiments, $R^{A1}$ of formula XIV, XIVa, or XIVb is a substituted or unsubstituted alkynyl group. In some embodiments, $R^{A1}$ of formula XIV, XIVa, or XIVb is an acyl group. In some embodiments, $R^{A1}$ of formula XIV, XIVa, or XIVb is an amino group. In other embodiments, $R^{A1}$ of formula XIV, XIVa, or XIVb is a protected amino group.

In some embodiments, $R^{A2}$ of formula XIV, XIVa, or XIVb is hydrogen. In other embodiments, $R^{A2}$ of formula XIV, XIVa, or XIVb is a halogen. In certain embodiments, $R^{A2}$ of formula XIV, XIVa, or XIVb is chloro, bromo, or iodo. In certain embodiments, $R^{A2}$ of formula XIV, XIVa, or XIVb is bromo. In certain embodiments, $R^{A2}$ of formula XIV, XIVa, or XIVb is a hydroxyl or alkoxyl group. In some embodiments, $R^{A2}$ of formula XIV, XIVa, or XIVb is a substituted or unsubstituted aliphatic group. In certain embodiments, $R^{A2}$ of formula XIV, XIVa, or XIVb is a substituted or unsubstituted alkyl group. In certain embodiments, $R^{A2}$ of formula XIV, XIVa, or XIVb is a substituted or unsubstituted aryl group. In certain embodiments, $R^{A2}$ of formula XIV, XIVa, or XIVb is a substituted or unsubstituted alkenyl group. In certain other embodiments, $R^{A2}$ of formula XIV, XIVa, or XIVb is a substituted or unsubstituted alkynyl group. In some embodiments, $R^{A2}$ of formula XIV, XIVa, or XIVb is an acyl group. In some embodiments, $R^{A2}$ of formula XIV, XIVa, or XIVb is an amino group. In other embodiments, $R^{A2}$ of formula XIV, XIVa, or XIVb is a protected amino group.

In some embodiments, $R^{A3}$ of formula XIV, XIVa, or XIVb is hydrogen. In other embodiments, $R^{A3}$ of formula XIV, XIVa, or XIVb is a halogen. In certain embodiments, $R^{A3}$ of formula XIV, XIVa, or XIVb is chloro, bromo, or iodo. In certain embodiments, $R^{A3}$ of formula XIV, XIVa, or XIVb is chloro. In certain embodiments, $R^{A3}$ of formula XIV, XIVa, or XIVb is a hydroxyl or alkoxyl group. In some embodiments, $R^{A3}$ of formula XIV, XIVa, or XIVb is a substituted or unsubstituted aliphatic group. In certain embodiments, $R^{A3}$ of formula XIV, XIVa, or XIVb is a substituted or unsubstituted alkyl group. In certain embodiments, $R^{A3}$ of formula XIV, XIVa, or XIVb is a substituted or unsubstituted aryl group. In certain embodiments, $R^{A3}$ of formula XIV, XIVa, or XIVb is a substituted or unsubstituted alkenyl group. In certain other embodiments, $R^{A3}$ of formula XIV, XIVa, or XIVb is a substituted or unsubstituted alkynyl group. In some embodiments, $R^{A3}$ of formula XIV, XIVa, or XIVb is an acyl group. In some embodiments, $R^{A3}$ of formula XIV, XIVa, or XIVb is an amino group. In other embodiments, $R^{A3}$ of formula XIV, XIVa, or XIVb is a protected amino group.

In some embodiments, $R^{A4}$ of formula XIV, XIVa, or XIVb is hydrogen. In some embodiments, $R^{A4}$ of formula XIV, XIVa, or XIVb is a halogen. In certain embodiments, $R^{A4}$ of formula XIV, XIVa, or XIVb is chloro, bromo, or iodo. In certain embodiments, $R^{A4}$ of formula XIV, XIVa, or XIVb is chloro. In certain embodiments, $R^{A4}$ of formula XIV, XIVa, or XIVb is bromo. In certain embodiments, $R^{A4}$ of formula XIV, XIVa, or XIVb is a hydroxyl or alkoxyl group. In some embodiments, $R^{A4}$ of formula XIV, XIVa, or XIVb is a substituted or unsubstituted aliphatic group. In certain embodiments, $R^{A4}$ of formula XIV, XIVa, or XIVb is a substituted or unsubstituted alkyl group. In certain embodiments, $R^{A4}$ of formula XIV, XIVa, or XIVb is a substituted or unsubstituted aryl group. In certain embodiments, $R^{A4}$ of formula XIV, XIVa, or XIVb is a substituted or unsubstituted alkenyl group. In certain other embodiments, $R^{A4}$ of formula XIV, XIVa, or XIVb is a substituted or unsubstituted alkynyl group. In some embodiments, $R^{A4}$ of formula XIV, XIVa, or XIVb is an acyl group. In some embodiments, $R^{A4}$ of formula XIV, XIVa, or XIVb is an amino group. In other embodiments, $R^{A4}$ of formula XIV, XIVa, or XIVb is a protected amino group.

In certain embodiments, $R_C$ of formula XIV, XIVa, or XIVb is a suitable hydroxyl protecting group, as defined herein. In certain embodiments, $R_C$ of formula XIV, XIVa, or XIVb is an acyl group. In certain embodiments, $R_C$ of formula XIV, XIVa, or XIVb is an ester group. In certain embodiments, $R_C$ of formula XIV, XIVa, or XIVb is an aliphatic group. In certain embodiments, $R_C$ of formula XIV, XIVa, or XIVb is a heteroaliphatic group. In certain embodiments, —$OR_C$ of formula XIV, XIVa, or XIVb is a phosphate group. In certain other embodiments, —$OR_C$ of formula XIV, XIVa, or XIVb is a sulfate group.

In certain embodiments, Z of formula XIV, XIVa, or XIVb is =O. In certain other embodiments, Z of formula XIV, XIVa, or XIVb is =N—NHR$_D$, wherein R$_D$ is as defined herein.

In some embodiments, compounds of formula XIV, XIVa, or XIVb are of the following formulae:

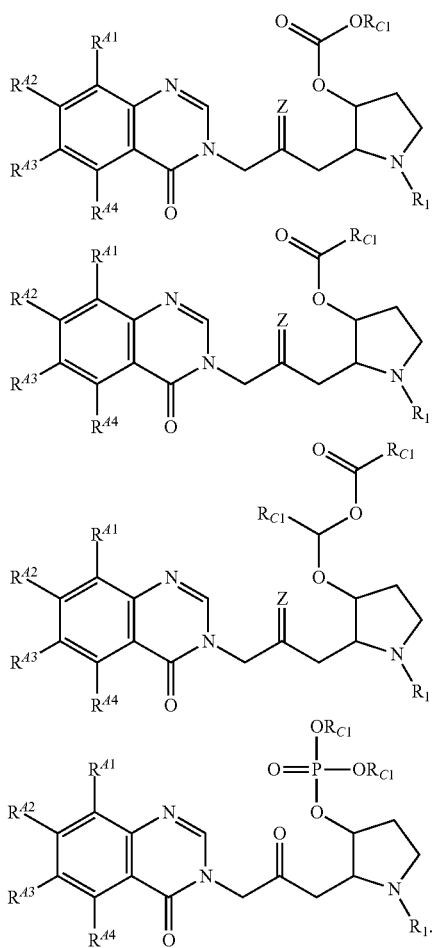

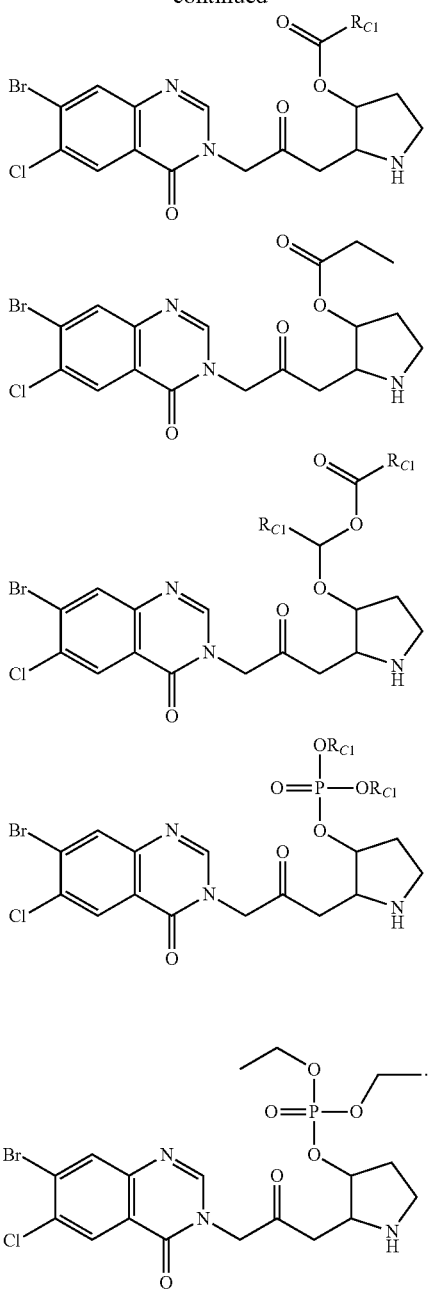

In some embodiments, compounds of formula XIV, XIVa, or XIVb are of the following formulae:

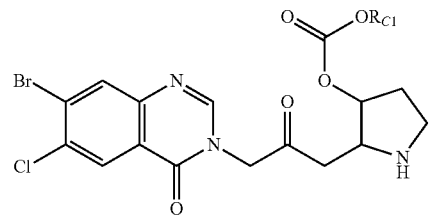

In some embodiments, compounds of formula XIV or XIVa are of the following formulae:

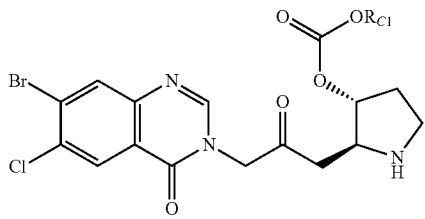

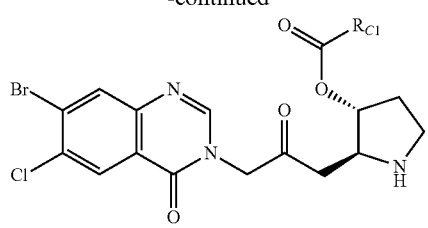
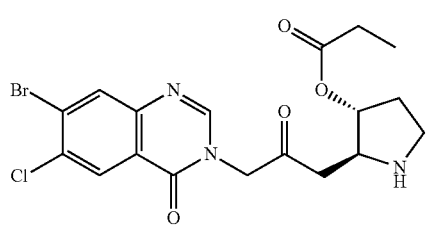
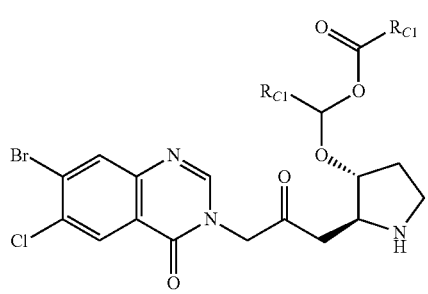
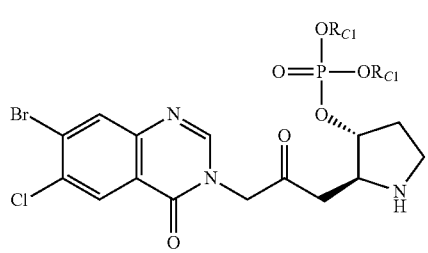
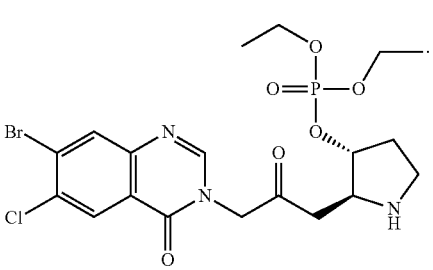
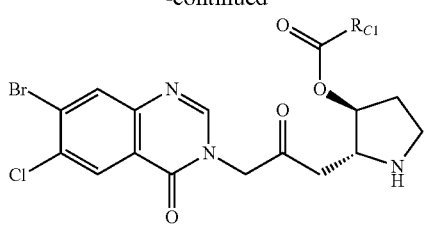
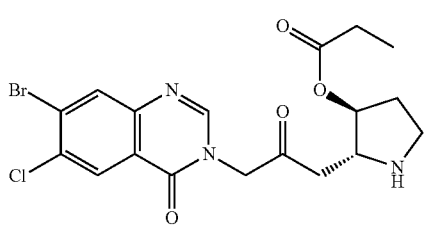
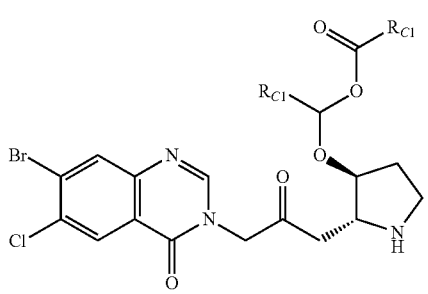
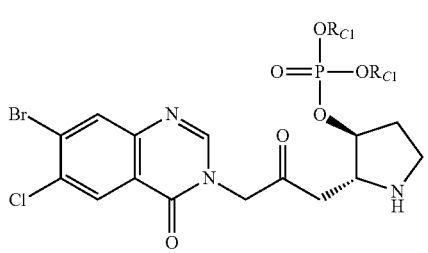
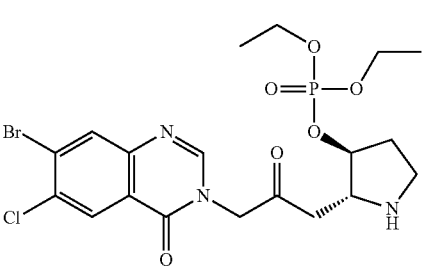
In some embodiments, compounds of formula XIV or XIVb are of the following formulae:
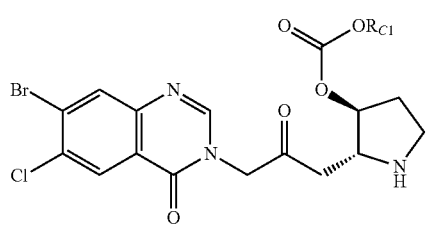
In some embodiments, compounds of formula XIV, XIVa, or XIVb are of the following formulae:
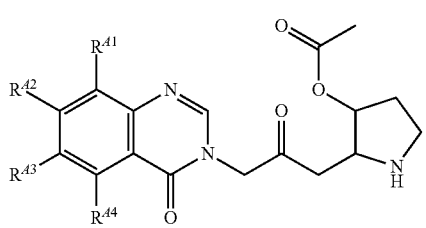

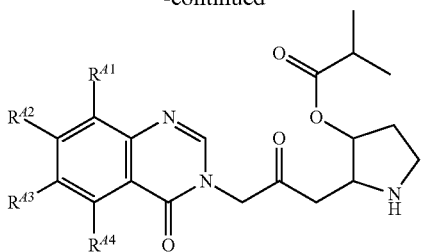
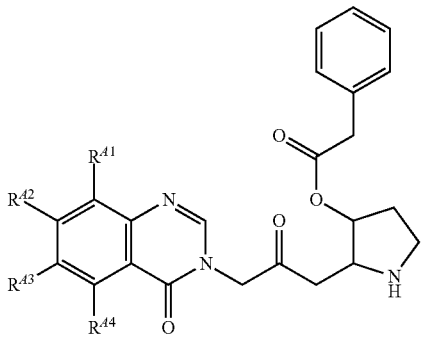
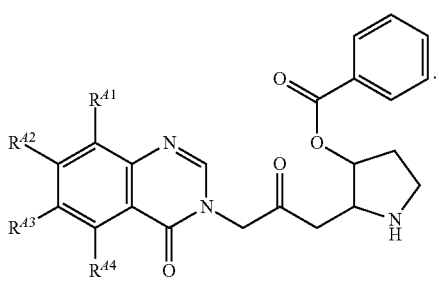
In some embodiments, compounds of formula XIV or XIVa are of the following formulae:
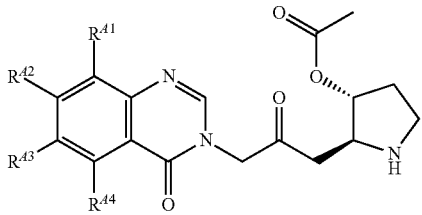
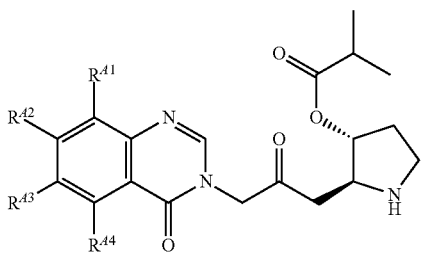
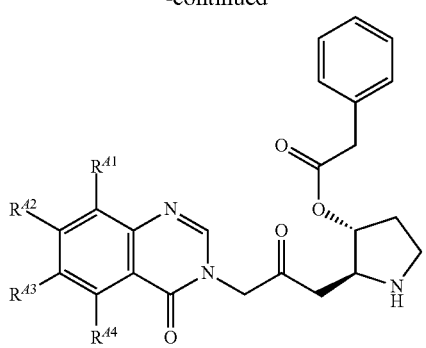
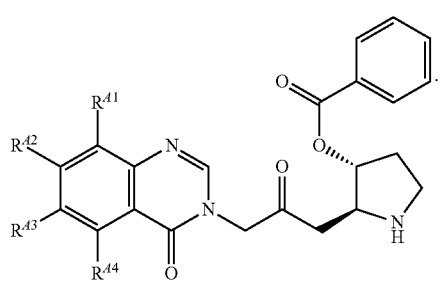
In some embodiments, compounds of formula XIV or XIVb are of the following formulae:
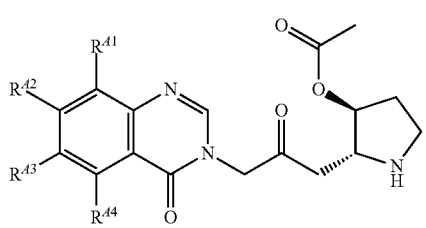
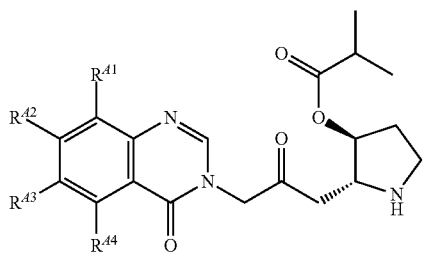
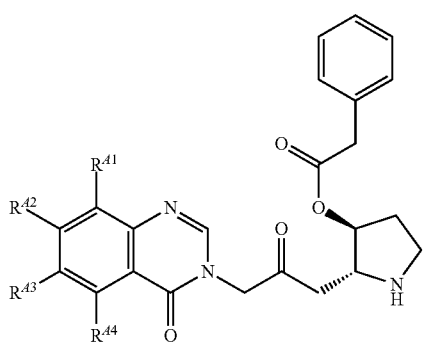

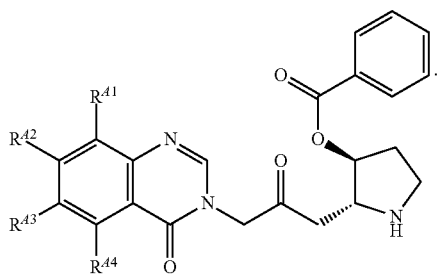
In some embodiments, compounds of formula XIV, XIVa, or XIVb are of the following formulae:
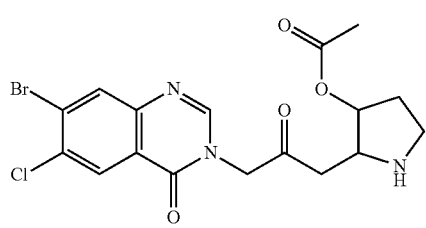
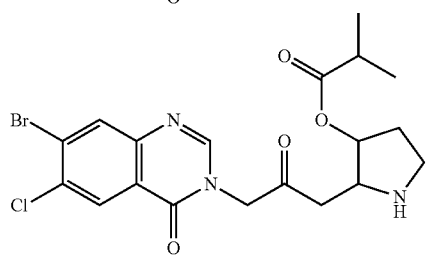
In some embodiments, compounds of formula XIV or XIVa are of the following formulae:
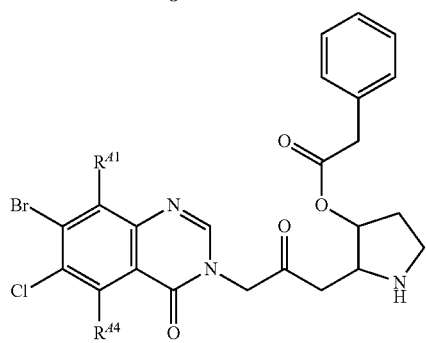
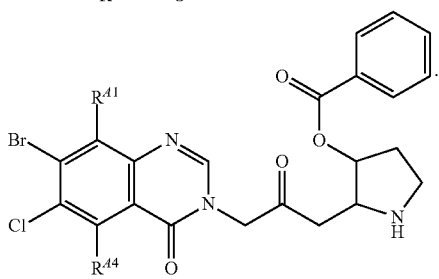
In some embodiments, compounds of formula XIV or XIVb are of the following formulae:
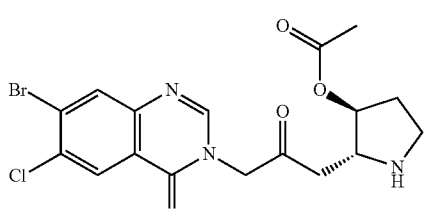
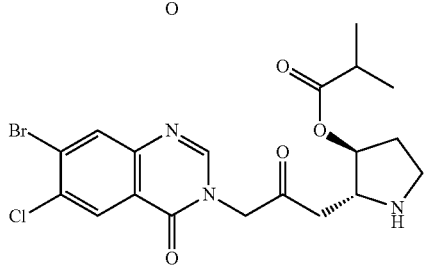

123
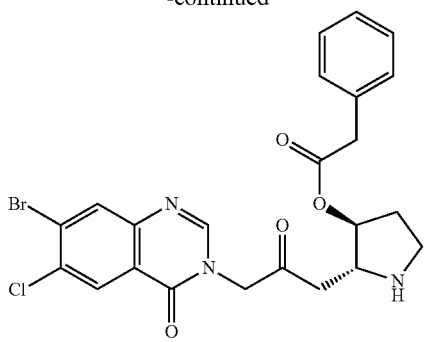
124
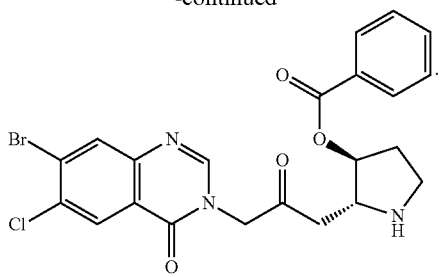
Exemplary compounds of the invention include:
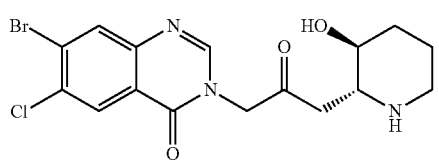
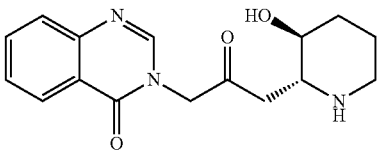
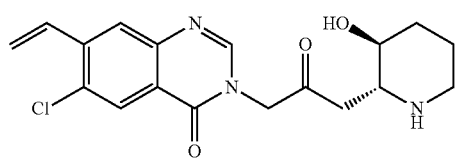
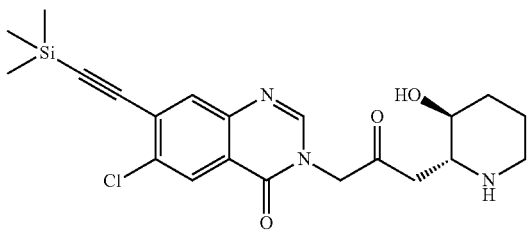
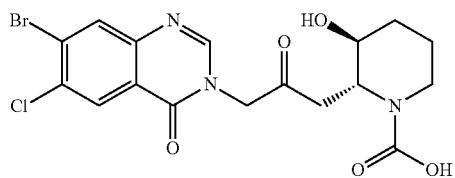
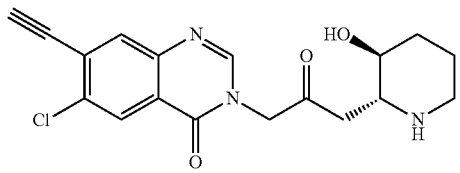
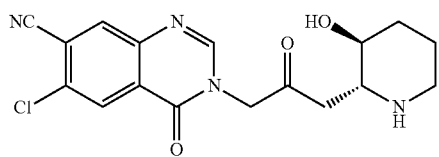
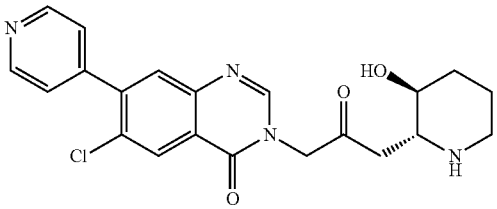
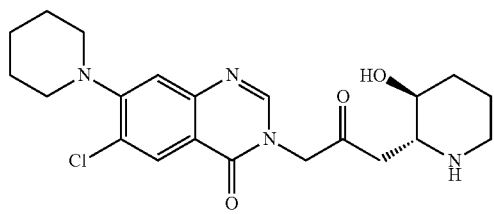
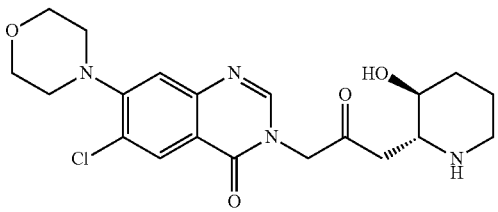
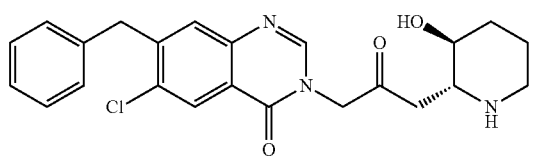

125 126
-continued
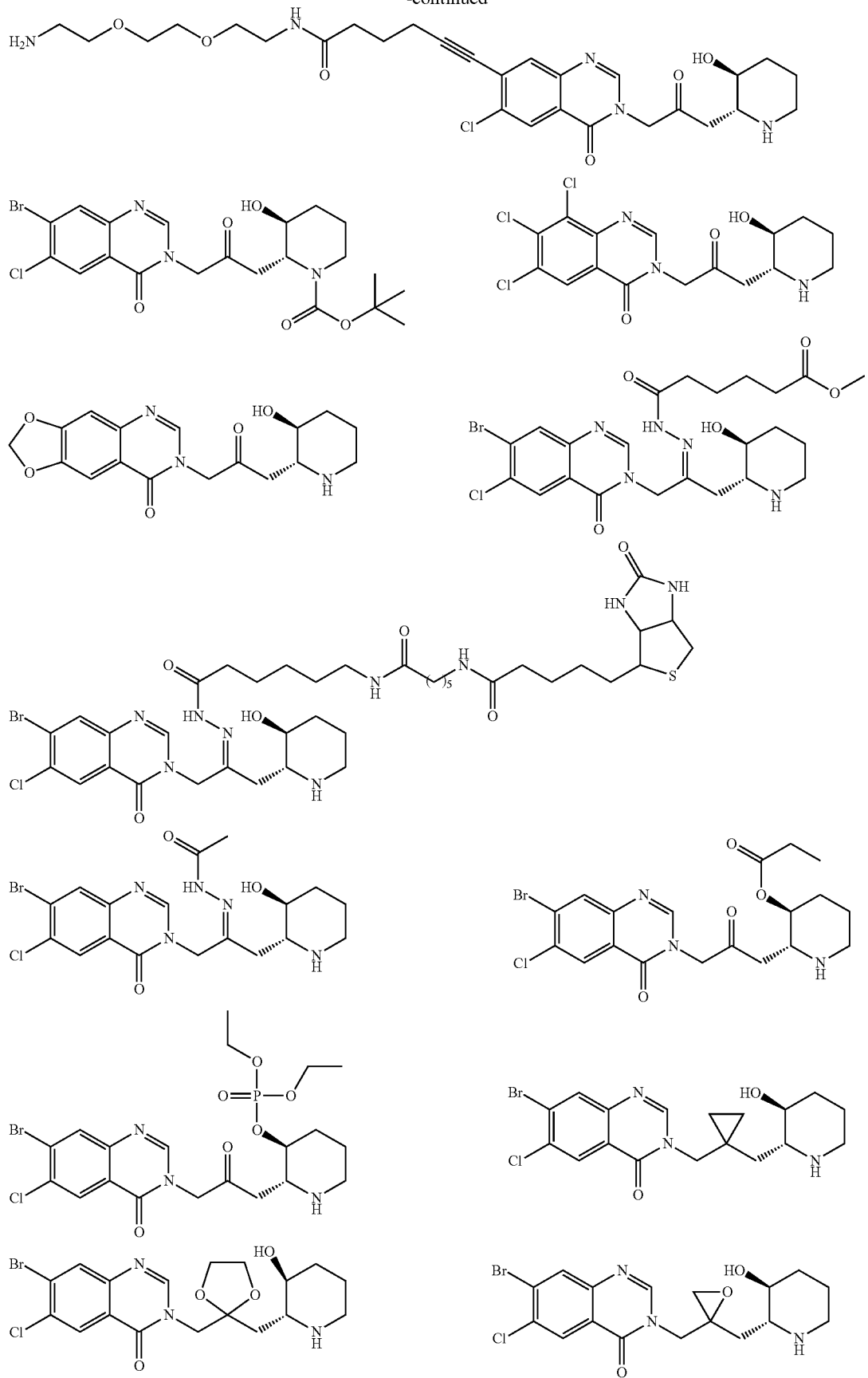

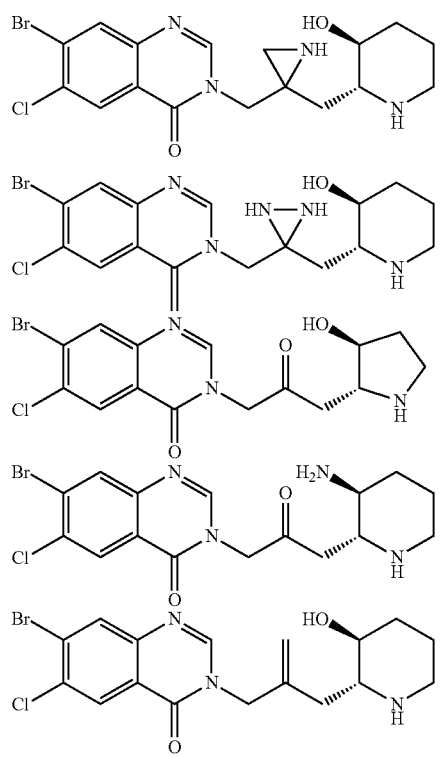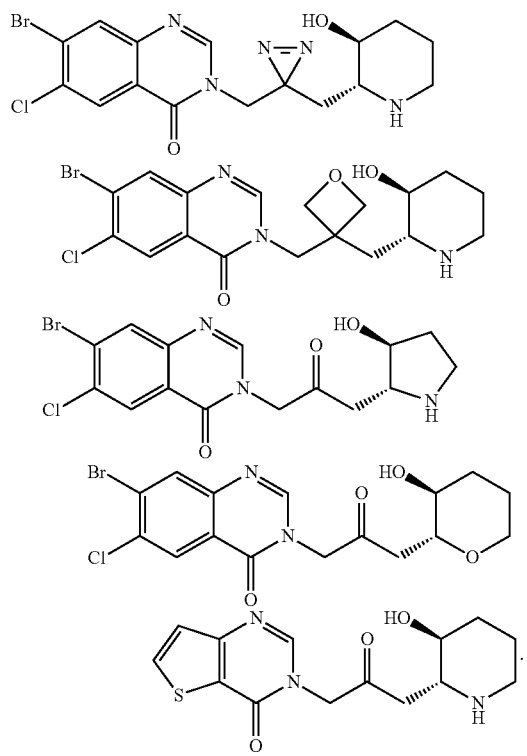
Exemplary compounds of the invention include:
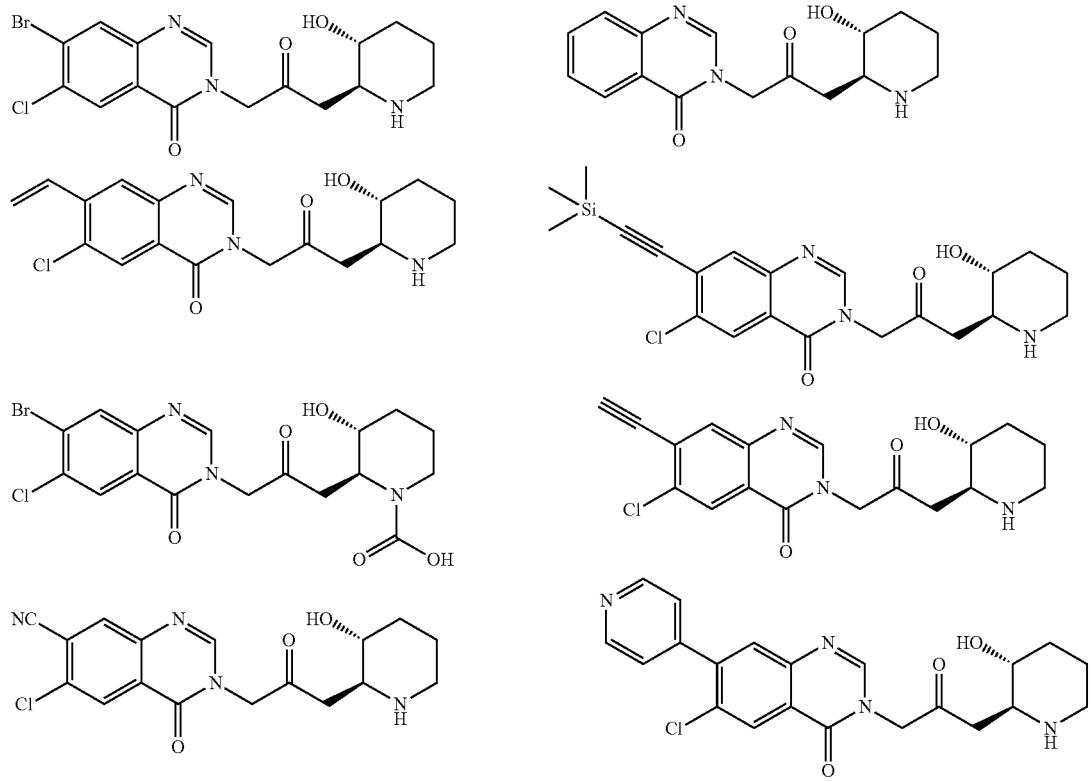

129
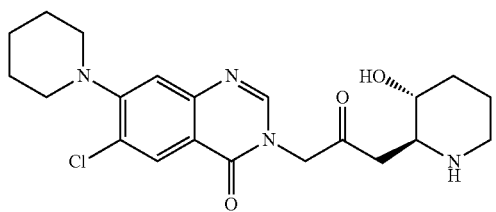
130
-continued
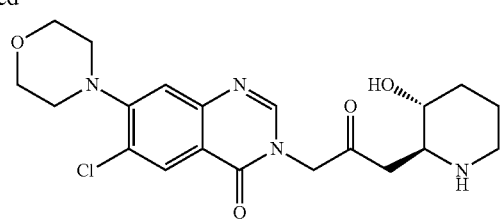
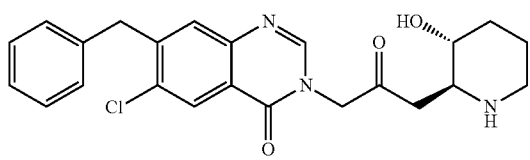
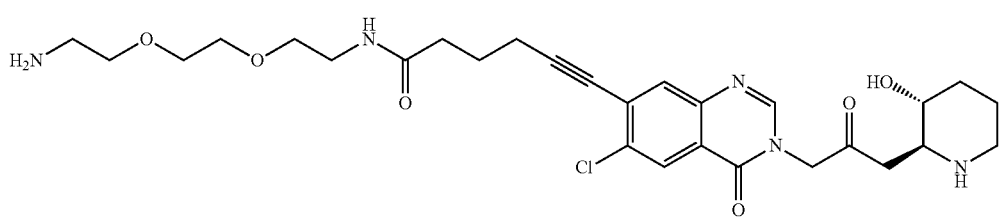
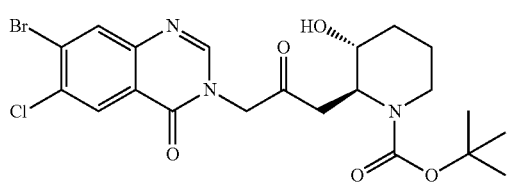
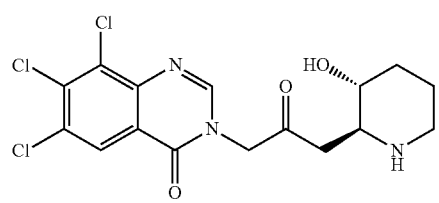
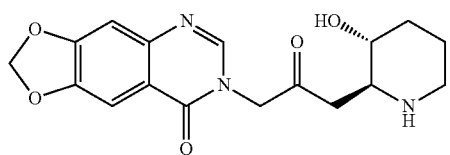
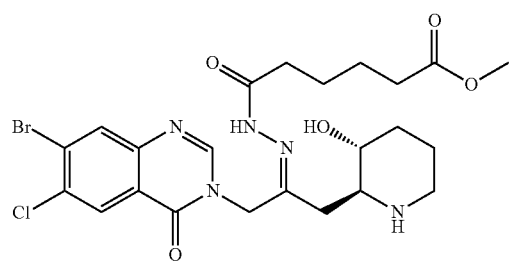
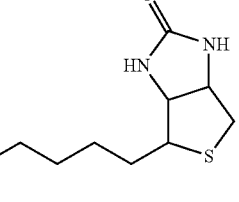
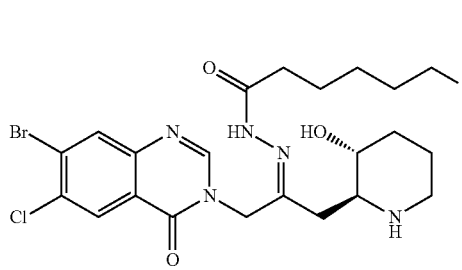
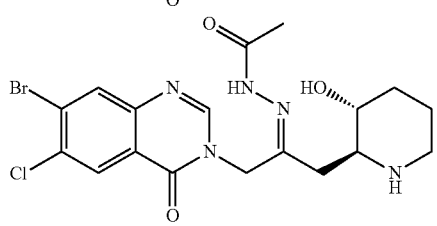
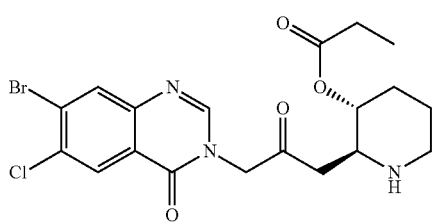

-continued

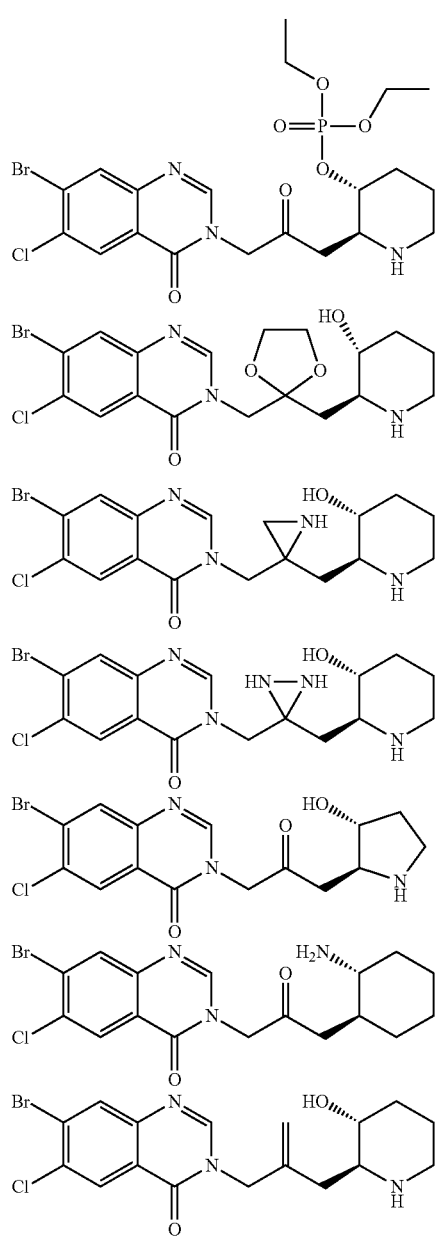
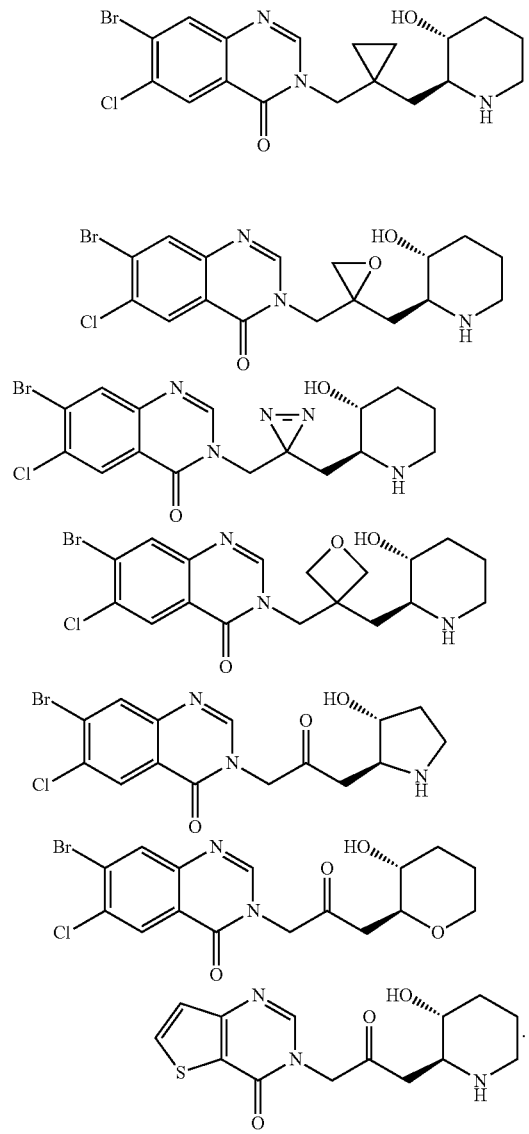

Synthesis of Inventive Compounds

The compounds provided by the present invention may be prepared via any synthetic route known to one of skill in the art. For example, the compounds may be prepared from simple, commercially available starting materials, of the compounds may be prepared semi-synthetically using more complex starting materials such as halofuginone or febrifugine. The inventive compounds may be prepared from literature procedures. U.S. Pat. No. 4,762,838; U.S. Patent Application Publication 2008/0188498; Emmanuvel et al., "A concise enantioselective synthesis of (+)-febrifugine" Tetrahedron: Asymmetry 20(1):84-88, 2009; Ooi et al., "A Concise Enantioselective Synthesis of Antimalarial Febrifugine Alkaloids" Organic Letters 3(6):953-955, 2001; Ashoorzadeh et al., "Synthetic evaluation of an enantiopure tetrahydropyridine N-oxide. Synthesis of (+)-febrifugine" Tetrahedron 65(24):4671-4680, 2009; Sukemoto et al., "Concise asymmetric synthesis of (+)-febrifugine utilizing trans-selective intramolecular conjugate addition" Synthesis (19):3081-3087, 2008; Kikuchi et al., "Exploration of a New Type of Antimalarial Compounds Based on Febrifugine" Journal of Medicinal Chemistry 49(15):4698-4706, 2006; Takaya et al., "New Type of Febrifugine Analogues, Bearing a Quinolizidine Moiety, Show Potent Antimalarial Activity against Plasmodium Malaria Parasite" Journal of Medicinal Chemistry 42(16):3163-3166, 1999. The inventive compounds may also be prepared from commercially available starting materials using the following synthetic schemes. The following are only meant to exemplify the routes available to a synthetic organic chemist for preparing the inventive compounds. As would be readily apparent to one of skill in this art, these exemplary schemes may be modified to use different starting materials, reagents, and/or reaction conditions.

Various groups such as cyano, alkenyl, alkynyl, aryl, and amino may be substituted for the bromine of halofuginone or derivatives thereof as shown in the scheme below:

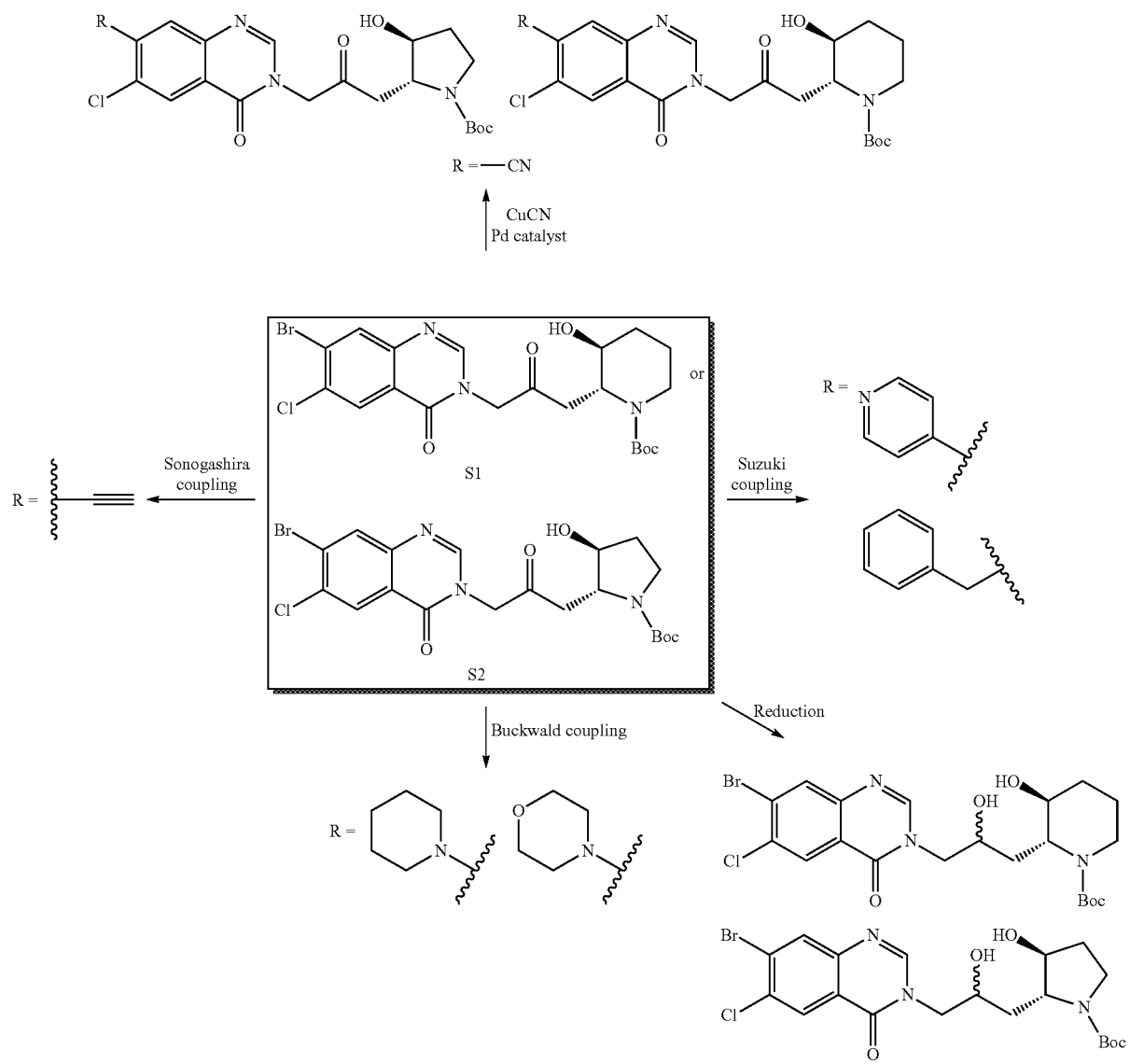

* A de-Boc step will be done after each coupling reaction to obtain the final product.

The starting material S1 can be prepared according to literature procedures for closely related compounds. See, e.g., Kikuchi et al., *J. Med. Chem.* 49(15):4698-4706, 2006; Ooi et al., *Org. Lett.* 3:953-55, 2001; JP2002201192; CN1583729. The starting material S2 can be prepared according to literature procedures for closely related compounds. See, e.g., U.S. Patent Application Publication US 2008/0188498.

In certain embodiments, inventive compounds are prepared wherein the phenyl moiety of the bicyclic quinazolinone ring system of halofuginone is replaced with a heteroaryl moiety such as thiophenyl, furanyl, pyridinyl, or pyrimidinyl. Such compounds may be prepared by the scheme:

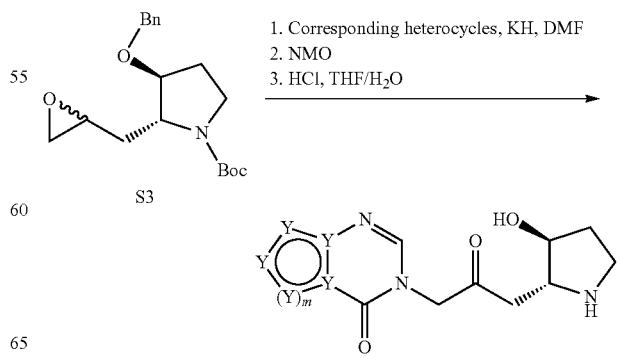

The starting material S3 can be prepared according to U.S. Patent Application Publication US 2008/0188498. Corresponding heterocycles for preparing such inventive compounds are either commercially available or can be prepared following literature procedures. Song, *Heterocyclic Communications* 13(1):33-34, 2007; Peng et al., *Journal of Combinatorial Chemistry* 9(3):431-436, 2007; Robba et al., *Bulletin de la Societe Chimique de France* 3-4(Pt. 2):587-91, 1975; Reigan et al., *Bioorganic & Medicinal Chemistry Letters* 14(21):5247-5250, 2004; Al-Shaar et al., *Journal of the Chemical Society, Perkin Transactions* 1: *Organic and Bio-Organic Chemistry* 21:2789-811, 1992; Hanami et al., *Tetrahedron Letters* 48(22):3801-3803, 2007; Vogel et al., *Helvetica Chimica Acta* 58(3):761-71, 1975; Heim-Riether et al., *Journal of Organic Chemistry* 70(18):7331-7337, 2005; Patil et al., *Journal of Heterocyclic Chemistry* 31(4):781-6, 1994.

Inventive compounds with an amino group off the phenyl moiety of halofuginone or derivatives thereof may be prepared by the following exemplary route:

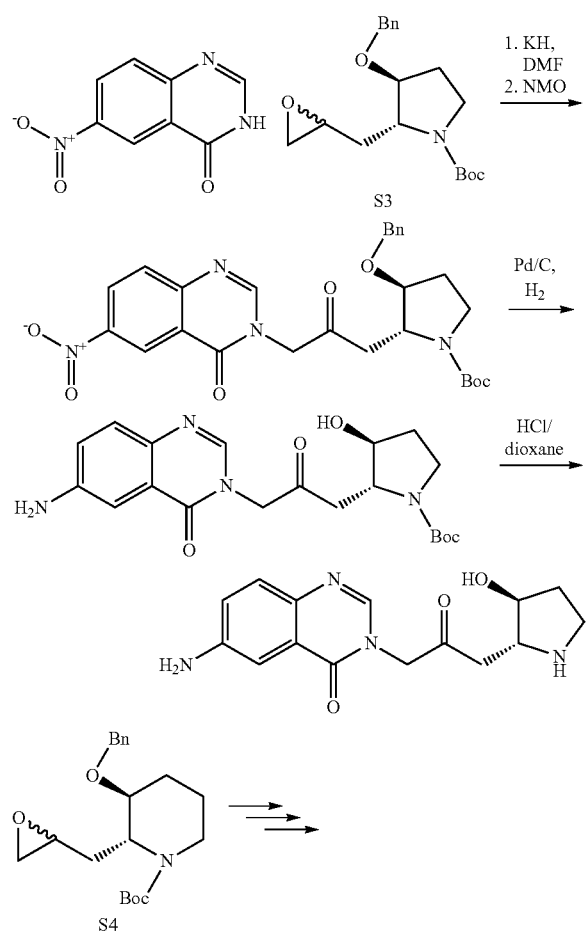

Prodrugs (e.g., esters of the hydroxyproline) may be prepared by the following exemplary scheme:

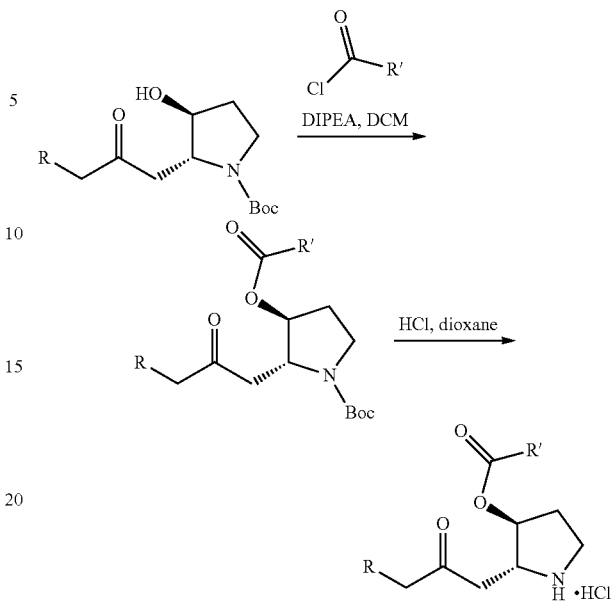

In Scheme 1 below, intermediate 1A is either commercially available or is be prepared as described in literature procedures. Song, *Heterocyclic Communications* 13(1):33-34, 2007; Peng et al., *Journal of Combinatorial Chemistry* 9(3): 431-436, 2007; Robba et al., *Bulletin de la Societe Chimique de France* 3-4(Pt. 2):587-91, 1975; Reigan et al., *Bioorganic & Medicinal Chemistry Letters* 14(21):5247-5250, 2004; Al-Shaar et al., *Journal of the Chemical Society, Perkin Transactions* 1: *Organic and Bio-Organic Chemistry* 21:2789-811, 1992. Intermediate 1B can be prepared following literature procedures with modest variations if necessary. U.S. Patent Application Publication 2008/0188498; Emmanuvel et al., "*A concise enantioselective synthesis of (+)-febrifugine*" *Tetrahedron: Asymmetry* 20(1):84-88, 2009; Ooi et al., "*A Concise Enantioselective Synthesis of Antimalarial Febrifugine Alkaloids*" *Organic Letters* 3(6):953-955, 2001; Ashoorzadeh et al., "Synthetic evaluation of an enantiopure tetrahydropyridine N-oxide. Synthesis of (+)-febrifugine" *Tetrahedron* 65(24):4671-4680, 2009; Sukemoto et al., "Concise asymmetric synthesis of (+)-febrifugine utilizing trans-selective intramolecular conjugate addition" *Synthesis* (19):3081-3087, 2008; Kikuchi et al., "Exploration of a New Type of Antimalarial Compounds Based on Febrifugine" *Journal of Medicinal Chemistry* 49(15):4698-4706, 2006; Takaya et al., "New Type of Febrifugine Analogues, Bearing a Quinolizidine Moiety, Show Potent Antimalarial Activity against Plasmodium Malaria Parasite" *Journal of Medicinal Chemistry* 42(16):3163-3166, 1999. Compound 1C can be prepared by reacting the nucleophilic 1A with the electrophilic 1B in the presence of a base, e.g., KH or $K_2CO_3$.

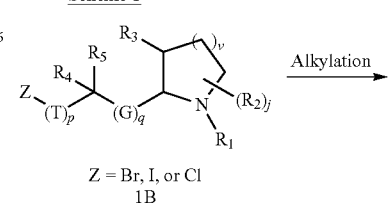

-continued

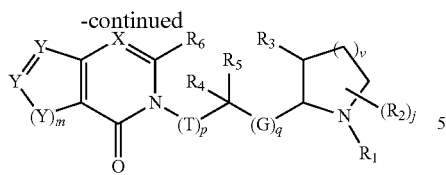

1C

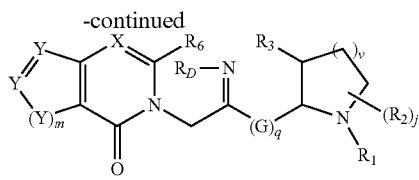

3A

When R₄ and R₅ are taken together to form =O, or R₄ is hydrogen and R₅ is hydroxyl, compounds 2C and 2D can be prepared following Scheme 2. Intermediate 2B is prepared following literature procedures with modest variations if necessary. U.S. Patent Application Publication 2008/0188498; Kikuchi et al., "Exploration of a New Type of Antimalarial Compounds Based on Febrifugine" *Journal of Medicinal Chemistry* 49(15):4698-4706, 2006. Compound 2C is prepared by reacting the nucleophilic 1A with the electrophilic 2B in the presence of a base, e.g., KH or K₂CO₃. Compound 2C is then oxidized to provide compound 2D. In certain embodiments, the reaction conditions comprise TPAP and NMO at room temperature in the presence of ground molecular sieves.

When R₄ and R₅ are taken together to form =N—NR$_D$ or =N—N(R$_D$)₂, compound 4A or compound 4B can be prepared according to Scheme 4. A mixture of intermediate 2D and the corresponding hydrazine are refluxed in methanol, ethanol, or another suitable solvent, optionally in the presence of an acid catalyst (e.g., acetic acid) to yield compound 4A or 4B.

Scheme 2

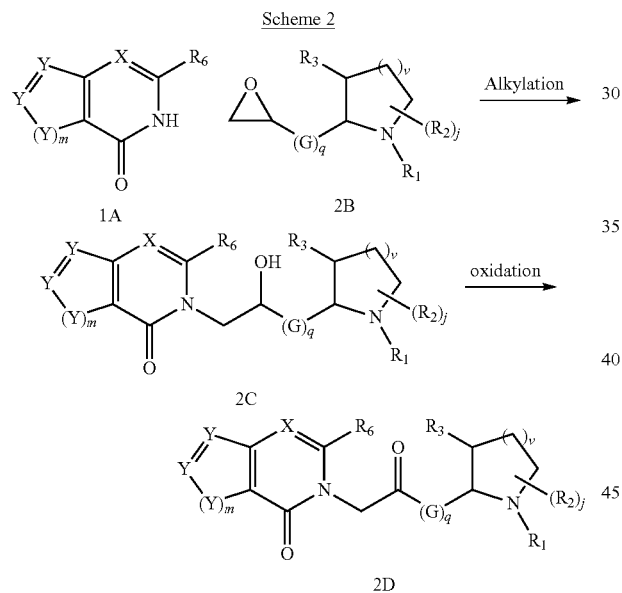

Scheme 4

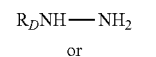
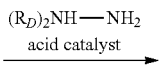
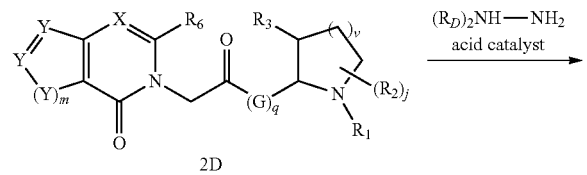

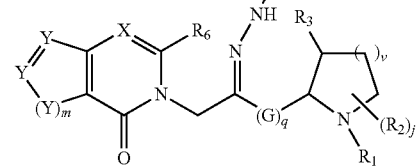

4A or

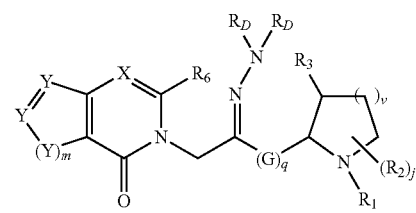

4B

When R₄ and R₅ are taken together to form =NR$_D$, compound 3A is prepared according to Scheme 3. Reaction of compound 2D with primary amine R$_D$—NH₂ in the presence of an acid catalyst (e.g., formic acid, acetic acid, TiCl₄) yields compound 3A.

Scheme 3

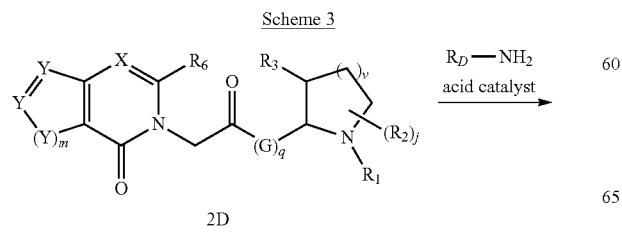

When R₄ and R₅ are taken together to form =N—OR$_D$, compound 5A can be prepared according to Scheme 5. A mixture of intermediate 2D and the corresponding hydroxylamine are refluxed in methanol, ethanol, or another suitable solvent, optionally in the presence of a base (e.g., pyridine, sodium acetate) to yield compound 5A.

Scheme 5

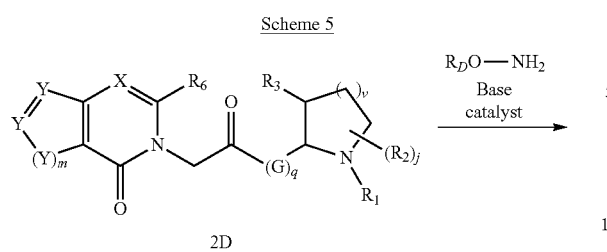

2D

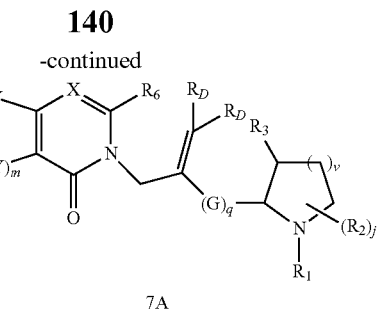

7A

When $R_4$ and $R_5$ are taken together with a neighboring atom to form a cyclopropyl ring, compound 8A can be prepared according to Scheme 8. Intermediate 7A can be prepared following Scheme 7. Treatment of 7A with the corresponding carbene reagent yields the cyclopropyl compound 8A.

Scheme 8

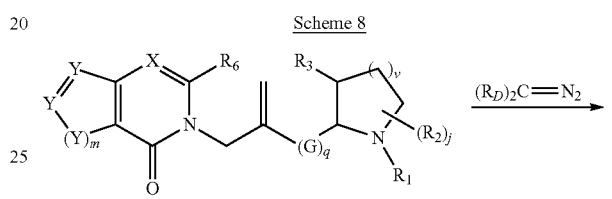

7A

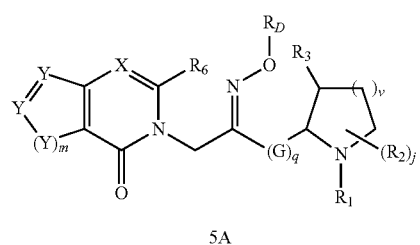

5A

When $R_4$ and $R_5$ are taken together to form =S, compound 6A can be prepared according to Scheme 6. Compound 6A can be prepared by treating intermediate 2D with Lawesson's reagent.

Scheme 6

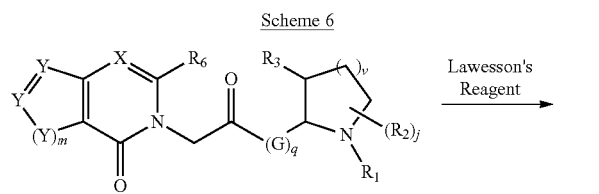

2D

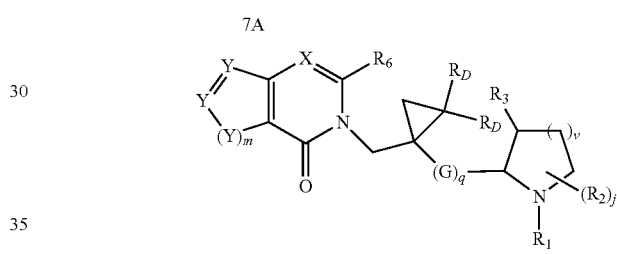

8A

When $R_4$ and $R_5$ are taken together with a neighboring atom to form an epoxide ring, compounds 9A can be prepared according to Scheme 9. Reaction of intermediate 7A with oxygen donors such as MCPBA, hydrogen peroxide, or tert-butyl peroxide provides compound 9A as the product.

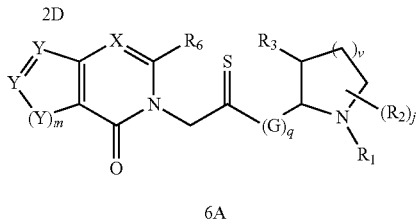

6A

Scheme 9

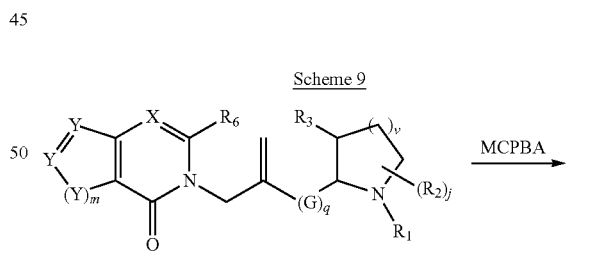

7A

When $R_4$ and $R_5$ are taken together to form $=C(R_D)_2$, compound 7A can be prepared according to Scheme 7. Reaction of the ketone intermediate 2D with the corresponding Wittig reagent yields compound 7A.

Scheme 7

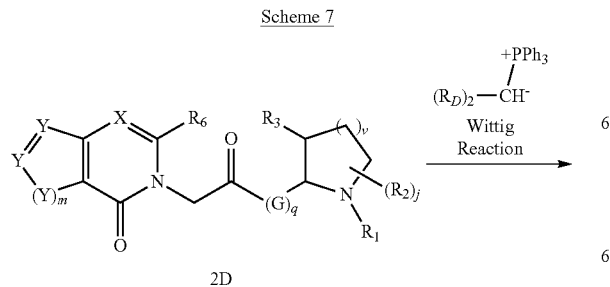

2D

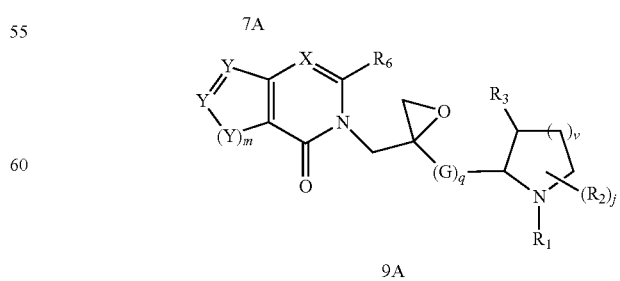

9A

When $R_4$ and $R_5$ are taken together with a neighboring atom to form an aziridine ring, compound 10A can be prepared according to Scheme 10. Compound 10A is prepared by first reacting 7A with ICl and NaN$_3$ in MeCN, followed by reductive ring closure with LiAlH$_4$ in Et$_2$O.

Scheme 10

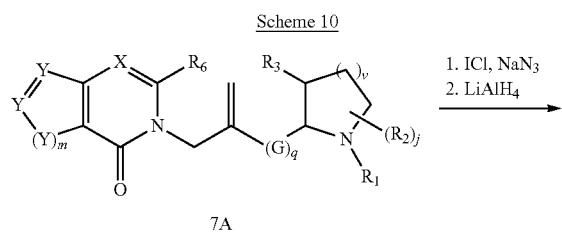

7A

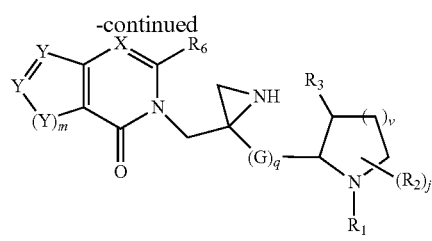

10A

In Scheme 11, compounds 11A-E can be prepared starting with the ketone intermediate 2D. Reductive amination of 2D with corresponding amine $R_D$—NH$_2$ with a catalytic amount of acetic acid and NaCNBH$_3$ (or NaBH(OAc)$_3$) in DCE can provide compound 11A. Subsequently, reaction of 11A with the corresponding acid chloride yields compound 11B; reaction of 11A with the corresponding sulfonyl chloride yields compound 11C; reaction of 11A with the corresponding chloroformate yields compound 11D; and reaction of 11A with the corresponding isocyanate yields compound 11E.

Scheme 11

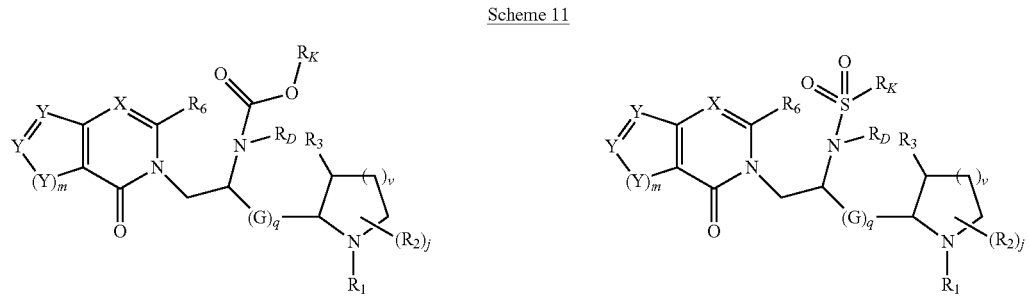

11D                                    11C

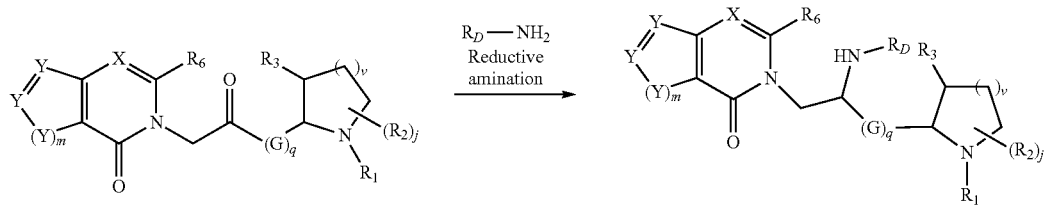

2D                                     11A

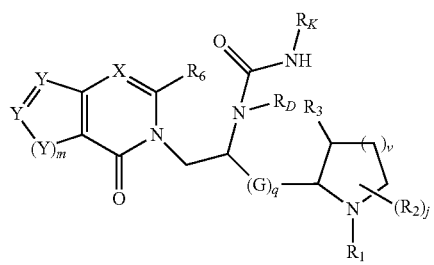

11E

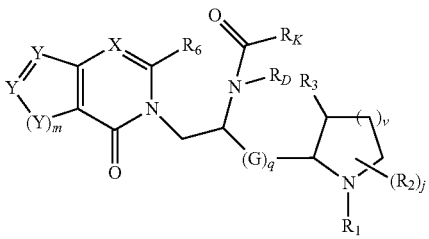

11B

In Scheme 12, reduction of intermediate 7A using H₂ in the presence of a palladium or platinum catalyst, yields compounds 12A.

Scheme 12

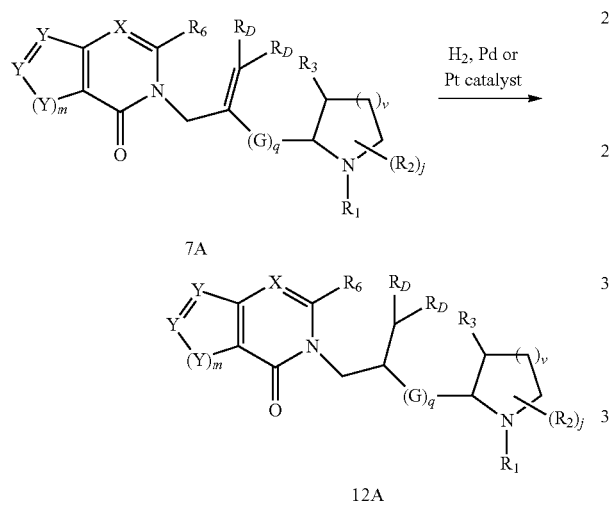

In Scheme 13, the diaziridine compound 13A can be prepared by treating intermediate 2D with HOSO₂ONH₂ and NH₃ in MeOH. Oxidation of 13A with Ag₂O in Et₂O then provides compound 13B.

Scheme 13

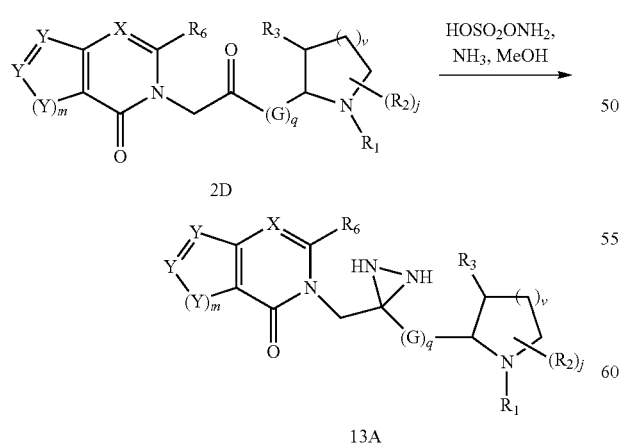

-continued

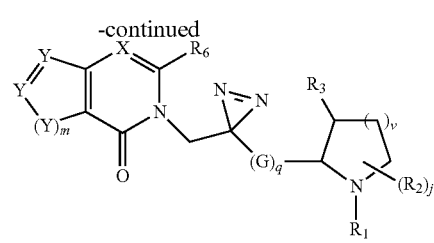

13B

In Scheme 14, treatment of intermediate 2D with the corresponding 1,2-ethanediol in the presence of p-tosyl acid in toluene or another suitable solvent under reflux conditions yields compound 14A.

Scheme 14

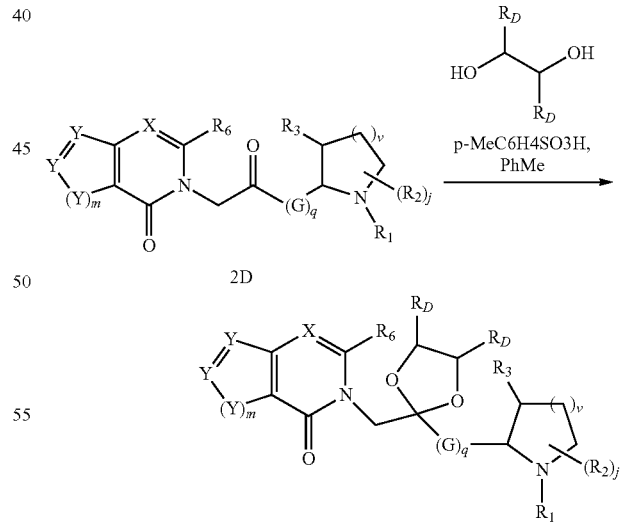

14A

In Scheme 15, refluxing of intermediate 2D with the corresponding 2-aminoethanol in toluene or another suitable solvent yields compound 15A.

Scheme 15
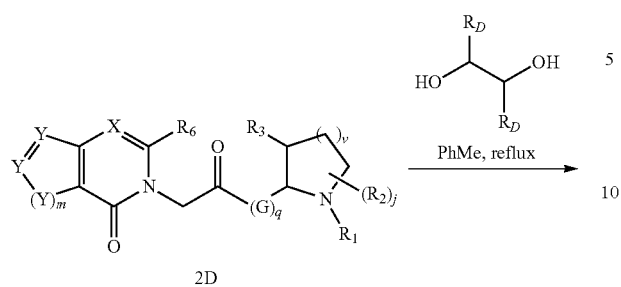
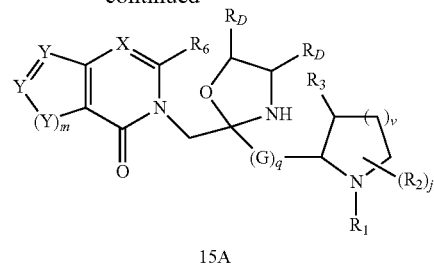
In Scheme 16, intermediate 1C is prepared according to Scheme 1. Reaction of 1C with the corresponding chloroformate, acid chloride, isocyanate, or sulfonyl chloride provides compounds 16A, 16B, 16C, and 16D, respectively.
Scheme 16
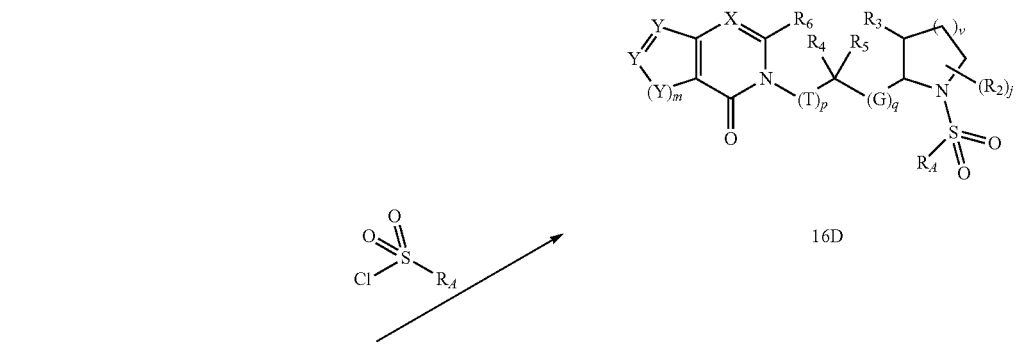
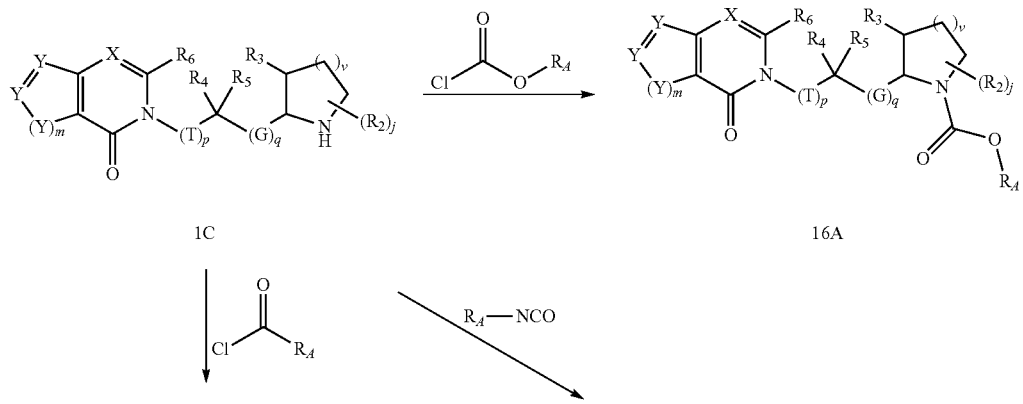
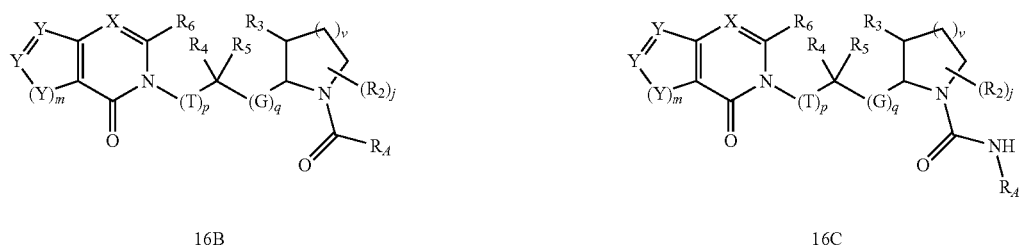

In Scheme 17, alkylation of intermediate 1C with electrophile $(R_A)_3C$—Br (the leaving group can also be I, Cl, OMs, or OTs) provides compound 17A. Alternatively, reductive amination of 1C with the corresponding aldehyde (or ketone) provides compound 17B.

Scheme 17

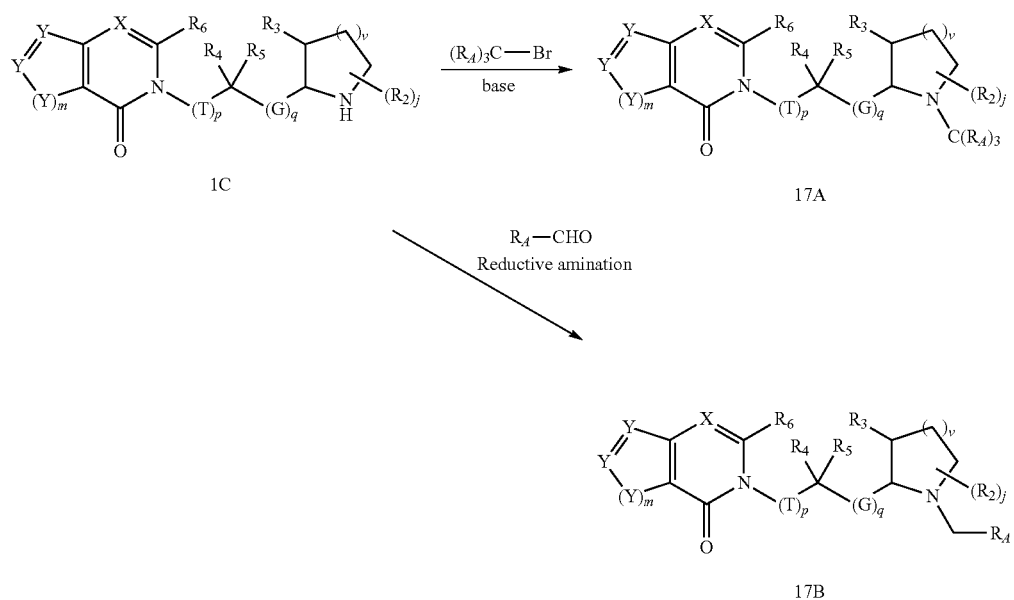

In Scheme 18, cross-coupling of 1C with aryl bromide in the presence of a copper or palladium catalyst provides compound 18A.

Scheme 18

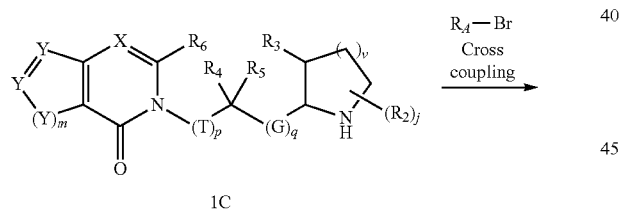

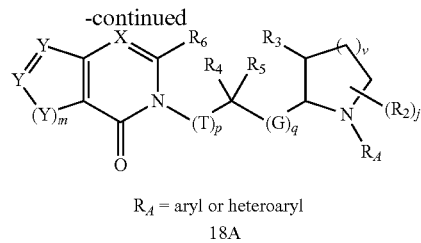

$R_A$ = aryl or heteroaryl

18A

In Scheme 19, intermediate 1C can be prepared according to Scheme 1. Reaction of compound 1C with the corresponding acid chloride, chloroformate, isocyanate, or phosphorochloridate yield compounds 19A, 19B, 19C, or 19D, respectively.

Scheme 19

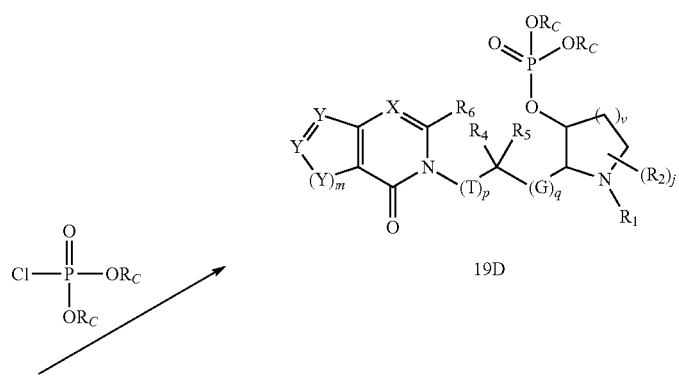

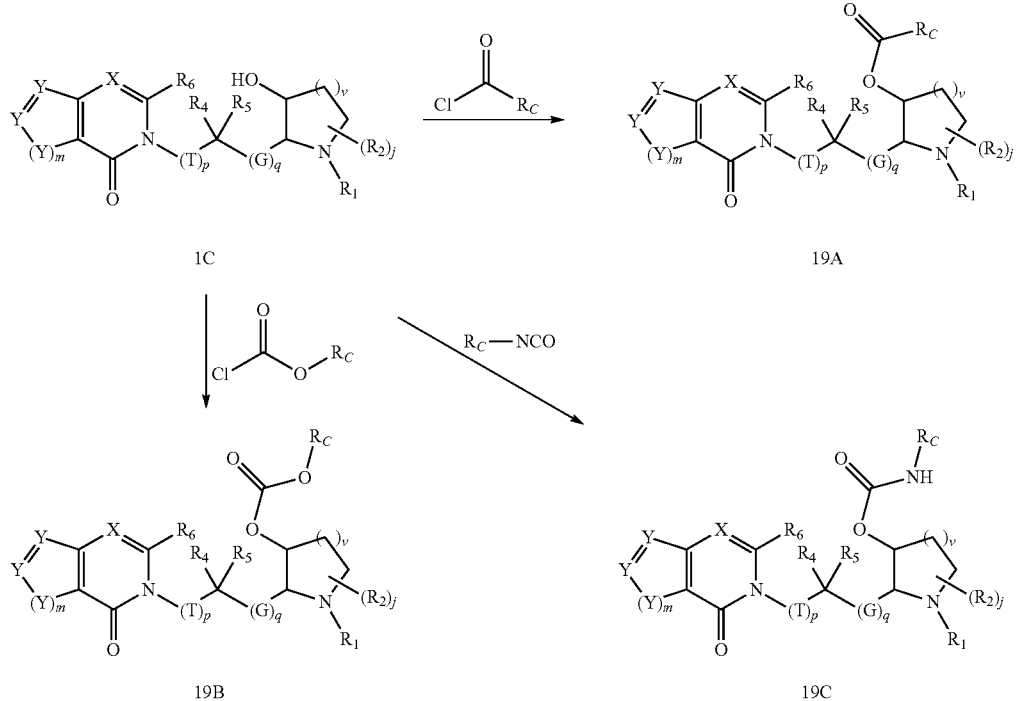

Inhibition of Glutamyl-Prolyl tRNA Synthetase (EPRS)

Some of the analogs of halofuginone (1) described herein act as inhibitors of metazoan glutamyl-prolyl tRNA synthetase (EPRS) or non-metazoan prolyl tRNA synthetase. See FIGS. 21 and 22. In certain embodiments, the EPRS is a eukaryotic EPRS. In certain embodiments, the EPRS is a human EPRS. In certain embodiments, the prolyl tRNA synthetase is a protozoan prolyl tRNA synthetase. A structural feature of these inhibitors is a piperidine or pyrrolidine ring, or an analog thereof. Without wishing to be bound by a particular theory, it is believed that the piperidine ring of halofuginone (1) acts by binding in the active site of the tRNA synthetase like the pyrrolidine ring of proline, thus preventing the charging of the amino acid proline to the tRNA synthetase.

Figure 1:
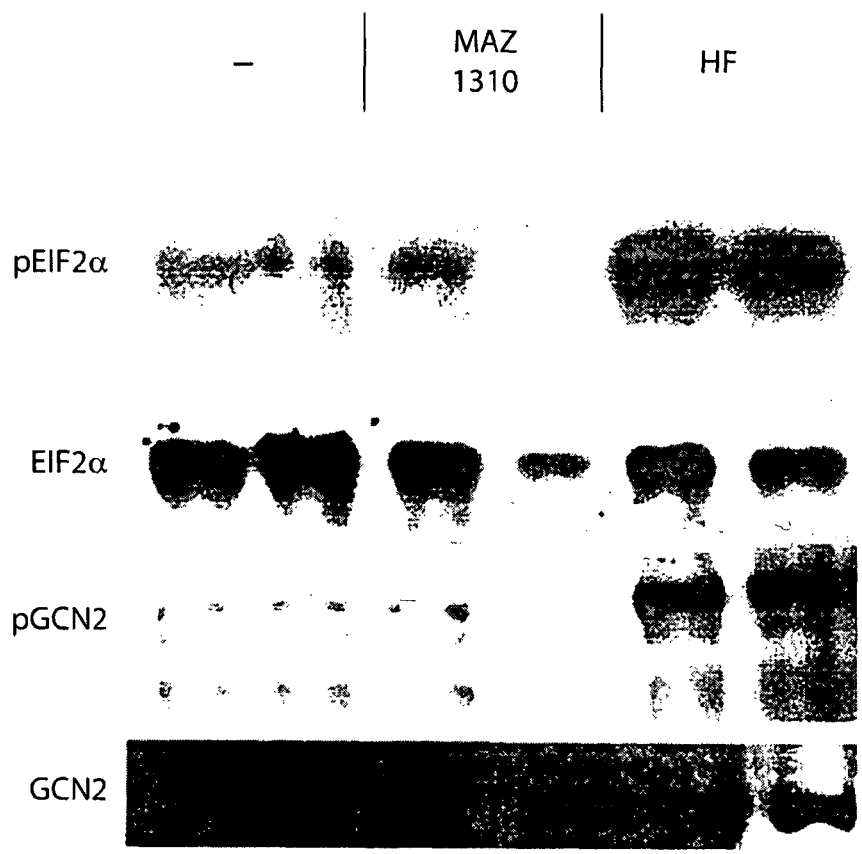
FIG. 1 depicts western blot analysis showing that halofuginone (HF) stimulates the amino acid response (AAR) in a fibroblastic cell line.

Inhibition of EPRS or other tRNA synthetases leads to the accumulation of uncharged prolyl tRNAs, which in turn activates the amino acid starvation response (AAR, FIG. 1). Activation of the AAR in T-cells suppresses the differentiation of a subset of effector T-cells (Th17 cells) that promote autoimmunity. AAR also suppresses pro-fibrotic gene expression and viral gene expression, replication, and maturation. AAR may contribute to the protection of organs from stress (e.g., ER stress in the pancreas during the development of diabetes).

Inhibition of EPRS suppresses the synthesis and accumulation of proteins such as polyglutamine-containing proteins that cause neurodegenerative diseases such as Huntington's disease. This class of EPRS inhibitors also promotes autophagy, a process that clears protein aggregates in diseases such as Huntington's disease, Alzheimer's disease, Parkinson's disease, and amyotrophic lateral sclerosis (ALS). Halofuginone and similarly active compounds are therefore useful as promoters of autophagy.

The specific inhibition of EPRS (as opposed to other tRNA synthetases) also inhibits the synthesis of proline-rich proteins such as collagen, which may be useful for the inhibition of scarring and fibrosis due to excess collagen deposition. Inhibition of collagen synthesis may be useful for cosmetic and therapeutic applications. The role of collagen in fibrosis makes the inventive compounds useful in various cosmetic and therapeutic applications associated with the accumulation of collagen.

The synthesis of collagen and the degradation and remodelling of the ECM are also involved in a number of physiological and pathological conditions, including angiogenesis, systemic sclerosis, graft-versus-host disease (GVHD), pulmonary and hepatic fibrosis, and autoimmune diseases. These disease are many times associated with the excessive production of connective tissue components, particularly collagen, which results in the destruction of normal tissue architecture and function. Therefore, the inventive compounds may be useful in treating or preventing these diseases associated with collagen accumulation or the degradation and remodelling of the ECM.

Molecular Target of Halofuginone

Figure 2:
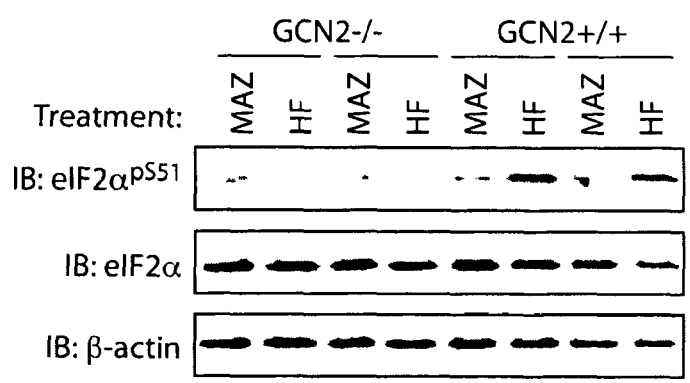
FIG. 2 depicts western blot analysis showing that phosphorylation of eIF2alpha by halofuginone is GCN2-dependent.

Halofuginone activates phosphorylation of eIF2alpha, a downstream component of the amino acid starvation response. The activation of eIF2alpha leads to the stimulation of an upstream kinase, GCN2, the activation of which is monitored by measuring its state of phosphorylation. FIG. 1 shows that GCN2 is phosphorylated in response to halofuginone but not an inactive derivative of halofuginone. The ability of halofuginone to stimulate eIF2alpha phosphorylation is dependent on GCN2, as the ability to stimulate eIF2alpha is lost in cells lacking GCN2 (FIG. 2). Activation of GCN2 is well established to be regulated by the accumulation of uncharged tRNAs (Dong, et al., *Mol. Cell*. (2000) 6: 269-279). These data indicate that halofuginone acts either to limit the availability of amino acids for tRNA charging or to inhibit the enzymes that charge tRNA, the amino-acyl tRNA synthetases. The data detailed below show that halofuginone inhibits an amino-acyl tRNA synthetase, in particular, EPRS.

Figure 3:
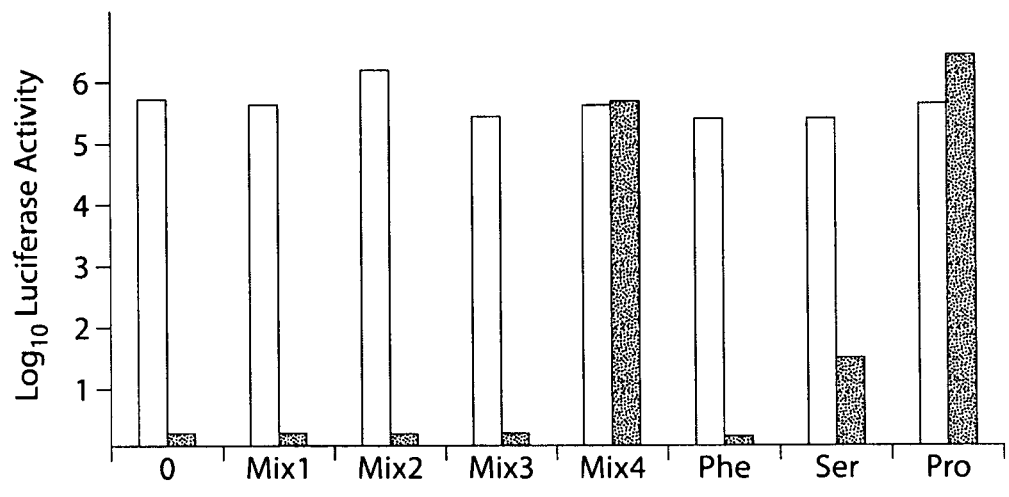
FIG. 3 is a graph showing that proline rescues translational inhibition by halofuginone.

To distinguish these possibilities, the effect of halofuginone on protein translation was examined in an in vitro system (rabbit reticulocyte lysate) in which amino acids are already present at levels adequate to support protein synthesis. In this system, halofuginone at 400 nM inhibits translation of luciferase by 5-6 orders of magnitude (FIG. 3), ruling out the possibility that halofuginone modifies amino acid synthesis or transport and indicating that it blocks tRNA synthetase activity. Distinct tRNA synthetases catalyze the charging of individual tRNA species with their cognate amino acid. To determine which tRNA synthetase is inhibited by halofuginone, several amino acid mixtures were added to the in vitro translation system to determine which, if any, could reverse the inhibition of translation by halofuginone (FIG. 3). When a mixture containing serine, phenylalanine, and proline was found to reverse the effect of halofuginone (FIG. 3, Mix 4), the effect of each amino acid was tested. Only proline could rescue halofuginone inhibition, indicating that glutamyl-prolyl tRNA synthetase (EPRS), the enzyme responsible for proline tRNA aminoacylation, is specifically inhibited by halofuginone. To examine whether proline could specifically rescue the effect of halofuginone in intact cells, the ability of each amino acid to reverse the effect of halofuginone on eIF2alpha phosphorylation in T-cells or to prevent halofuginone inhibition of Th17 differentiation was tested (FIG. 4). Only proline had an effect in these assays, confirming that EPRS is the target for halofuginone in intact cells. Inhibition of EPRS with compounds of the current invention can inhibit Th17 differentiation.

In Vitro Methods

Compounds of the invention may be screened to identify biological activity, e.g., the ability to modulate the development and/or expansion of Th17 cells by inhibiting EPRS, e.g., IL-17 secreting cells, in a subject. An assay for screening selective inhibitors of IL-17 expressing cell development and/or expansion, such as IL-17 expressing effector T-cell development and/or expansion, e.g., Th17 development and/or expansion includes contacting a naïve T-cell population with a test compound under conditions sufficient to allow T-cell development and/or expansion, culturing the cell population, and detecting the level of IL-17 expression and/or the number of Th17 cells in the cell population, wherein no change or a decrease in the level of IL-17 expression in the cell population indicates that the test compound is a selective Th17 inhibitor and/or wherein no change or a decrease in the number of Th17 cells in the cell population indicates that the test compound is a selective Th17 inhibitor. Determining the level of IL-17 expression and/or the number of Th17 cells in the cell population can be accomplished for example by using a detection agent that binds to IL-17 or other marker for Th17 cells, for example, the Th17-specific transcription factor RORgammat (RORγt). The detection agent is, for example, an antibody. The detection agent can be coupled with a radioisotope or enzymatic label such that binding of the detection agent to IL-17 or other Th17 marker can be determined by detecting the labeled compound. For example, the detection agent can be labeled with $^{125}I$, $^{35}S$, $^{14}C$, or $^{3}H$, either directly or indirectly, and the radioisotope detected by direct counting of radioemission or by scintillation counting. Alternatively, detection agents can be enzymatically labeled with, for example, horseradish peroxidase, alkaline phosphatase, or luciferase, and the enzymatic label detected by determination of conversion of an appropriate substrate to product.

Methods of Modulating Th17 Cell Differentiation and/or Proliferation and Other Cellular Functions Using Halofuginone Analogs and Compositions Thereof Halofuginone and analogs thereof have been found to specifically alter the development of T-cells away from the Th17 lineage, which is associated with cell-mediated damage, persistent inflammation, and autoimmunity.

Th17 cells secrete several cytokines that may have a role in promoting inflammation and fibrosis, including IL-17, IL-6, IL-21, and GM-CSF. Of these cytokines, IL-17 is a specific product of Th17 cells, and not other T-cells. Whether Th17 cells are the only source of IL-17 during inflammatory response is not clear, but elevated IL-17 levels are in general thought to reflect expansion of the Th17 cell population.

Diseases that have been associated with expansion of a Th17 cell population or increased IL-17 production include, but are not limited to, rheumatoid arthritis, multiple sclerosis, Crohn's disease, inflammatory bowel disease, dry eye syndrome, Lyme disease, airway inflammation, transplantation rejection, graft versus host disease, lupus, psoriasis, scleroderma, periodontitis, systemic sclerosis, coronary artery disease, myocarditis, atherosclerosis, diabetes, and inflammation associated with microbial infection (e.g., viral, protazoal, fungal, or bacterial infection).

Halofuginone analogs can be useful for treatment of any of these diseases by suppressing the chronic inflammatory activity of IL-17 expressing cells, such as IL-17 expressing effector T-cells, e.g., Th17 cells. In some instances, this may address the root cause of the disease (e.g., self-sustaining inflammation in rheumatoid arthritis); in other cases (e.g., diabetes, periodontitis) it may not address the root cause but may ameliorate the symptoms associated with the disease.

IL-17 expressing effector T-cells, e.g., Th17 cells, and their associated cytokine IL-17 provide a broad framework for predicting or diagnosing diseases potentially treatable by halofuginone analogs. Specifically, pre-clinical fibrosis and/or transplant/graft rejection could be identified and treated with a halofuginone analog, or with a halofuginone analog in combination with other Th17 antagonists. Additionally, diseases that are not currently associated with Th17 cell damage and persistence of inflammation may be identified through the measurement of Th17 cell expansion, or of increased IL-17 levels (e.g., in serum or synovial fluid). Alternatively, or in addition, the use of gene profiling to characterize sets of genes activated subsequent to Th17 differentiation may allow detection of Th17-affected tissues, prior to histological/pathologic changes in tissues.

Halofuginone analogs could be used in combination with other agents that act to suppress Th17 development to achieve synergistic therapeutic effects. Current examples of potential synergistic agents would include anti-IL-21 antibodies or antigen binding fragments thereof, retinoic acid, or anti-IL-6 antibodies or antigen binding fragments thereof, all of which can reduce Th17 differentiation.

Halofuginone analogs could be used in combination with other agents that act to suppress inflammation and/or immunological reactions, such as steroids (e.g., cortisol (hydrocortisone), dexamethasone, methylprednisolone, and/or prednisolone), non-steroidal anti-inflammatory drugs (NSAIDs; e.g., ibuprofen, acetominophin, aspirin, celecoxib, valdecoxib, etoricoxib, lumiracoxib, parecoxib, rofecoxib, nimesulide, and/or naproxen), or immunosuppressants (e.g., cyclosporine, rapamycin, and/or FK506). In certain embodiments, halofuginone analogs are used in combination with agents that are immunomodulatory (e.g., modulators of the mTOR pathway; thalidomide and derivatives thereof such as lenalidomide and actimid; biguanides such as metformin, phenformin, buformin, and proguanil; and HDAC inhibitors such as trichostatin A, depsipeptide, SAHA, PXD101, LAQ824, LBH589, MS275, CI994, MGCD0103, and valproic acid. In some embodiments, an agent that inhibits a tRNA synthetase is used in combination with an inhibitor of a proinflammatory cytokine. Proinflammatory cytokines that can be targeted (in addition to IL-6 and IL-21, discussed above) include TNFα, IFNγ, GM-CSF, MIP-2, IL-12, IL-1α, IL-Iβ, and IL-23. Examples of such inhibitors include antibodies that bind to the cytokine or that bind to a receptor of the cytokine and block its activity, agents that reduce expression of the cytokine (e.g., small interfering RNA (siRNA) or antisense agents), soluble cytokine receptors, and small molecule inhibitors (see, e.g., WO 2007/058990).

In some embodiments, agents that inhibit tRNA synthetases are used in combination with an inhibitor of TNFα. In some embodiments, an inhibitor of TNFα comprises an anti-TNFα antibody or antigen binding fragment thereof. In some embodiments, the anti-TNFα antibody is adalimumab (Humira™). In some embodiments, the anti-TNFα antibody is infliximab (Remicade™). In some embodiments, the anti-TNFα antibody is CDP571. In some embodiments, an inhibitor of TNFα comprises a TNFα receptor. For example, in some embodiments, the TNFα inhibitor is etanercept (Enbrel™), which is a recombinant fusion protein having two soluble TNF receptors joined by the Fc fragment of a human IgG1 molecule. In some embodiments, an inhibitor of TNFα comprises an agent that inhibit expression of TNFα, e.g., such as nucleic acid molecules that mediate RNA interference (RNAi) (e.g., a TNFα selective siRNA or shRNA) or antisense oligonucleotides. For example, a TNFα inhibitor can include, e.g., a short interfering nucleic acid (siNA), a short interfering RNA (siRNA), a double-stranded RNA (dsRNA), or a short hairpin RNA (shRNA)(see, e.g., U.S. Patent Application No. 20050227935, incorporated herein by reference).

Halofuginone analogs can be evaluated in animal models. To determine whether a particular halofuginone analog suppresses graft rejection, allogeneic or xenogeneic grafting (e.g., skin grafting, organ transplantion, or cell implantation) can be performed on an animal such as a rat, mouse, rabbit, guinea pig, dog, or non-human primate. Strains of mice such as C57B1-10, B10.BR, and B10.AKM (Jackson Laboratory, Bar Harbor, Me.), which have the same genetic background but are mismatched for the H-2 locus, are well suited for assessing various organ grafts.

In another example, heart transplantation is performed, e.g., by performing cardiac grafts by anastomosis of the donor heart to the great vessels in the abdomen of the host as described by Ono et al., *J. Thorac. Cardiovasc. Surg.* 57:225, 1969. See also Corry et al., *Transplantation* 16:343, 1973. Function of the transplanted heart can be assessed by palpation of ventricular contractions through the abdominal wall. Rejection is defined as the cessation of myocardial contractions. A halofuginone analog would be considered effective in reducing organ rejection if animals treated with the inhibitor experience a longer period of myocardial contractions of the donor heart than do untreated hosts.

In another example, effectiveness of a halofuginone analog at reducing skin graft rejection is assessed in an animal model. To perform skin grafts on a rodent, a donor animal is anesthetized and a full thickness skin is removed from a part of the tail. The recipient animal is also anesthetized, and a graft bed is prepared by removing a patch of skin (e.g., 0.5× 0.5 cm) from the shaved flank. Donor skin is shaped to fit the graft bed, positioned, covered with gauze, and bandaged. Grafts are inspected daily beginning on the sixth post-operative day and are considered rejected when more than half of the transplanted epithelium appears to be non-viable. A halofuginone analog that causes a host to experience a longer period of engraftment than seen in an untreated host would be considered effective in this type of experiment.

In another example, a halofuginone analog is evaluated in a pancreatic islet cell allograft model. DBA/2J islet cell allografts can be transplanted into rodents, such as 6-8 week-old B6AF1 mice rendered diabetic by a single intraperitoneal injection of streptozotocin (225 mg/kg; Sigma Chemical Co., St. Louis, Mo.). As a control, syngeneic islet cell grafts can be transplanted into diabetic mice. Islet cell transplantation can be performed by following published protocols (for example, see Emamaullee et al., *Diabetes* 56(5):1289-98, 2007). Allograft function can be followed by serial blood glucose measurements (Accu-Check III™; Boehringer, Mannheim, Germany). A rise in blood glucose exceeding normal levels (on each of at least 2 successive days) following a period of primary graft function is indicative of graft rejection. The NOD (non-obese diabetic) mouse model is another model that can be used to evaluate ability of a halofuginone analog to treat or prevent type I diabetes.

In another example, a tRNA synthetase inhibitor is evaluated in a model of dry eye disease (DED). In one such model, DED is induced in mice in a controlled environment chamber by administering scopolamine hydrobromide into the skin four times daily. Chamber conditions include a relative humidity <30%, airflow of 15 L/min, and constant temperature (21-23° C.). Induction of dry eye can be confirmed by measuring changes in corneal integrity with corneal fluorescein staining (see, e.g., Chauhan et al., *J. Immunol.* 182:1247-1252, 2009; Barabino et al., *Invest. Ophthamol. Visual Sci.* 46:2766-2771, 2005; and Rashid et al., *Arch. Ophthamol.* 126: 219-225, 2008).

Numerous autoimmune diseases have been modeled in animals, including rheumatic diseases, such as rheumatoid arthritis and systemic lupus erythematosus (SLE), type I diabetes, dry eye syndrome, and autoimmune diseases of the thyroid, gut, and central nervous system. For example, animal models of SLE include MRL mice, BXSB mice, and NZB mice and their F1 hybrids. The general health of the animal as well as the histological appearance of renal tissue can be used to determine whether the administration of a halofuginone analog can effectively suppress the immune response in an animal model of one of these diseases.

Animal models of intestinal inflammation are described, for example, by Elliott et al. (Elliott et al., 1998, Inflammatory Bowel Disease and Celiac Disease. In: The Autoimmune Diseases, Third ed., N. R. Rose and I. R. MacKay, eds. Academic Press, San Diego, Calif.). Some mice with genetically engineered gene deletions develop chronic bowel inflammation similar to IBD. See, e.g., Elson et al., *Gastroenterology* 109:1344, 1995; Ludviksson et al., *J. Immunol.* 158:104, 1997; and Mombaerts et al., *Cell* 75:274, 1993). One of the MRL strains of mice that develops SLE, MRL-lpr/lpr, also develops a form of arthritis that resembles rheumatoid arthritis in humans (Theofilopoulos et al., *Adv. Immunol.* 37:269, 1985).

Models of autoimmune disease in the central nervous system (CNS), such as experimental allergic encephalomyelitis (EAE), can also be experimentally induced, e.g., by injection of brain or spinal cord tissue with adjuvant into the animal (see, e.g., Steinman and Zamvil, Ann Neurol. 60:12-21, 2006). In one EAE model, C57B/6 mice are injected with an immunodominant peptide of myelin basic protein in Complete Freund's Adjuvant. EAE disease correlates such as limp tail, weak/altered gait, hind limb paralysis, forelimb paralysis, and morbidity are monitored in animals treated with a halofuginone analog as compared to controls.

In addition to T cell differentiation processes, halofuginone analogs can specifically alter processes such as fibrosis and angiogenesis. Fibrosis can be assayed in vitro by observing the effect of a halofuginone analog on fibroblast behavior. In one exemplary assay for use in evaluating halofuginone analogs, primary dermal fibroblasts are cultured in a matrix of Type I collagen, which mimics the interstitial matrix of the dermis and hypodermis, such that fibroblasts attach to the substratum and spread. Inhibition of fibroblast attachment and spreading in the presence of a halofuginone analog indicates that the halofuginone analog has anti-fibrotic properties. Biological effects of halofuginone analogs on non-immune cell functions can also be evaluated in vivo. In some embodiments, a halofuginone analog reduces extracellular matrix deposition (e.g., in an animal model of wound healing; see, e.g., Pines et al., *Biol. Bone Marrow Transplant* 9:417-425, 2003). In some embodiments, a halofuginone analog reduces extracellular matrix deposition at a concentration lower than the concentration at which it inhibits another cellular function, such as cell proliferation or protein synthesis.

The invention further provides methods of treating a disease using a halofuginone analog. The inventive method involves the administration of a therapeutically effective amount of a halofuginone analog to a subject (including, but not limited to a human or other animal).

Compounds and compositions described herein are useful for the inhibition of glutamyl-prolyl tRNA synthetase (EPRS) Inhibition of EPRS leads to the accumulation of uncharged tRNAs, which in turn activate the amino acid starvation response (AAR). Activation of this response suppresses 1) pro-fibrotic gene expression; 2) the differentiation of naïve T-cells into Th17 cells that promote autoimmunity; 3) viral gene expression, replication, and maturation; and/or 4) stress to organs (e.g., during transplantation).

In some embodiments, halofuginone analog that inhibits EPRS has anti-fibrotic properties in vivo. For example, an EPRS inhibitor, halofuginone, potently reduces dermal extracellular matrix (ECM) deposition (Pines et al., *Biol. Blood Marrow Transplant* 9: 417-425, 2003). Halofuginone inhibits the transcription of a number of components and modulators of ECM function, including Type I collagen, fibronectin, the matrix metallopeptidases MMP-2 and MMP-9, and the metalloprotease inhibitor TIMP-2 (Li et al., *World J. Gastroenterol.* 11: 3046-3050, 2005; Pines et al., *Biol. Blood Marrow Transplant* 9: 417-425, 2003). The major cell types responsible for altered ECM deposition, tissue thickening, and contracting during fibrosis are fibroblasts and myofibroblasts. Myofibroblasts mature/differentiate from their precursor fibroblasts in response to cytokine release, often following tissue damage and mechanical stress, and can be distinguished from fibroblasts in a wide range of organs and pathological conditions (Border et al., *New Eng. J. Med.* 331: 1286-1292, 1994; Branton et al., *Microbes Infect.* 1: 1349-1365, 1999; Flanders, *Int. J. Exp. Pathol.* 85: 47-64, 2004). Halofuginone has been studied extensively as a potential anti-fibrotic therapeutic and has progressed to phase 2 clinical trials for applications stemming from these properties.

In animal models of wound healing and fibrotic disease, halofuginone reduces excess dermal ECM deposition when introduced intraperitoneally, added to food, or applied locally (Pines et al., *Biol. Blood Marrow Transplant* 9: 417-425, 2003). Halofuginone is currently in phase 2 clinical trials as a treatment for scleroderma (Pines et al., *Biol. Blood Marrow Transplant* 9: 417-425, 2003), bladder cancer (Elkin et al., *Cancer Res.* 59: 4111-4118, 1999), and angiogenesis during Kaposi's sarcoma, as well as in earlier stages of clinical investigation for a wide range of other fibrosis-associated disorders (Nagler et al., *Am. J. Respir. Crit. Care Med.* 154: 1082-1086, 1996; Nagler et al., *Arterioscler. Thromb. Vasc. Biol.* 17: 194-202, 1997; Nagler et al., *Eur. J. Cancer* 40: 1397-1403, 2004; Ozcelik et al., *Am. J. Surg.* 187: 257-260, 2004). The results presented herein indicate that the inhibition of fibrosis may be due at least in part to the inhibition of glutamyl-prolyl tRNA synthetase (EPRS).

In some embodiments, a halofuginone analog inhibits pro-fibrotic activities of fibroblasts. Thus, in certain embodiments, the present invention provides a method for treating a fibroblast-associated disorder comprising the step of administering to a patient in need thereof a halofuginone analog or pharmaceutically acceptable composition thereof.

As used herein, the term "fibroblast-associated" disorders means any disease or other deleterious condition in which fibroblasts are known to play a role. Accordingly, another embodiment of the present invention relates to treating or lessening the severity of one or more diseases in which fibroblasts are known to play a role including, but not limited to, fibrosis.

While halofuginone at high concentrations (between 20-40 nM) does generally inhibit $CD4^+$ T cell, $CD8^+$ T cell, and $B220^+$ B cell activation, halofuginone also specifically inhibits the development of Th17 cells, i.e., the T helper subset that exclusively expresses high levels of the pro-inflammatory cytokine interleukin IL-17, at low concentrations (PCT/US08/09774, filed Aug. 15, 2008, which claims priority to U.S. Ser. No. 60/964,936, filed Aug. 15, 2007, the entirety of each of which is incorporated herein by reference). Th17 cells, as a function of their IL-17 secretion, play causal roles in the pathogenesis of two important autoimmune diseases in the mouse, experimental autoimmune encephalomyelitis (EAE) and type II collagen-induced arthritis (CIA). EAE and CIA are murine models of the human autoimmune pathologies, multiple sclerosis (MS) and rheumatoid arthritis (RA). Halofuginone has been shown to be active in these models. Halofuginone-mediated specific inhibition of IL-17 expressing cell development, such as IL-17 expressing effector T cell development, e.g., Th17 cell development, takes place at remarkably low concentrations, with 50% inhibition being achieved around 3 nM. Therefore, halofuginone treatment specifically inhibits the development of Th17-mediated and/or IL-17 related diseases, including autoimmune diseases, persistent inflammatory diseases, and infectious diseases, while not leading to profound T cell dysfunction, either in the context of delayed-type hypersensitivity or infection. Halofuginone analogs can also be used to inhibit the development of Th17-mediated and/or IL-17 related diseases.

Halofuginone and analogs thereof interfere with the differentiation of naïve T-cells into IL-17-expressing Th17 cells. Thus, in certain embodiments, the present invention provides a method for treating a Th17-mediated or IL-17-mediated disorder comprising the step of administering to a patient in need thereof a halofuginone analog or a pharmaceutically acceptable composition thereof.

As used herein, the terms "Th17-mediated" disorder and "IL-17-mediated" disorder means any disease or other deleterious condition in which Th17 or IL-17 is known to play a role. Accordingly, another embodiment of the present invention relates to treating or lessening the severity of one or more diseases in which Th17 or IL-17 is known to play a role including, but not limited to, autoimmune diseases, inflammatory diseases, infectious diseases, angiogenesis, and organ protection during transplantation.

The compounds and pharmaceutical compositions of the present invention may be used in treating or preventing diseases or conditions including, but not limited to, asthma, arthritis, inflammatory diseases (e.g., Crohn's disease, rheumatoid arthritis, psoriasis, dry eye syndrome), proliferative diseases (e.g., cancer, benign neoplasms, diabetic retinopathy), cardiovascular diseases, and autoimmune diseases (e.g., rheumatoid arthritis, lupus, multiple sclerosis, psoriasis, scleroderma, or dry eye syndrome). Halofuginone analogs and pharmaceutical compositions thereof may be administered to animals, preferably mammals (e.g., domesticated animals, cats, dogs, mice, rats), and more preferably humans. Any method of administration may be used to deliver the agent or pharmaceutical composition to the animal. In certain embodiments, the agent or pharmaceutical composition is administered orally. In other embodiments, the agent or pharmaceutical composition is administered parenterally.

In certain embodiments, the present invention provides methods for treating or lessening the severity of autoimmune diseases including, but not limited to, acute disseminated encephalomyelitis, alopecia universalis, alopecia areata, Addison's disease, ankylosing spondylosis, antiphospholipid antibody syndrome, aplastic anemia, arthritis, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, celiac disease, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, dry eye syndrome, endometriosis, dysautonomia, essential mixed cryoglobulinemia, fibromyalgia-fibromyositis, glomerulonephritis, idiopathic pulmonary fibrosis, Goodpasture's syndrome, Graves' disease, Guillain-Barre syndrome, Hashimoto's thyroiditis, IgA neuropathy, inflammatory bowel disease, interstitial cystitis, juvenile arthritis, lichen planus, Meniere's disease, mixed connective tissue disease, type 1 or immune-mediated diabetes mellitus, juvenile arthritis, multiple sclerosis, myasthenia gravis, neuromyotonia, opsoclonus-myoclonus syndrome, optic neuritis, Ord's thyroiditis, osteoarthritis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiffman syndrome, Still's disease, systemic lupus erythematosus, takayasu arteritis, temporal arteristis/giant cell arteritis, idiopathic thrombocytopenic purpura, ulcerative colitis, uveitis, vasculitides such as dermatitis herpetiformis vasculitis, vitiligo, vulvodynia, warm autoimmune hemolytic anemia, and Wegener's granulomatosis.

In some embodiments, the present invention provides a method for treating or lessening the severity of one or more diseases and conditions, wherein the disease or condition is selected from immunological conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of an inflammatory disease including, but not limited to, asthma, appendicitis, Blau syndrome, blepharitis, bronchiolitis, bronchitis, bursitis, cervicitis, cholangitis, cholecystitis, chronic obstructive pulmonary disease (COPD), chronic recurrent multifocal osteomyelitis (CRMO), colitis, conjunctivitis, cryopyrin associated periodic syndrome (CAPS), cystitis, dacryoadenitis, dermatitis, dermatomyositis, dry eye syndrome, encephalitis, endocarditis, endometritis, enteritis, enterocolitis, epicondylitis, epididymitis, familial cold-induced autoinflammatory syndrome, familial Mediterranean fever (FMF), fasciitis, fibrositis, gastritis, gastroenteritis, hepatitis, hidradenitis suppurativa, laryngitis, mastitis, meningitis, mevalonate kinase deficiency (MKD), Muckle-Well syndrome, myelitis myocarditis, myositis, nephritis, oophoritis, orchitis, osteitis, inflammatory osteolysis, otitis, pancreatitis, parotitis, pericarditis, peritonitis, pharyngitis, pleuritis, phlebitis, pneumonitis, pneumonia, proctitis, prostatitis, pulmonary fibrosis, pyelonephritis, pyoderma gangrenosum and acne syndrome (PAPA), pyogenic sterile arthritis, rhinitis, salpingitis, sinusitis, stomatitis, synovitis, systemic juvenile rheumatoid arthritis, tendonitis, TNF receptor associated periodic syndrome (TRAPS), tonsillitis, undifferentiated spondyloarthropathy, undifferentiated arthropathy, uveitis, vaginitis, vasculitis, vulvitis, or chronic inflammation resulting from chronic viral or bacteria infections, psoriasis (e.g., plaque psoriasis, pustular psoriasis, erythrodermic psoriasis, guttate psoriasis or inverse psoriasis).

In certain embodiments, the present invention provides methods for treating or lessening the severity of arthropathies and osteopathological diseases including, but not limited to, rheumatoid arthritis, osteoarthritis, gout, polyarthritis, and psoriatic arthritis.

In certain embodiments, the present invention provides methods for treating or lessening the severity of hyperproliferative diseases including, but not limited to, psoriasis or smooth muscle cell proliferation including vascular proliferative disorders, atherosclerosis, and restenosis. In certain embodiments, the present invention provides methods for treating or lessening the severity of endometriosis, uterine fibroids, endometrial hyperplasia, and benign prostate hyperplasia.

In certain embodiments, the present invention provides methods for treating or lessening the severity of acute and chronic inflammatory diseases including, but not limited to, ulcerative colitis, inflammatory bowel disease, Crohn's disease, dry eye syndrome, allergic rhinitis, allergic dermatitis, cystic fibrosis, chronic obstructive bronchitis, and asthma.

In some embodiments, the present invention provides a method for treating or lessening the severity of a cardiovascular disorder including, but not limited to, myocardial infarction, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis, ischemic stroke, cardiac hypertrophy, and heart failure.

The present invention further includes a method for the treatment of mammals, including humans, which are suffering from one of the above-mentioned conditions, illnesses, disorders, or diseases. The method comprises that a pharmacologically active and therapeutically effective amount of one or more of the halofuginone analogs according to this invention is administered to the subject in need of such treatment.

The invention further relates to the use of the halofuginone analogs according to the present invention for the production of pharmaceutical compositions which are employed for the treatment and/or prophylaxis and/or amelioration of the diseases, disorders, illnesses, and/or conditions as mentioned herein.

The invention further relates to the use of halofuginone analogs according to the present invention for the production of pharmaceutical compositions.

The invention further relates to the use of the halofuginone analogs according to the present invention for the production of pharmaceutical compositions for inhibiting or treating fibrosis.

The invention further relates to the use of halofuginone analogs according to the present invention for the production of pharmaceutical compositions which can be used for treating, preventing, or ameliorating of diseases responsive to inhibiting IL-17 production, such as autoimmune or inflammatory diseases, such as any of those diseases mentioned herein.

The exact amount required will vary from subject to subject, depending on the species, age, and general condition of the subject, the particular agent, its mode of administration, its mode of activity, and the like. The compounds of the invention are preferably formulated in dosage unit form for ease of administration and uniformity of dosage. It will be understood, however, that the total daily usage of the agents of the present invention will be decided by the attending physician within the scope of sound medical judgment. The specific therapeutically effective dose level for any particular patient or organism will depend upon a variety of factors including the disorder being treated and the severity of the disorder; the specific agent employed; the age, body weight, general health, sex, and diet of the patient; the time of administration, route of administration, and rate of excretion of the specific agent employed; the duration of the treatment; drugs used in combination or coincidental with the specific agent employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, an agent of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, a halofuginone analog is administered at a dose that is below the dose at which the agent causes non-specific effects. In certain embodiments, a halofuginone analog is administered at a dose that does not cause generalized immunosuppression in a subject.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active agent.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of an agent to the body. Such dosage forms can be made by dissolving or dispersing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the agents and pharmaceutical compositions of the present invention can be employed in combination therapies, that is, the agents and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a halofuginone analog may be administered concurrently with another agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

Methods of Identifying Subjects in Need of Th17 Modulation

In various embodiments of the invention, suitable in vitro or in vivo studies are performed to determine whether administration of a specific therapeutic that modulates the development of IL-17 expressing cells, such as IL-17 expressing effector T-cells, e.g., Th17 cells is indicated for treatment of a given subject or population of subjects. For example, subjects in need of treatment using a compound that modulates IL-17 expressing cell development, such as IL-17 expressing effector T-cell development, e.g., Th17 cell development, are identified by obtaining a sample of IL-17 expressing cells, such as IL-17 expressing effector T-cells, e.g., Th17 cells from a given test subject and expanding the sample of cells. If the concentration of any of a variety of inflammatory cytokine markers, including IL-17, IL-17F, IL-6, IL-21, IL-2, and TNFα, also increases as the cell population expands, then the test subject is a candidate for treatment using any of the compounds, compositions, and methods described herein.

Subjects in need of treatment are also identified by detecting an elevated level of IL-17 expressing cells, such as IL-17 expressing effector T-cells, e.g., Th17 cells or a Th17 cell-associated cytokine or a cytokine that is secreted by a Th17 cell. Cytokine levels to be evaluated include IL-17, IL-17F, IL-6, IL-21, TNFα, and GM-CSF. The cytokine IL-17, as well as other cytokines such as IL-6, IL-21, IL-2, TNFα, and GM-CSF, are typically induced during inflammation and/or infection. Thus, any elevated level of expression of these cytokines in a subject or biological sample as compared to the level of expression of these cytokines in a normal subject is useful as an indicator of a disease state or other situation where treatment with an inventive compound is desirable. Studies have shown that the levels of IL-17 in healthy patient serum is less than 2 pg/mL (i.e., below the detection limit of the assay used), while patients with liver injury had levels of IL-17 expression in the range of 2-18 pg/mL and patients with rheumatoid arthritis had levels greater than 100 pg/mL (see Yasumi et al., *Hepatol Res*. (2007) 37: 248-254, and Ziolkowska et al., *J Immunol*. (2000) 164: 2832-2838, each of which is incorporated herein by reference). Thus, detection of an expression level of IL-17 greater than 2 pg/mL in a subject or biological sample is useful in identifying subjects in need of treatment.

A subject suffering from or at risk of developing a Th17-related and/or IL-17-related diseases such as an autoimmune disease, a persistent inflammatory disease, or an infectious disease is identified by methods known in the art. For example, subjects suffering from an autoimmune disease, persistent inflammatory disease, or an infectious disease are diagnosed based on the presence of one or more symptoms associated with a given autoimmune, persistent inflammatory, or infectious disease. Common symptoms include, for example, inflammation, fever, loss of appetite, weight loss, abdominal symptoms, such as, for example, abdominal pain, diarrhea, or constipation, joint pain or aches (arthralgia), fatigue, rash, anemia, extreme sensitivity to cold (Raynaud's phenomenon), muscle weakness, muscle fatigue, change in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function.

Subjects suffering from an autoimmune disease such as, e.g., multiple sclerosis, rheumatoid arthritis, Crohn's diseases, are identified using any of a variety of clinical and/or laboratory test such as, physical examination, radiological examination and blood, urine, and stool analysis to evaluate immune status. For example, subjects suffering from an infectious disease such as Lyme disease are identified based on symptoms, objective physical findings (such as erythema migrans, facial palsy, or arthritis), and a history of possible exposure to infected ticks. Blood test results are generally used to confirm a diagnosis of Lyme disease.

Determination of the Biological Effect of Th17 Modulation

In various embodiments of the invention, suitable in vitro or in vivo studies are performed to determine the effect of a specific therapeutic that modulates the development of IL-17 expressing cells, such as IL-17 expressing effector T-cells, e.g., Th17 cells, and whether its administration is indicated for treatment of a given subject or population of subjects. For example, the biological effect of a selective Th17 inhibitor therapeutic, such as a compound of the invention, is monitored by measuring level of IL-17 production and/or the number of IL-17 expressing cells, such as IL-17 expressing effector T-cells, e.g., Th17 cells in a patient-derived sample. The biological effect of a therapeutic is also measured by physical and/or clinical observation of a patient suffering from, or at risk of developing, a Th17-related and/or Il-17-related disease such as an autoimmune disease, persistent inflammatory disease, and/or an infectious disease. For example, administration of a specific Th17 inhibitor to a patient suffering from a Th17-related disease and/or an IL-17-related disease is considered successful if one or more of the symptoms associated with the disorder is alleviated, reduced, inhibited, or does not progress to a further, i.e., worse, state.

These and other aspects of the present invention will be further appreciated upon consideration of the following Examples, which are intended to illustrate certain particular embodiments of the invention but are not intended to limit its scope, as defined by the claims.

EXAMPLES

Example 1

The Amino Acid Starvation Response (AAR) is Activated by HF in Cultured Fibroblastic Cells SV-MES mesangial cells were stimulated for 2 hours with halofuginone (20 nM), or an inactive derivative of halofuginone 9 (MAZ1310, 20 nM) or control buffer, lysed and analyzed by SDS-PAGE/Western blot for total or Ser51 phosphorylated eIF2alpha, and total or Thr 898 phosphorylated GCN2. FIG. 1 shows the results of the experiment. Duplicate cell samples are shown. Phosphorylation of GCN2 at Thr898 is a defining characteristic of AAR activation, therefore the activation of GCN2 phosphorylation at this site following HF treatment indicates that HF activates the AAR. Activated GCN2 phosphorylates eif2alpha at Ser 51, therefore this is an expected downstream outcome of AAR activation.

Example 2

GCN-2 Dependency of Halofuginone Stimulated eIF2alpha Phosphorylation

CD4+ CD25− T cells purified from wild type of GCN2−/− mice were activated through TCR for 4 hours in the presence of halofuginone (10 nM) or 9 (MAZ1310, 10 nM). Results are shown in FIG. 2. Whole cell lysates were analyzed by SDS PAGE/Western blot and antibodies indicated. Treatment with Halofuginone, but not the inactive derivative 9, leads to phosphorylation of Ser51 of eif2alpha only in wild type cells and not in GCN2−/− cells, establishing the eif2alpha phosphorylation following halofuginone stimulation occurs through activation of the AAR/GCN2 pathway.

Example 3

Proline Rescue of Translation Inhibition by Halofuginone

Translation in vitro was performed using rabbit reticulocyte lysates and luciferase mRNA as template. Translation was measured as arbitrary units of luciferase activity using a luminometer based luminescence assay. Results are shown in FIG. 3. Log scale presentation of background-subtracted data is shown. Translations were performed without (dark bars) or with (light bars) 400 nM halofuginone, in the absence of amino acids (0), or with the following additions: Mix 1: 1 mM Asn, 1 mM Arg; Mix 2: 1 mM Lys, 1 mM Ile, 1 mM Tyr; Mix 3: 1 mM His, 1 mM Met, 1 mM Leu; Mix 4: 1 mM Ser, 1 mM Phe, 1 mM Pro, Phe: 2 mM Phe; Pro: 2 mM Pro; Ser: 2 mM Ser. Addition of proline, either alone or in combination with phenylaline and serine, rescues inhibition of translation by halofuginone, establishing that proline utilization for translation (by glutamyl prolyl tRNA synthetase) is the critical target of halofuginone action.

Example 4

Halofuginone-Induced eIF2alpha Phosphorylation is Rescued by Proline Addition

Naïve T-cells were treated to stimulate the T-cell receptor (TCR) in the presence or absence of 10 nM halofuginone in the presence of 1 mM added amino acid, and then assayed for eIF2alpha activity phosphorylation by SDS PAGE/Western blot. Results are shown in FIG. 4A. Phosphorylation induced by halofuginone is blocked by added proline. These data establish that utilization of proline is inhibited by halofuginone, leading to activation of the AAR.

Example 5

Rescue of Halofuginone Inhibited Th17 Differentiation by Proline

Figure 4B:
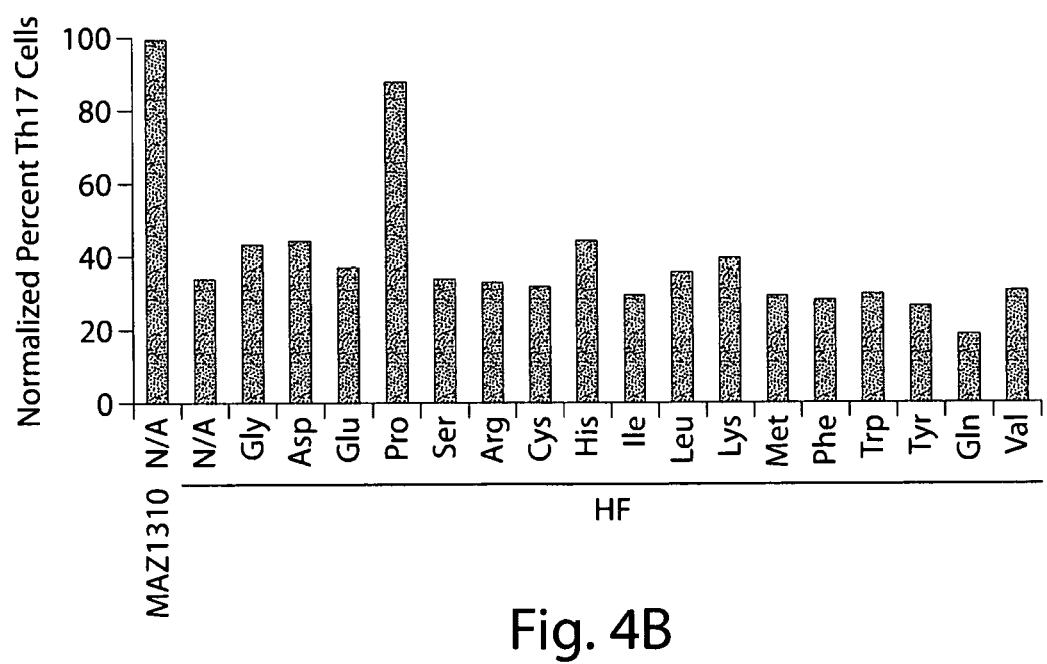
FIG. 4B is a graph showing that halofuginone-inhibited Th17 differentiation is blocked by added proline.

Naïve T-cells were stimulated to differentiate in the presence or absence of 10 nM halofuginone, with 1 mM of the indicated amino acids added to the medium, and stained for Th17 differentiation on day 4. Results are shown in FIG. 4B. Naïve murine T cells were activated in the presence or absence of TGFβ plus IL-6 as indicated, expanded in for 4 days and restimulated with PMA and ionomycin for intracellular cytokine staining. For intracellular cytokine staining, fixed cells were washed twice with staining buffer (PBS/1% BSA/0.1% NaN$_3$) and then permeabilized with perm buffer III (BD Pharmingen) on ice for 30 minutes. Cells were then washed and stored in staining buffer prior to data acquisition All FACS data was acquired on a FACSCalibur flow cytometer (BD Pharmingen) and analyzed using FlowJo software (Treestar, Inc., Ashland, Oreg.). FACS sorting was performed on a FACS-Diva cytometer (BD Pharmingen). Bars indicate percentage of cells differentiation as Th17 as indicated by IL17 expression. Proline, and no other added amino acid, rescues the inhibition of Th17 differentiation by halofuginone, confirming that proline utilization is the critical target for halofuginone inhibition of Th17 differentiation.

Example 6

Inhibition of Cell Spreading by Halofuginone Analogs in a Fibroblast Model

The ability of halofuginone and analogs thereof to inhibit the spreading of freshly plated primary dermal fibroblasts was examined. Human primary dermal fibroblasts were replated and halofuginone added immediately after replating; spreading of cells was assessed by light microscopy 28 hours after treatment with compound. "+++" vs. "++" vs. "+" in general denotes ~4-fold differences in potency. "−" denotes no activity at any dose tested, up to 1000× the effective dose of halofuginone. These data establish that several analogs of halofuginone act similarly to halofuginone in this assay, and that these activities correlate well with activities described in Tables 2 and 3 below.

TABLE 1

Inhibition of cell spreading by halofuginone analogs in a fibroblast model

| Compound # | Fibroblast inhibition |
|---|---|
| 1 | +++ |
| 2 | − |
| 3 | ++ |
| 4 | − |
| 5 | ++ |
| 6 | − |
| 7 | +++ |
| 8 | + |
| 9 | − |
| 10 | +++ |
| 11 | + |
| 12 | ++ |
| 13 | ++ |
| 15 | +++ |
| 16 | − |

Example 7

Inhibition of Th17 Differentiation by Halofuginone Analogs

The effect of different halofuginone and analogs thereof on differentiation of naïve T-cells was assayed as described in legend for FIG. 4 above. Differentiation of primary naïve T-cells into Th17 cells following T-cell receptor stimulation+IL-6+TGFb. "+++" vs. "++" vs. "+" in general denotes ~4-fold differences in potency. "−" denotes no activity at any dose tested, up to 1000× the effective dose of halofuginone. These data establish that several analogs of halofuginone act similarly to halofuginone in this assay.

TABLE 2

Inhibition of Th17 differentiation by halofuginone analogs.

| Compound # | Inhibition of Th17 differentiation |
|---|---|
| 1 | +++ |
| 2 | − |
| 3 | ++ |
| 4 | − |
| 7 | +++ |
| 9 | − |
| 10 | +++ |
| 11 | + |
| 13 | ++ |

Example 8

Translational Inhibition by Halofuginone Analogs in Rabbit Reticulocyte Lysates

Inhibition of translation of luciferase RNA by halofuginone and analogs thereof was measured as described in FIG. 3 above. Results are shown of translation of a luciferase RNA reporter in a rabbit reticulocyte lysate. "+++" vs. "++" vs. "+" in general denotes ~4-fold differences in potency. "−" denotes no activity at any dose tested, up to 1000× the effective dose of halofuginone. These data establish that several analogs of halofuginone act similarly to halofuginone in this assay, and that these activities correlate well with activities described in Tables 1 and 2 above.

TABLE 3

Translational inhibition by halofuginone analogs in rabbit reticulocyte lysates

| Compound # | Translational inhibition |
| --- | --- |
| 1 | +++ |
| 2 | − |
| 3 | ++ |
| 4 | − |
| 7 | +++ |
| 8 | + |
| 9 | − |
| 12 | ++ |
| 13 | ++ |
| 14 | ++ |
| 15 | + |
| 16 | − |

Example 9

Inhibition of Th17 Cell Development Through Activation of an Amino Acid Starvation Response This example shows that the aminoacyl tRNA synthetase inhibitor, halofuginone (HF), imparts a selective block of Th17 differentiation in both human and mouse T cells by inducing the AAR response.

To investigate whether HF can modulate T cell differentiation or effector function, purified murine CD4$^+$ CD25$^-$ T cells were treated with HF or its inactive derivative 9 (MAZ1310) and stimulated in the absence or presence of polarizing cytokines to induce Th1, Th2, iTreg, or Th17 differentiation. Dose-response experiments revealed a remarkably selective effect of HF on Th17 differentiation (defined here as the percentage of IL-17$^+$ IFNγ$^-$ cells following restimulation on day 4-5). HF repressed Th17 differentiation in a dose-dependent manner with an IC$_{50}$ of 3.6 nM±0.4 nM (FIG. 5A, 5B). Low concentrations of HF (1-10 nM) that strongly reduced IL-17 production (FIG. 5A, 5B, FIG. 9A) did not affect T cell proliferation, CD25 upregulation, or production of IL-2, TNF, or IFNγ (FIG. 9B). Low-dose HF also failed to modulate Th1, Th2 or iTreg differentiation as assessed by IFNγ, IL-4, or Foxp3 expression, respectively (FIG. 9A). At approximately 10-fold higher concentrations (>20 nM), HF induced a general inhibition of T and B cell activation, proliferation, and effector function (FIG. 5A, 5B).

The selective inhibition of Th17 differentiation by low-dose HF was stereospecific: the HPLC-purified D-enantiomer of HF inhibited IL-17 expression more potently than a racemic mixture, whereas the L-enantiomer was completely inactive (FIG. 5C). Inhibition of IL-17 expression was most pronounced when HF was added during a 12-hour window at the start of the culture period (FIG. 5D) and HF treatment impaired expression of both IL-17 and IL-17f mRNA (FIG. 9C). These results suggest that HF regulates early events, possibly involved in Th17 lineage commitment, rather than influencing the expansion of Th17 cells or preventing acute cytokine expression upon restimulation. Inhibition by HF was not due to perturbation of cell cycle progression or selective survival; HF inhibited IL-17 expression in a dose-dependent manner even when considering only cells that had completed an equivalent number of cell divisions based on CFSE dilution (FIG. 5E). HF also reduced IL-17 expression in cultures where IFNγ and IL-4, cytokines known to inhibit Th17 differentiation (Park et al., Nat. Immunol. 6:1133, 2005), were blocked by addition of neutralizing antibodies. Thus, HF-mediated inhibition of Th17 cell development is not secondary to effects on T cell proliferation or auxiliary cytokine production.

In light of reports that IL-17 expression may be differentially regulated in murine versus human T cells (Manel et al., Nat. Immunol. 9:641, 2008; Wilson et al., Nat. Immunol. 8:950, 2007; Acosta-Rodriguez et al., Nat. Immunol. 8:942, 2007), HF modulation of IL-17 expression by human CD4$^+$ T cells was investigated. These experiments showed that HF treatment greatly reduced both the percentage of human T cells expressing IL-17 and the amount of IL-17 produced (FIG. 5F, 5G). In striking contrast, IFNγ expression was essentially unaffected by HF treatment (FIG. 5F, 5G). Therefore, HF selectively limits IL-17 expression in both human and mouse T cells.

Th17 differentiation is synergistically regulated by TGFβ and the pro-inflammatory cytokines IL-6 and IL-21. Although reports had indicated that HF can attenuate TGFβ signaling at high concentrations (>50 nM) (Gnainsky et al., Cell Tiss. Res. 328:153, 200; Flanders, Int. J. Exp. Pathol. 85:47, 2004), it was discovered that low dose HF inhibited neither TGFβ-induced Smad phosphorylation nor a variety of other lymphocyte responses to TGFβ (Li et al., Ann. Rev. Immunol. 24:99, 2006; Glimcher et al., Nat. Rev. Immunol. 4:900, 2004; van Vlasselaer et al., J. Immunol. 148:2062, 1992), in contrast to the type 1 TGFβ receptor kinase inhibitor SB-431542, which abrogated all responses to TGFβ (FIG. 10). Since STAT3 is the major transducer of IL-6 and IL-21 signaling, the kinetics of STAT3 phosphorylation in HF-treated T cells were examined. HF did not interfere with STAT3 activation during the first 6 hours of Th17 differentiation, but rather decreased the maintenance of STAT3 phosphorylation, beginning around 12 hours post activation (FIG. 6A, 6B).

Next, it was investigated whether inhibition of Th17 differentiation by HF could be restored by transgenic expression of a hyperactive STAT3 protein (STAT3C) (Bromberg et al., Cell 98:295, 1999). T cells isolated from homozygous mice containing a floxed stop-STAT3C-IRES-EGFP (STAT3C-GFPfl/fl) or stop-YFP (YFPfl/fl) cassette inserted into the ROSA26 locus were transduced with a cell-permeant TAT-Cre fusion protein to delete the stop cassette and these cells were activated in the presence of TGFβ plus IL-6, with either HF or 9 (MAZ1310). As expected, HF strongly impaired Th17 differentiation of cells expressing YFP or those not expressing a transgene (FIG. 6C, top three panels); in contrast, T cells expressing STAT3C (defined by their concomitant expression of GFP) remained capable of differentiating into Th17 cells even in the presence of 10 nM HF (FIG. 6C, bottom panel). Data from a number of similar experiments are quantified and summarized in FIG. 6D. Collectively, these results suggest that HF inhibits Th17 differentiation through its ability to prevent sustained activation of STAT3. STAT3 promotes Th17 lineage commitment through the induction of the orphan nuclear receptors RORγt and RORα (Yang et al., J. Biol. Chem. 282:9358, 2007; Ivanov et al., Cell 126:1121, 2006; Yang et al., Immunity 28:29, 2008). Consistent with the finding that HF did not affect STAT3 phosphorylation during the first 12 hours of stimulation, HF did not interfere with the upregulation of RORγt or RORα during Th17 differentiation (FIG. 11A). Moreover, HF inhibited Th17 differentiation as effectively in T cells retrovirally transduced with RORγt-expressing retroviruses as in those transduced with empty retroviruses (FIG. 11B, 11C). T cells differentiated in the presence of HF showed enhanced Foxp3 expression (FIG. 6E), as expected from the observations that HF inhibits STAT3 signaling and Th17 differentiation (Yang et al., J. Biol.

*Chem.* 282:9358, 2007). This result suggested that HF redirects developing Th17 cells to the iTreg lineage rather than simply blocking their effector function. However, upregulation of Foxp3 by HF was neither necessary nor sufficient to inhibit Th17 differentiation; retroviral expression of FOXP3 in T cells did not decrease IL-17 expression induced by TGFβ plus IL-6 (FIG. 12A), though it markedly reduced IL-2 and IFNγ production in T cells cultured under non-polarizing conditions. Moreover, HF strongly repressed IL-17 expression in T cells lacking Foxp3 (FIG. 12B). Therefore, the inhibitory effects of HF on Th17 differentiation are not exerted indirectly through the upregulation of Foxp3. Rather, HF impairs the maintenance of STAT3 phosphorylation in developing Th17 cells, resulting in a reciprocal increase in iTreg cell development.

The 12-hour lag period between the addition of HF to T cell cultures and the ensuing effect on STAT3 phosphorylation strongly suggested an indirect effect. To identify more proximal cellular effects of HF treatment, we used DNA microarrays to define the transcriptional profiles of HF- and MAZ 1310-treated T cells activated in Th17-priming conditions for 3 or 6 hours. Eighty-one annotated genes that were differentially expressed at both time points in HF-versus MAZ1310-treated cells were identified, the majority of which were upregulated following HF treatment (FIG. 7A, FIG. 15). Among the HF-inducible transcripts, a large number of genes functionally associated with amino acid synthesis and transport, as well as protein synthesis, were observed (FIG. 7A, FIG. 15). Similar gene expression profiles have been observed during cellular responses to amino acid starvation (Fafournoux et al., *Biochem. J.* 351:1, 2000; Peng et al., *Mol. Cell Biol.* 22:5575, 2002). Insufficient cellular levels of amino acids lead to the accumulation of uncharged tRNAs that, in turn, activate the amino acid response (AAR) pathway via the protein kinase GCN2. Activated GCN2 phosphorylates and inhibits eukaryotic translation initiation factor 2A (eIF2α), thereby reducing overall protein translation, while specifically enhancing translation of the transcription factor ATF4 (Harding et al., *Mol. Cell* 11:619, 2003; Harding et al., *Mol. Cell* 6:1099, 2000). Indeed, a number of stress-induced genes reportedly regulated by ATF4 in mouse embryonic fibroblasts (Harding et al., *Mol. Cell* 11:619, 2003) were over-represented among the genes induced by HF treatment in T cells (FIG. 7B, FIG. 16). These analyses suggest that at least a portion of the transcriptional response to HF is mediated by ATF4. Furthermore, quantitative real-time PCR (qPCR) experiments confirmed that at least three known AAR-associated genes (Asns, Gpt2, eIF4Ebp1) were induced by HF treatment within 4 hours of T cell activation (FIG. 7C).

To directly address whether HF activates the AAR pathway, eIF2α phosphorylation and ATF4 protein levels in HF-treated T cells was examined. HF induced detectable eIF2α phosphorylation at 2.5 nM, and this effect plateaued at 5-10 nM HF (FIG. 7D). ATF4 expression levels were highest in T cells treated with 5-10 nM HF and were reduced in cells treated with higher concentrations of HF (20-40 nM) (FIG. 7D), demonstrating a positive correlation between the concentrations of HF that induce ATF4 expression and those that selectively inhibit Th17 differentiation (FIG. 5A). In kinetic analyses, eIF2α phosphorylation in HF-treated cells reached maximum levels by 2 hours and ATF4 protein continued to accumulate until 4 hours (FIG. 7E), indicating that HF activates the AAR pathway before any detectable effects on STAT3 phosphorylation or IL-17 production are observed. AAR activation was a general consequence of HF treatment; HF induced eIF2α phosphorylation, not only in T cells activated in Th17-priming conditions, but also in resting naïve T cells and T cells activated in ThN, Th1, Th2, and iTreg polarizing conditions (FIG. 7F). HF treatment also increased eIF2α phosphorylation in cultured fibroblasts (FIG. 13) and microarray analyses of fibroblasts revealed that HF induced a pattern of early gene induction similar to that seen in T cells. These data demonstrate that activation of the AAR pathway by HF is not a cell type-specific effect. HF treatment induced ATF4 expression in all differentiated T cells, but not in naïve T cells (FIG. 7F). This result most likely reflects the low metabolic rate and relatively inefficient translation capacity of naïve T cells (Rathmell et al., *Eur. J. Immunol.* 33:2223, 2003). Thus, the rapid activation of the AAR pathway by HF could underlie both its selective inhibition of Th17 differentiation and its effects on fibroblasts (Pines and Nagler, *Gen. Pharmacol.* 30:445, 1998).

A variety of other cellular stresses (ER stress, oxidative stress, viral infection) also result in eIF2α phosphorylation and ATF4 translation, a phenomenon termed the integrated stress response (ISR) (Harding et al., *Mol. Cell* 11:619, 2003; Harding et al., *Mol. Cell* 6:1099, 2000). Individual stressors, however, can also activate stress type-specific pathways. For instance, the unfolded protein response (UPR), which is activated by ER stress, results in expression of the transcription factor Xbp-1 through a mechanism involving IRE-1-dependent splicing, as well as nuclear translocation of the ER-sequestered transcription factor ATF6 in addition to eIF2α phosphorylation catalyzed by the protein kinase Perk (Ron and Walter, *Nat. Rev. Mol. Cell Biol.* 8:519, 2007; Brunsing et al., *J. Biol. Chem.* 283, 17954, 2008; Lin et al., *Science* 318:944, 2007). Xbp-1 and ATF6, in turn, upregulate ER chaperones such as GRP78/BiP and calreticulin, whose expression is specific to the UPR and independent of the eIF2α/ATF4 ISR pathway (Ron and Walter, *Nat. Rev. Mol. Cell Biol.* 8:519, 2007; Lee et al., *Mol. Cell Biol.* 23: 7448, 2003). However, HF did not induce the expression of these and other hallmark ER stress response genes.

To delineate the stress response pathway activated by HF, the effects of amino acid starvation with those of tunicamycin (an inducer of ER stress) or HF treatment during T cell activation were compared. As expected, cells deprived of cysteine (Cys) and methionine (Met) displayed eIF2α phosphorylation, ATF4 expression, and upregulation of AAR-associated genes but did not induce Xbp-1 splicing (FIG. 8A, FIG. 14A, 14B). In contrast, tunicamycin treatment induced eIF2α phosphorylation and ATF4 expression together with Xbp-1 splicing (FIG. 8A), as characteristic of the UPR. The effects of HF treatment closely resembled those of amino acid starvation, inducing eIF2α phosphorylation without promoting Xbp-1 splicing (FIG. 8A). Taken together, these data indicate that HF specifically induces an AAR.

Next, the effects of amino acid starvation on Th17 differentiation and STAT3 activation were investigated. It was discovered that the functional consequences of Cys/Met-deprivation were remarkably similar to those of HF treatment in T cells. Cys/Met deprivation profoundly and selectively impaired Th17 differentiation in a manner directly related to the concentration of these amino acids in the culture medium. T cells cultured under limiting Cys/Met concentrations showed greatly diminished Th17 differentiation but upregulated CD25 expression and differentiated into Th1, Th2, and iTreg subsets as effectively as T cells cultured in complete medium (FIG. 8B, FIG. 14C). As shown for HF (FIG. 5E), inhibition of IL-17 expression by amino acid starvation was unrelated to cell survival or proliferation (FIG. 14D). Further similar to the effects of HF, Cys/Met-deprivation did not affect the early phase of STAT3 phosphorylation but impaired the maintenance of STAT3 phosphorylation (FIG. 8C, 8D).

Moreover, L-tryptophanol, a tryptophan derivative that competitively inhibits tryptophanyl-tRNA loading, or limiting concentrations of a different amino acid, leucine, also impaired IL-17 production (FIG. 8E), suggesting that inhibition of Th17 differentiation is a general consequence of amino acid starvation. The mammalian target of rapamycin (mTOR) pathway represents a second, complementary mechanism through which cells respond to amino acid availability (Fingar and Blenis, *Oncogene* 23:3151, 2004). However, early transcriptional responses induced by HF and the mTOR inhibitor rapamycin are distinct (Peng et al., *Mol. Cell Biol.* 22:5575, 2002 and FIG. 15), and HF did not inhibit signaling downstream of mTOR in fibroblasts.

To test whether inhibition of IL-17 expression was specific to stress induced by amino acid starvation, the influence of tunicamycin on T cell activation and differentiation was tested. Surprisingly, low concentrations of tunicamycin had little influence on IL-17 expression in T cells (FIG. 8F, FIG. 14C) but instead preferentially impaired Th1 and Th2 differentiation (FIG. 8F, FIG. 14C). These data suggest that individual stress response pathways can regulate distinct aspects of T cell differentiation and effector function but also indicate that eIF2α phosphorylation and ATF4 translation (shared consequences of both AAR and UPR) are not sufficient to explain the selective regulation of Th17 differentiation by HF or amino acid deprivation. The impact of cellular stress on the immune system is complex. Data herein show here that Th17 differentiation is particularly susceptible to stress induced by amino acid deprivation, whereas ER stress blunts Th1 and Th2 differentiation. In addition to these effects on T cell effector function, eIF2α phosphorylation induced during ER stress may have cytoprotective effects in oligodendrocytes and pancreatic β cells during acute inflammation associated with autoimmune encephalomyelitis and diabetes (Puccetti and Grohmann, *Nat. Rev. Immunol.* 7:817, 2007; Lin et al., *J. Clin. Invest.* 117:448, 2007). Diverse cellular responses to stress may regulate both T cell function and the downstream cellular targets of inflammatory cytokine signaling during tissue inflammation.

The distinctive sensitivity of Th17 cells to AAR pathway activation may have a role during adaptive immune responses in vivo. For example, indoleamine 2,3-dioxygenase (IDO), an IFNγ-induced enzyme that breaks down tryptophan, has been shown to cause local depletion of tryptophan at sites of inflammation and activate the AAR pathway in resident T cells (Puccetti and Grohmann, *Nat. Rev. Immunol.* 7:817, 2007; Munn et al., *Immunity* 22:633, 2005). While local IDO accumulation is most often associated with proliferative impairment in T cells, expansion or conversion of Foxp3+ T cells also has been reported following upregulation of IDO (Puccetti and Grohmann, *Nat. Rev. Immunol.* 7:817, 2007; Park et al., *Arthritis Res.* 10:R11, 2008). Given the reciprocal relationship between the development of pro-inflammatory Th17 cells and tissue protective iTreg cells, it is postulated that IDO-mediated immune tolerance involves local AAR mediated inhibition of Th17 differentiation and consequent skewing of the Th17: iTreg balance in favor of iTreg cells (Romani et al., *J. Immunol.* 180:5157, 2008).

Materials and Methods
Mice

Mice were housed in specific pathogen-free barrier facilities and were used in accordance with protocols approved by the animal care and use committees of the Immune Disease Institute and Harvard Medical School. Wild-type C57B/6 mice were purchased from Jackson laboratories (Bar Harbor, Me.) and were used for all in vitro culture experiments unless otherwise noted. ROSA26-YFPfl/fl (Srinivas et al., *BMC Dev. Biol.* 1:4, 2001) and ROSA26-STAT3C-GFPfl/fl (Mesaros et al., *Cell. Metab.* 7:236, 2008) mice have been described. Dr. Alexander Rudensky provided lymphoid organs from Foxp3gfp and Foxp3ko mice (Gavin et al., *Nature* 445:771, 2007).

Cell Isolation

Primary murine T and B cells were purified by cell sorting. CD4$^+$ CD25$^-$ T cells were positively selected using CD4 dynabeads and detachabeads (Dynal, Oslo, Norway) per manufacturers instructions followed by nTreg depletion using a CD25 microbead kit (Miltenyi biotech, Auburn, Calif.). Naïve (CD4$^+$ CD62Lhi CD44lo Foxp3gfp- or CD4$^+$ CD62Lhi CD44lo CD25$^-$) T cells were purified from Foxp3gfp or Foxp3ko mice, respectively, by FACS sorting. CD8$^+$ T cells or B cells were isolated from CD4$^-$ fractions using CD8 negative isolation kit (Dynal) or CD43 negative isolation kit (Miltenyi biotech), respectively. Resting human CD4$^+$ T cells were isolated from PBMC of healthy human donors using Dynal CD4 Positive Isolation Kit (Invitrogen, Carlsbad, Calif.) as previously described (Sundrud et al., *Blood* 106:3440, 2005). CD4$^+$ cells were further purified to obtain memory T cells by staining with PE-conjugated anti-human CD45RO-PE antibodies (BD Biosciences), and sorting on a FACSAria cytometer (BD Biosciences). Following purification, cells were greater than 99% CD4$^+$ CD45RO$^+$. CD14$^+$ monocytes were isolated from autologous PBMC by MACS sorting using a magnetic separator (AutoMACS, Miltenyi Biotech) and were more then 99% pure following isolation.

Cytokines, Antibodies and Cell Culture

Purified CD4$^+$ CD25$^-$ T cells were activated in vitro as previously described (Djuretic et al., *Nat. Immunol.* 8:145, 2007) using 0.3 µg/ml hamster anti-mouse CD3 (clone 145-2C11) (ATCC, Manassas, Va.) and 0.5 µg/ml hamster anti-mouse CD28 (BD Pharmingen, San Jose, Calif.). Activated cell cultures were differentiated using the following combinations of cytokines and antibodies: iTreg—recombinant human TGFβ1 (3 ng/ml—R&D systems, Minneapolis, Minn.), Th17-TGFβ1 (3 ng/ml) plus recombinant mouse IL-6 (30 ng/ml—R&D systems). Th1 and Th2 differentiation was performed as previously described (Djuretic et al., *Nat. Immunol.* 8:145, 2007). Human IL-2 supernatant (National Cancer Institute) was used in culture at 0.01 U/ml and was added at 48 hours-post activation when T cells were split into tissue culture wells lacking CD3 and CD28 antibodies, with the exception of Th17 cultures that were maintained in the absence of exogenous IL-2. CD8$^+$ T cells were activated with 1 µg/ml anti-CD3 and 1 µg/ml anti-CD28 and were expanded in 0.1 U/ml IL-2 until day 6 post activation. CD43-depleted B cells were activated in vitro by culturing with 25 µg/ml LPS (Sigma, St. Louis, Mo.) for 3-4 days in the presence or absence of TGFβ. All reagents (see below) were added at the time of T cell activation and again at 48 hours post activation unless indicated otherwise. For some experiments, purified CD4$^+$ CD25$^-$ T cells, CD8$^+$ T cells or B cells were labeled with 1 µM CFSE (Invitrogen) prior to activation in accordance with manufacturer's instructions. Human T cell activation was performed by plating purified monocytes in a 96-well flat bottom plate at a concentration of 2×10$^4$ cells per well in complete medium overnight. 10$^5$ purified human memory T cells were added to monocyte cultures in the presence of soluble anti-CD3/anti-CD28 beads (Dynabeads, Invitrogen). T cells were expanded in the presence HF or 9 (MAZ1310) for up to 6 days.

Inhibitors and Amino Acid Starvation 1 kg of 10% pure HF was received as a gift from Hangpoon Chemical Co. (Seoul, Korea), which was further purified via HPLC to >99% purity and used for experiments. Compound 9 (MAZ1310, Kamberov, Ph. D. Dissertation, Harvard University, 2008) was generated by chemical derivatization of halofuginone and was used at equal concentrations as a negative control. HF and 9 were prepared as 100 mM stock solutions in DMSO and diluted to the indicated concentrations. SB-431542 (Inman et al., *Mol. Pharmacol.* 62:65, 2002) (Tocris Bioscience, Ellisville, Mo.) was prepared as a 10 mM stock solution in DMSO and was used in culture at 10 μM. L-tryptophanol was prepared as a 20 mM stock solution in 0.1 M NaOH, pH 7.4 and was used at 0.2 mM. For amino acid starvation experiments, T cells were activated and differentiated as above in D-MEM medium without L-cysteine and L-methionine (Invitrogen, Carlsbad, Calif.), or D-MEM medium without L-leucine. Stocks containing 20 mM L-cysteine (Sigma, St. Louis, Mo.) plus 10 mM L-methionine (Sigma), or 400 mM L-leucine (Sigma) were prepared in ddH2O, pH 1.0 and were added to medium at the indicated concentrations.

Tat-Cre Transduction

6×His-TAT-NLS-Cre (HTNC—herein called TAT-Cre) was prepared as previously described (Peitz et al., *Proc. Nat. Acad. Sci. USA* 99:4489, 2002). Purified T cells where rested in complete medium for 30 minutes, washed 3 times in ADCF-Mab serum free medium (Hyclone, Logan, Utah) and resuspended in pre-warmed serum free medium supplemented with 50 μg/ml of TATCre. Following a 45 minute incubation at 37° C., transduction was stopped using media containing 10% FCS and T cells were rested for 4-6 hours in complete medium prior to activation.

Retroviral Transduction

MIG and MIG.RORγt retroviral cDNA were gifts from Dr. Dan Littman. pRV and pRV.FOXP3 retroviral constructs have been described previously (Wu et al., *Cell* 126:375, 2006). Retroviral particles were generated using the phoenix-Eco system (ATCC). Supernatants were concentrated by centrifugation and stored at −80° C. prior to use in culture. Thawed retroviral supernatants were added to T cell cultures 12 hours after T cell activation in the presence of 8 μg/ml polybrene (American Bioanalytical, Natick, Mass.) and centrifuged for 1 hour at room temperature to enhance infections.

Detection of Cytokine Production

Cytokines secreted into media supernatant were measured using the mouse Th1/Th2 cytometric bead array (CBA—BD Pharmingen) in accordance with manufacturers instructions. Briefly, CD4+ CD25− T cells were activated in anti-CD3/anti-CD28-coated tissue culture wells (see above) and supernatants were collected at the indicated times.

For detection of intracellular cytokines in murine cells, cultured T or B cells were stimulated with 10 nM PMA (Sigma) and 1 mM ionomycin (Sigma) for 4-5 hours in the presence of 10 mM brefeldin A (Sigma). Stimulated cells were harvested, washed with PBS and fixed with PBS plus 4% paraformaldehyde at room temperature for 20 minutes. Cells were then washed with PBS, permeabilized with PBS supplemented with 1% BSA and 0.5% saponin (Sigma) at room temperature for 10 minutes before cytokine-specific antibodies were added and incubated with cells for an additional 20 minutes at room temperature. Human T cells were restimulated with PMA (20 ng/ml) (Sigma) and Ionomycin (500 ng/ml) (Sigma) for 6 hours in the presence of golgi plug (BD Biosciences) and intracellular staining was performed using cytofix/cytoperm kit (BD Biosciences) per manufacturers instructions. All stained cells were stored at 4° C. in PBS plus 1% paraformaldehyde prior to FACS analyses.

FACS Analyses and Sorting

All cell surface staining was performed in FACS buffer (PBS/2% FBS/0.1% NaN₃) and antibodies were incubated with cells on ice for 20-30 minutes. Cells were washed with FACS buffer and fixed with FACS buffer plus 1% paraformaldehyde prior to data acquisition. For phospho-STAT3 intracellular staining, stimulated T cells cultured with or without TGFβ plus IL-6 for the indicated times were harvested on ice and fixed in PBS plus 2% paraformaldehyde for 10 minutes at 37° C. Fixed cells were washed twice with staining buffer (PBS/1% BSA/0.1% NaN₃) and then permeabilized with perm buffer III (BD Pharmingen) on ice for 30 minutes. Cells were then washed twice with staining buffer and PE-conjugated anti-STAT3 (pY705) (BD Pharmingen) was added per the manufacturer's instructions and incubated with cells at room temperature for 45-60 minutes. Cells were then washed and stored in staining buffer prior to data acquisition. Foxp3 intracellular staining was performed using a Foxp3 intracellular staining kit (eBioscience, San Diego, Calif.) in accordance with the manufacturer's instructions. Fluorescent-conjugated antibodies purchased from BD Pharmingen were percp-Cy5.5-conjugated anti-CD4, PE-conjugated anti-CD25, PE-conjugated anti-IL-17, PE-conjugated anti-phospho-STAT3 and APC-conjugated anti-human IFNγ. Fluorescent conjugated antibodies purchased from eBioscience include FITC-conjugated anti-CD8, APC-conjugated anti-mouse/rat Foxp3, PE-conjugated anti-IL-4, APC-conjugated anti-IFNγ, PE-conjugated anti-granzyme B, APC-conjugated streptavidin, PE-conjugated anti-IL-6, and PE-conjugated anti-human IL-17. Biotin-conjugated anti-IgA antibody was purchased from Southern biotech (Birmingham, Ala.). All FACS data was acquired on a FACSCalibur flow cytometer (BD Pharmingen) and analyzed using FlowJo software (Treestar, Inc., Ashland, Oreg.). FACS sorting was performed on a FACS-Diva cytometer (BD Pharmingen).

Quantitative Real-Time PCR

T cells were activated as described above, collected at the indicated times and pellets were flash-frozen in liquid nitrogen. Total RNA was obtained by RNeasy (Quiagen, Valencia, Calif.) column purification per manufacturers instructions. RORγt expression was determined after reverse transcription using the message sensor kit (Ambion—Austin, Tex.) per the manufacturer's instructions and taqman primers and probe as described elsewhere (Ivanov et al., *Cell* 126:1121, 2006). Sybrgreen quantitative real-time PCR was performed on T cell RNA samples following reverse transcription via SuperScript II first-strand cDNA synthesis kit (Invitrogen, Carlsbad, Calif.). All PCR data was collected on an iCycler thermal cycler (Biorad, Hercules, Calif.). Primer sequences used for detecting stress response genes are listed below.

```
Asns forward:
                                    (SEQ ID NO: 1)
5'-TGACTGCCTTTCCGTGCAGTGTCTGAG-3'

Asns reverse:
                                    (SEQ ID NO: 2)
5'-ACAGCCAAGCGGTGAAAGCCAAAGCAGC-3'

Gpt2 forward:
                                    (SEQ ID NO: 3)
5'-TAGTCACAGCAGCGCTGCAGCCGAAGC-3'

Gpt2 reverse:
                                    (SEQ ID NO: 4)
5'-TACTCCACCGCCTTCACCTGCGGGTTC-3'
```

-continued eIF4Ebp1 forward:
(SEQ ID NO: 5)
5'-ACCAGGATTATCTATGACCGGAAATTTC-3' eIF4Ebp1 reverse:
(SEQ ID NO: 6)
5'-TGGGAGGCTCATCGCTGGTAGGGCTAG-3'

Hprt forward:
(SEQ ID NO: 7)
5'-GGGGGCTATAAGTTCTTTGCTGACC-3'

Hprt reverse:
(SEQ ID NO: 8)
5'-TCCAACACTTCGAGAGGTCCTTTTCAC-3'

Western Blotting

Whole cell lysates were generated from T cells activated for the indicated times. For STAT3 and Smad2/3 western blots cells were harvested, washed in PBS and lysed in 50 mM Tris, pH 7.4, 0.1% SDS, 1% Triton-X100, 140 mM NaCl, 1 mM EDTA, 1 mM EGTA supplemented with protease inhibitors tablets (Roche, Germany), 1 mM NaF and 1 mM $Na_3VO_4$. For eIF2α and ATF4 western blots, cells were harvested as above and lysed in 50 mM Tris, pH 7.4, 2% SDS, 20% glycerol and 2 mM EDTA supplemented with protease and phosphatase inhibitors as above. All lysates were cleared via centrifugation and 15-30 μg of protein was resolved by SDS-PAGE. Protein was transferred to nitrocellulose membranes, blocked and blotted using specific antibodies. Antibodies used for western blot analysis were anti-phospho-Smad2, anti-STAT3 (pY705), anti-STAT3, anti-eIF2α$^{pS51}$, anti-eIF2α (all from Cell Signaling Technology, Danvers, Mass.). Anti-ATF4/CREB2 and anti-β-actin were purchased from Santa Cruz Biotechnology (Santa Cruz, Calif.). HRP-conjugated secondary antibodies were all purchased from Sigma, with the exception of HRP-conjugated anti-armenian hamster antibody (Jackson Immunoresearch, West Grove, Pa.).

Microarrays, Data Analyses and Statistics

RNA prepared from activated T cells treated with 10 nM HF or MAZ1310 for either 3 or 6 hours, was amplified, biotin-labeled (MessageAmp II Biotin-Enhanced kit, Ambion, Austin, Tex.), and purified using the RNeasy Mini Kit (Qiagen, Valencia, Calif.). Resulting cRNAs were hybridized to M430 2.0 chips (Affymetrix, Inc.). Raw data were normalized using the RMA algorithm implemented in the "Expression File Creator" module from the GenePattern software package (Reich et al., *Nat. Gen.* 38:500, 2006) (available on the internet at the following address: broad.mit.edu/cancer/software/genepattern/). Data were visualized using the GenePattern "Multiplot" modules. Gene expression distribution analyses were performed using Chi-squared statistical tests. For all other statistical comparisons, p values were generated using one-tailed student T-tests on duplicate or triplicate samples.

Example 10

Depletion of Amino Acids or tRNA Synthetase Inhibition with L-Tryptophanol Inhibits Th17 Differentiation T cells were cultured in complete medium (complete—200 μM Cys/100 μM Met/4 mM Leu), medium containing 0.1×, 0.2×, or 1× cysteine and methionine (Cys/Met), medium containing 0.1× leucine (Leu), or complete medium plus 0.2 mM L-tryptophanol. Cells were activated in the presence or absence of TGFβ plus IL-6, expanded for 4 days and restimulated with PMA and ionomycin for intracellular cytokine staining. For intracellular cytokine staining, fixed cells were washed twice with staining buffer (PBS/1% BSA/0.1% $NaN_3$) and permeabilized with perm buffer III (BD Pharmingen) on ice for 30 minutes. Cells were then washed and stored in staining buffer prior to data acquisition. All FACS data were acquired on a FACSCalibur flow cytometer (BD Pharmingen) and analyzed using FlowJo software (Treestar, Inc., Ashland Oreg.). FACS sorting was performed on a FACS-Diva cytometer (BD Pharmingen). The results, depicted in FIG. 17, show that depletion of Cys/Met, depletion of Leu, and treatment with tryptophanol all inhibited Th17 differentiation.

Example 11

Modulation of Th17-Mediated Effects In Vivo

The ability of systemic HF treatment to block IL-17 expression and associated autoimmune inflammation in vivo was examined using two distinct models of experimental autoimmune encephalomyelitis (EAE). The first model used is referred to as adjuvant-driven EAE and is actively induced by immunization of wild-type mice with the immunodominant myelin-derived peptide antigen $MOG_{33-55}$ emulsified in Complete Freund's Adjuvant (CFA). The second model, a passive model of EAE induction, is initiated by the transfer of myelin proteolipid protein (PLP)-reactive T cells into lymphopenic hosts.

Adjuvant-driven EAE was induced in 8 week-old wild-type B6 mice purchased from Charles River laboratories (Kingston, N.Y.) by subcutaneous injection of $MOG_{33-55}$ peptide emulsified in Incomplete Freund's Adjuvant (IFA) plus 5 mg/ml heat-killed *M. tuburculosis* (BD Biosciences) in both dorsal flanks as described in Veldhoen et al. (*Nat. Immunol.* 7(11):1151-1156, 2006).

Passive EAE was induced by intravenous transfer of purified CD3$^+$ splenic T cells isolated from PLP TCR transgenic B10.S mice into syngeneic RAG2-deficient mice (3×10$^6$ cells/mouse) (Waldner et al., *J. Clin. Invest.* 113(7):990-997, 2004).

Mice were injected daily with HF (2 μg/mouse) or vehicle control (DMSO) i.p. Clinical signs of EAE were assessed according to the following score: 0, no signs of disease; 1, flaccid tail; 2, weak gait/hind limb paresis; 3, hind limb paralysis; 4, tetraplegia; 5, moribund. Cytokine production during EAE was determined either in peripheral T cells isolated from spleen or lymph nodes of mice prior to disease onset (day 6-10) or in mononuclear cells isolated from the brain and spinal cords of mice with severe disease (clinical score ≥2) between days 15-20. Briefly, splenocytes were stained for intracellular cytokines following erythrocyte lysis with ammonium chloride buffer. T cells were isolated from brain and spinal cords of mice with active EAE following perfusion with cold PBS. Minced CNS tissue was digested with liberase C1 (0.33 mg/ml, Roche Diagnostics) or collagenase D (10 mg/ml, Roche Diagnostics) at 37° C. for 30-45 minutes. Cell suspensions were passed through 70 μm cell strainers (VWR) and fractionated by 70%/30% Percoll gradient centrifugation. Mononuclear cells were collected from the interphase, washed, and used for intracellular cytokine analysis.

The adjuvant-driven EAE model is associated with infiltration of both IL-17- and IFNγ-expressing CD4+ T cells into the CNS (FIG. 18A). Low-dose HF treatment (2 μg HF daily, ~0.1 mg/kg) significantly reduced both the severity of adjuvant-driven EAE disease and frequency of disease onset (FIG. 18B). The second, passive model of EAE induction leads to a predominant Th1 response, rather than Th17 response, within CNS infiltrates (FIG. 18C). In marked contrast to the adjuvant-driven EAE model, HF-treated mice in the passive EAE model developed disease symptoms with kinetics and severity similar to control treated animals (FIG. 18D). The contrasting effects of HF in these two models of EAE support the notion that HF selectively inhibits IL-17-associated inflammatory T cell function without inducing general T cell hyporesponsiveness. Taken together, these data suggest that HF can modulate autoimmune inflammation associated with Th17, but not Th1, responses.

HF-mediated protection from adjuvant-driven EAE was accompanied by a reduction in T cell-derived IL-17-expression, both in peripheral lymph nodes prior to disease onset and in CNS tissue during active disease (FIG. 18E), as well as an overall reduction in CD4+ T cell infiltrates into the CNS (FIG. 19). Consistent with in vitro results, HF impaired IL-17 production but did not affect IFNγ expression in the same T cell populations. Moreover, splenocytes isolated ex vivo from HF-injected mice displayed increased eIF2α phosphorylation and expression of AAR-associated transcripts (FIG. 18F). Thus, systemic administration of low doses of HF activates the AAR, leading to a selective impairment of Th17 differentiation, and concomitant blunting of IL-17 associated inflammatory responses in vivo.

Thus, consistent with in vitro data, it was discovered that HF protects mice from adjuvant-driven EAE through in vivo activation of the AAR. HF selectively reduced the number of IL-17 expressing T cells in vivo, but had no effect on the number of IFNγ T-cells. These data are consistent with reports showing that adjuvant-driven EAE disease is particularly sensitive to modulation of IL-17 expression. Notably, HF had no effect on an independent, passive model of EAE that develops in the absence of a Th17 response, demonstrating that HF is neither globally immunosuppressive nor generically protective against CNS inflammation. Both Th1 and Th17 cells can drive EAE pathogenesis when transferred into mice. In the adjuvant-driven EAE model described above, a roughly equal induction of Th1 and Th17 cells was observed, whereas in the passive model of EAE, encephalitogenic T cells were biased towards a Th1 response. Thus, the lack of an effect of HF in the passive model, in comparison to the adjuvant-driven EAE is likely due to the distinctive inflammatory T cell responses in the two models.

Two follow-on experiments were performed to further determine the therapeutic benefit of HF on EAE. In one, HF was injected into mice immunized to produce EAE as described above, with the exception that HF was not introduced into the animals until day 10 following immunization. These data demonstrate that HF controls autoimmune inflammation even after inflammatory pathogenesis is evident, providing a more accurate representation of autoimmune disease in humans. See FIG. 24. In the other experiment, HF was injected into mice immunized to produce EAE as described above, with the exception that HF injection was terminated at day 10 following immunization. These data as shown in FIG. 25 demonstrate that HF exerts a protective effect that extends well beyond the time of treatment, consistent with its proposed role in preventing the differentiation of pro-inflammatory Th17 cells. Therefore, HF has been shown to have a therapeutic benefit in EAE after the onset of symptoms as well as to prevent the development of the symptoms of EAE.

Example 12

Synthesis of (2S/R,3R/S)-tert-butyl 2-(3-(7-bromo-6-chloro-4-oxoquinazolin-3(4H)-yl)-2-oxopropyl)-3-hydroxypiperidine-1-carboxylate (9)

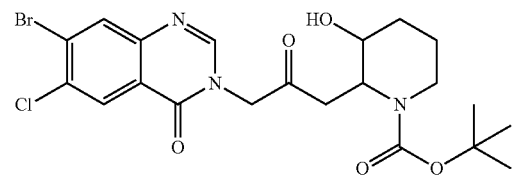 [SMILES: CC(C)(C)OC(=O)N1CCCC(O)C1CC(=O)Cn1cnc2cc(Br)c(Cl)cc2c1=O]

Di-tert-butyldicarbonate (982 mg) in 10 mL DMF was added to a solution of 1.5 g halofuginone hydrobromide and 1.3 mL diisopropylethylamine in 100 mL. The reaction mixture was stirred for 16 h at room temperature. After addition of water the aqueous layer was extracted three times with diethyl ether. The combined organic layers were dried over sodium sulfate and evaporated to dryness. The crude product was purified on silica gel with dichloromethane/methanol to yield the desired Boc protected product as white solid in quantitative yield.

Example 13

Synthesis of tert-butyl 2-(2-(2-hex-5-ynamidoethoxy)ethoxy)ethylcarbamate

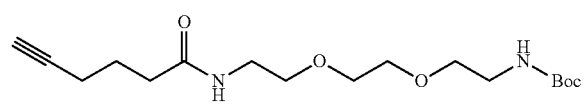 [SMILES: C#CCCCC(=O)NCCOCCOCCNC(=O)OC(C)(C)C]

PyBOP (2.34 g) in 5 mL dichloromethane were added to a solution of 476 mg hex-5-ynoic acid and 1.16 g diisopropylethylamine in 20 mL dichloromethane. After 2 min 700 mg Boc-2,2'-(ethane-1,2-diylbis(oxy))diethanamine were added and the reaction mixture was stirred for 3 h at room temperature. The reaction mixture was washed with citric acid solution and saturated sodium bicarbonate solution. The organic layer was then dried over sodium sulfate and evaporated to dryness. The crude product was purified on silica gel with dichloromethane and methanol to yield the desired product as colorless oil (820 mg).

Example 14

Synthesis of (2S/R,3R/S)-tert-butyl 2-(3-(6-chloro-7-(2,2-dimethyl-4,15-dioxo-3,8,11-trioxa-5,14-diaza-icos-19-yn-20-yl)-4-oxoquinazolin-3(4H)-yl)-2-oxo-propyl)-3-hydroxypiperidine-1-carboxylate

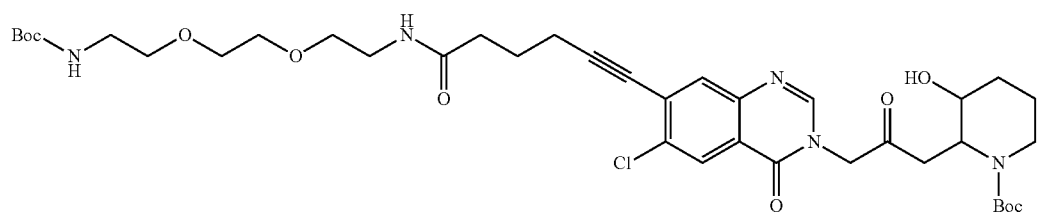 [SMILES: CC(C)(C)OC(=O)NCCOCCOCCNC(=O)CCCC#Cc1cc2ncn(CC(=O)CC3C(O)CCCN3C(=O)OC(C)(C)C)c(=O)c2cc1Cl]

(2S/R,3R/S)-tert-butyl 2-(3-(7-bromo-6-chloro-4-oxo-quinazolin-3(4H)-yl)-2-oxopropyl)-3-hydroxypiperidine-1-carboxylate (100 mg) and 130 mg tert-butyl 2-(2-(2-hex-5-ynamidoethoxy)ethoxy)ethylcarbamate were dissolved in 5 mL triethylamine and 5 mL THF. The solution was degassed and 50 mg tetrakis(triphenylphosphine)palladium and 40 mg copper iodide are added. The reaction mixture was stirred at 50° C. for 16 h. After cooling to room temperature dichloromethane was added and the organic layer was washed with brine. The organic layer was dried over sodium sulfate and evaporated to dryness. The crude product was purified on silica with hexanes and ethyl acetate (5:1) as eluent to afford 130 mg of the product as off white solid.

Example 15

Synthesis of N-(2-(2-(2-aminoethoxy)ethoxy)ethyl)-6-(6-chloro-3-(3-((2S/R,3R/S)-3-hydroxypiperidin-2-yl)-2-oxopropyl)-4-oxo-3,4-dihydroquinazolin-7-yl)hex-5-ynamide (8)

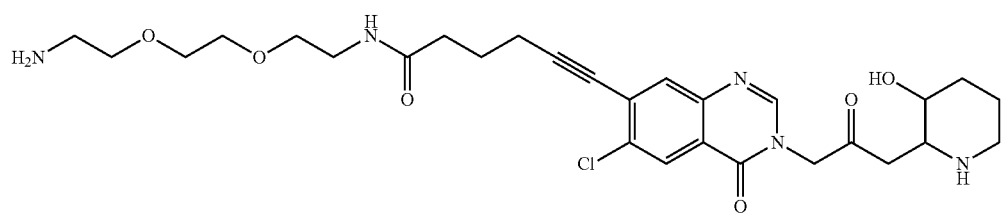 [SMILES: NCCOCCOCCNC(=O)CCCC#Cc1cc2ncn(CC(=O)CC3NCCCC3O)c(=O)c2cc1Cl]

(2S/R,3R/S)-tert-butyl 2-(3-(6-chloro-7-(2,2-dimethyl-4,15-dioxo-3,8,11-trioxa-5,14-diazaicos-19-yn-20-yl)-4-oxo-quinazolin-3(4H)-yl)-2-oxopropyl)-3-hydroxypiperidine-1-carboxylate (6 mg) was dissolved in 1 mL dichloromethane, followed by the addition of 200 uL TFA. The reaction mixture was stirred at room temperature for 16 hours and the solvent was removed under reduced pressure. The product was used without further purification as trifluoroacetate.

Example 16

Synthesis of (2S/R,3R/S)-tert-butyl 2-(3-(6-chloro-4-oxo-7-((trimethylsilyl)ethynyl)quinazolin-3(4H)-yl)-2-oxopropyl)-3-hydroxypiperidine-1-carboxylate

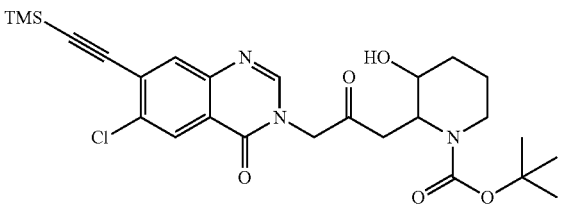 [SMILES: CC(C)(C)OC(=O)N1CCCC(O)C1CC(=O)Cn1cnc2cc(C#C[Si](C)(C)C)c(Cl)cc2c1=O]

(2S/R,3R/S)-tert-butyl 2-(3-(7-bromo-6-chloro-4-oxo-quinazolin-3(4H)-yl)-2-oxopropyl)-3-hydroxypiperidine-1-carboxylate (55 mg) and 24 mg ethynyltrimethylsilane were dissolved in 5 mL triethylamine. The solution was degassed and 11.5 mg tetrakis(triphenylphosphine)palladium and 8 mg copper iodide were added. The reaction mixture was stirred at 50° C. for 16 h. After cooling to room temperature dichloromethane and water were added and the aqueous layer was extracted twice with dichloromethane. The organic layer was dried over sodium sulfate and evaporated to dryness. The crude product was purified on basic alumina with dichlo-

Example 17

Synthesis (2S/R,3R/S)-tert-butyl 2-(3-(6-chloro-7-ethynyl-4-oxoquinazolin-3(4H)-yl)-2-oxopropyl)-3-hydroxypiperidine-1-carboxylate

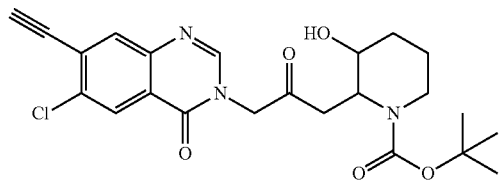 [SMILES: C#Cc1cc2ncn(CC(=O)CC3C(O)CCCN3C(=O)OC(C)(C)C)c(=O)c2cc1Cl]

(2S/R,3R/S)-tert-butyl 2-(3-(6-chloro-4-oxo-7-((trimethylsilyl)ethynyl)quinazolin-3(4H)-yl)-2-oxopropyl)-3-hydroxypiperidine-1-carboxylate (11 mg) was dissolved in 500 uL methanol, followed by the addition of 3 mg potassium carbonate. The reaction mixture was stirred for 2 h at room temperature. The solvent was removed and the product was purified on basic alumina with dichloromethane and methanol as eluent to afford 6 mg of the desired product as white solid.

Example 18

Synthesis of 6-chloro-3-(3-((2S/R,3R/S)-3-hydroxypiperidin-2-yl)-2-oxopropyl)-7-((trimethylsilyl)ethynyl)quinazolin-4(3H)-one (5)

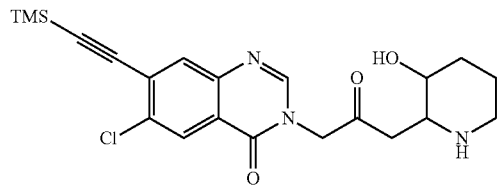 [SMILES: C[Si](C)(C)C#Cc1cc2ncn(CC(=O)CC3NCCCC3O)c(=O)c2cc1Cl]

(2S/R,3R/S)-tert-butyl 2-(3-(6-chloro-4-oxo-7-((trimethylsilyl)ethynyl)quinazolin-3(4H)-yl)-2-oxopropyl)-3-hydroxypiperidine-1-carboxylate (10 mg) was dissolved in 500 uL dichloromethane, followed by the addition of 50 uL TFA. The reaction mixture was stirred at room temperature for 5 h and the solvent was removed under reduced pressure. The product was used without further purification as the trifluoroacetate salt.

Example 19

6-chloro-7-ethynyl-3-(3-((2S/R,3R/S)-3-hydroxypiperidin-2-yl)-2-oxopropyl)quinazolin-4(3H)-one (7)

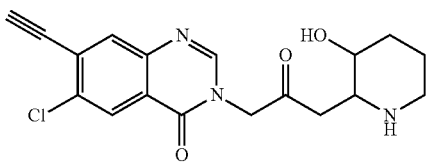 [SMILES: C#Cc1cc2ncn(CC(=O)CC3NCCCC3O)c(=O)c2cc1Cl]

(2S/R,3R/S)-tert-butyl 2-(3-(6-chloro-7-ethynyl-4-oxoquinazolin-3(4H)-yl)-2-oxopropyl)-3-hydroxypiperidine-1-carboxylate (6 mg) was dissolved in 500 µL dichloromethane, followed by the addition of 50 µL TFA. The reaction mixture was stirred at room temperature for 5 h and the solvent was removed under reduced pressure. The product was purified by HPLC (water/MeCN) to yield 3 mg of the desired product as white solid.

Example 20

(2S/R,3R/S)-tert-butyl 2-((Z)-3-(7-bromo-6-chloro-4-oxoquinazolin-3(4H)-yl)-2-hydrazonopropyl)-3-hydroxypiperidine-1-carboxylate

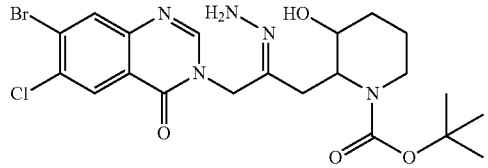 [SMILES: CC(C)(C)OC(=O)N1CCCC(O)C1C/C(Cn1cnc2cc(Br)c(Cl)cc2c1=O)=N/N]

(2S/R,3R/S)-tert-butyl 2-(3-(7-bromo-6-chloro-4-oxoquinazolin-3(4H)-yl)-2-oxopropyl)-3-hydroxypiperidine-1-carboxylate (40 mg) and 40 uL hydrazine were dissolved in 2 mL absolute ethanol and heated for 16 h. The solvent was evaporated and the crude product was purified on silica with dichloromethane and methanol to yield 15 mg of the desired hydrazone as white solid.

Example 21

Synthesis of 7-bromo-6-chloro-3-((Z)-2-hydrazono-3-((2S/R,3R/S)-3-hydroxypiperidin-2-yl)propyl)quinazolin-4(3H)-one

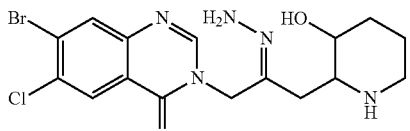

Halofuginone trifluoroacetate (24 mg) and 40 uL hydrazine were dissolved in 2 mL absolute ethanol. The reaction mixture was stirred for 5 h at room temperature whereby the desired product precipitated as white solid. The product was filtered off and washed twice with ethanol to yield 16 mg of the desired hydrazone without further purification.

Example 22

Synthesis of (Z)—N'-(1-(7-bromo-6-chloro-4-oxoquinazolin-3(4H)-yl)-3-((2S/R,3R/S)-3-hydroxypiperidin-2-yl)propan-2-ylidene)acetohydrazide (14)

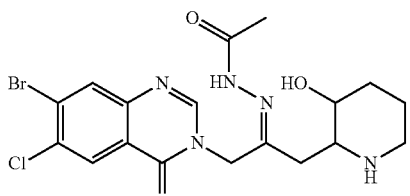

Halofuginone trifluoroacetate (24 mg) and 14 mg acetohydrazide were dissolved in 2 mL absolute ethanol. The reaction mixture was stirred for 1 h at room temperature followed by the removal of the solvent under reduced pressure. The crude product was purified by HPLC to yield the desired product as colorless oil (16 mg).

Example 23

Synthesis of methyl 6-((Z)-2-(1-(7-bromo-6-chloro-4-oxoquinazolin-3(4H)-yl)-3-((2S/R,3R/S)-3-hydroxypiperidin-2-yl)propan-2-ylidene)hydrazinyl)-6-oxohexanoate (12)

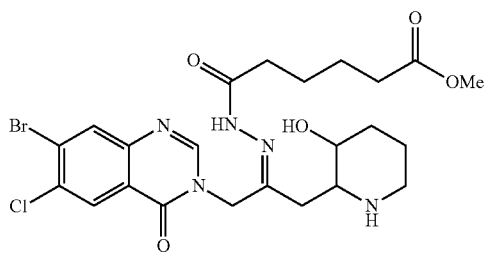 [SMILES: COC(=O)CCCCC(=O)N/N=C(/CC1NCCCC1O)Cn1cnc2cc(Br)c(Cl)cc2c1=O]

Halofuginone trifluoroacetate (50 mg) and 50 mg methyl 6-hydrazinyl-6-oxohexanoate were dissolved in 2 mL absolute ethanol. The reaction mixture was stirred for 24 h at room temperature followed by the removal of the solvent under reduced pressure.

Example 24

Synthesis of N-(6-((Z)-2-(1-(7-bromo-6-chloro-4-oxoquinazolin-3(4H)-yl)-3-((2S/R,3R/S)-3-hydroxypiperidin-2-yl)propan-2-ylidene)hydrazinyl)-6-oxohexyl)-6-(5-(2-oxohexahydro-1H-thieno[3,4-d]imidazol-4-yl)pentanamido)hexanamide (13)

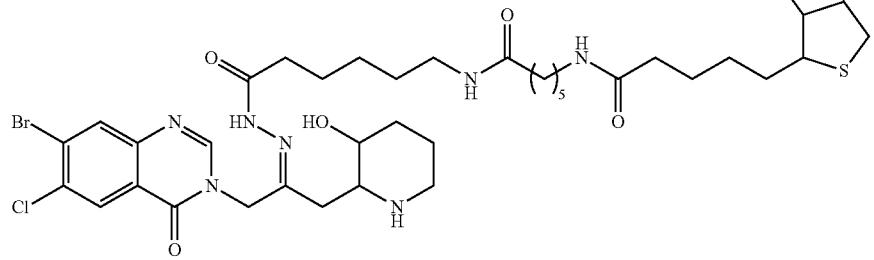

Halofuginone trifluoroacetate (25 mg) and 25 mg N-(6-hydrazinyl-6-oxohexyl)-6-(5-(2-oxohexahydro-1H-thieno[3,4-d]imidazol-4-yl)pentanamido)hexanamide were dissolved in 2 mL absolute ethanol. The reaction mixture was stirred for 48 h at 65° C. followed by the removal of the solvent under reduced pressure. The crude product was purified by HPLC to yield the desired product as colorless oil (30 mg).

Example 25

Synthesis of (2S/R,3R/S)-tert-butyl 2-(3-(7-bromo-6-chloro-4-oxoquinazolin-3(4H)-yl)-2-oxopropyl)-3-(diethoxyphosphoryloxy)piperidine-1-carboxylate

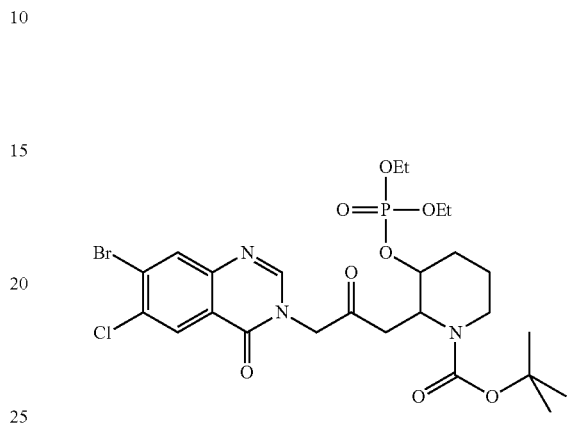

(2S/R,3R/S)-tert-butyl 2-(3-(7-bromo-6-chloro-4-oxoquinazolin-3(4H)-yl)-2-oxopropyl)-3-hydroxypiperidine-1-carboxylate (52 mg), 15 mg triethylamine and 17.2 mg diethyl phosphorochloridate were dissolved in 2 mL dichloromethane followed by the addition of 40 uL titaniumtetraisopropoxide. After 16 h stirring at room temperature additional 0.5 eq phosphochloride and 0.2 eq titaniumtetraisopropoxide were added and the reaction mixture was stirred for additional 24 hours. After addition of few drops water and methanol the solvent was removed under reduced pressure and the crude product was purified by HPLC to yield the desired phosphate as white solid (10 mg).

Example 26

Synthesis of (2S/R,3R/S)-2-(3-(7-bromo-6-chloro-4-oxoquinazolin-3(4H)-yl)-2-oxopropyl)piperidin-3-yl diethyl phosphate (16)

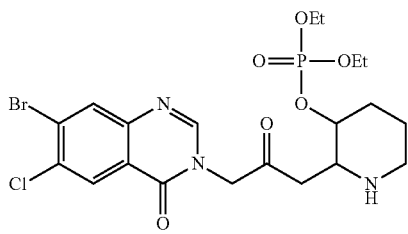 [SMILES: CCOP(=O)(OCC)OC1CCCNC1CC(=O)Cn1cnc2cc(Br)c(Cl)cc2c1=O]

(2S/R,3R/S)-tert-butyl 2-(3-(7-bromo-6-chloro-4-oxo-quinazolin-3(4H)-yl)-2-oxopropyl)-3-(diethoxyphosphoryloxy)piperidine-1-carboxylate (6 mg) was dissolved in 2 mL dichloromethane followed by the addition of 0.1 mL trifluoroacetic acid. The reaction mixture was stirred for 2 h followed by the removal of the solvent under reduced pressure. The product was used without further purification.

Example 27

MAZ1320 and MAZ1686 Inhibit Th17 Differentiation

Two novel derivatives of halofuginone (MAZ1320 and MAZ 1686, shown below) selectively inhibit the differentiation of Th17 cells without inhibiting Th1 differentiation. Methods for determining Th17 differentiation and FACS analysis are described above. Shown in FIG. 20 is FACS analysis of CD4+ CD25− T cells analyzed according to IL17 expression (marking Th17 differentiation, y-axis) and Th1 (IFNgamma, x-axis) following differentiation in the presence of the indicated concentrations of HF or derivatives thereof (MAZ1320, MAZ1685, MAZ1686).

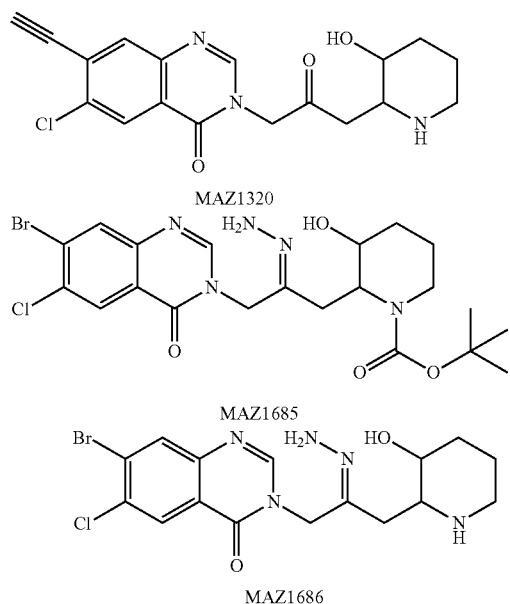

Example 28

HF Inhibits the Incorporation of Proline into tRNA

Rabbit reticulocyte lysate was incubated with total bovine tRNA, 0.1 µM puromycin (to prevent translation), and $^{14}$C-labeled proline or $^{35}$S-labeled methionine for minutes in the presence or absence of HF or MAZ1310 (an inactive HF derivative). Total RNA was extracted with acidic phenol-chloroform and tRNA was isolated using miRVANA microRNA isolation kit. Radioisotope incorporation into tRNA was measured in a scintillation counter. FIG. 21 shows data normalized to control (no HF or MAZ1310 addition) material. HF is an inhibitor of prolyl-tRNA synthetase (EPRS) but not a different tRNA synthetase (methionyl tRNA synthetase) in a crude in vitro translation system.

Example 29

HF Inhibits Purified EPRS

Prolyl-tRNA synthetase (EPRS) purified from rabbit liver was tested for its ability to incorporate $^{14}$C-labeled proline into tRNA in the presence of the indicated concentration of HF or its inactive derivative, MAZ1310. Purified enzyme was incubated with 100 µg/ml bovine tRNA, 50 µM $^{14}$C-labeled proline, 5 mM ATP, and 10 mM $MgCl_2$ for 20 minutes. Charged tRNA was isolated by precipitation on Whatman filter paper and washing with cold 5% TCA. TCA precipitable counts were assayed by scintillation counting. FIG. 22 shows the TCA preciptiable counts for 10 µM HF, 4 µM HF, 1 µM HF, and MAZ1310. HF directly inhibits purified mammalian EPRS.

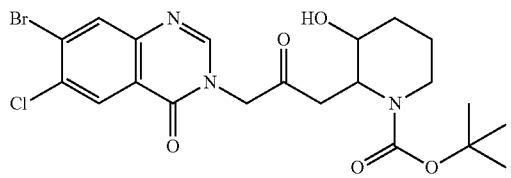

MAZ1310

Example 30

A tRNA Synthetase Inhibitor Structurally Unrelated to HF Selectively Inhibits Th17 Differentiation Borrelidin, a threonyl tRNA synthetase inhibitor structurally unrelated to HF was tested for its ability to alter T-cell differentiation. Methods for determining Th17 differentiation and FACS analysis are described above. Shown in FIG. 23 is FACS analysis of CD4+ CD25− T cells analyzed according to IL17 expression (marking Th17 differentiation), IFNgamma expression (marking Th1 differentiation), FoxP3 expression (marking Tref differentiation), or IL4 (marking Th2 differentiation) following differentiation under conditions for polarization of each effector T-cell subtype in the presence of the indicated concentrations of HF (10 nM) or borrelidin. Borrelidin inhibits Th17 differentiation without affecting Th1, Th2, or Treg differentiation or cell number, a selectivity identical to that of HF. tRNA synthetase inhibition therefore provides a general approach to the selective inhibition of Th17 differentiation without generalized immunosuppression.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A compound of formula (I):

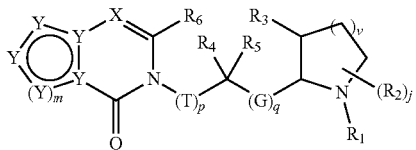

wherein
j is an integer between 0 and 10, inclusive;
p is an integer between 0 and 6, inclusive;
q is an integer between 0 and 6, inclusive;
m is 1 or 2;
v is an integer between 1 and 3, inclusive;
X is N or $CR_X$, wherein $R_X$ is hydrogen; halogen; substituted or unsubstituted aliphatic; substituted or unsubstituted heteroaliphatic; substituted or unsubstituted aryl; substituted or unsubstituted heteroaryl; —$OR_F$; —$SR_F$; —$N(R_F)_2$; and —$C(R_F)_3$; wherein each occurrence of $R_F$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
each occurrence of Y is independently S, O, N, $NR_Y$, C or $CR_Y$, wherein each occurrence of $R_Y$ is independently hydrogen; halogen; substituted or unsubstituted heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; or —$NHC(O)R_G$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety, wherein one, two, or three occurrences of Y are CH;
each occurrence of T and G is independently —S—, —O—, —$NR_E$—, or —$C(R_E)_2$—, wherein each occurrence of $R_E$ is independently hydrogen; halogen; substituted or unsubstituted aliphatic; substituted or unsubstituted heteroaliphatic; substituted or unsubstituted aryl; substituted or unsubstituted heteroaryl; —$OR_G$; —$SR_G$; —$N(R_G)_2$; and —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;
$R_3$ is halogen; —OH; or —$CO_2R_C$; wherein each occurrence of $R_C$ is independently a hydrogen; a protecting group; an aliphatic moiety; a heteroaliphatic moiety; an acyl moiety; an aryl moiety; or a heteroaryl moiety;

R$_4$ and R$_5$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_D$; —C(=O)R$_D$; —CO$_2$R$_D$; —C(=O)N(R$_D$)$_2$; —CN; —SCN; —SR$_D$; —SOR$_D$; —SO$_2$R$_D$; —NO$_2$; —N(R$_D$)$_2$; —NHC(O)R$_D$; or —C(R$_D$)$_3$; wherein each occurrence of R$_D$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and R$_6$ is hydrogen; halogen; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_K$; —C(=O)R$_K$; —CO$_2$R$_K$; —C(=O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

and pharmaceutically acceptable salts thereof.

2. The compound of claim 1 of formula:

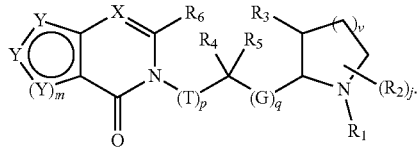

3. The compound of claim 1, wherein R$_6$ is hydrogen.

4. The compound of claim 1 of formula:

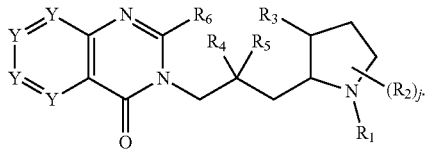

5. A compound of formula (VI):

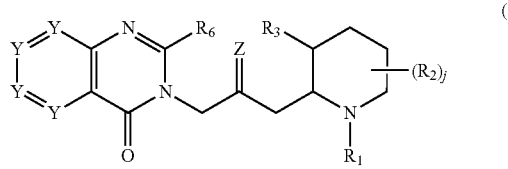

(VI)

wherein j is an integer between 1 and 8, inclusive;

each occurrence of Y is S, O, N, or CR$_Y$, wherein each occurrence of R$_Y$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_G$; —C(=O)R$_G$; —CO$_2$R$_G$; —C(=O)N(R$_G$)$_2$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

Z is =O or =N—NHR$_D$, wherein R$_D$ is a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —C(=O)R$_A$; —C(=O)OR$_A$; —C(=O)N(R$_A$)$_2$; or —C(R$_A$)$_3$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of R$_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_B$; —C(=O)R$_B$; —CO$_2$R$_B$; —C(=O)N(R$_B$)$_2$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_C$; —C(=O)R$_C$; —CO$_2$R$_C$; —C(=O)N(R$_C$)$_2$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and $R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and pharmaceutically acceptable salts thereof;

provided that at least one instance of Y is not $CR_Y$.

6. The compound of claim 5 of formula:

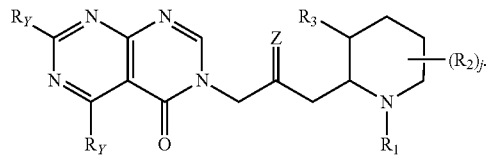

7. The compound of claim 5 of formula:

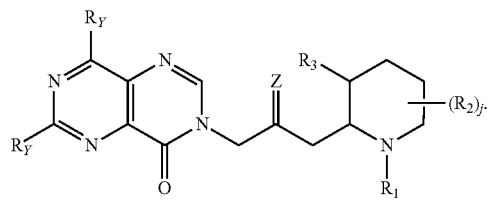

8. A compound of formula (XI):

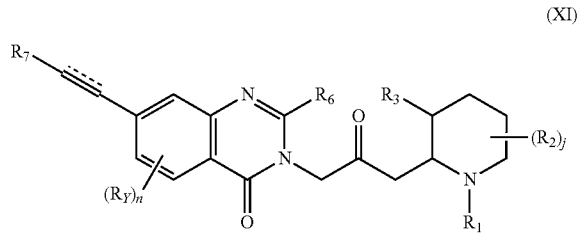

(XI)

wherein

═══ represents a double or triple bond;

n is an integer between 0 and 3, inclusive;

j is an integer between 0 and 8, inclusive;

$R_1$ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$C(=O)R_A$; —$C(=O)OR_A$; —$C(=O)N(R_A)_2$; or —$C(R_A)_3$; wherein each occurrence of $R_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_G$; —$C(=O)R_G$; —$CO_2R_G$; —$C(=O)N(R_G)_2$; —CN; —SCN; —$SR_G$; —$SOR_G$; —$SO_2R_G$; —$NO_2$; —$N(R_G)_2$; —$NHC(O)R_G$; or —$C(R_G)_3$; wherein each occurrence of $R_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

each occurrence of $R_2$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_B$; —$C(=O)R_B$; —$CO_2R_B$; —$C(=O)N(R_B)_2$; —CN; —SCN; —$SR_B$; —$SOR_B$; —$SO_2R_B$; —$NO_2$; —$N(R_B)_2$; —$NHC(O)R_B$; or —$C(R_B)_3$; wherein each occurrence of $R_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_C$; —$C(=O)R_C$; —$CO_2R_C$; —$C(=O)N(R_C)_2$; —CN; —SCN; —$SR_C$; —$SOR_C$; —$SO_2R_C$; —$NO_2$; —$N(R_C)_2$; —$NHC(O)R_C$; or —$C(R_C)_3$; wherein each occurrence of $R_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

$R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —$OR_K$; —$C(=O)R_K$; —$CO_2R_K$; —$C(=O)N(R_K)_2$; —CN; —SCN; —$SR_K$; —$SOR_K$; —$SO_2R_K$; —$NO_2$; —$N(R_K)_2$; —$NHC(O)R_K$; or —$C(R_K)_3$; wherein each occurrence of $R_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and R₇ is hydrogen; halogen; cyclic or acyclic, unsubstituted, branched or unbranched alkyl; cyclic or acyclic, substituted or unsubstituted, branched or unbranched alkenyl; cyclic or acyclic, substituted or unsubstituted, branched or unbranched alkynyl; cyclic or acyclic, substituted or unsubstituted, branched or unbranched carbocyclyl; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_C$; —C(═O)R$_C$; —CO$_2$R$_C$; —C(═O)N(R$_C$)$_2$; —CN; —SCN; —SR$_C$; —SOR$_C$; —SO$_2$R$_C$; —NO$_2$; —N(R$_C$)$_2$; —NHC(O)R$_C$; —Si(R$_C$)$_3$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and pharmaceutically acceptable salts thereof.

9. A compound of Formula (XIII):

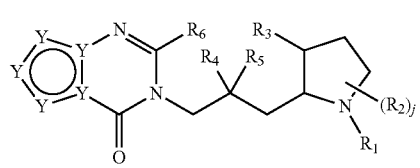

(XIII)

wherein
j is an integer between 0 and 6, inclusive;
each occurrence of Y is independently S, O, N, C or CR$_Y$, wherein each occurrence of R$_Y$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_G$; —C(═O)R$_G$; —CO$_2$R$_G$; —C(═O)N(R$_G$)$_2$; —CN; —SCN; —SR$_G$; —SOR$_G$; —SO$_2$R$_G$; —NO$_2$; —N(R$_G$)$_2$; —NHC(O)R$_G$; or —C(R$_G$)$_3$; wherein each occurrence of R$_G$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety, wherein one, two, or three occurrences of Y are CH;

R₁ is hydrogen; a protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —C(═O)R$_A$; —C(═O)OR$_A$; —C(═O)N(R$_A$)$_2$; or —C(R$_A$)$_3$; wherein each occurrence of R$_A$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; provided that R₁ is not a tert-butoxycarbonyl group;

each occurrence of R₂ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_B$; —C(═O)R$_B$; —CO$_2$R$_B$; —C(═O)N(R$_B$)$_2$; —CN; —SCN; —SR$_B$; —SOR$_B$; —SO$_2$R$_B$; —NO$_2$; —N(R$_B$)$_2$; —NHC(O)R$_B$; or —C(R$_B$)$_3$; wherein each occurrence of R$_B$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety;

R₃ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_C$; —C(═O)R$_C$; —CO$_2$R$_C$; —C(═O)N(R$_C$)$_2$; —CN; —SCN; —SR$_C$; —SOR$_C$; —SO$_2$R$_C$; —NO$_2$; —N(R$_C$)$_2$; —NHC(O)R$_C$; or —C(R$_C$)$_3$; wherein each occurrence of R$_C$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino, alkylamino, dialkylamino, heteroaryloxy; or heteroarylthioxy moiety; provided that R₃ is not —OCH₂Ph;

R₄ and R₅ are independently hydrogen or —OH; and
R₆ is hydrogen; halogen; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR$_K$; —C(═O)R$_K$; —CO$_2$R$_K$; —C(═O)N(R$_K$)$_2$; —CN; —SCN; —SR$_K$; —SOR$_K$; —SO$_2$R$_K$; —NO$_2$; —N(R$_K$)$_2$; —NHC(O)R$_K$; or —C(R$_K$)$_3$; wherein each occurrence of R$_K$ is independently a hydrogen; a halogen; a protecting group; an aliphatic moiety; a heteroaliphatic moiety; an acyl moiety; an aryl moiety; a heteroaryl moiety; alkoxy; aryloxy; alkylthioxy; arylthioxy; amino; alkylamino; dialkylamino; heteroaryloxy; or heteroarylthioxy moiety; and pharmaceutically acceptable salts thereof.

10. A pharmaceutical composition comprising a compound of claim 1 or a pharmaceutically acceptable salt thereof; and a pharmaceutically acceptable excipient or vehicle.

11. The compound of claim 1, wherein X is N.
12. The compound of claim 11, wherein T is —C(R$_E$)$_2$—.
13. The compound of claim 12, wherein G is —C(R$_E$)$_2$—.
14. The compound of claim 13, wherein p is 1.
15. The compound of claim 14, wherein q is 1.
16. The compound of claim 1, wherein R$_C$ is hydrogen.
17. The compound of claim 1, wherein one occurrence of Y is CH.
18. The compound of claim 1, wherein two occurrences of Y are CH.
19. The compound of claim 1, wherein three occurrences of Y are CH.
20. The compound of claim 1, wherein m is 1 and v is 1 or 2.
21. The compound of claim 1, wherein m is 2 and v is 1 or 2.
22. The compound of claim 5, wherein R₆ is hydrogen.

23. The compound of claim 22 of formula:
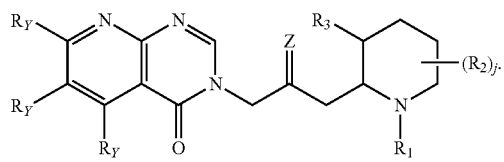
24. The compound of claim 22 of formula:
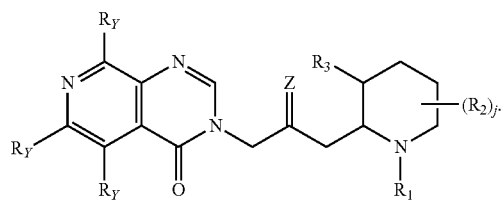
25. The compound of claim 22 of formula:
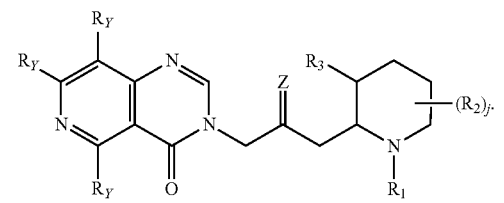
26. The compound of claim 22 of formula:
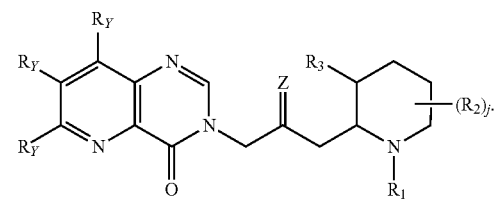
27. The compound of claim 8, wherein $R_6$ is hydrogen.
28. The compound of claim 27, wherein the compound is one of the following:
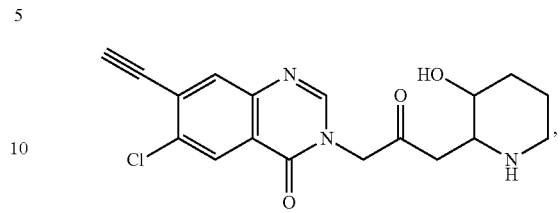
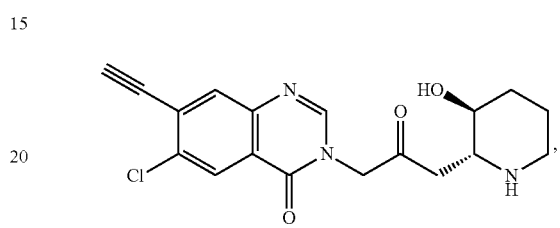
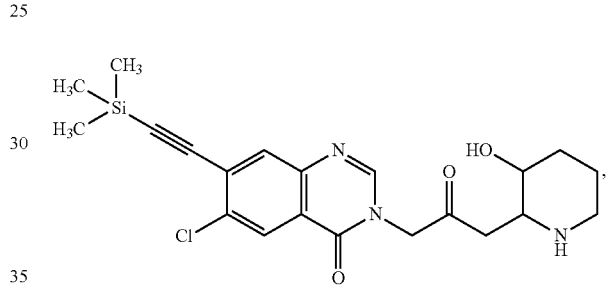
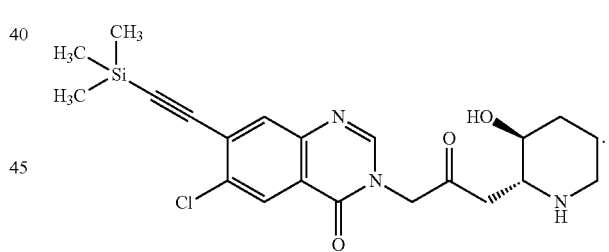
29. A compound selected from the group consisting of:
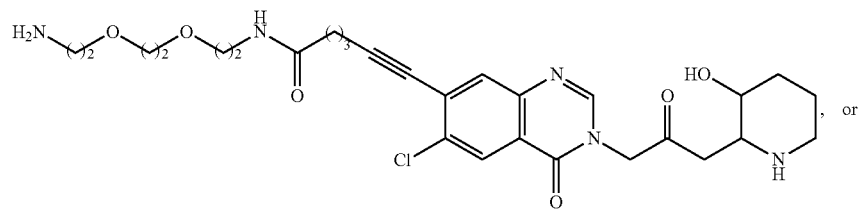

-continued
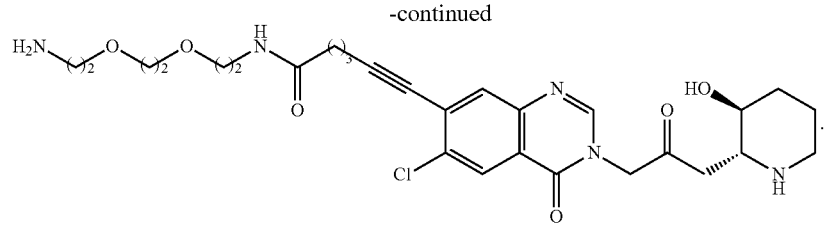
* * * * *